US008772236B2

(12) United States Patent
Timmerman et al.

(10) Patent No.: US 8,772,236 B2
(45) Date of Patent: Jul. 8, 2014

(54) TRUNCATED CYSTINE-KNOT PROTEINS

(75) Inventors: Peter Timmerman, Lelystad (NL); Wouter C. Puijk, Lelystad (NL); Tilman M. Hackeng, Cadier en Keer (NL); Arjan W. Griffioen, Heemstede (NL)

(73) Assignees: Pepscan Systems B.V., Lelystad (NL); Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 0 days.

(21) Appl. No.: 13/138,372

(22) PCT Filed: Feb. 5, 2010

(86) PCT No.: PCT/NL2010/050053

§ 371 (c)(1), (2), (4) Date: Nov. 19, 2011

(87) PCT Pub. No.: WO2010/090523

PCT Pub. Date: Aug. 12, 2010

(65) Prior Publication Data

US 2012/0231000 A1 Sep. 13, 2012

(30) Foreign Application Priority Data

Feb. 6, 2009 (EP) .................................... 09152305

(51) Int. Cl.
*A61K 38/18* (2006.01)
*A61K 38/16* (2006.01)
*A61K 38/00* (2006.01)

(52) U.S. Cl.
USPC ........... 514/13.3; 514/8.1; 514/21.3; 514/1.1; 530/324

(58) Field of Classification Search
None
See application file for complete search history.

(56) References Cited

U.S. PATENT DOCUMENTS

| | | | | |
|---|---|---|---|---|
| 6,706,687 | B1 | 3/2004 | Eriksson et al. | |
| 7,105,481 | B2 * | 9/2006 | Uutela et al. | 514/8.2 |
| 7,972,993 | B2 | 7/2011 | Slootstra et al. | |
| 2005/0250936 | A1 | 11/2005 | Oppermann et al. | |
| 2006/0073518 | A1 | 4/2006 | Timmerman et al. | |
| 2008/0139407 | A1 | 6/2008 | Slootstra et al. | |
| 2010/0322945 | A1 | 12/2010 | Timmerman et al. | |

FOREIGN PATENT DOCUMENTS

| | | |
|---|---|---|
| WO | WO 91/05565 A1 | 5/1991 |
| WO | WO 00/20449 A2 | 4/2000 |
| WO | WO 00/27879 A | 5/2000 |
| WO | WO 00/37025 | 6/2000 |
| WO | WO 2010/090523 A1 | 8/2010 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Ferrara et al. 2005. BBRC 333:328-335.*
Michels et al. 2005. Opthalmology 112:1035-1047.*
Stevens (1995. excerpted from Hanly et al. Ilar Jr. 37:93-125).*
Scappalicci 2002. J. Clin Oncol. 20:3906-3927.*
Huang et al. 2005. J. Cell. Biochem. 96:447-462.*
Groppe et al. 2002. Nature 420:636-642.*
Bell et al., N-linked oligosaccharides play a role in disulphide-dependent dimerization of intestinal mucin Muc2, Biochemical Journal, 2003, pp. 893-900, vol. 373, The Biochemical Society.
Wilczynski et al., Abstract, Structural characterization and pharmacology of a potent (Cys101-Cys119, Cys110-Cys117) bycyclic agouti-related protein (AGRP) melanocortin receptor antagonist, Journal of Medicinal Chemistry, 2004, pp. 3662-3673, vol. 47, No. 23, American Chemical Society.
Hua et al., Abstract, The combination of VEGF-C expressing vector and the detection of expression in Tca8113 cell, Chemical Abstracts Service, Columbus, Ohio, US.
PCT International Search Report, PCT/NL2010/050053, dated Jun. 4, 2010.
U.S. Appl. No. 13/101,894, filed May 5, 2011, Indentification of Protein Binding Sites, Slootstra et al.

* cited by examiner

*Primary Examiner* — Shulamith H Shafer
(74) *Attorney, Agent, or Firm* — TraskBritt, P.C.

(57) ABSTRACT

The invention relates to the fields of protein chemistry, biology and medicine. More specifically, it relates to the design and preparation of proteinmimics of members of the cystine-knot growth factor superfamily. Further, the invention relates to the use of these proteinmimics as a medicament or prophylactic agent. The invention provides proteinmimics of members of the cystine-knot growth factor superfamily, preferably for use in immunogenic and/or therapeutic compositions.

12 Claims, 43 Drawing Sheets

| | Seq Nr. | Full protein name | Species | X0 | |
|---|---|---|---|---|---|
| | | cys-knot trunc | | XXXXXXXXXX | C1 |
| Family 1 | | TGF-beta like | consensus sequence: | | |
| | 1 | protein 60A | fruit fly | LLEPMESTRS | C |
| | 2 | Artemin | human | SRARAAGARG | C |
| | 3 | bone morphogenetic protein-10 | human | RIRRNAKCNY | C |
| | 4 | bone morphogenetic protein-15 | human | KHSGPPENNQ | C |
| | 5 | bone morphogenetic protein 2 | human | HKQRKRLKSS | C |
| | 6 | bone morphogenetic protein 3 | human | QWIEPRN | C |
| | 7 | bone morphogenetic protein 3b | human | QWDEPRV | C |
| | 8 | bone morphogenetic protein 4 | human | SQRARKKNKN | C |
| | 9 | bone morphogenetic protein 5 | human | DYNTSEQKQA | C |
| | 10 | bone morphogenetic protein 6 | human | DYNSSELKTA | C |
| | 11 | bone morphogenetic protein 7 | human | AENSSSDRQA | C |
| | 12 | bone morphogenetic protein-8 | human | DVRGSHGRQV | C |
| | 13 | Dauer larva development regulatory growth factor daf-7 | C. elegans | SHAKPV | C |
| | 14 | Protein decapentaplegic | fruit fly | PTRRKNHDDT | C |
| | 15 | Protein decapentaplegic | red flour beatle | RRHRKNLKDP | C |
| | 16 | Derriere protein | frog | PTPSNI | C |
| | 17 | Dorsalin-1 | chicken | SIGANH | C |
| | 18 | protein DVR-1 | frog | SKLPFTASNI | C |
| | 19 | protein DVR-1 homolog | urchin | SASSLNSDWQ | C |
| | 20 | Growth/differentation factor 11 | human | NLGLD | C |
| | 21 | Growth/differentation factor 15 | human | ARARNGDH | C |
| | 22 | Embryonic growth/differentation factor 1 | human | PVLGGGPGGA | C |
| | 23 | Growth/differentation factor 2 | human | SAGAGSH | C |
| | 24 | Growth/differentation factor 3 | human | PVPKLSCKNL | C |
| | 25 | Growth/differentation factor 5 | human | KRPSKNLKAR | C |
| | 26 | Growth/differentation factor 6 | human | KRHGKKSRLR | C |

FIG. 10A

| Seq Nr. | X1<br>XXXXXXXXXXXXXXXXXXXXXXXX | C2 | X2<br>XXXXXXXXXXXXXXX | C3 |
|---|---|---|---|---|
| | [LIVM]XXPXX[FY]XXXX | C | XGX | C |
| Family 1 | | | | |
| 1 | QMQTLYIDFKDLGWHDWIIAPEGYGAFY | C | SGE | C |
| 2 | RLRSQLVPVRALGLGHRSDELVRFRF | C | SGS | C |
| 3 | KRTPLYIDFKEIGWDSWIIAPFGYEAYE | C | RGV | C |
| 4 | SLHPFQISFRQLGWDHWIIAPPFYTPNY | C | KGT | C |
| 5 | KRHPLYVDFSDVGWNDWIVAPPGYHAFY | C | HGE | C |
| 6 | ARRYLKVDFADIGWSEWIISPKSFDAYY | C | SGA | C |
| 7 | SRRYLKVDFADIGWNEWIISPKSFDAYY | C | AGA | C |
| 8 | RRHSLYVDFSDVGWNDWIVAPPGYQAFY | C | HGD | C |
| 9 | KKHELYVSFRDLGWQDWIIAPEGYAAFY | C | DGE | C |
| 10 | RKHELYVSFQDLGWQDWIIAPKGYAANY | C | DGE | C |
| 11 | KKHELYVSFRDLGWQDWIIAPEGYAAYY | C | EGE | C |
| 12 | RRHELYVSFQDLGWLDWVIAPQGYSAYY | C | EGE | C |
| 13 | NAEAQSKGCCLYDLEIEFEKIGWDWIVAPRYNAYM | C | RGD | C |
| 14 | RRHSLYVDFSDVGWDDWIVAPLGYDAYY | C | HGK | C |
| 15 | RRRQMYVDFGSVGWNDWIVAPLGYDAYY | C | GGE | C |
| 16 | KKRRLYIDFKDVGWQNWVIAPRGYMANY | C | HGE | C |
| 17 | RRTSLHVNFKEIGWDSWIIAPKDYEAFE | C | KGG | C |
| 18 | KKRHLYVEFKDVGWQNWVIAPQGYMANY | C | YGE | C |
| 19 | KRKNLFVNFEDLDWQEWIIAPLGYVAFY | C | QGE | C |
| 20 | DEHSSESRCCRYPLTVDFEAFGWDWIIAPKRYKANY | C | SGQ | C |
| 21 | PLGPGRCCRLHTVRASLEDLGWADWVLSPREVQVTM | C | IGA | C |
| 22 | RARRLYVSFREVGWHRWVIAPRGFLANY | C | QGQ | C |
| 23 | QKTSLRVNFEDIGWDSWIIAPKEYEAYE | C | KGG | C |
| 24 | HRHQLFINFRDLGWHKWIIAPKGFMANY | C | HGE | C |
| 25 | SRKALHVNFKEMGWDDWIIAPLEYEAFH | C | EGL | C |
| 26 | SKKPLHVNFKELGWDDWIIAPLEYEAYH | C | EGV | C |

FIG. 10B

| Seq Nr. cys-knot trunc | Full protein name | Species | XO XXXXXXXXXX | C1 |
|---|---|---|---|---|
| 27 | Growth/differentation factor 7 | human | RGHGRRGRSR | C |
| 28 | Growth/differentation factor 8 | human | DFGLD | C |
| 29 | Growth/differentation factor 9 | human | FRQFLLPQNE | C |
| 30 | Glial cell line-derived neurotrophic factor | human | RGGQRGKNRG | C |
| 31 | Inhibin alfa chain | human | PPEEPAAHAN | C |
| 32 | Inhibin beta chain | fruit fly | TRRVRRRAVD | C |
| 33 | Inhibin beta-A chain | human | PHRRRRRGLE | C |
| 34 | Inhibin beta-B chain | human | RHRIRKRGLE | C |
| 35 | Inhibin beta-C chain | human | KHQIHRRGID | C |
| 36 | Inhibin beta-E chain | human | AGRARRRTPT | C |
| 37 | left-right determination factor 2 | human | DLRDYGAQGD | C |
| 38 | Muellerian-inhibiting factor [Precursor] | human | SAGATAADGP | C |
| 39 | Nodal homolog 2-A | African clawed frog | IPSRSVGKTL | C |
| 40 | Nodal homolog 4-A | African clawed frog | VPPADSSRTL | C |
| 41 | Nodal homolog | human | HHLPDRSQL | C |
| 42 | neurturin | human | RLGARP | C |
| 43 | persephin | human | ALSGP | C |
| 44 | Protein screw | fruit fly | PVDLYRPPQS | C |
| 45 | transforming growth factor beta-1 | human | NYCFSSTEKN | C |
| 46 | transforming growth factor beta-2 | human | AYCFRNVQDN | C |
| 47 | transforming growth factor beta-3 | human | NYCFRNLEEN | C |
| 48 | Univin | urchin | SFPTASLTNL | C |
| 49 | Mullerian inhibitory substance | hatcheri | GLDSPSGSNI | C |
| 50 | Decapentaplegic-like protein | sea anemone | GGAKRRRPQY | C |
| 51 | decapentaplegic protein homolog | roundworm | HHNTEAESNL | C |

FIG. 10C

| Seq Nr. | X1<br>XXXXXXXXXXXXXXXXXXXXXXXX | C2 | X2<br>XXXXXXXXXXXXXXX | C3 |
|---|---|---|---|---|
| 27 | SRKPLHVDFKELGWDDWIIAPLDYEAYH | C | EGL | C |
| 28 | DEHSTESRCCRYPLTVDFEAFGWDWIIAPKRYKANY | C | SGE | C |
| 29 | ELHDFRLSFSQLKWDNWIVAPHRYNPRY | C | KGD | C |
| 30 | VLTAIHLNVTDLGLGYETKEELIFRY | C | SGS | C |
| 31 | HRVALNISFQELGWERWIVYPPSFIFHY | C | HGG | C |
| 32 | GGALNGQCCKESFYVSFKALGWDDWIIAPRGYFANY | C | RGD | C |
| 33 | DGKVNICCKKQFFVSFKDIGWNDWIIAPSGYHANY | C | EGE | C |
| 34 | DGRTNLCCRQQFFIDFRLIGWNDWIIAPTGYYGNY | C | EGS | C |
| 35 | QGGSRMCCRQEFFVDFREIGWHDWIIQPEGYAMNF | C | IGQ | C |
| 36 | EPATPLCCRRDHYVDFQELGWRDWILQPEGYQLNY | C | SGQ | C |
| 37 | DPEAPMTEGTRCCRQEMYIDLQGMKWAKNWVLEPPGFLAYE | C | VGT | C |
| 38 | ALRELSVDLRAERSVLIPETYQANN | C | QGV | C |
| 39 | RRVDMIVDFEKIEWGDRIVYPKRFNAYR | C | EGA | C |
| 40 | RRVDFFVDFKQIGWDSWIIHPMKYNAYR | C | EGE | C |
| 41 | RKVKFQVDFNLIGWGSWIIYPKQYNAYR | C | EGE | C |
| 42 | GLRELEVRVSELGLGYASDETVLFRY | C | AGA | C |
| 43 | QLWSLTLSVAELGLGYASEEKVIFRY | C | AGS | C |
| 44 | ERLNFTVDFKELHMHNWVIAPKKFEAYF | C | GGG | C |
| 45 | CVRQLYIDFRKDLGWKWIHEPKGYHANF | C | LGP | C |
| 46 | CLRPLYIDFKRDLGWKWIHEPKGYNANF | C | AGA | C |
| 47 | CVRPLYIDFRQDLGWKWVHEPKGYYANF | C | SGP | C |
| 48 | QRHRLFVSFRDVGWENWIIAPMGYQAYY | C | DGE | C |
| 49 | GLRSLTVSFEKLLLGPQTANINN | C | QGS | C |
| 50 | RRHPLYVDFTDVGWNDWIVAPPGYHAFY | C | TGV | C |
| 51 | RRTDFYVDFDDLNWQDWIMAPKGYDAYQ | C | QGS | C |

FIG. 10D

| | Seq Nr. | Full protein name | Species | X0 XXXXXXXXXX | C1 |
|---|---|---|---|---|---|
| | | cys-knot trunc | | | |
| | 52 | CG1901-PB, isoform B | fruit fly | TNNCYKLHQR | C |
| | 53 | CG16987-PA, isoform A (CG16987-PB, isoform B) (GH144433p) | fruit fly | SINCSSGMTE | C |
| | 54 | Myoglianin | fruit fly | DCTENDHDMR | C |
| | 55 | CBR-DBL-1 protein | roundworm | HHNTEAESNL | C |
| | 56 | CBR-UNC-129 protein | roundworm | RVVLLQNKNR | C |
| Family 2a/b | | Cys-knot: GLHB-like | consensus sequences: | | |
| | 57 | choriogonadotropin-beta v1 | human | SKEPLRPR | C |
| | 58 | choriogonadotropin-beta v2 | human | SKEPLRPR | C |
| | 59 | choriogonadotropin-beta | human | SKEPLRPR | C |
| | 60 | follicle-stimulating hormone-beta | human | NS | C |
| | 61 | glycoprotein hormone beta-5 | human | SSGNLRTFVG | C |
| | 62 | gonadotropin beta-1 chain | eel | | C |
| | 63 | gonadotropin beta-2 chain | eel | SLLLP | C |
| | 64 | gonadotropin beta chain | eel | SVLQP | C |
| | 65 | luteinizing hormone beta | human | SREPLRPW | C |
| | 66 | thyroid-stimulating hormone beta | human | F | C |
| | 67 | putative uncharacterized protein (Glycoprotein hormone beta 5) | roundworm | | C |
| Family 3 | | NGF-like | consensus sequence: | | |
| | 68 | Brain-derived neurotrophic factor | human | DPARRGELSV | C |
| | 69 | Venom nerve growth factor 1 | viper | PVHNQGEYSV | C |
| | 70 | Venom nerve growth factor 2 | snake | PVNDHGEYSV | C |
| | 71 | Venom nerve growth factor 3 | snake | PVHNQGEHSV | C |
| | 72 | Venom nerve growth factor 4 | snake | PVHNQGEHSV | C |
| | 73 | Venom nerve growth factor 5 | snake | PVYNRGEHSV | C |
| | 74 | Venom nerve growth factor | snake | PVHNLGEHSV | C |

FIG. 10E

| | Seq Nr. | X1<br>XXXXXXXXXXXXXXXXXXXXXXX | C2 | X2<br>XXXXXXXXXXXXXX | C3 |
|---|---|---|---|---|---|
| | 52 | CRNQLDVAFKSIKGFEFILPQKVFDAGY | C | HGR | C |
| | 53 | CREHLYISFRDIGWSNWILKPEGYNAYF | C | RGS | C |
| | 54 | CRYPLKVNFTSFGWHFVVAPTSFDAYF | C | SGD | C |
| | 55 | RRTDLYVDFDDLGWQDWIMAPKGYDAYQ | C | QGS | C |
| | 56 | HKEGTLVSLKHFGWDKFVMEPRTIETSF | C | KGK | C |
| Family 2a/b | | | C | [STAGM]G[HFYL] | C |
| | 57 | RPINATLAVEKEGCPVCITVNTTI | C | AGY | C |
| | 58 | RPINATLAVEKEGCPVCITVNTTI | C | AGY | C |
| | 59 | RPINATLAVEKEGCPVCITVNTTI | C | AGY | C |
| | 60 | ELTNITIAIEKEECRFCISINTTW | C | AGY | C |
| | 61 | AVREFTFLAKKPGCRGLRITTDA | C | WGR | C |
| | 62 | GLANISISVENEECGGCITFNTTA | C | AGL | C |
| | 63 | EPINETISVEKDGCPKCLVFQTSI | C | SGH | C |
| | 64 | QPINETISVEKDGCPKCLVFQTSI | C | SGH | C |
| | 65 | HPINAILAVEKEGCPVCITVNTTI | C | AGY | C |
| | 66 | IPTEYTMHIERRECAYCLTINTTI | C | AGY | C |
| | 67 | MRLVPGFNPLRQVDANGKECRGNVELPF | C | KGY | C |
| Family 3 | | | | [GSRE] | C |
| | 68 | DSISEWVTAADKKTAVDMSGGTVTVLEKVPVSKGQLKQYFYETK | C | NPMGYTKEG | C |
| | 69 | DSVSVWVANKTTATDIRGNLVTVMVDINLNNNVYKQYFFETK | C | RNPNPVPSG | C |
| | 70 | DSVSVWVNKTTATDIKGKPVTVMVDVNLNNHVYKQYFFETK | C | KNPNPVPSG | C |
| | 71 | DSVSDWVIKTTATDIRGNMVTVMVDINRDNEVYKQYFFETK | C | RNPNPNPVQSE | C |
| | 72 | DSVSDWVIKTTATDIRGNVVTVMEDINLNNEVYKQYFFETK | C | RNPNPNPVQSE | C |
| | 73 | DSVSVWVTNKTKATDIKGNMVTVMVDINLNNEVYKQYFFETK | C | RNPNPVPSG | C |
| | 74 | DSISVWVTNKTKATDIKDNMVTVMVDINLNNEVYKQYFFETK | C | RNPNPVPSG | C |

FIG. 10F

| | Seq Nr. | Full protein name | Species | X0 XXXXXXXXXX | C1 |
|---|---|---|---|---|---|
| | | cys-knot trunc | | | |
| | 75 | Beta-nerve growth factor | human | PIFHRGEFSV | C |
| | 76 | Beta-nerve growth factor | rat | PVFHMGEFSV | C |
| | 77 | Neurotrophic factor-3 | human | HKSHRGEYSV | C |
| | 78 | Neurotrophic factor-4/5 | human | PASRRGELAV | C |
| | 79 | Neurotrophin-7 | zebrafish | DFLHRGEYSV | C |
| Family 4 | | PDGF-like | consensus sequence: | | |
| | 80 | Plateled-derived growth factor A | human | SIEEAVPAV | C |
| | 81 | Plateled-derived growth factor B | human | TIAEPAMIAE | C |
| | 82 | Plateled-derived growth factor C | human | LLTEEVRLYS | C |
| | 83 | Plateled-derived growth factor D | human | RLNDDAKRYS | C |
| | 84 | Placenta growth factor | human | PFQEVWGRSY | C |
| | 85 | PDGF-related-transforming protein sis | monkey sarcoma virus | SVAEPAMIAE | C |
| | 86 | Vascular Endothelial Growth Factor toxin | snake | PFMEVYRHSV | C |
| | 87 | Vascular Endothelial Growth Factor toxin | snake | PFLEVHERSA | C |
| | 88 | Vascular Endothelial Growth Factor A | human | KFMDVYQRSY | C |
| | 89 | Vascular Endothelial Growth Factor B | human | SWIDVYTRAT | C |
| | 90 | Vascular Endothelial Growth Factor C | human | SIDNEWRKTQ | C |
| | 91 | Vascular Endothelial Growth Factor D | human | VIDEEWQRTQ | C |
| | 92 | Vascular Endothelial Growth Factor homolog | orf-virus strain NZ2 | GWSEVLKGSE | C |
| | 93 | Vascular Endothelial Growth Factor homolog | orf-virus strain NZ7 | DWMRTLDKSG | C |
| | 94 | Vascular Endothelial Growth Factor A-A | zebrafish | PFMDVYKKSA | C |
| | 95 | VEGF-like protein | orf-virus | KWPEVLEGSK | C |
| | 96 | C-sis proto oncogene | cat | TVAEPAMIAE | C |
| Family 5 | | GLHA-like | consensus sequence: | | |
| | 97 | glycoprotein hormones alfa chain 1 | salmon | SDMTNVGCEE | C |

FIG. 10G

| | Seq Nr. | X1<br>XXXXXXXXXXXXXXXXXXXXXXXX | C2 | X2<br>XXXXXXXXXXXXXXX | C3 |
|---|---|---|---|---|---|
| | 75 | DSVSVWVGDKTTATDIKGKEVMVLGEVNINNSVFKQYFFETK | C | RDPNPVDSG | C |
| | 76 | DSVSVWVGDKTTATDIKGKEVTVLGEVNINNSVFKQYFFETK | C | RAPNPVESG | C |
| | 77 | DSESLWVTDKSSAIDIRGHQVTVLGEIKTGNSPVKQYFYETR | C | KEARPVKNG | C |
| | 78 | DAVSGWVTDRRTAVDLRGREVEVLGEVPAAGGSPLRQYFFETR | C | KADNAEEGGPGAGGGG | C |
| | 79 | DSEEHWVGNLTHATDLGGNEVMVLPHFRINNVVKKQLFYETT | C | RVKKPIGAPKPGQGASGVKAGTSS | C |
| Family 4 | | P[PSR]CVXXXR | C | [GSTA]GC | C |
| | 80 | KTRTVIYEIPRSQVDPTSANFLIWPPCVEVKR | C | TGC | C |
| | 81 | KTRTEVFEISRRLIDRTNANFLVWPPCVEVQR | C | SGC | C |
| | 82 | TPRNFSVSIREELKRTDTIFWPGCLLVKR | C | GGN | C |
| | 83 | TPRNYSVNIREELKLANVVFFPRCLLVQR | C | GGN | C |
| | 84 | RALERLVDVVSEYPSEVEHMFSPSCVSLLR | C | TGC | C |
| | 85 | KTRTEVFEISRRLIDRTNANFLVWPPCVEVQR | C | SGC | C |
| | 86 | QPRETLVSILEEYPCEIAHIFRPSCVTALR | C | GGC | C |
| | 87 | QARETLVSILQEYPDEISDIFRPSCVAVLR | C | SGC | C |
| | 88 | HPIETLVDIFQEYPDEIEYIFKPSCVPLMR | C | GGA | C |
| | 89 | QPREVVVPLTVELMGTVAKQLVPSCVTVQR | C | GGC | C |
| | 90 | MPREVAIDVGKEFGVATNTFFKPPCVSVYR | C | GGC | C |
| | 91 | SPRETAVEVASELGKSTNTFFKPPCVNVFR | C | GGC | C |
| | 92 | KPRPIVVPVSETHPELTSQRFNPPCVTLMR | C | GGC | C |
| | 93 | KPRDTVVYLGEEYPESTNLQYNPRCVTVKR | C | SGC | C |
| | 94 | KTRELLVDIIQEYPDEIEHTYIPSCVVLMR | C | AGC | C |
| | 95 | KPRPTVLSVNGEHPELTSQRFNPPCVTLMR | C | GGC | C |
| | 96 | KTRTEVFEVSRRLIDRTNANFLVWPPCVEVQR | C | SGC | C |
| Family 5 | | | C | XGC | C |
| | 97 | KLKENKVFSNPGAPVYQ | C | TGC | C |

FIG. 10H

| Family | Seq Nr. | Full protein name | Species | X0 XXXXXXXXXX | C1 |
|---|---|---|---|---|---|
| | | cys-knot trunc | | | |
| | 98 | glycoprotein hormones alfa chain 2 | salmon | CEE | C |
| | 99 | glycoprotein hormones alfa chain | human | APDVQDCPE | C |
| | 100 | glycoprotein hormones alfa chain | macaque | GEFTMQDCPE | C |
| Family 6 | | Noggin-like | no consensus sequence defined | | |
| | 101 | Noggin | human | LQMWLWSQTF | C |
| | 102 | Noggin-1 | zebrafish | LQMWLWSYSF | C |
| | 103 | Noggin-2 | zebrafish | FLQWLWMYTH | C |
| | 104 | Noggin-3 | zebrafish | LQLWLWSYTF | C |
| | 105 | Noggin-4 | chicken | LRRWLVERAS | C |
| | 106 | Noggin-5 | zebrafish | MRRWMWSYTR | C |
| | 107 | Noggin-I | sponge | AIRRTLNTLN | C |
| | 108 | Noggin-like protein | dugesia japonica | IRRWMVQQAA | C |
| | 109 | Noggin-like protein 1 | flatworm | IRRWMVQQAT | C |
| Family 7 | | Coagulin-like | no consensus sequence defined | | |
| | 110 | Coagulogen [precursor](contains AB-chains + pept.C) | horseshoe crab | FFPFHHFPSE | C |
| | 111 | Coagulogen (contains AB-chains + pept.C) | crab | FPPFVHFTSE | C |
| Family 2c/8 | | CTCK-like | consensus sequence: | | |
| | 112 | Bursicon | fruit fly | TDNDITHLGD | C |
| | 113 | Partner of bursicon | fruit fly | RYSQGTGDEN | C |
| | 114 | protein CEF-10 | chicken | SYASLKKGKK | C |
| | 115 | Cerberus | human | IKSHEVHWET | C |
| | 116 | Connective tissue growth factor | human | LEENIKKGKK | C |
| | 117 | protein CYR61 | human | VYSSLKKGKK | C |
| | 118 | DAN domain family member 5 | human | LNPQEVIQGM | C |
| | 119 | DAN domain family member 5 | xenla | IGQDALKRSR | C |

FIG. 10I

| Seq Nr. | X1<br>XXXXXXXXXXXXXXXXXXXXXXXX | C2 | X2<br>XXXXXXXXXXXXXXX | C3 |
|---|---|---|---|---|
| 98 | TLKPNTIFPNIMQ | C | TGC | C |
| 99 | TLQENPFFSQPGAPILQ | C | MGC | C |
| 100 | KPRENKFFSKPGAPIYQ | C | MGC | C |
| Family 6 | | | | |
| 101 | PVLYAWNDLGSRFWPRYVKVGS | C | FSKRS | C |
| 102 | PVLYAWNDLGSRFWPRFVRAGS | C | YTKRS | C |
| 103 | PVLYTWKDLGLRFWPRYIKEGN | C | FSERS | C |
| 104 | PVVHTWQDLGNRFWPRYLKVGS | C | YNKRS | C |
| 105 | RLTSAWVDLGPVFWPRWVRHTA | C | RTGPPA | C |
| 106 | PVLSMWKDLGVRFWPRYVKEGQ | C | STERS | C |
| 107 | RVTYNWADAGVNFFPRYFSAGS | C | FERR | C |
| 108 | KIDYLWKRLDDTHWPSFIKHGV | C | NSRES | C |
| 109 | KTDYIWKRLDETHWPSWIKHGI | C | SSTEP | C |
| Family 7 | | | | |
| 110 | PVSVSACEPTFGYTTSNELRIIVQAPKAGFRQCVWQHK | C | RAYGSNF | C |
| 111 | PVSTRDCEPVFGYTVAGEFRVIVQAPRAGFRQCVWQHK | C | R-YGSNN | C |
| Family 2c/8 | | | | |
| 112 | QVTPVIHVLQYPGCVPKPIPSFA | C | VGR | C |
| 113 | ETLKSEIHLIKEEFDELGRMQRTCNADVIVNK | C | EGL | C |
| 114 | TKTKKSPSPVRFTYAGCSSVKKYRPKY | C | GS | C |
| 115 | RTVPFSQTITHEGCEKVVVQNNL | C | FGK | C |
| 116 | IRTPKISKPIKFELSGCTSMKTYRAKF | C | GV | C |
| 117 | SKTKKSPEPVRFTYAGCLSVKKYRPKY | C | GS | C |
| 118 | KAVPFVQVFSRPGCSAIRLRNHL | C | FGH | C |
| 119 | HALPFIQNVFRKNCFPVRLPNKF | C | FGQ | C |
| ... | | | | |

FIG. 10J

| Seq Nr. | Full protein name<br>cys-knot trunc | Species | XO<br>XXXXXXXXXX | C1 |
|---|---|---|---|---|
| 120 | Gremlin-1 | human | TERKYLKRDW | C |
| 121 | Gremlin-2 | human | TERKYLKRDW | C |
| 122 | mucin-19 | human | KKCCYTCKNN | C |
| 123 | mucin-2 | human | CTPRNETRVP | C |
| 124 | mucin-5AC | human | EPPPYQNQST | C |
| 125 | mucin-5B | human | GCCYSCEEDS | C |
| 126 | mucin-6 | human | GTPTPTSPGV | C |
| 127 | Norrie disease protein | human | SFIMDSDPRR | C |
| 128 | protein NOV homolog | human | EQPTDKKGKK | C |
| 129 | Otogelin-like protein C12orf64 | human | CKICKREERI | C |
| 130 | Otogelin | human | CRTCKEDGRS | C |
| 131 | Slit homolog 1 protein | human | SGELCEQESE | C |
| 132 | Slit homolog 2 protein | human | TGDSCDREIS | C |
| 133 | Slit homolog 3 protein | human | SGEHCQQENP | C |
| 134 | Protein slit | drosophila | EPPTVTAAST | C |
| 135 | sclerostin domain-containing protein 1 | human | LDRNTRVQVG | C |
| 136 | sclerostin | human | FETKDVSEYS | C |
| 137 | SCO-spondin | human | VLEPGSCCPS | C |
| 138 | von Willebrand factor | human | TCCDTCEEPE | C |
| 139 | WNT1-inducible-signalling pathway protein 1 | human | IHTLIKAGKK | C |
| 140 | WNT1-inducible-signalling pathway protein 3 | human | LKTIKIPKGK | C |
| 141 | Hemolectin | drosophila | SEPLVEDKSS | C |
| 142 | glycoprotein hormone alfa-2 | human | QEAVIPG | C |
| 143 | glycoprotein hormone alfa-2 | mouse | HSPETAIPG | C |
| 144 | Protein jagged-1 | human | LDANECEAKP | C |
| 145 | Protein jagged-2 | human | LDANECEGKP | C |

FIG. 10K

| Seq Nr. | X1<br>XXXXXXXXXXXXXXXXXXXXXXXX | C2 | X2<br>XXXXXXXXXXXXXXX | C3 |
|---|---|---|---|---|
| 120 | KTQPLKQTIHEEGCNSRTIINRF | C | YGQ | C |
| 121 | KTQPLRQTVSEEGCRSRTILNRF | C | YGQ | C |
| 122 | RSSLVNVTVIYSGCKKRVQMAK | C | TGE | C |
| 123 | STVPVTTEVSYAGCTKTVLMNH | C | SGS | C |
| 124 | AVYHRSLIIQQQGCSSSEPVRLAY | C | RGN | C |
| 125 | QVRINTTILWHQGCETEVNITF | C | EGS | C |
| 126 | SVREQQEEITFKGCMANVTVTR | C | ECA | C |
| 127 | MRHHYVDSISHPLYKCSSKMVLLAR | C | EGH | C |
| 128 | LRTKKSLKAIHLQFKNCTSLHTYKPRF | C | GV | C |
| 129 | QKVIIKSVIRKQDCMSQSPINVAS | C | DGK | C |
| 130 | KKVTIRMTIRKNECRSSTPVNLVS | C | DGR | C |
| 131 | RGDPVRDFHQVQRGYAICQTTRPLSWVE | C | RGS | C |
| 132 | RGERIRDYYQKQQGYAACQTTKKVSRLE | C | RGG | C |
| 133 | LGQVVREVIRRQKGYASCATASKVPIME | C | RGG | C |
| 134 | RKEQVREYYTENDCRSRQPLKYAK | C | VGG | C |
| 135 | RELRSTKYISDGQCTSISPLKELV | C | AGE | C |
| 136 | RELHFTRYVTDGPCRSAKPVTELV | C | AGE | C |
| 137 | RREAPEEQSPSCQLLTELRNFTKGTCYLDQVEVSY | C | SGY | C |
| 138 | NDITARLQYVKVGSCKSEVEVDIHY | C | QGK | C |
| 139 | LAVYQPEASMNFTLAGCISTRSYQPKY | C | GV | C |
| 140 | QPTFQLSKAEKFVFSGCSSTQSYKPTF | C | GI | C |
| 141 | LPVSLAESRTKEILKFPVQGHGTCVNADPIQGFTD | C | EGA | C |
| 142 | HLHPFNVTVRSDRQGTCQGSHVAQA | C | VGH | C |
| 143 | HLHPFNVTVRSDRLGTCQGSHVAQA | C | VGH | C |
| 144 | VNAKSCKNLIASYYCDCLPGWNGQNCDININD | C | LGQ | C |
| 145 | LNAFSCKNLIGGYYCDCIPGWKGINCHINVND | C | RGQ | C |

FIG. 10L

| Seq Nr. | X3<br>XXXXXXXXXXXXXXXXXXXXXXXXXXXXXXXXX | C4 |
|---|---|---|
| Family 1 | | |
| 1 | NFPLNAHMNATNHAIVQTLVHLLEPKKVPKPC | C |
| 2 | RRARSPHDLSLASLLGAGALRPPPGSRPVSQPC | C |
| 3 | NYPLAEHLTPTKHAIIQALVHLKNSQKASKAC | C |
| 4 | LRVLRDGLNSPNHAIIQNLINQLVDQSVPRPS | C |
| 5 | PFPLADHLNSTNHAIVQTLVNSVNSKIPKAC | C |
| 6 | QFPMPKSNHATIQSIVRAVGVVPGIPEPC | C |
| 7 | EFPMPKIVRPSNHATIQSIVRAVGIIPGIPEPC | C |
| 8 | PFPLADHLNSTNHAIVQTLVNSVNSSIPKAC | C |
| 9 | SFPLNAHMNATNHAIVQTLVHLMFPDHVPKPC | C |
| 10 | SFPLNAHMNATNHAIVQTLVHLMNPEYVPKPC | C |
| 11 | AFPLNSYMNATNHAIVQTLVHFINPETVPKPC | C |
| 12 | SFPLDSCMNATHAILQSLVHSMKPNAVPKAC | C |
| 13 | PSQFRAANMHAQIKTSLHRLKPDTVPAPC | C |
| 14 | PFPLADHFNSTNHAVVQTLVNNMNPGKVPKAC | C |
| 15 | EYPIPDHMNTTNHAIVQSLVNSMKPKEVPGPC | C |
| 16 | PYPLTEMLRGTNHAVLQTLVHSVEPENTPLPC | C |
| 17 | FFPLTDNVTPTKHAIVQTLVHLQNPKKASKAC | C |
| 18 | PYPLTEILNGSNHAILQTLVHSIEPEDIPLPC | C |
| 19 | AFPLNGHANATNHAIVQTLVHHMSPSHVPQPC | C |
| 20 | EYMFMQKYPHTHLVQQANPRGSAGPC | C |
| 21 | PSQFRAANMHAQIKTSLHRLKPDTVPAPC | C |
| 22 | ALPVALSGSGGPPALNHAVLRALMHAAAPGAADLPC | C |
| 23 | FFPLADDVTPTKHAIVQTLVHLKFPTKVGKAC | C |
| 24 | PFSLTISLNSSNYAFMQALMHAVDPEIPQAV | C |
| 25 | EFPLRSHLEPTNHAVIQTLMNSMDPESTPPTC | C |

FIG. 10M

| Seq Nr. | X4 | C5 | X5 | C6 | X6 |
|---|---|---|---|---|---|
| | XXXXXXXXXXXXXXXXXXXXXXXXXXXXXXXXX | C5 | X | C6 | XXXXXXXXXX |
| Family 1 | | | | | |
| 1 | APTRLGALPVLYHLNDENVNLKKYRNMIVKS | C | G | C | H |
| 2 | RPTRYEAVSFMDVNSTWRTVDRLSATA | C | G | C | LG |
| 3 | VPTKLEPISILYLDKGVVTYKFKYEGMAVSE | C | G | C | R |
| 4 | VPYKYVPISVLMIEANGSILYKEYEGMIAES | C | T | C | R |
| 5 | VPTELSAISMLYLDENEKVVLKNYQDMVVEG | C | G | C | R |
| 6 | VPEKMSSLSILFFDENKNVVLKVYPNMTVES | C | A | C | R |
| 7 | VPDKMNSLGVLFLDENRNVVLKVYPNMSVDT | C | A | C | R |
| 8 | VPTELSAISMLYLDEYDKVVLKNYQEMVVEG | C | G | C | R |
| 9 | APTKLNAISVLYFDDSSNVILKKYRNMVVRS | C | G | C | H |
| 10 | APTKLNAISVLYFDDNSNVILKKYRNMVVRA | C | G | C | H |
| 11 | APTQLNAISVLYFDDSSNVILKKYRNMVVRA | C | G | C | H |
| 12 | APTKLSATSVLYYDSSNNVILRKHRNMVVKA | C | G | C | H |
| 13 | VPASYNPMVLIQKTDTGVSLQTYDDLLAKD | C | H | C | I |
| 14 | VPTQLDSVAMLYLNDQSTVVLKNYQEMTVVG | C | G | C | R |
| 15 | VPTQLGQMSMLYLGSDGSVILKNYKEMVVVG | C | G | C | R |
| 16 | APTKLSPISMLYYDNNDNVVLRHYEDMVVDE | C | G | C | K |
| 17 | VPTKLDAISILYKDDAGVPTLIYNYEGMKVAE | C | G | C | R |
| 18 | VPTKMSPISMLFYDNNDNVVLRHYENMAVDE | C | G | C | R |
| 19 | APTKLSPITVLYYDDSRNVVLKKYKNMVVRA | C | G | C | L |
| 20 | TPTKMSPINMLYFNDKQQIIYGKIPGMVVDR | C | G | C | S |
| 21 | VPASYNPMVLIQKTDTGVSLQTYDDLLAKD | C | H | C | I |
| 22 | VPARLSPISVLFFDNSDNVVLRQYEDMVVDE | C | G | C | R |
| 23 | VPTKLSPISVLYKDDMGVPTLKYHYEGMSVAE | C | G | C | R |
| 24 | IPTKLSPISMLYQDNNDNVILRHYEDMVVDE | C | G | C | G |
| 25 | VPTRLSPISILFIDSANNVVYKQYEDMVVES | C | G | C | R |

FIG. 10N

| Seq Nr. | X3<br>XXXXXXXXXXXXXXXXXXXXXXXXXXXXXXXXX | C4 |
|---|---|---|
| 26 | DFPLRSHLEPTNHAIIQTLMNSMDPGSTPPSC | C |
| 27 | DFPLRSHLEPTNHAIIQTLLNSMAPDAAPASC | C |
| 28 | EFVFLQKYPHTHLVHQANPRGSAGPC | C |
| 29 | PRAVGHRYGSPVHTMVQNIIYEKLDSSVPRPS | C |
| 30 | DAAETTYDKILKNLSRNRRLVSDKVGQAC | C |
| 31 | GLHIPPNLSLPVPGAPPTPAQPYSLLPGAQPC | C |
| 32 | TGSFRTPDTFQTFHAHFIEEYRKMGLMNGMRPC | C |
| 33 | PSHIAGTSGSSLSFHSTVINHYRMRGHSPFANLKSC | C |
| 34 | PAYLAGVPGSASSFHTAVVNQYRMRGLNPGTVNSC | C |
| 35 | PLHIAGMPGIAASFHTAVLNLLKANTAAGTTGGGSC | C |
| 36 | PPHLAGSPGIAASFHSAVFSLLKANNPWPASTSC | C |
| 37 | QQPPEALAFNWPFLGPRQ | C |
| 38 | GWPQSDRNPRYGNHVVLLLKMQVRGAALARPPC | C |
| 39 | PIPLNETFKPTNHAYIKSLVKLYDQEKVECSS | C |
| 40 | PSPVNESVKPNNHAYMQSLLNYVKGKAPEVC | C |
| 41 | PNPVGEEFHPTNHAYIQSLLKRYQPHRVPSTC | C |
| 42 | EAAARVYDLGLRRLRQRRRLRRERVRAQPC | C |
| 43 | PRGARTQHGLALARLQGQERAHGGPC | C |
| 44 | NFPLGTKMNATNHAIVQTLMHLKQPHLPKPC | C |
| 45 | PYIWSLDTQYSKVLALYNQHNPGASAAPC | C |
| 46 | PYLWSSDTQHSRVLSLYNTINPEASASPC | C |
| 47 | PYLRSADTTHSTVLGLYNTLNPEASASPC | C |
| 48 | PFPLGERLNGTNHAIIQTLVNSIDNRAVPKVC | C |
| 49 | AFPLTNGNNHAVLLNSHVESGNANERAPC | C |
| 50 | PYPIAKHLNATNHAIVQTIMNTVD-SNVPNAC | C |
| 51 | PNPMPAQLNATNHAIIQSLLHSLRPDEVPPPC | C |

FIG. 10O

| Seq Nr | X4<br>xxxxxxxxxxxxxxxxxxxxxxxxxxxxxxxxxx | C5 | X5<br>X | C6 | X6<br>XXXXXXXXXX |
|---|---|---|---|---|---|
| 26 | VPTKLTPISILYIDAGNNVVYKQYEDMVVES | C | G | C | R |
| 27 | VPARLSPISILYIDAANNVVYKQYEDMVVEA | C | G | C | R |
| 28 | TPTKMSPINMLYFNGKEQIIYGKIPAMVVDR | C | G | C | S |
| 29 | VPAKYSPLSVLTIEPDGSIAYKEYEDMIATK | C | T | C | R |
| 30 | RPIAFDDDLSFLDDNLVYHILRKHSAKR | C | G | C | I |
| 31 | AALPGTMRPLHVRTTSDGGYSFKYETVPNLLTQH | C | A | C | I |
| 32 | APIKFSSMSLIYYGDDGIIKRDLPKMVVDE | C | G | C | P |
| 33 | VPTKLRPMSMLYYDDGQNIIKKDIQNMIVEE | C | G | C | S |
| 34 | IPTKLSTMSMLYFDDEYNIVKRDVPNMIVEE | C | G | C | A |
| 35 | VPTARRPLSLLYYDRDSNIVKTDIPDMVVEA | C | G | C | S |
| 36 | VPTARRPLSLLYLDHNGNVVKTDVPDMVVEA | C | G | C | S |
| 37 | IASETASLPMIVSIKEGGRTRPQVVSLPNMRVQK | C | S | C | ASDGALVPRR |
| 38 | VPTAYAGKLLISLSEERISAHHVPNMVATE | C | G | C | R |
| 39 | VPVKMSPLSMLLYEDGEVVLKHHEDMIVDE | C | G | C | N |
| 40 | VPIRMSSLSMVYYDHDDIAFQNHEGMIVEE | C | G | C | Q |
| 41 | APVKTKPLSMLYVDNGRVLLDHHKDMIVEE | C | G | C | L |
| 42 | RPTAYEDEVSFLDAHSRYHTVHELSARE | C | A | C | V |
| 43 | RPTRYTDVAFLDDRHRWQRLPQLSAAA | C | G | C | G |
| 44 | VPTVLGAITILRYLNEDIIDLTKYQKAVAKE | C | G | C | H |
| 45 | VPQALEPLPIVYYVGRKPKVEQLSNMIVRS | C | K | C | S |
| 46 | VSQDLEPLTILYYIGKTPKIEQLSNMIVKS | C | K | C | S |
| 47 | VPQDLEPLTILYYVGRTPKVEQLSNMVVKS | C | K | C | S |
| 48 | APTKLSGISMLYFDNNENVVLRQYEDMVVEA | C | G | C | R |
| 49 | VPVAYDPLEVMDWNAEESFLSIKPDMIVKE | C | G | C | R |
| 50 | IPTTLNPISILSLNEFDKVVLKNYKDMVIEG | C | G | C | R |
| 51 | VPTETSPLSILYMDVDKVIVIREYADMRVES | C | G | C | R |

FIG. 10P

| Seq Nr. | X3 | |
|---|---|---|
| | XXXXXXXXXXXXXXXXXXXXXXXXXXXXXXXXXX | C4 |
| 52 | PPRHNPAHHHALLQSLIWQEDHKRAPRPC | C |
| 53 | SSVASVTQAASHHSSIMKILSTSGANKSLELVPC | C |
| 54 | KVGYLEQYPHTHLAALTTSATPC | C |
| 55 | PNPMPAQLNATNHAIIQSLLHSLKPDEVPPPC | C |
| 56 | AKPMLASGKASNHAMLQSLFAAEPVC | C |
| Family 2a/b X[ST] | | |
| 57 | PTMTRVLQGVLPALPQVV | C |
| 58 | PTMTRVLQGVLPALPQVV | C |
| 59 | PTMTRVLQGVLPALPQVV | C |
| 60 | YTRDLVYKDPARPKIQKT | C |
| 61 | ETWEKPILEPPYIEAHHRV | C |
| 62 | FTQDSVYKSSLKSYPQQA | C |
| 63 | ITKDPSYKSPLSTVYQRV | C |
| 64 | ITKDPSYKSPLSTVYQRV | C |
| 65 | PTMMRVLQAVLPPLPQVV | C |
| 66 | MTRDINGKLFLPKYALSQDV | C |
| 67 | KTSESGTHGFPPRVQNSKV | C |
| Family 3 | [KRL]G[LIVT][DE]XXX[YW]XSX | C |
| 68 | RGIDKRHWNSQ | C |
| 69 | RGIDARHWNSY | C |
| 70 | RGIDSRHWNSY | C |
| 71 | RGIDSRLWNSY | C |
| 72 | RGIDSRLWNSY | C |
| 73 | RGTDSRHWNSY | C |
| 74 | RGTDSRHWNSY | C |
| 75 | RGIDSKHWNSY | C |

FIG. 10Q

| Seq Nr | X4 | | C5 | X5 | C6 | X6 |
|---|---|---|---|---|---|---|
| | xxxxxxxxxxxxxxxxxxxxxxxxxxxxxxxxx | | C5 | X | C6 | xxxxxxxxxx |
| 52 | TPSKLEMLEILHVDENHSDKLKISTWSDMQVVE | | C | A | C | S |
| 53 | TAKQYSSLQLVVMDSSNTATVKTLPNMVVES | | C | G | C | R |
| 54 | SPTKMSSLSLLYFDDNHNLVLSVIPNMSVEG | | C | S | C | S |
| 55 | VPTETSPLSILYMDVDKVIVIREYADMRVDS | | C | G | C | R |
| 56 | APTNLKSLNFLYRDEKGRTVIRNYSKMLIGS | | C | S | C | L |
| Family 2a/b | | [PA]VAXX | C | X | C | XXCXXXX[STDAI][DEY]C |
| 57 | NYRDVRFESIRLPGCPRGVNPVVSYAVALS | | C | Q | C | ALCRRSTTDC |
| 58 | NYRDVRFESIRLPGCPRGVNPVVSYAVALS | | C | Q | C | ALCRRSTTDC |
| 59 | NYRDVRFESIRLPGCPRGVNPVVSYAVALS | | C | Q | C | ALCRRSTTDC |
| 60 | TFKELVYETVRVPGCAHHADSLYTYPVATQ | | C | H | C | KCDSDSTDCT |
| 61 | TYNETKQVTVKLPNCAPGVDPFYTYPVAIR | | C | D | C | GACSTATTEC |
| 62 | NFRDVVYETVHLPGCPSGMDLHFTYPVALS | | C | E | C | SKCNTDSTDC |
| 63 | TYRDVRYETVRLPDCRPGVDPHVTFPVALS | | C | D | C | NLCTMDTSDC |
| 64 | TYRDVRYETVRLPDCRPGVDPHVTFPVALS | | C | D | C | NLCTMDTSDC |
| 65 | TYRDVRFESIRLPGCPRGVDPVVSFPVALS | | C | R | C | GPCRRSTSDC |
| 66 | TYRDFIYRTVEIPGCPLHVHPYFSYPVALS | | C | K | C | GKCNTDYSDC |
| 67 | TLVTTSTRKVVLDDCDDGADESVKFVMVPHGTD | | C | E | C | SAVPLEQHHS |
| Family 3 | | | | | | |
| 68 | RTTQSYVRALTMDSKKRIGWRFIRIDTS | | C | V | C | TLTIKRGR |
| 69 | TTTHTYVRALTKE-GNQASWRFIRIDTA | | C | V | C | VISRITENFG |
| 70 | TTTQSFVKALTKEGNQASWRFIRIDTA | | C | V | C | VISRKTGNF |
| 71 | TTTRTFVRALTMEGNQASWRFIRIDTA | | C | V | C | VIIRKTDNF |
| 72 | TTTQTFVRALTMEGNQASWRFIRIDTA | | C | V | C | VIIRKTDNF |
| 73 | TTTQTFVRALTMEGNQASWRFIRIDTA | | C | V | C | VIIRKTDNF |
| 74 | TTTQTFVKALTMEGNRASWRFIRIDTA | | C | V | C | VISRKTDNF |
| 75 | TTTHTFVKALTMDGKQAAWRFIRIDTA | | C | V | C | VLSRKAVRRA |

FIG. 10R

| Seq Nr. | X3 | |
|---|---|---|
| | XXXXXXXXXXXXXXXXXXXXXXXXXXXXXXXX | C4 |
| 76 | RGIDSKHWNSY | C |
| 77 | RGIDDKHWNSQ | C |
| 78 | RGVDRRHWVSE | C |
| 79 | RGIDSKHWVSY | C |
| Family 4 | | |
| 80 | NTSSVK | C |
| 81 | NNRNVQ | C |
| 82 | ACCLHNCNECQ | C |
| 83 | GCCGTVNWRSCT | C |
| 84 | GDENLH | C |
| 85 | NNRNVQ | C |
| 86 | TDESLE | C |
| 87 | TDESLK | C |
| 88 | NDEGLE | C |
| 89 | PDDGLE | C |
| 90 | NSEGLQ | C |
| 91 | NEESLI | C |
| 92 | NDESLE | C |
| 93 | NGDGQI | C |
| 94 | NDEALE | C |
| 95 | NDESLE | C |
| 96 | NNRNVQ | C |
| Family 5 | [FY]S[RQS]A[FY]PTP | |
| 97 | FSRAYPTPLQSKKAMLVPKNITSEATC | C |

FIG. 10S

| Seq Nr | X4 | C5 | X5 | C6 | X6 |
|---|---|---|---|---|---|
| | XXXXXXXXXXXXXXXXXXXXXXXXXXXXXXXXXX | C5 | X | C6 | XXXXXXXXXX |
| 76 | TTTHTFVKALTTDDKQAAWRFIRIDTA | C | V | C | VLSRKAARRG |
| 77 | KTSQTYVRALTSENNKLVGWRWIRIDTS | C | V | C | ALSRKIGRT |
| 78 | KAKQSYVRALTADAQGRVGWRWIRIDTA | C | V | C | TLLSRTGRA |
| 79 | TNTHTYVRALTSYKNQIAWRFIRINAA | C | V | C | VLSRNSWRHG |
| Family 4 | | | | | |
| 80 | QPSRVHHRSVKVAKVEYVRKKPKLKEVQVRLEEHLE | C | A | C | ATSLNPDYRE |
| 81 | RPTQVQLRPVQVRKIEIVRKKPIFKKATVTLEDHLA | C | K | C | ETVAAARPVT |
| 82 | VPSKVTKKYHEVLQLRPKTGVRGLHKSLTDVALEHHEE | C | D | C | VCRGSTGG |
| 83 | NSGKTVKKYHEVLQFEPGHIKRRGRAKTMALVDIQLDHHER | C | D | C | ICSSRPPR |
| 84 | VPVETANVTMQLLKIRSGDRPSYVELTFSQHVR | C | E | C | RHSPGRQSPD |
| 85 | RPTQVQLRPVQVRKIEIVRKKPIFKKATVTLEDHLA | C | K | C | EIVAAARAVT |
| 86 | TATGKRSVGREIMRLSPHKGTSEKEVMQFTEHTD | C | E | C | RPRSASGVNS |
| 87 | TPVGKHTVDLQIMRVNPRTQSSKMEVMKFTEHTA | C | E | C | RPRRKQGEPD |
| 88 | VPTEESNITMQIMRIKPHQGQHIGEMSFLQHNK | C | E | C | RPKKDRARQE |
| 89 | VPTGQHQVRMQILMIRYPSSQLGEMSLEEHSQ | C | E | C | RPKKKDSAVK |
| 90 | MNTSTSYLSKTLFEITVPLSQGPKPVTISFANHTS | C | R | C | MSKLDVYRQV |
| 91 | MNTSTSYISKQLFEISVPLTSVPELVPVKVANHTG | C | K | C | LPTAPRHPYS |
| 92 | VPTEEVNVSMELLGASGSGSNGMQRLSFVEHKK | C | D | C | RPRFTTTPPT |
| 93 | TAVETRNTTVTVSVTGVSSSSGTNSGVSTNLQRISVTEHTK | C | D | C | IGRTTTTPTT |
| 94 | VPTETRNVTMEVLRVKQRVSQHNFQLSFTEHTK | C | E | C | RPKAEVKAKK |
| 95 | VPTEEANVTMEFMGVGVSSTGSSVSTQHLEFVEHTK | C | D | C | PRGGQQTTPP |
| 96 | RPTQVQLRLVQVRKIEIVRKRPVFKKATVTLEDHLA | C | K | C | ETVVAARPVT |
| Family 5 | | | | | |
| 97 | VAKEGERVVVDNIKLTNHTE | C | W | C | NTCYHHKS |

FIG. 10T

| Seq Nr. | X3<br>XXXXXXXXXXXXXXXXXXXXXXXXXXXXXXXXXX | C4 |
|---|---|---|
| 98 | FSRAYPTPLRSKQTMLVPKNITSEATC | C |
| 99 | FSRAYPTPLRSKKTMLVQKNVTSESTC | C |
| 100 | FSRAYPTPLRSKKTMLVQKNVTSESTC | C |
| Family 6 | | |
| 101 | SVPEGMV | C |
| 102 | SVPEGMV | C |
| 103 | SFPEGMS | C |
| 104 | SVPEGMV | C |
| 105 | SWPPGMA | C |
| 106 | SLPEGMF | C |
| 107 | SIPDRADFL | C |
| 108 | SWPPGMN | C |
| 109 | SWPPGMA | C |
| Family 7 | | |
| 110 | QRTGR | C |
| 111 | GFSGR | C |
| Family 2c/8 | C | C |
| 112 | ASYIQVSGSKIWQMERSCMC | C |
| 113 | NSQVQPSVITPTGFLKECYC | C |
| 114 | VDGRC | C |
| 115 | GSVHFPGAAQHSHTSCSH | C |
| 116 | TDGRC | C |
| 117 | VDGRC | C |
| 118 | SSLYIPGSDPTPLVLCNS | C |
| 119 | NSFYVPGWPAGLSQPCTS | C |

FIG. 10U

| | Seq Nr | X4 | C5 | X5 | C6 | X6 |
|---|---|---|---|---|---|---|
| | | XXXXXXXXXXXXXXXXXXXXXXXXXXXXXXXXXX | | X | | XXXXXXXXXX |
| | 98 | VAKEGERVTTKDGFPVTNHTE | C | H | C | STCYYHKS |
| | 99 | VAKSYNRVTVMGGFKVENHTA | C | H | C | STCYYHKS |
| | 100 | VAKSLTRVMVMGNVRVENHTQ | C | H | C | STCYYHKF |
| Family 6 | | | | | | |
| | 101 | KPSKSVHLTVLRWRCQRRGGQRCGWIPIQYPIISE | C | K | C | SC |
| | 102 | KPAKSTHITLLRWRCVARRGALKCAWIPVQYPIITE | C | K | C | SCAN |
| | 103 | KPVKAVTKTFLRWYCQGFMRQKYCTWIQVQYPIISQ | C | K | C | SC |
| | 104 | KPPKSSHLIVLRWRCVQRKGGLKCAWIPVQYPVISE | C | K | C | SCPN |
| | 105 | RPAQLAHLKLLAWHCWAARPPGPPHCAWRQVPYPVVVA | C | K | C | SCR |
| | 106 | KPVQSVSVTLLRWHCQQGSRALKRCAWIRAHYPVISQ | C | A | C | AC |
| | 107 | RPDVFNQEQMGTLTALRWDCCWEVVETIVRGRRGRTFRRLSRRYNCGWRRIRFPIVCD | C | D | C | NCPGNRPRI |
| | 108 | RPNDQKLLKILKWTCISDPLGKRWNEFRESIFADKRKRRLRRHKIKRHLSQKRKTNKVIRPKRMKRLVKRYLYRTSKYVSGYLCQWKPIDYTVHQS | C | T | C | SCQG |
| | 109 | KQSDKKTLKVLKWTCLSDPLGEKWNAFRELMHEDRKRRRLRRHQFKRHLSQKRKIGVKKVKKPKQLKRLVKRYLYKISKYASGYLCQWKPIDYTVYES | C | T | C | SC |
| Family 7 | | | | | | |
| | 110 | TQQRSVVRLVTYDLEKGVFFCENVRTCCG | C | P | C | RS |
| | 111 | TQQRSVVRLVTYNLEKDGFLCESFRTCCG | C | P | C | RNY |
| Family 2c/8 | | XXXXXXXXXXXXXCXX[GN]XXXXXXXXXXXX | C | X | C | (X)nC (n=2-4) |
| | 112 | QESGEREAAVSLFCPKVKPGERKFKKVLTKAPLE | C | M | C | RPCTSIEESG |
| | 113 | RESFLKEKVITLTHCYDPDGTRLTSPGEMGSMDIRLREPTE | C | K | C | FKCGDFTR |
| | 114 | TPQQTRTVKIRFRCDDGETFTKSVMMIQS | C | R | C | NYNCPHANEA |
| | 115 | LPAKFTTMHLPLNCTELSSVIKVVMLVEE | C | Q | C | KVKTEHEDGH |
| | 116 | TPHRTTTLPVEFKCPDGEVMKKNMMFIKT | C | A | C | HYNCPGDNDI |
| | 117 | TPQLTRTVKMRFRCEDGETFSKNVMMIQS | C | K | C | NYNCPHANEA |
| | 118 | MPARKRWAPVVLWCLTGSSASRRRVKISTMLIEG | C | H | C | SPKA |
| | 119 | APSRSRRISLPLRCRSGHLAWQEVELVEE | C | E | C | ETRYDRNTVE |

FIG. 10V

| Seq Nr. | X3<br>XXXXXXXXXXXXXXXXXXXXXXXXXXXXXXXXX | C4 |
|---|---|---|
| 120 | NSFYIPRHIRKEEGSFQSCSF | C |
| 121 | NSFYIPRHVKKEEESFQSCAF | C |
| 122 | EKTAKYNHDILLLEHSCLC | C |
| 123 | GTFVMYSAKAQALDHSCSC | C |
| 124 | GDSSSMYSLEGNTVEHRCQC | C |
| 125 | PGASKYSAEAQAMQHQCTC | C |
| 126 | TSAASFNIITQQVDARCSC | C |
| 127 | SQASRSEPLVSFSTVLKQPFRSSCHC | C |
| 128 | SDGRC | C |
| 129 | PSATIYNINIESHLRFCKC | C |
| 130 | PSASIYNYNINTYARFCKC | C |
| 131 | PGQGC | C |
| 132 | AGGQC | C |
| 133 | GPQC | C |
| 134 | GSQC | C |
| 135 | LPLPVLPNWIGGGYGTKYWSRRSSQEWR | C |
| 136 | GPARLLPNAIGRGKWWRPSGPDFR | C |
| 137 | PSSTHVMPEEPYLQSQCDC | C |
| 138 | ASKAMYSIDINDVQDQCSC | C |
| 139 | MDNRC | C |
| 140 | LDKRC | C |
| 141 | SSGSKYNTLTDMHEKFCTC | C |
| 142 | ESSAFPSRYSVLVASGYRHNITSVSQC | C |
| 143 | ESSAFPSRYSVLVASGYRHNITSSSQC | C |
| 144 | QNDASCRDLVNGYRCICPPGYAGDH | C |
| 145 | QHGGTCKDLVNGYQCVCPRGFGGRH | C |

FIG. 10W

| Seq Nr | X4<br>XXXXXXXXXXXXXXXXXXXXXXXXXXXXXXXXX | C5 | X5<br>X | C6 | X6<br>XXXXXXXXXX |
|---|---|---|---|---|---|
| 120 | KPKKFTTMMVTLNCPELQPPTKKKRVTRVKQ | C | R | C | ISIDLD |
| 121 | KPQRVTSVLVELECPGLDPPFRLKKIQKVKQ | C | K | C | MSVNLS |
| 122 | REENYELRDIVLDCPDGSTIPYQYKHITT | C | S | C | LDICQLYTTF |
| 123 | KEEKTSQREVVLSCPNGGSLTHTYTHIES | C | Q | C | QDTVCGLPTG |
| 124 | QELRTSLRNVTLHCTDGSSRAFSYTEVEE | C | G | C | MGRRCP |
| 125 | QERRVHEETVPLHCPNGSAILHTYTHVDE | C | G | C | TPFCV |
| 126 | RPLHSYEQQLELPCPDPSTPGRRLVLTLQVFSH | C | V | C | SSVACG |
| 127 | RPQTSKLKALRLRCSGGMRLTATYRYILS | C | H | C | EECNS |
| 128 | TPHNTKTIQAEFQCSPGQIVKKPVMVIGT | C | T | C | HTNCPKNNEA |
| 129 | RENGVRNLSVPLYCSGNGTEIMYTLQEPID | C | T | C | QWN |
| 130 | REVGLQRRSVQLFCTNATWVPYTVQEPTD | C | A | C | QWS |
| 131 | QGLRLKRRKFTFECSDCTSFAEEVEKPTK | C | G | C | ALCA |
| 132 | GPLRSKRRKYSFECTDGSSFVDEVEKVVK | C | G | C | TRCV |
| 133 | QPTRSKRRKYVFQCTDGSSFVEEVERHLE | C | G | C | LACS |
| 134 | AAKIVRRRKVRMVCSNNRKYIKNLDIVRK | C | G | C | TKKCY |
| 135 | VNDKTRTQRIQLQCQDGSTRTYKITVVTA | C | K | C | KRYTRQHNES |
| 136 | IPDRYRAQRVQLLCPGGEAPRARKVRLVAS | C | K | C | KRLTRFHNQS |
| 137 | SYRLDPESPVRILNLRCLGGHTEPVVLPVIHS | C | Q | C | SSCQGGDFSK |
| 138 | SPTRTEPMQVALHCTNGSVVYHEVLNAME | C | K | C | SPRKCSK |
| 139 | IPYKSKTIDVSFQCPDGLGFSRQVLWINA | C | F | C | NLSCRNPNDI |
| 140 | IPNKSKMITIQFDCPNEGSFKWKMLWITS | C | V | C | QRNCREPGDI |
| 141 | SIKSYHPISVKMICDDGHTFTQKHEVPSN | C | G | C | SPCSEFSDSA |
| 142 | TISGLKKVKVQLQCVGSRREELEIFTARA | C | Q | C | DMCRLSRY |
| 143 | TISSLRKVRVWLQCVGNQRGELEIFTARA | C | Q | C | DMCRFSRY |
| 144 | ERDIDECASNPCLNGGHCQNEINRFQ | C | L | C | PTGFSGNLCQ |
| 145 | ELERDECASSPCHSGGLCEDLADGFH | C | H | C | PQGFSGPLCE |

TRUNCATED CYSTINE-KNOT PROTEINS

CROSS-REFERENCE TO RELATED APPLICATIONS

This is a national phase entry under 35 U.S.C. §371 of International Patent Application PCT/NL2010/050053, filed Feb. 5, 2010, published in English as International Patent Publication WO 2010/090523 A1 on Aug. 12, 2010, which claims the benefit under Article 8 of the Patent Cooperation Treaty to European Patent Application Serial No. 09152305.0, filed Feb. 6, 2009.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "P82942US00 seqlist.ST25 DJM.txt," which is 176 KB and created on Oct. 14, 2011.

TECHNICAL FIELD

The invention relates to the fields of protein chemistry, biology and medicine. More specifically, it relates to the design and preparation of proteinmimics of members of the cystine-knot growth factor superfamily. Further, the invention relates to the use of these proteinmimics as a medicament or prophylactic agent.

BACKGROUND

The cystine-knot three-dimensional structure is found in many extracellular molecules and is conserved among divergent species.[ref 4] The cystine-knot structure is formed by the arrangement of six cysteines which, through their disulfide bonds, form a knot. A typical consensus motif for a cystine-knot structure is: X0-C1-X1-C2-X2-C3-X3-C4-X4-C5-X5-C6-X6 (amino acids of SEQ ID NO:2), wherein cysteines 2, 3, 5 and 6 form a ring that includes X2 and X3, by disulfide bonding of cysteines 2 and 5, and cysteines 3 and 6. The third disulfide bond between cysteines 1 and 4 penetrates the ring, thus forming a knot.[ref 2,3] FIG. 11 represents a schematic representation of a protein comprising a cystine-knot structure. This cystine-knot folding leads to the formation of three distinct domains, with two distorted beta-hairpin (beta-1 and beta-3) loops protruding from one side of the knot, and a single (beta-2) hairpin loop protruding from the other side of the knot. The beta-1 hairpin loop is formed by the stretch of amino acids between C1 and C2 and is designated "X1" in the above-mentioned consensus motif; the beta-2 ("X3") and beta-3 ("X4") hairpin loops are formed by the amino acid stretch between C3 and C4, and between C4 and C5, respectively.

Growth factors represent a large group of polypeptides that share the property of inducing cell multiplication both in vivo and in vitro. Although the level of sequence similarity between growth factors is low, they can be classified into subfamilies based on their structural and functional similarities. For instance, the following growth factor subfamilies all show the cystine-knot conformation described above: glycoprotein hormone-beta (GLHB) subfamily, the platelet-derived growth factor (PDGF) subfamily, the transforming growth factor beta (TGF-beta) subfamily, the nerve growth factor (NGF) subfamily, the glycoprotein hormone-alpha (GLHA) subfamily, CTCK subfamily, Noggin-like subfamily, Coagulin subfamily, Mucin-like subfamily, Mucin-like BMP-antagonist subfamily, Mucin-like hemolectin subfamily, Slit-like subfamily, and Jagged-like subfamily. However, the different sub-families have, for instance, different consensus lengths for X1, X2, X3, X4 and/or X5. Further, the different subfamilies have quite different functions and target organs. For instance, the GLHA and GLHB subfamilies are important for physiologic processes involved in reproduction, whereas members of the NGF subfamily exert their function mainly on nerve cells, and members of the PDGF subfamily mainly on endothelial cells.

Next to the cysteines involved in cystine-knot formation, other cysteines can be present in a cystine-knot protein, which are normally used to create further disulfide bonds within the cystine-knot, within the protruding domains, or between two proteins, for instance, during dimerization.

There has been extensive research on cystine-knot growth factors in health and disease, and therapeutic examples, for instance, are the use of vascular endothelial growth factor-specific antibodies (VEGF; a sub-subfamily of the PDGF subfamily) in the treatment of cancer, Bevacizumab (Avastin™), a monoclonal antibody developed by Genentech was approved in 2004 by the Food and Drug Administration (FDA) for the treatment of colorectal cancer, and the development of a follicle-stimulating hormone (FSH; a member of the GLHA/B subfamily) vaccine as a contraceptive for men. Major drawbacks of the therapeutic VEGF-specific monoclonal antibody Bevacizumab are the high production costs and relatively large amounts needed for treatment, sometimes low tumor penetration and its side effects. Furthermore, the antibody must be administered many times during a few months putting a high burden onto the patient.

DISCLOSURE

Provided are proteinmimics of members of the cystine-knot growth factor superfamily, which are preferably capable of inducing an immune response against the members. Also provided are alternative means and methods for treatment and/or prophylaxis of cystine-knot protein-related conditions.

Provided are proteinmimics of members of the cystine-knot growth factor superfamily, which may or may not be used in immunogenic and/or therapeutic compositions.

As said before, cystine-knot proteins have a complex conformation comprising a ring that is constituted of at least two amino acid stretches and two disulfide bonds connecting the amino acid stretches. A third disulfide bond penetrates the ring, forming a knot. All members of the cystine-knot growth factor superfamily further have in common that the amino acid stretches between the first and the second cysteine and the fourth and fifth cysteine form beta-hairpin loops that protrude in one direction, whereas another amino acid stretch, which is situated between cysteines three and four, protrudes from the opposite site of the molecule. (FIG. 11.)

In a first embodiment, the invention provides a proteinmimic of a member of the cystine-knot growth factor superfamily, the proteinmimic having the motif X0-C1-X1-C2-X2-C3-X3-C4-X4-C5-X5-C6-X6 (SEQ ID NO:1 of the incorporated herein Sequence Listing), wherein C1 to C6 are cysteine residues that form a cystine-knot structure in which C1 is linked to C4, C2 is linked to C5 and C3 is linked to C6;

and wherein X0 and X6 represent, independently from each other, an amino acid sequence with a length of zero to ten amino acids, preferably zero to five amino acids, more preferably zero to three amino acids, more preferably zero to two amino acids, even more preferably zero or one amino acid, most preferably zero amino acids; X2 represents an amino acid sequence with a length of 2 to 24 amino acid residues with at least 70%, preferably at least 80%, more preferably at least 90%, most preferably at least 95% sequence identity to the amino acid sequence located between C2 and C3 of a member of the cystine-knot growth factor superfamily; X5 represents an amino acid sequence with a length of 1 amino acid residue; X1 represents an amino acid sequence with a length of 15 to 50 amino acids with at least 70%, preferably at least 80%, more preferably at least 90%, most preferably at least 95% sequence identity to the amino acid sequence located between C1 and C2 of a member of the cystine-knot growth factor superfamily; X3 represents an amino acid sequence with a length of 3 to 36 amino acids with at least 70%, preferably at least 80%, more preferably at least 90%, most preferably at least 95% sequence identity to the amino acid sequence located between C3 and C4 of a member of the cystine-knot growth factor superfamily; and X4 represents an amino acid sequence with a length of 15 to 50 amino acids with at least 70%, preferably at least 80%, more preferably at least 90%, most preferably at least 95% sequence identity to the amino acid sequence located between C4 and C5 of a member of the cystine-knot growth factor superfamily. Preferably, C2, C3, C5 and C6 form a ring by a bond between C2 and C5, and between C3 and C6, wherein the third bond between C1 and C4 penetrates the ring, thus forming a cystine-knot.

In a particular embodiment, a peptidomimetic hereof is provided for which the total number of amino acids equals 130 or less, preferably 110 or less, more preferably 100 or less, even more preferably 90 or less, most preferably 80 or less.

In a particular embodiment, a proteinmimic hereonf is provided wherein X1, X2, X3 and X4 each represent an amino acid sequence with at least 70%, preferably at least 80%, more preferably at least 90%, most preferably at least 95% sequence identity to an amino acid sequence of the same member of the cystine-knot growth factor superfamily. This thus means that provided is a proteinmimic of a member of the cystine-knot growth factor superfamily, the proteinmimic having the motif X0-C1-X1-C2-X2-C3-X3-C4-X4-C5-X5-C6-X6 (SEQ ID NO:2), wherein C1 to C6 are cysteine residues that form a cystine-knot structure in which C1 is linked to C4, C2 is linked to C5 and C3 is linked to C6; and wherein X0 and X6 represent, independently from each other, an amino acid sequence with a length of zero to ten amino acids, preferably zero to five amino acids, more preferably zero to three amino acids, more preferably zero to two amino acids, more preferably zero or one amino acid, most preferably zero amino acids; X2 represents an amino acid sequence with a length of 2 to 24 amino acid residues with at least 70%, preferably at least 80%, more preferably at least 90%, most preferably at least 95% sequence identity to the amino acid sequence located between C2 and C3 of the member of the cystine-knot growth factor superfamily; X5 represents an amino acid sequence with a length of one amino acid residue; X1 represents an amino acid sequence with a length of 15 to 50 amino acids with at least 70%, preferably at least 80%, more preferably at least 90%, most preferably at least 95% sequence identity to the amino acid sequence located between C1 and C2 of the member of the cystine-knot growth factor superfamily; X3 represents an amino acid sequence with a length of 3 to 36 amino acids with at least 70%, preferably at least 80%, more preferably at least 90%, most preferably at least 95% sequence identity to the amino acid sequence located between C3 and C4 of the member of the cystine-knot growth factor superfamily; and X4 represents an amino acid sequence with a length of 15 to 50 amino acids with at least 70%, preferably at least 80%, more preferably at least 90%, most preferably at least 95% sequence identity to the amino acid sequence located between C4 and C5 of the member of the cystine-knot growth factor superfamily. Preferably, C2, C3, C5 and C6 form a ring by a bond between C2 and C5, and between C3 and C6, wherein the third bond between C1 and C4 penetrates the ring, thus forming a cystine-knot.

In a particular embodiment, a peptidomimetic hereof is provided for which the total number of amino acids equals 130 or less, preferably 110 or less, more preferably 100 or less, even more preferably 90 or less, most preferably 80 or less.

A member of the cystine-knot growth factor superfamily is herein defined as any protein that forms a typical cystine-knot three-dimensional structure as described above, thus with at least six cysteines that form a cystine-knot and three hairpin loops protruding from the knot, wherein cysteines 2, 3, 5 and 6 form a ring by a bond between cysteines 2 and 5, as well as between cysteines 3 and 6, and wherein the third bond between cysteines 1 and 4 penetrates the ring, thus forming the knot. A person skilled in the art is able, for instance, by a combination of pattern search and pair-wise alignments, to identify structural motifs, present in members of the cystine-knot growth factor superfamily. A person skilled in the art may be guided in his search, for instance, by known cystine-knot proteins belonging to the cystine-knot growth factor superfamily, for instance, by the non-limiting examples provided in FIG. 10A-X.

The inventors have provided the insight that so-called "truncated cystine-knot proteins" according to the invention are especially useful for treating or preventing cystine-knot protein-related disorders. They have, for instance, shown that a truncated VEGF according to the invention shows negligible hormonal activity, whereas its immunological properties are excellent. One of the advantages of the negligible hormonal activity of truncated VEGF according to the invention is, for instance, that a significant amount of truncated VEGF can be administered to an animal without the hormonal side effects of the whole protein. Another advantage of truncated VEGF in comparison to the native protein or smaller fragments thereof, is that truncated VEGF is immunogenic per se. This is due to the fact that, in contrast to smaller fragments, truncated VEGF is large enough to be immunogenic without being coupled to a carrier protein and, in contrast to the native protein, is "non-native" enough to be seen as non-self by the immune system. With "non-self" is meant that the immune system does not consider the protein or parts of the protein as a self-protein and, therefore, mounts an immune response toward the protein.

Without being bound to theory, the fact that a truncated protein according to the invention is seen as "non-self" is explained, for instance, by the concept of "cryptic peptides." Cryptic peptides are defined as peptides that are part of a (self-)protein, but under normal conditions, are not presented to the immune system. The immune system is "ignorant" of these cryptic peptides. Proteins taken up by antigen-presenting cells are processed, i.e., cut in small peptide fragments. Under normal conditions, these small peptide fragments of a given protein are more or less identical after each processing. These are so-called "dominant peptides". Each time a given protein is processed, it produces, for instance, peptides x, y and z in sufficient amounts to be effectively presented to the immune system. The immune system, constantly being exposed to peptides x, y and z of self proteins, ignores these dominant peptides of self proteins, whereas dominant peptides of non-self proteins, which are occasionally present, are reacted to. If, however, a self protein is, for instance, truncated according to the invention, the peptide fragments after processing in antigen-presenting cells differ from those of the whole native protein. As a result, so-called "cryptic peptides," peptides that are not normally presented, are being generated and presented to the immune system in sufficient amounts. Instead of, for instance, the dominant self peptides x, y and z, peptides x, z and w are generated and presented to the immune system. As the immune system has not been exposed to cryptic peptide w previously, the immune system regards peptide w as non-self, and initiates an immune reaction. Without being bound to theory, this phenomenon may explain the enhanced immunogenicity of the truncated protein according to the invention as compared to the native protein.

Further shown is that the cystine-knot structure is important for the immunological properties of the protein. This is especially true if the native protein is to be immunologically mimicked. The inventors have, for instance, shown that a truncated VEGF protein in which the cysteines were blocked, disabling cystine-knot formation, is not recognized by the therapeutic VEGF monoclonal antibody Bevacizumab, whereas a truncated VEGF in which a cystine-knot is presented, is recognized by the antibody. What is said above for VEGF is equally true for other members of the cystine-knot growth factor superfamily. If, for instance, a proteinmimic of FSH is used, it is preferred that the biological or hormonal activity is negligible, whereas the proteinmimic is preferably able to induce antibodies, preferably neutralizing antibodies that are capable of cross-reacting with the native protein. The same holds true for other members of the GLHA/GLHB subfamily, or members of other subfamilies.

A "truncated cystine-knot protein" is defined herein as a cystine-knot protein in which at least part of the native amino acid sequence has been deleted, preferably N-terminal and/or C-terminal of the cystine-knot sequence. More preferably, the amino acid sequences N-terminal of C1 and C-terminal of C6 have been completely deleted. In a particular embodiment, therefore, provided is a proteinmimic hereof, wherein the proteinmimic has the motif C1-X1-C2-X2-C3-X3-C4-X4-C5-X5-C6 (SEQ ID NO:2). C2, C3, C5 and C6 may form a ring by a bond between C2 and C5, and between C3 and C6, and a third bond between C1 and C4 penetrates the ring, thus forming a cystine-knot.

In a more preferred embodiment, a peptidomimetic hereof is provided, for which the total number of amino acids equals 130 or less, preferably 110 or less, more preferably 100 or less, even more preferably 90 or less, most preferably 80 or less so that biological activity, e.g., hormonal side effects, are significantly reduced.

In a particular embodiment, a proteinmimic according to the invention is provided wherein X1 represents an amino acid sequence with at least 70%, preferably at least 80%, more preferably at least 90%, most preferably at least 95% sequence identity to an amino acid sequence of a member of the cystine-knot growth factor superfamily and wherein X2, X3 and/or X4 represent an amino acid sequence with at least 70%, preferably at least 80%, more preferably at least 90%, most preferably at least 95% sequence identity to an amino acid sequence of at least one other member of the cystine-knot growth factor superfamily. This is called a "chimeric proteinmimic" because the proteinmimic contains amino acid sequences with at least 70%, preferably at least 80%, more preferably at least 90%, most preferably at least 95% sequence identity to sequences of at least two different members of the cystine-knot growth factor superfamily. Such a chimeric proteinmimic preferably comprises loops, at least one of which representing a loop from another member of the cystine-knot growth factor superfamily than the other loops. In a preferred embodiment, each of the loops represents another member of the cystine-knot growth factor superfamily.

Also provided is a proteinmimic according to the invention, wherein the proteinmimic comprises the motif C1-X1-C2-X2-C3-X3-C4-X4-C5-X5-C6 (SEQ ID NO:1), wherein each of X1, X2, X3, X4 and X5 represents an amino acid sequence that has at least 80%, preferably at least 85%, more preferably at least 90%, most preferably at least 95% sequence identity with the corresponding part of a sequence selected from any of the sequences 1 to 145 of FIG. 10A-X. In a most preferred embodiment, each of X1, X2, X3, X4 and X5 represents an amino acid sequence that is identical to the corresponding part of a sequence selected from sequences 1 to 145 of FIG. 10A-X.

It is especially useful to substitute at least one loop of one member of a cystine-knot growth factor superfamily with a loop of another member of a cystine-knot growth factor superfamily, wherein the latter loop is smaller, i.e., comprises lesser amino acids, than the loop that is substituted. One advantage of a substation with a smaller loop is that the proteinmimic is manufactured more easily. In a working example, the invention, for instance, shows that the substitution of the b2 loop (represented by "X3") of Transforming Growth Factor-B2 (TGFB2) consisting of 29 amino acids with the b2 loop of VEGF consisting of six amino acids provides a proteinmimic that is successfully used to induce antibodies that fully cross-react with the full-length TGFB2 protein.

In a preferred embodiment, therefore, provided is a proteinmimic hereof, wherein X3 represents an amino acid sequence with at least 70%, preferably at least 80%, more preferably at least 90%, most preferably at least 95% sequence identity to an amino acid sequence of a member of the cystine-knot growth factor superfamily and wherein X1, X2 and/or X4 represent an amino acid sequence with at least 70%, preferably at least 80%, more preferably at least 90%, most preferably at least 95% sequence identity to an amino acid sequence of at least one other member of the cystine-knot growth factor superfamily, preferably wherein at least one other member of the cystine-knot growth factor superfamily is a member of the TGF-beta subfamily, more preferably TGFB2. Preferably X1, X2 and X4 each represent an amino acid sequence with at least 70%, preferably at least 80%, more preferably at least 90%, most preferably at least 95% sequence identity to an amino acid sequence of the corresponding part of the same cystine-knot growth factor superfamily, whereas X3 represents an amino acid sequence with at least 70%, preferably at least 80%, more preferably at least 90%, most preferably at least 95% sequence identity to an amino acid sequence of the corresponding part of another member of the cystine-knot growth factor superfamily. Preferably X1, X2 and X4 represent an amino acid sequence with at least 70%, preferably at least 80%, more preferably at least 90%, most preferably at least 95% sequence identity to an amino acid sequence of a member of the TGF-beta subfamily, more preferably to an amino acid sequence of TGFB2.

In a particular embodiment, the chimeric proteinmimic consists of the amino acid sequence: C1 ALRPLYIDFKRDLGWKWIHEPKGYNANFC2AGAC3-NDEGLEC4VSQDLEPLTILYYIGKTPKIEQLSNMIVKS- C5KC6 (SEQ ID NO:35) ($TGFB2_{15-111/\Delta 49-77}$-$VEGF_{62-67}$), optionally comprising flanking sequences with a length of at most five amino acids. In a particular embodiment, the flanking sequences have a length of at most two amino acids, preferably at most one amino acid. In a most preferred embodiment, the proteinmimic does not comprise flanking sequences.

TGF2B2 is a member of the TGF-beta subfamily. It is a secreted protein (cytokine) that performs many cellular functions and has a vital role during embryonic development. It is also known as Glioblastoma-derived T-cell suppressor factor, G-TSF, BSC-1 cell growth inhibitor, Polyergin, and Cetermin. It is known to suppress the effects of interleukin-dependent T-cell tumors.

In another preferred embodiment, provided is a proteinmimichereof, wherein X0 represents acetyl and/or X6 represents amide. In a more preferred embodiment, X0 represents acetyl and X6 represents amide. Acetylation of the N-terminus and/or amidation of the C-terminus has several advantages, for instance, the acetylated and amidated peptide ends are uncharged so they mimic natural peptides, stability toward digestions by aminopeptidases is enhanced and peptide ends are blocked against synthetase activities.

In another preferred embodiment, provided is a proteinmimic of a member of the cystine-knot growth factor superfamily, the proteinmimic having an identical sequence as the member, with the exception that the protein is truncated at position 0 to 10, preferably at position 0 to 5, more preferably at position 0 to 3, even more preferably at position 0 to 2, most preferably at position 0 or 1 N-terminal of C1 and at position 0 to 10, preferably at position 0 to 5, more preferably at position 0 to 3, even more preferably at position 0 to 2, more preferably at position 0 or 1, most preferably at position 0 C-terminal of C6.

Instead of the native sequence of a given member, consensus sequences of a subfamily can be used for designing a proteinmimic useful in the invention.

For the cystine-knot growth factor superfamily, several consensus sequences have been described.[(ref 1,3)] For instance, for all but the Noggin-, Coagulin- and NGF-like cystine-knot proteins, X2 consists of two or three amino acids that can be defined as X2a-G-X2b, wherein X2a is any amino acid or none, G is glycine, and X2b is any amino acid. In a preferred embodiment, therefore, a proteinmimic according to the invention is provided wherein X2 has the amino acid sequence X2a-G-X2b, wherein X2a is any amino acid or none, G is glycine, and X2b is any amino acid. Other consensus sequences are known, for instance, for TGF-beta, GLHB, NGF, PDGF, GLHA, and CTCK. Known consensus sequences are depicted for the respective subfamilies in FIG. 10A-X.

In another preferred embodiment, a proteinmimic according to the invention is provided, which comprises at least one of the following consensus sequences:

```
                                    (SEQ ID NO: 4)
[GSRE]C3[KRL]G[LIVT][DE]XXX[YW]XSXC4;

                                    (SEQ ID NO: 5)
P[PSR]CVXXXRC2[GSTA]GCC3;

                                    (SEQ ID NO: 6)
[LIVM]XXPXX[FY]XXXXC2XGXC3;

                                    (SEQ ID NO: 7)
C2[STAGM]G[HFYL]C3X[ST];
```

-continued

```
                                    (SEQ ID NO: 8)
[PA]VAXXC5XC6XXCXXXX[STDAI][DEY]C;

                                    (SEQ ID NO: 9)
C2XGCC3[FY]S[RQS]A[FY]PTP;
or

                           (SEQ ID NOS: 10 and 11)
CC4(X)13C(X)2[GN](X)12C5XC6(X)2,4C;
```

wherein C2 to C6 are cysteine residues that are part of a cystine-knot structure;

X means any amino acid;

[GSRE] means G or S or R or E; [KRL] means K or R or L;

[LIVT] means L or I or V or T; [DE] means D or E; [YW] means Y or W;

[PSR] means P or S or R; [GSTA] means G or S or T or A;

[LIVM] means L or I or V or M; [FY] means F or Y;

[STAGM] means S or T or A or G or M; [HFYL] means H or F or Y or L;

[ST] means S or T; [PA] means P or A; [STDAI] means S or T or D or A or I;

[DEY] means D or E or Y; [GN] means G or N; [RQS] means R or Q or S;

(X)13 means a sequence of 13 amino acids; (X)2 means a sequence of two amino acids;

(X)12 means a sequence of 13 amino acids and (X)2,4 means a sequence of two, three, or four amino acids.

It is preferred to use a proteinmimic that shows a considerable % sequence identity with a native amino acid sequence of the cystine-knot protein in order to produce antibodies and/or T-cells that are capable of cross-reacting towards the native protein. With "considerable % sequence identity" is meant: at least 70%, preferably at least 80%, more preferably at least 90%, most preferably at least 95% sequence identity with the native amino acid sequence of the cystine-knot protein. This is especially true if the proteinmimic is used as a vaccine to induce an immune response that is cross-reactive with a native cystine-knot protein, but also if the proteinmimic is used to induce T-cells and/or antibodies to be used as a medicament. The T-cells and/or antibodies that are raised against the proteinmimic are especially useful if they are able to cross-react with a native cystine-knot protein. However, in another embodiment, it can be especially useful to not generate antibodies against the native protein, for instance, if the proteinmimic is to be used as an antagonist of a cystine-knot protein. In such a case, a proteinmimic according to the invention with a lower sequence identity with the native protein is designed, preferably between 70% and 90%, more preferably between 70% and 80%, most preferably between 70% and 75% sequence identity with the native amino acid sequence of the cystine-knot protein. Administration of such a proteinmimic with antagonistic properties to an individual preferably does not induce a T-cell and/or antibody response in the individual. In order to act as an antagonist, the proteinmimic preferably does not convey protein function to a receptor.

"% sequence identity" is defined herein as the percentage of residues in a candidate amino acid sequence that is identical with the residues in a reference sequence after aligning the two sequences and introducing gaps, if necessary, to achieve the maximum percent identity.

Methods and computer programs for the alignment are well known in the art. One computer program that may be used or adapted for purposes of determining whether a candidate sequence falls within this definition is "Align 2," authored by Genentech, Inc., which was filed with user documentation in the United States Copyright Office, Washington, D.C. 20559, on Dec. 10, 1991.

In a particular embodiment, a proteinmimic according to the invention is provided wherein the proteinmimic has an amino acid sequence with at least 70% sequence identity, preferably at least 80%, more preferably at least 85%, most preferably at least 90% sequence identity to the corresponding native amino acid sequence of the member of the cystine-knot growth factor superfamily. In another preferred embodiment, the invention provides a proteinmimic according to the invention, wherein the member of the cystine-knot growth factor superfamily is a member selected from the group consisting of the GLHB subfamily, the PDGF subfamily, the TGF-beta subfamily, the NGF subfamily, the GLHA subfamily, the CTCK subfamily, the Noggin-like subfamily, the Mucin-like subfamily, the Mucin-like BMP antagonist subfamily, the Mucin-like hemolectin subfamily, the Slit-like subfamily, and the Jagged-like subfamily.

In another preferred embodiment, a proteinmimic hereof is provided wherein the proteinmimic has an amino acid sequence with between 70% and 90%, more preferably between 70% and 80%, most preferably between 70% and 75% sequence identity to the corresponding native amino acid sequence of the member of the cystine-knot growth factor superfamily. In another preferred embodiment, the invention provides a proteinmimic according to the invention, wherein the member of the cystine-knot growth factor superfamily is a member selected from the group consisting of the GLHB subfamily, the PDGF subfamily, the TGF-beta subfamily, the NGF subfamily, the GLHA subfamily, the CTCK subfamily, the Noggin-like subfamily, the Mucin-like subfamily, the Mucin-like BMP antagonist subfamily, Mucin-like hemolectin subfamily, the Slit-like subfamily, and the Jagged-like subfamily.

It is also useful to design a proteinmimic according to the invention with at least 70% sequence identity, preferably at least 80%, more preferably at least 85%, most preferably at least 90% sequence identity to the corresponding native amino acid sequence of the member of the cystine-knot growth factor superfamily, wherein at least one of the amino acid sequences represented by X1, X3, or X4 is at least partly deleted and/or modified. This is, for instance, especially useful if the amino acid sequence comprises an immunodominant peptide, or if the amino acid sequence has no function, for instance, if the sequence it is not part of the immunogenic determinant of the member. Deletion of such an amino acid sequence can, for instance, significantly facilitate the manufacturing process, reduce manufacturing costs or improve solubility of the proteinmimic according to the invention. In a preferred embodiment, therefore, the invention provides a proteinmimic according to the invention, wherein at least one of the amino acid sequences represented by X1, X3, or X4 is at least partly deleted and/or modified.

For instance, PDGF plays a role in embryonic development, cell proliferation, cell migration, and angiogenesis. PDGF has also been linked to several diseases such as atherosclerosis, fibrosis and malignant diseases. Especially the VEGF family, a sub-subfamily of the PDGF subfamily, has been linked to angiogenesis related to tumor growth and metastasis. Accordingly, in a preferred embodiment, the invention provides a proteinmimic according to the invention, wherein the member is a member of the PDGF subfamily, and wherein X2 represents an amino acid sequence with a length of three amino acids, X5 represents an amino acid sequence with a length of one amino acid, X1 represents an amino acid sequence with a length of 29 to 32 amino acids, X3 represents an amino acid sequence with a length of six to twelve amino acids, and X4 represents an amino acid sequence with a length of 32 to 41 amino acids.

In a more preferred embodiment, a proteinmimic is provided wherein the member is human Vascular Endothelial Growth Factor (hVEGF), and wherein X0 comprises amino acid sequence KFMDVYQRSY (amino acids 1-10 of SEQ ID NO:12), X1 comprises amino acid sequence HPIETLVDIFQEYDPEIEYIFKPSAVPLMR (amino acids 12-41 of SEQ ID NO:12), X2 comprises GGA, X3 comprises NDEGLE (amino acids 47-52 of SEQ ID NO:12), X4 comprises VPTEESNITMQIMRIKPHQGQHIGEMSFLQHNK (amino acids 54-86 of SEQ ID NO:12), X5 comprises E, and X6 comprises RPKKDRARQE (amino acids 90-99 of SEQ ID NO:12).

In another more preferred embodiment, a proteinmimic is provided that has at least 70% sequence identity to X0-X6 of hVEGF, wherein X0-X6 are the respective hVEGF amino acid sequences depicted in FIG. 10A-X. Preferably, the proteinmimic has at least 80%, more preferably at least 90%, most preferably at least 95% sequence identity to X0-X6 of hVEGF.

In yet another more preferred embodiment, a proteinmimic according to the invention is provided wherein the member is human Vascular Endothelial Growth Factor (hVEGF), and wherein the proteinmimic consists of the amino acid sequence C1 HPIETLVDIFQEYDPEIEYIFKPSAVPLMRC2GGAC3NDEGLEC4VPTEESNITMQIMRIKPHQGQHIGEMSFLQHNKC5EC6 (SEQ ID NO:26), optionally comprising flanking sequences with a length of at most five amino acids. In a preferred embodiment, the flanking sequences have a length of at most two amino acids, preferably at most one amino acid. In a most preferred embodiment, the proteinmimic does not comprise flanking sequences.

Placental growth factor (PLGF) is a member of the PDGF subfamily (subfamily 4) and a key molecule in angiogenesis and vasculogenesis, in particular, during embryogenesis. The main source of PLGF during pregnancy is the placental trophoblast. PLGF is also expressed in many other tissues, including the villous trophoblast. PLGF expression within human atherosclerotic lesions is associated with plaque inflammation and neovascular growth.

Serum levels of PLGF and sFlt-l (soluble fms-like tyrosine kinase-1, also known as soluble VEGF receptor-1) are altered in women with preeclampsia. Studies show that in both early and late onset preeclampsia, maternal serum levels of sFlt-l are higher and PLGF lower in women presenting with preeclampsia. In addition, placental sFlt-l levels were significantly increased and PLGF decreased in women with preeclampsia as compared to those with uncomplicated pregnancies. This suggests that placental concentrations of sFlt-l and PLGF mirror the maternal serum changes. This is consistent with the view that the placenta is the main source of sFlt-l and PLGF during pregnancy.

In yet another preferred embodiment, a proteinmimic according to the invention is provided wherein the member is human Placental Growth Factor (hPLGF), and wherein X0 comprises amino acid sequence PFQEVWGRSY (amino acids 1-10 of SEQ ID NO:13), X1 comprises amino acid sequence RALERLVDVVSEYPSEVEHMFSPSAVSLLR (amino acids 12-41 of SEQ ID NO:13), X2 comprises TGA, X3 comprises GDENLH (amino acids 47-52 of SEQ ID NO:13), X4 comprises VPVETANVTMQLLKIRSGDRPSYVELTFSQHVR (amino acids 54-86 of SEQ ID NO:13), X5 comprises E, and X6 comprises RHSPGRQSPD (amino acids 90-99 of SEQ ID NO:13).

In another more preferred embodiment, a proteinmimic is provided that has at least 70% sequence identity to X0-X6 of PLGF, wherein X0-X6 are the respective PLGF amino acid sequences depicted in FIG. 10. Preferably, the proteinmimic has at least 80%, more preferably at least 90%, most preferably at least 95% sequence identity to X0-X6 of PLGF.

In another more preferred embodiment, a proteinmimic is provided that has at least 70% sequence identity to X0-X6 of PLGF, wherein X0-X6 are the respective PLGF amino acid sequences depicted in FIG. 10A-X. Preferably, the proteinmimic has at least 80%, more preferably at least 90%, most preferably at least 95% sequence identity to X0-X6 of PLGF.

In yet another preferred embodiment, a proteinmimic according to the invention is provided wherein the member is human Platelet-Derived Growth Factor A (hPDGF-A), and wherein X0 comprises amino acid sequence SIEEAVPAV (amino acids 1-9 of SEQ ID NO:15), X1 comprises amino acid sequence KTRTVIYEIPRSQVDPTSANFLIWPPCVEVKR (amino acids 11-42 of SEQ ID NO:15), X2 comprises TGC, X3 comprises NTSSVK (amino acids 48-53 of SEQ ID NO:15), X4 comprises QPSRVHHRSVKVAKVEYVRKKPKLKEVQVRLEEHLE (amino acids 55-90 of SEQ ID NO:15), X5 comprises A, and X6 comprises ATSLNPDYRE (amino acids 92-103 of SEQ ID NO:15). In another more preferred embodiment, a proteinmimic is provided that has at least 70% sequence identity to X0-X6 of hPDGF-A, wherein X0-X6 are the respective hPDGF-A amino acid sequences depicted in FIG. 10A-X. Preferably, the proteinmimic has at least 80%, more preferably at least 90%, most preferably at least 95% sequence identity to X0-X6 of hPDGF-A.

In yet another preferred embodiment, a proteinmimic according to the invention is provided wherein the member is human Platelet-Derived Growth Factor A (hPDGF-C), and wherein X0 comprises amino acid sequence LLTEEVRLYS (amino acids 1-10 of SEQ ID NO:16), X1 comprises amino acid sequence TPRNFSVSIREELKRTDTIFWPGCLLVKR (amino acids 12-40 of SEQ ID NO:16), X2 comprises GGN, X3 comprises ACCLHNCNECQ (amino acids 46-56 of SEQ ID NO:16), X4 comprises VPSKVTKKYHEVLQLRPKTGVRGLHKSLTDVALEHHEE (amino acids 58-95 of SEQ ID NO:16), X5 comprises D, and X6 comprises VCRGSTGG (amino acids 99-106 of SEQ ID NO:16).

In another more preferred embodiment, a proteinmimic is provided that has at least 70% sequence identity to X0-X6 of hPDGF-C, wherein X0-X6 are the respective hPDGF-C amino acid sequences depicted in FIG. 10A-X. Preferably, the proteinmimic has at least 80%, more preferably at least 90%, most preferably at least 95% sequence identity to X0-X6 of hPDGF-C.

In yet another preferred embodiment, a proteinmimic according to the invention is provided wherein the member is human Vascular Endothelial Growth Factor C (hVEGF-C), and wherein X0 comprises amino acid sequence SIDNEWRKTQ (amino acids 1-10 of SEQ ID NO:17), X1 comprises amino acid sequence MPREVAIDVGKEFGVATNTFFKPPCVSVYR (amino acids 12-41 of SEQ ID NO:17), X2 comprises GGC, X3 comprises PDDGLE (amino acids 47-53 of SEQ ID NO:17), X4 comprises VPTGQHQVRMQILMIRYPSSQLGEMSLEEHSQ (amino acids 54-85 of SEQ ID NO:17), X5 comprises E, and X6 comprises RPKKKDSAVK (amino acids 89-98 of SEQ ID NO:17).

In another more preferred embodiment, a proteinmimic is provided that has at least 70% sequence identity to X0-X6 of hVEGF-C, wherein X0-X6 are the respective hVEGF-C amino acid sequences depicted in FIG. 10A-X. Preferably, the proteinmimic has at least 80%, more preferably at least 90%, most preferably at least 95% sequence identity to X0-X6 of hVEGF-C.

Other subfamilies of the cystine-knot growth factor superfamily include the GLHA and GLHB subfamily. Members of these subfamilies comprise the glycoprotein hormone-alpha and glycoprotein hormone-beta subunits, respectively, that after dimerization, form luteinizing hormone (LH), thyroid-stimulating hormone (TSH), chorionic gonadotropin (CG) and follicle-stimulating hormone (FSH). These hormones all play a role in reproduction in mammals. For instance, FSH stimulates testicular and ovarian functions through binding to a G-protein-coupled receptor on either Sertoli (male) or granulose (female) cells. Amongst other things, LH stimulates ovulation and sustains the corpus luteum during menstrual cycle, whereas CG, for instance, sustains the corpus luteum during pregnancy. TSH is important for Sertoli cell maturation and ovulatory function. The present invention also provides proteinmimics of this GLHB subfamily.

Thus, in another preferred embodiment, the member of the cystine-knot growth factor superfamily is a member of the GLHB subfamily, X2 represents an amino acid sequence with a length of three amino acids, X5 represents an amino acid sequence with a length of one amino acid, X1 represents an amino acid sequence with a length of 23 to 28 amino acids, X3 represents an amino acid sequence with a length of 18 to 20 amino acids, and X4 represents an amino acid sequence with a length of 30 to 33 amino acids.

In a more preferred embodiment, a proteinmimic according to the invention is provided wherein the member is human Follicle-Stimulating Hormone (hFSH), and wherein X0 comprises amino acid sequence NS, X1 comprises amino acid sequence ELTNITIAIEKEECRFCISINTTW (amino acids 4-27 of SEQ ID NO:18), X2 comprises AGY, X3 comprises YTRDLVYKDPARPKIQKT (amino acids 33-50 of SEQ ID NO:18), X4 comprises TFKELVYETVRVPGCAHHADSLYTYPVATQ (amino acids 52-81 of SEQ ID NO:18), X5 comprises H, and X6 comprises KCDSDSTDCT (amino acids 85-94 of SEQ ID NO:18).

In another more preferred embodiment, a proteinmimic is provided that has at least 70% sequence identity to X0-X6 of FSH, wherein X0-X6 are the respective FSH amino acid sequences depicted in FIG. 10A-X. Preferably, the proteinmimic has at least 80%, more preferably at least 90%, most preferably at least 95% sequence identity to X0-X6 of FSH.

In yet another more preferred embodiment, a proteinmimic according to the invention is provided wherein the member is human Choriogonadotropin (hCG), and wherein X0 comprises amino acid sequence SKEPLRPR (amino acids 1-8 of SEQ ID NO:19), X1 comprises amino acid sequence RPINATLAVEKEGCPVCITVNTTI (amino acids 10-33 of SEQ ID NO:19), X2 comprises AGY, X3 comprises PTMTRVLQGVLPALPQVV (amino acids 39-56 of SEQ ID NO:19), X4 comprises NYRDVRFESIRLPGCPRGVNPVVSYAVALS (amino acids 58-87 of SEQ ID NO:19), X5 comprises Q, and X6 comprises ALCRRSTTDC (amino acids 91-100 of SEQ ID NO:19).

In another more preferred embodiment, a proteinmimic is provided that has at least 70% sequence identity to X0-X6 of hCG, wherein X0-X6 are the respective hCG amino acid sequences depicted in FIG. 10A-X. Preferably, the proteinmimic has at least 80%, more preferably at least 90%, most preferably at least 95% sequence identity to X0-X6 of hCG.

In yet another preferred embodiment, the invention provides a proteinmimic according to the invention, wherein the member of the cystine-knot growth factor superfamily is a member of the glycoprotein hormone-alpha (GLHA) subfamily, and wherein X2 represents an amino acid sequence with a length of three amino acids, X5 represents an amino acid sequence with a length of one amino acid, X1 represents an amino acid sequence with a length of 13 to 17 amino acids, X3 represents an amino acid sequence with a length of 27 amino acids, and X4 represents an amino acid sequence with a length of 20 to 21 amino acids.

In yet another preferred embodiment, a proteinmimic according to the invention is provided wherein the member of the cystine-knot growth factor superfamily is a member of the nerve growth factor (NGF) subfamily, and wherein X2 represents an amino acid sequence with a length of 9 to 24 amino acids, X5 represents an amino acid sequence with a length of one amino acid, X1 represents an amino acid sequence with a length of 41 to 44 amino acids, X3 represents an amino acid sequence with a length of eleven amino acids, and X4 represents an amino acid sequence with a length of 27 or 28 amino acids.

In a more preferred embodiment, a proteinmimic according to the invention is provided wherein the member is human Nerve Growth Factor (hNGF), and wherein X0 comprises amino acid sequence PIFHRGEFSV (amino acids 1-10 of SEQ ID NO:20), X1 comprises amino acid sequence DSVSVWVGDKTTATDIKGKEVMVLGEVNINNSVFKQYFFETK (amino acids 12-53 of SEQ ID NO:20), X2 comprises RDPNPVDSG (amino acids 55-63 of SEQ ID NO:20), X3 comprises RGIDSKHWNSY (amino acids 65-75 of SEQ ID NO:20), X4 comprises TTTHTFVKALTMDGKQAAWRFIRIDTA (amino acids 77-103 of SEQ ID NO:20), X5 comprises V, and X6 comprises VLSRKAVRRA (amino acids 107-116 of SEQ ID NO:20).

In another more preferred embodiment, a proteinmimic is provided that has at least 70% sequence identity to X0-X6 of hNGF, wherein X0-X6 are the respective hNGF amino acid sequences depicted in FIG. 10A-X. Preferably, the proteinmimic has at least 80%, more preferably at least 90%, most preferably at least 95% sequence identity to X0-X6 of hNGF.

Members of the NGF subfamily play a role in survival and maintenance of sympathetic and sensory neurons and have been associated with Alzheimer disease. NGF plays a role in the repair, regeneration, and protection of neurons, and a proteinmimic of a member of the NGF subfamily according to the invention is thus especially useful for treating or preventing a neurodegenerative disorder.

Yet another subfamily of the cystine-knot growth factor superfamily is the TGF-beta subfamily. TGF-beta controls proliferation, cellular differentiation, and other functions in most cells. It plays a role in immunity, cancer, heart disease and in Marfan syndrome, a genetic disorder of the connective tissue.

In another preferred embodiment, therefore, the invention provides a proteinmimic according to the invention, wherein the member of the cystine-knot growth factor superfamily is a member of the transforming growth factor beta (TGF-beta) subfamily, and wherein X2 represents an amino acid sequence with a length of three amino acids, X5 represents an amino acid sequence with a length of one amino acid, X1 represents an amino acid sequence with a length of 23 to 41 amino acids, X3 represents an amino acid sequence with a length of 18 to 36 amino acids, and X4 represents an amino acid sequence with a length of 27 to 34 amino acids.

In a more preferred embodiment, a proteinmimic according to the invention is provided wherein the member is human Transforming Growth Factor beta2 (hTGF-beta2), and wherein X0 comprises amino acid sequence AYCFRNVQDN (amino acids 1-10 of SEQ ID NO:21), X1 comprises amino acid sequence CLRPLYIDFKRDLGWKWIHEPKGYNANF (amino acids 12-39 of SEQ ID NO:21), X2 comprises AGA, X3 comprises PYLWSSDTQHSRVLSLYNTINPEASASPC (amino acids 45-73 of SEQ ID NO:21), X4 comprises VSQDLEPLTILYYIGKTPKIEQLSNMIVKS (amino acids 75-104 of SEQ ID NO:21), X5 comprises K, and X6 comprises S.

In another more preferred embodiment, a proteinmimic is provided that has at least 70% sequence identity to X0-X6 of hTGF-beta2, wherein X0-X6 are the respective hTGF-beta2 amino acid sequences depicted in FIG. 10A-X. Preferably, the proteinmimic has at least 80%, more preferably at least 90%, most preferably at least 95% sequence identity to X0-X6 of hTGF-beta2.

Functional diverse modular proteins share a conserved domain of about 90 amino acids in their C-terminal cysteine-rich region, that has been proposed to be structurally related to the cystine-knot family and that is, therefore, called C-terminal cystine-knot (CTCK). Members of the C-terminal cystine-knot family are, amongst others, von Willebrand factor (vWF), a multifunctional protein that is involved in maintaining homeostasis, mucins, CCN family members (cef-10/cyr61/CTFG/fisp-12/nov protein family),[ref 5] Drosophila slit protein, which is essential for development of midline glia and commissural axon pathways, Norrie disease protein (NDP), which may be involved in neuroectodermal cell-cell interaction and in a pathway that regulates neural cell differentiation and proliferation, and Silk moth hemocytin, a humoral lectin that is involved in a self-defense mechanism. The teaching of the present invention also encompasses this CTCK family.

In another preferred embodiment, therefore, the invention provides a proteinmimic according to the invention, wherein the member of the cystine-knot growth factor superfamily is a member of the CTCK subfamily, and wherein X2 represents an amino acid sequence with a length of two to three amino acids, X5 represents an amino acid sequence with a length of one amino acid, X1 represents an amino acid sequence with a length of 22 to 35 amino acids, X3 represents an amino acid sequence with a length of 4 to 28 amino acids, and X4 represents an amino acid sequence with a length of 29 to 41 amino acids.

Sclerostin (or SOST) is also a member of the CTCK-subfamily of the cystine-knot growth factor super family. Sclerostin, the product of the SOST gene, was originally believed to be a non-classical bone morphogenetic protein (BMP) antagonist. More recently, sclerostin has been identified as binding to LRP5/6 receptors and inhibiting the Wnt-signaling pathway. Wnt-activation under these circumstances is antagonistic to bone formation. More recently, it has been revealed that the antagonism of BMP-induced bone formation by sclerostin is mediated by Wnt signaling, but not BMP-signaling pathways. The successful synthesis of $SOST_{67-144}$ in one of the examples serves to demonstrate that truncated cystine-knot proteins/peptides with an additional SS-bridge between $C_{71}$ (loop-1; X1) and $C_{125}$ (loop-3; X4) perfectly form the correctly folded cystine-knot structure in the presence of the additional disulfide bond.

In a more preferred embodiment, a proteinmimic according to the invention is provided wherein the member is sclerostin, and wherein X0 comprises amino acid sequence FETKDVSEYS (amino acids 1-10 of SEQ ID NO:22), wherein X1 comprises amino acid sequence RELHFTRYVTDGPCRSAKPVTELV (amino acids 12-35 of SEQ ID NO:22), X2 comprises SGQ, X3 comprises GPARLLPNAIGRGKWWRPSGPDFR (amino acids 41-64 of SEQ ID NO:22), X4 comprises IPDRYRAQRVQLLCPGGEAPRARKVRLVAS (amino acids 66-95 of SEQ ID NO:22), X5 comprises K, and X6 comprises KRLTRFHNQS (amino acids 99-108 of SEQ ID NO:22).

In another more preferred embodiment, a proteinmimic is provided that has at least 70% sequence identity to X0-X6 of sclerostin, wherein X0-X6 are the respective sclerostin amino acid sequences depicted in FIG. 10A-X. Preferably, the proteinmimic has at least 80%, more preferably at least 90%, most preferably at least 95% sequence identity to X0-X6 of sclerostin.

In yet another more preferred embodiment, a proteinmimic according to the invention is provided wherein the member is sclerostin, and wherein the proteinmimic consists of the amino acid sequence GGGC1RELHFTRYVTDGPCRSAKPVTELVC2SGQC3GPARLLPNAIGRGKWWRPSGPDFRC4IPDRYRAQRVQLLCPGGEAPRARKVRLVASC5KC6 (SEQ ID NO:23), optionally comprising flanking sequences with a length of at most five amino acids. In a preferred embodiment, the flanking sequences have a length of at most two amino acids, preferably at most one amino acid. In a most preferred embodiment, the proteinmimic does not comprise flanking sequences.

Members of the Noggin-like subfamily are, for instance, known to inhibit TGF-beta signal transduction by binding to TGF-beta family ligands and preventing them from binding to their corresponding receptors. Noggin plays a key role in neural induction by inhibiting BMP4. A proteinmimic of a member of the Noggin-like subfamily is thus especially useful for regulating TGF-beta and/or BMP4 activity.

In another preferred embodiment, therefore, the invention provides a proteinmimic according to the invention, wherein the member of the cystine-knot growth factor superfamily is a member of the Noggin-like subfamily, and wherein X2 represents an amino acid sequence with a length of four to six amino acids, X5 represents an amino acid sequence with a length of one amino acid, X1 represents an amino acid sequence with a length of 22 amino acids, X3 represents an amino acid sequence with a length of seven to nine amino acids, and X4 represents an amino acid sequence with a length of 35 to 98 amino acids.

A proteinmimic of a member of the Coagulin-like subfamily is, for instance, especially useful for treating coagulation disorders. Clinical trials have been started, for instance, with gene therapy-based coagulin B supplementation for hemophilia B. However, a proteinmimic of a member of the coagulin-like subfamily as provided herewith is suitable for inhibiting coagulin B, for instance, to reduce blood clotting, thereby preventing thrombosis.

In another preferred embodiment, therefore, the invention provides a proteinmimic according to the invention, wherein the member of the cystine-knot growth factor superfamily is a member of the Coagulin-like subfamily, and wherein X2 represents an amino acid sequence with a length of seven amino acids, X5 represents an amino acid sequence with a length of one amino acid, X1 represents an amino acid sequence with a length of 38 amino acids, X3 represents an amino acid sequence with a length of five amino acids, and X4 represents an amino acid sequence with a length of 29 amino acids.

Members of the jagged-like subfamily are, for instance, ligands of the Notch family of receptors. The Notch signaling pathway plays a crucial role during embryonic pattern formation, controls many conserved cell determination events and defines a fundamental mechanism controlling cell fate. It is involved in lineage cell decisions in a variety of tissues. It plays a role in hematopoiesis, vascular development and angiogenesis, myogenesis, neurogenesis, somitogenesis, in kidney, eye, ear, and tooth development, etc. Proteinmimics based on jagged-like members are especially useful for controlling the before-mentioned biological processes.

In another preferred embodiment, therefore, provided is a proteinmimic, wherein the member of the cystine-knot growth factor superfamily is a member of the Jagged-like subfamily, and wherein X2 represents an amino acid sequence with a length of three amino acids, X5 represents an amino acid sequence with a length of one amino acid, X1 represents an amino acid sequence with a length of 32 amino acids, X3 represents an amino acid sequence with a length of 25 amino acids, and X4 represents an amino acid sequence with a length of 26 amino acids.

As said before, FIG. 10A-X depicts non-limiting examples of truncated proteins belonging to several cystine-knot growth factor subfamilies. It is especially useful to introduce small mutations, for instance, exchange at least one cysteine, not being one of the conserved cysteines one to six that are necessary for cystine-knot formation, in order to prevent, for instance, dimer formation. In a preferred embodiment, therefore, a proteinmimic according to the invention is provided, wherein X1 represents an amino acid sequence with at least 80%, preferably at least 85%, more preferably at least 90%, most preferably at least 95% sequence identity with any one of the sequences identified as a X1 in FIG. 10A-X, and/or wherein X3 represents an amino acid sequence with at least 80%, preferably at least 85%, more preferably at least 90%, most preferably at least 95% sequence identity with any one of the sequences identified as X3 in FIG. 10A-X, and/or wherein X4 represents an amino acid sequence with at least 80%, preferably at least 85%, more preferably at least 90%, most preferably at least 95% sequence identity with any one of the sequences identified as X4 in FIG. 10A-X, wherein X1, X3 and X4 are taken from a single amino acid sequence of FIG. 10A-X.

In a more preferred embodiment, at least one cysteine in any of the sequences represented by X1, X2, X3, X4, and X6, is replaced by another amino acid, preferably alanine. In another preferred embodiment, X1 represents an amino acid sequence that is identical with any one of the sequences identified as X1 in FIG. 10A-X, and/or X3 represents an amino acid sequence that is identical with any one of the sequences identified as X3 in FIG. 10A-X, and/or X4 represents an amino acid sequence that is identical with any one of the sequences identified as X4 in FIG. 10A-X, wherein X1, X3 and X4 are taken from a single amino acid sequence of FIG. 10A-X.

In another preferred embodiment, a proteinmimic according to the invention is provided wherein X2 represents an amino acid sequence with at least 80%, preferably at least 85%, more preferably at least 90%, most preferably at least 95% sequence identity with any of the sequences identified as X2 in FIG. 10A-X, and/or wherein X5 represents an amino acid sequence that is identical to any of the sequences identified as X5 in FIG. 10A-X, wherein X2 and X5 are taken from a single amino acid sequence of FIG. 10A-X.

In a more preferred embodiment, at least one cysteine in any of the sequences represented by X1, X2, X3, X4, and X6, is replaced by another amino acid, preferably alanine. In another more preferred embodiment, X2 represents an amino acid sequence which is identical with a sequence identified as X2 in FIG. 10, wherein X2 and X5 are taken from a single amino acid sequence of FIG. 10A-X.

In another preferred embodiment, the invention provides a proteinmimic according to the invention, wherein the proteinmimic comprises the motif C1-X1-C2-X2-C3-X3-C4-X4-C5-X5-C6 (SEQ ID NO:1), wherein the sequence has at least 80%, preferably at least 85%, more preferably at least 90%, most preferably at least 95% sequence identity with a sequence selected from sequences 1 to 145 of FIG. 10A-X. In a most preferred embodiment, the proteinmimic sequence is identical to a sequence selected from sequences 1 to 145 of FIG. 10A-X. Such a proteinmimic is especially useful for induction of a cross-reactive, preferably a neutralizing antibody response, because the proteinmimic is identical to a part of the native protein.

In a particular embodiment, a proteinmimic hereof is provided wherein C1 is linked to C4 through a disulfide bond and/or C2 is linked to C5 through a disulfide bond, and/or C3 is linked to C6 through a disulfide bond. In a more preferred embodiment, C1 is linked to C4 through a disulfide bond and C2 is linked to C5 through a disulfide bond, and C3 is linked to C6 through a disulfide bond.

Now that proteinmimics of members of the cystine-knot growth factor superfamily are provided, also provided is the insight that a proteinmimic hereof is especially useful for inducing an immune response, preferably, the immune response is cross-reactive to a member of the cystine-knot growth factor superfamily. With "cross-reactive" is meant that the antibody produced not only specifically binds the proteinmimic against which the antibody was raised, but also specifically binds to at least one of the members of the cystine-knot growth factor superfamily. In one embodiment therefore, an immunogenic composition is provided, comprising a proteinmimic according to the invention. The immunogenic composition preferably further comprises a therapeutically acceptable carrier, adjuvant, diluent and/or excipient. "Immunogenic composition" is defined herein in its broad sense to refer to any type of biological agent in an administrable form capable of inducing and/or stimulating an immune response in an animal. In one preferred embodiment, an immunogenic composition according to the invention at least comprises a proteinmimic according to the invention and a pharmaceutically acceptable adjuvant.

In another preferred embodiment, an immunogenic composition according to the invention is provided wherein the proteinmimic is coupled to an immunogenic carrier, preferably diphtheria toxin (DT) and/or keyhole limpet haemocyanin (KLH).

Further provided is a pharmaceutical composition comprising a proteinmimic according to the invention and a pharmaceutically acceptable carrier, diluent and/or excipient. Suitable carriers, diluents, excipients and the like are commonly known in the art of pharmaceutical formulation and may be readily found, and applied by the skilled artisan, in references, for instance, Remmington's Pharmaceutical Sciences, Mace Publishing Company, Philadelphia Pa., 17th ed. 1985.

Members of the cystine-knot growth factor super-family are, as already mentioned before, associated with many diseases, including diseases of the nervous system, hematopoietic development, coagulation disorders, cancer, angiogenesis, etc. In one embodiment, therefore, the invention provides a use of a proteinmimic according to the invention for the preparation of a medicament and/or prophylactic agent for the treatment and/or prevention of a disorder associated with a member of the cystine-knot growth factor superfamily.

Thus provided is the use of a proteinmimic in an immunogenic composition. Such immunogenic composition comprising a proteinmimic according to the invention is suitable for inducing an immune reaction in an animal, preferably a human. In a preferred embodiment, a proteinmimic of the invention is used to induce antibodies, which are preferably able to cross-react with the native protein. Even more preferably, the antibodies are neutralizing antibodies, i.e., the function and/or activity of the native cystine-knot protein is diminished, inhibited, or at least reduced after binding of the native cystine-knot protein to the neutralizing antibody. It is possible to induce the antibodies in an individual in need thereof, for instance, by administering a vaccine comprising a proteinmimic according to the invention to the individual. It is also possible to induce the antibodies in a non-human animal by administering an immunogenic composition of the invention to the animal and use antibodies obtained from the animal for the manufacture of a medicament. However, it is also possible to use a proteinmimic according to the invention to directly antagonize the function and/or activity of the native cystine-knot protein. This can, for instance, be achieved if the proteinmimic binds to the receptor but does not or does not fully activate the receptor signal pathway. In one embodiment, the invention provides a use of a proteinmimic according to the invention, or an immunogenic compound comprising a proteinmimic according to the invention, as a partial or full antagonist of a member of the cystine-knot growth factor superfamily.

Now that the disclosure provides the insight that a proteinmimic according to the invention is useful as an antagonist and/or agonist for a member of the cystine-knot growth factor superfamily or suitable for raising an immune response against a member of the cystine-knot growth factor superfamily, a method is provided for treating or preventing a disorder associated with a member of the cystine-knot growth factor superfamily, comprising administering a therapeutically effective amount of a proteinmimic according to the invention to a subject suffering from, or at risk of suffering from, the disorder.

One subfamily of the cystine-knot growth factor superfamily is the subfamily of vascular endothelial growth factors (VEGF), which is a subfamily of the PDGF subfamily. VEGFs act through a family of cognate receptor tyrosine kinases in endothelial cells to stimulate blood vessel formation. Proteinmimics of, and/or antibodies specific for, VEGF are thus especially useful for treating a disorder related to vascularization. One such disorder is age-related macular degeneration (AMD), which causes rapid and severe visual loss. This loss is due to development of choroidal neovascularization under the macula. Inhibition of VEGF is, therefore, especially useful for the treatment and/or prevention of AMD. Another example of a disease that relates to vascularization is cancer. Tumors need neovascularization in order to grow. Fast-growing tissue needs a continuous supply of oxygen and nutrients and, therefore, the effective inhibition of neovascularization is thought to be one of the promising strategies for cancer therapy. This is, for instance, achieved by inhibiting, for instance, VEGF. As said before, Avastin™, a monoclonal antibody (Bevacizumab, Genentech) was approved in 2004 by the Food and Drug Administration (FDA) for the treatment of colorectal cancer when used with standard chemotherapy. In 2006, the FDA approved Bevacizumab® for the treatment of lung cancer in combination with standard first-line combination therapy.

The drawbacks of Bevacizumab®, such as the high production costs and the relative large amounts needed for treatment, sometimes low tumor penetration and frequent administration are reduced when a proteinmimic or an immunogenic composition of the invention is used. For instance, an immunogenic composition comprising a proteinmimic of the invention is administered in a dose of a few mg, preferably 0.1 to 10 mg per subject, in order to induce an immune response. Such an administration is generally repeated two or three times in order to induce a proper protective response.

In one embodiment, therefore, the invention provides use of a proteinmimic according to the invention for the preparation of a medicament and/or prophylactic agent for the treatment and/or prevention of a tumor-related disease and/or age-related macular degeneration (AMD), wherein the member of the cystine-knot growth factor superfamily is a member of the VEGF subfamily or the TGF-beta subfamily.

Another cystine-knot growth factor subfamily, TGF-beta, is also related to cancer. In normal cells, TGF-beta, acting through its signaling pathway, stops the cell cycle at the G1 stage to stop proliferation, induce differentiation, or promote apoptosis. When a cell is transformed into a cancer cell, parts of the TGF-beta signaling pathway are mutated, and TGF-beta no longer controls the cell. These cancer cells proliferate. The surrounding stromal cells (fibroblasts) also proliferate. Both cells increase their production of TGF-beta. This TGF-beta acts on the surrounding stromal cells, immune cells, endothelial and smooth-muscle cells. It causes immunosuppression and angiogenesis, which makes the cancer more invasive. TGF-beta also converts effector T-cells, which normally attack cancer with an inflammatory (immune) reaction, into regulatory (suppressor) T-cells, which turn off the inflammatory reaction. Inhibiting TGF-beta, for instance, with an antagonistic proteinmimic according to the invention and/or an antibody of the invention or functional part and/or functional equivalent thereof of the invention, wherein the member belongs to the TGF-beta subfamily, is thus especially useful for the treatment of cancer.

In a preferred embodiment, therefore, a method according to the invention is provided, wherein the disorder comprises a tumor-related disease and/or age-related macular degeneration (AMD), and wherein the member of the cystine-knot growth factor superfamily is a member of the VEGF subfamily or the TGF-beta subfamily. In a more preferred embodiment, the tumor-related disease is colorectal cancer or non-small cell lung cancer (NSCLC).

In another preferred embodiment, a method is provided wherein the disorder comprises a connective tissue disorder, preferably Marfan syndrome. Marfan syndrome is carried by a gene called FBN1, which encodes a connective protein called fibrillin-1. People have a pair of FBN1 genes. Because it is dominant, people who have inherited one affected FBN1 gene from either parent will have Marfan's. In addition to being a connective protein that forms the structural support for tissues outside the cell, fibrillin-1 binds to another protein, TGF-beta. TGF-beta can cause inflammation. Researchers now believe that the inflammatory effects of TGF-beta, at the lungs, heart valves, and aorta, weaken the tissues and cause the features of Marfan syndrome. A proteinmimic of TGF-beta is thus especially useful for treatment of Marfan syndrome.

In contrast, neovascularization (vascular regeneration) is especially useful for the treatment of ischemic disease including, but not limited to, arteriosclerotic occlusion of the lower limbs, angina pectoris/myocardial infarction or cerebral infarction in order to rescue the ischemic tissue by developing collateral circulation. In another preferred embodiment therefore, the disorder comprises an ischemic disorder, preferably, the ischemic disorder is taken from the group consisting of arteriosclerotic occlusion of the lower limbs, angina pectoris, myocardial infarction and cerebral infarction, wherein the member of the cystine-knot growth factor superfamily is a member of the VEGF subfamily.

As said before, members of the NGF subfamily are critical for the survival and maintenance of sympathetic and sensory neurons and have been associated with Alzheimer disease. As NGF plays a role in the repair, regeneration, and protection of neurons, a proteinmimic of a member for the NGF subfamily according to the invention is thus especially useful for treating a neurodegenerative disorder. Other possible applications are the use of a proteinmimic of a member of the NGF subfamily according to the invention, for instance, through induction of NGF-specific antibodies, to diminish and/or treat chronic and/or neurodegenerative pain. Further, such NGF-specific antibodies are considered especially useful for the treatment of breast tumors, as NGF is known to be a strong stimulator of breast cancer cell proliferation.

In another preferred embodiment, therefore, a method is provided, wherein the disorder comprises a disorder selected from the group consisting of a neurodegenerative disorder, preferably Alzheimer disease, a pain disorder, preferably a chronic and/or neuropathic pain disorder, and cancer, preferably breast cancer. In a more preferred embodiment, a method is provided wherein the member belongs to the NGF subfamily.

Further provided is a method for producing antibodies against a member of the cystine-knot growth factor superfamily, comprising administering a proteinmimic according to the invention and or an immunogenic composition according to the invention to a non-human animal, and obtaining antibodies against a member of the cystine-knot growth factor superfamily, which antibodies are produced by the animal. Also provided is the use of a proteinmimic according to the invention in an ex vivo method for producing an antibody, or a functional part or functional equivalent of an antibody, which is specifically directed against a member of the cystine-knot growth factor superfamily. The skilled artisan is aware of the different methods for producing an antibody ex vivo, such as B-cell hybrodima techniques, antibody phage display technologies and the like.

A functional part of an antibody is defined herewith as a part that has at least one same property as the antibody in kind, not necessarily in amount. The functional part is preferably capable of binding the same antigen as the antibody, albeit not necessarily to the same extent. A functional part of an antibody preferably comprises a single domain antibody, a single chain antibody, a Fab fragment or a $F(ab')_2$ fragment. A functional equivalent of an antibody is defined as an antibody that has been altered such that at least one property—preferably an antigen-binding property—of the resulting compound is essentially the same in kind, not necessarily in amount. An equivalent is provided in many ways, for instance, through conservative amino acid substitution, whereby an amino acid residue is substituted by another residue with generally similar properties (size, hydrophobicity, etc.), such that the overall functioning is likely not to be seriously affected.

The glycoprotein hormone subfamily (GLH), a subfamily of the cystine-knot superfamily of growth factors, comprises the hormones: luteinizing hormone, (LH), thyroid-stimulating hormone (TSH) and chorionic gonadotropin (CG) and follicle-stimulating hormone (FSH). These hormones all comprise an alpha and a beta subunit (GLHA and GLHB, respectively) and they play a role in reproduction in mammals. For instance, FSH stimulates testicular and ovarian functions through binding to a G-protein-coupled receptor on either Sertoli (male) or granulose (female) cells. Amongst other things, LH stimulates ovulation and sustains the corpus luteum during menstrual cycle, whereas CG, for instance, sustains the corpus luteum during pregnancy. TSH is important for Sertoli cell maturation and ovulatory function.

In a preferred embodiment, therefore, a method for treating or preventing a disorder associated with the presence of a member of the cystine-knot growth factor superfamily according to the invention is provided, wherein the disorder is a reproductive disorder. Apart from treating a reproductive disorder, a proteinmimic and/or an antibody or functional part or equivalent thereof according to the invention is also especially useful to prevent reproduction, i.e., prevent pregnancy.

By inhibition of a GLH, for instance, FSH, CG, LH or TSH, or inhibition of receptor binding and/or signaling of GLH in a female or a male, ovulatory or testicular function is disturbed and the chances of pregnancy are reduced. The invention thus provides a method for preventing pregnancy and/or reducing the chance of pregnancy in a female individual, comprising administering to the female or a sexual partner of the female an effective amount of a proteinmimic according to the invention, an immunogenic composition according to the invention, and/or an antibody obtainable by a method according to the invention or a functional part or functional equivalent of the antibody, wherein the member of the cystine-knot growth factor superfamily is a member of the GLHA or GLHB subfamily.

Further provided is a proteinmimic according to the invention, an immunogenic composition according to the invention, and/or an antibody obtainable by a method according to the invention, or a functional part or functional equivalent thereof, for use as a male and/or female contraceptive.

Further provided is a method for binding and/or neutralizing an antibody directed to a member of the cystine-knot growth factor superfamily, comprising administering a therapeutically effective amount of a proteinmimic according to any one of claims 1-17 to a subject comprising the antibody. Upon binding of the proteinmimic to the antibody, its activity is diminished. Antibodies that are specific for members of the cystine-knot protein are used in treatment protocols. One example thereof is Avastin™ specific for VEGF, which is used to treat metastatic cancer. Antibodies, once administered, have a half-life of several days, even up to several weeks. If, for instance, such an antibody is over-dosed or if the action of such antibody is not desired anymore, a proteinmimic of the invention is especially useful to counteract the action of the antibody by binding and/or neutralizing the antibody. A proteinmimic of the invention is especially useful because the proteinmimic as such is not or to a lesser extent bioactive and, therefore, does not interfere with a condition for which the antibody was initially administered. It is, of course, undesirable to treat a patient receiving, for instance, antibodies against VEGF with bio-active VEGF to neutralize the antibody. Bio-active VEGF administered in excess of the antibody present would exert its biological effect and would undermine the antibody treatment thus far received. An illustrative example that does not limit the invention is the use of a proteinmimic of VEGF that can be used to bind and/or neutralize a monoclonal antibody against VEGF, preferably Avastin™. Avastin™ is a commercially available monoclonal antibody against VEGF, which is administered, for instance, to treat metastatic cancers. Treatment with Avastin™, however, can lead to slow or incomplete wound healing (for example, when a surgical incision has trouble healing or staying closed). In some cases, this event resulted in fatality. It is, therefore, not recommended to start Avastin™ therapy for at least 28 days after surgery and until the surgical wound is fully healed. Of course, during Avastin™ therapy, surgery should be avoided. However, it is sometimes necessary to perform surgery on a person that receives Avastin™ therapy. In such a case, a truncated VEGF, preferably $VEGF_{26-104}$, is preferably administered to neutralize the circulating anti-VEGF antibodies without inducing much biological effect resembling the action of VEGF itself. Shortly after administration of the truncated VEGF and neutralization of the anti-VEGF antibodies, the patient may undergo surgery without the above-mentioned severe side effects that are normally observed after surgery during Avastin™ therapy.

In a preferred embodiment, therefore, a method for binding and/or neutralizing an antibody directed to a member of the cystine-knot growth factor superfamily comprising administering a therapeutically effective amount of a proteinmimic according to the invention to a subject comprising the antibody is provided, wherein the antibody is Avastin™ and the proteinmimic is $VEGF_{26-104}$.

Further provided is the use of a proteinmimic according to the invention for the manufacture of a medicament for neutralizing an antibody directed to a member of the cystine-knot growth factor superfamily. In a preferred embodiment, the antibody is Avastin™ and the proteinmimic is $VEGF_{26-104}$ as explained before.

Another member of the cystine-knot growth factor superfamily belonging to the TGF-beta subfamily is sclerostin, the secreted protein product of the SOST gene, which is an osteocyte-derived inhibitor of cultured osteoblasts. Sclerostin deficiency leads to sclerosteosis and van Buchem disease, two closely related, rare sclerosing disorders characterized by substantial increase in bone mass of good quality, which is due to increased bone formation. In contrast, osteoporosis, a disorder in which the density and quality of bone are reduced, leading to weakness of the skeleton and increased risk of fracture, particularly of the spine, wrist, hip, pelvis and upper arm, is possibly caused by an excess production of sclerostin, inhibiting bone formation. An agonistic or antagonistic proteinmimic of sclerostin and/or an antibody specific for sclerostin is thus especially useful for treatment of a bone disorder.

In a preferred embodiment, therefore, a method according to the invention is provided wherein the disorder comprises a disorder associated with disturbed bone regulation. In a more preferred embodiment, the disorder comprises osteoporosis or sclerosteosis.

The invention is further explained in the following examples that do not limit the scope of the invention, but merely serve to clarify specific aspects of the invention.

BRIEF DESCRIPTION OF THE FIGURES

FIG. 10A-X. Full protein name, species from which the protein was isolated, and amino acid sequence for all proteins known to be part of the cystine-knot growth factor superfamily, subdivided in TGF-beta, GLH-beta, NGF, PDGF, GLHA, Noggin-like, Coagulin-like, and CTCK-like subfamilies (SEQ ID NOS:36-180). Defined consensus sequences per subfamily are projected on top of the listing of sequences for each member.

Figure 1:
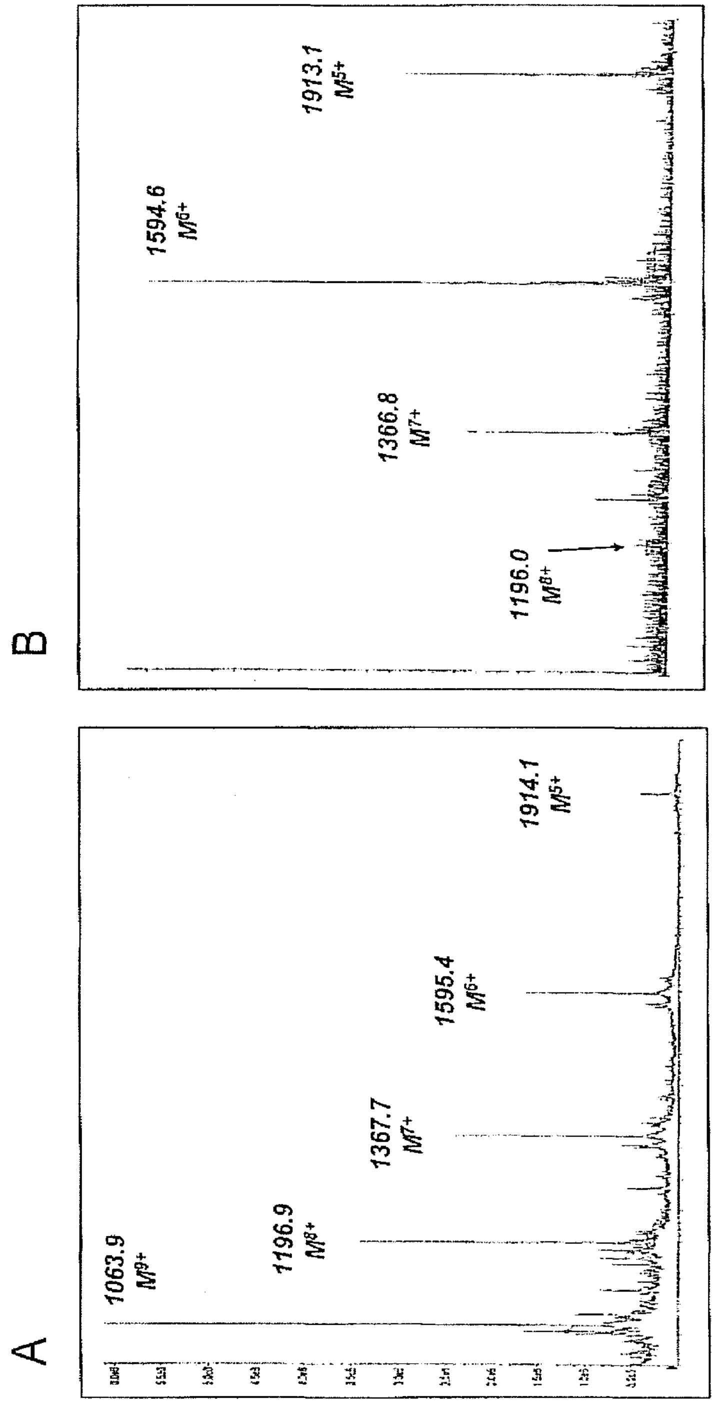
FIG. 1. Electro Spray Ionization Mass Spectrum (ESI/MS) of $humVEGF_{25-107}$ (Boc) in Panel A) fully reduced form ($MW_{calc}$=9569.1; $MW_{exp}$=9566.4), and Panel B) after oxidative folding ($MW_{calc}$=9563.1; $MW_{exp}$=9560.7). Folding conditions as described above.

humTGFB2trunc 1:

(SEQ ID NO: 24)

acetyl-C1ALRPLYIDFKRDLGWKWIHEPKGYNANFC2AGAC3NDEGLE

C4VSQDLEPLTILYYIGKTPKIEQLSNMIVKSC5KC6-amide humTGFB2trunc 2:

(SEQ ID NO: 25)

acetyl-C1ALRPLYIDFKRDLGWKWIHEPKGYNANFC2AGAC3PGGSPA

C4VSQDLEPLTILYYIGKTPKIEQLSNMIVKSC5KC6-amide

VEGFtrunc:

(SEQ ID NO: 26)

acetyl-C1HPIETLVDIFQEYPDEIEYIFKPSAVPLMRC2GGAC3NDEG

LEC4VPTEESNITMQIMRIKPHQGQHIGEMSFLQHNKC5EC6-amide

DETAILED DESCRIPTION OF THE INVENTION

Examples

Example 1A

Synthesis of Various Forms of VEGF-Truncated

Three different forms of VEGF-truncated were synthesized:

(SEQ ID NO: 27)
humVEGF$_{26-104}$; __$_{26}$Ac-C1HPIETLVDIFQEYPDEIEYIFKPSAVP

LMRC1GGAC3NDEGLEC4VPTEESNITMQIMRIKPHQGQHIGEMSFLQHN

KC5EC6#$_{104}$ (SEQ ID NO: 28)
humVEGF$_{25-107}$; __$_{25}$Ac-YC1HPIETLVDIFQEYPDEIEYIFKPSAV

PLMRC2GGAC3NDEGLEC4VPTEESNITMQIMRIKPHQGQHIGEMSFLQH

NKC5EC6RPK#$_{107}$ (SEQ ID NO: 29)
humVEGF$_{25-109}$: __$_{25}$Ac-YC1HPIETLVDIFQEYPDEIEYIFKPSAV

PLMRC2GGSC3NDEGLEC4VPTEESNITMQIMRIKPHQGQHIGEMSFLQH

NKC5EC6RPKKD#$_{109}$

Amino acids are indicated by the single-letter codes; "Ac" refers to N-terminal acetylation; "#" indicates C-terminal amidation; Cysteines (C1-C6) in boldface indicate cysteines involved in formation of the cystine-knot fold; alanines in boldface indicate native cysteines that were replaced by Ala.

Three different synthetic procedures were used:

I. Direct synthesis (Fmoc) of full-length peptide; only used for humVEGF$_{26-104}$.

II. Peptide-thioester synthesis using Fmoc-chemistry. Subsequent Native Chemical Ligation (NCL) of peptide fragments humVEGF$_{26-67}$(thioester)+humVEGF$_{68-104}$(free N-terminal cysteine) for humVEGF$_{26-104}$, humVEGF$_{25-67}$ (thioester)+humVEGF$_{68-107}$(free N-terminal cysteine) for humVEGF$_{25-107}$, and humVEGF$_{25-67}$(thioester)+humVEGF$_{68-109}$(free N-terminal cysteine) for humVEGF$_{25-109}$.

III. Peptide-thioester synthesis using Boc-chemistry. Subsequent Native Chemical Ligation (NCL) of peptide fragments humVEGF$_{25-67}$(thioester)+humVEGF$_{68-107}$(free N-terminal cysteine) for humVEGF$_{25-107}$ and humVEGF$_{26-67}$(thioester)+humVEGF$_{68-104}$(free N-terminal cysteine) or humVEGF$_{26-60}$(thioester)+humVEGF$_{61-104}$ (free N-terminal cysteine) for humVEGF$_{26-104}$.

Procedure I:

General Procedure (A) for Fmoc-Synthesis of Peptides:

Peptides were synthesized on solid-phase using a 4(2',4'-dimethoxyphenyl-Fmoc-aminomethyl)-phenoxy (RinkAmide) resin (BACHEM, Germany) on a Symphony (Protein Technologies Inc., USA), Voyager (CEM GmbH, Germany), or SyroII (MultiSyntech, Germany) synthesizer. All Fmoc-amino acids were purchased from Biosolve (Netherlands) or Bachem GmbH (Germany) with side-chain functionalities protected as N-t-Boc (KW), O-t-Bu (DESTY), N-Trt (HNQ), S-Trt (C), or N-Pbf (R) groups. A coupling protocol using a five-fold excess of HBTU/HOBt/amino acid/DIPEA (1:1:1:2) in NMP with a 20-minute activation time using double couplings was employed for every amino acid coupling step. Acetylation (Ac) of the peptide was performed by reacting the resin with NMP/$Ac_2O$/DIEA (10:1:0.1, v/v/v) for 30 minutes at room temperature. The acetylated peptide was cleaved from the resin by reaction with TFA (40 mL/mmol resin) containing 13.3% (w) phenol, 5% (v) thioanisole, 2.5% (v) 1,2-ethanedithiol, and 5% (v) milliQ-$H_2O$ for 2 hours at room temperature, unless indicated otherwise. Precipitation with ice-cold $Et_2O$+lyophilization of the precipitated material afforded the crude peptide.

humVEGF$_{26-104}$ was synthesized in one step following this procedure (resin-loading 0.88 mmol/g) on a Symphony synthesizer (Protein Technologies Inc., USA). In the first coupling step, a 4:1 (w/w) mixture of Ac-Cys(Trt)-OH and Fmoc-Cys(Trt)-OH was used. The acylated peptide was cleaved from the resin by reaction with a slightly different mixture: TFA (40 mL/mmol resin) containing 5% (v) TES, 2.5% (v) 1,2-ethanedithiol, and 2.5% (v) milliQ-$H_2O$. Finally, the peptide was purified by HPLC and folded by oxidation following procedure G.

The fragment peptides humVEGF$_{68-104}$, humVEGF$_{68-107}$, and humVEGF$_{68-109}$ (free N-terminal cysteine for NCL; see procedure II) were also synthesized following this procedure as described above for humVEGF$_{26-104}$ on a Rink-Made resin (loading 0.5 mmol/g) using a Liberty-synthesizer (CEM GmbH, Germany).

Procedure II:

Fmoc-Synthesis of Peptide Thioesters:

The fragment peptides humVEGF$_{25-67}$ and humVEGF$_{26-67}$ (free C-terminus) were synthesized on a SASRIN-resin (loading 0.5 mmol/g; Bachem GmbH, Germany) following the general procedure for Fmoc-synthesis of peptides as described in procedure I. The peptides were cleaved from the resin by repetitive treatment (20 cycles) with 1% TFA (40 mL/mmol resin) in DCM. The combined fractions were neutralized with pyridine, whereafter DCM was removed by evaporation under reduced pressure. Finally, the peptides were precipitated by addition of excess of $H_2O$, followed by centrifugation and lyophilization. The crude lyophilized peptides were dissolved in DCM (2.0 mM), twelve equivalents of 4-acetamidothiophenol in DCM (0.334 mg/mL, 2.0 mM), three equivalents of PyBOP in DCM (1.040 mg/mL, 2.0 mM), and 2.6 equivalents of DIPEA in DCM (1 vol %) were subsequently added and the mixture was stirred at room temperature for six hours. Then, another twelve equivalents of 4-acetamidothiophenol in DCM (0.334 mg/mL, 2.0 mM) were added and the mixture was stirred overnight at room temperature. Finally, the mixture was neutralized with ~2.6 equivalents of TFA and DCM was removed by evaporation under reduced pressure. The crude fragment peptide thioesters were then deprotected and purified by RP-HPLC following general procedures.

Native Chemical Ligation (NCL) of Fragment Peptides:

Condensation of fragment peptides humVEGF$_{68-104}$, humVEGF$_{68-107}$, or humVEGF$_{68-109}$ (A) with either fragment peptide thioesters humVEGF$_{25-67}$ or humVEGF$_{26-67}$ (B) by native chemical ligation was performed by mixing almost equimolar (1:1.2) solutions of A (10 mg/mL; ~2.0 mM) and B (10 mg/mL; ~2.0 mM) in working buffer (6 M guanHCl/20 mM TCEP/200 mM MPAA in 0.2 M phosphate buffer pH 8.0) and overnight stirring at room temperature. After mixing of the solutions (acidic!), the pH was adjusted to 6.5 by addition of 10 M NaOH (μL of NaOH is roughly equal to mg of MPAA used). Excess of MPAA was removed by Amicon filtration using working buffer (without MPAA!!) in the washing steps. Finally, the crude humVEGF$_{26-104}$, humVEGF$_{25-107}$, or humVEGF$_{25-109}$ in reduced form were purified by RP/HPLC following the standard procedure.

Oxidative Folding of Red-humVEGF$_{26-104}$, Red-humVEGF$_{25-107}$, and Red-humVEGF$_{25-109}$:

Fully reduced red-humVEGF$_{26-104}$, red-humVEGF$_{25-107}$, or red-humVEGF$_{25-109}$ were dissolved in 0.1 M Tris-buffer (pH 8.0), with or without 1 M guanidine.HCl, containing 1.0 mM cystine (SS-form) and 8.0 mM cysteine (SH-form) in a final concentration of 0.1 mg/mL and stirred at room temperature. Immediately, a sharp peak appears at a lower retention time (more polar) in addition to some broad peaks that correspond to incomplete or incorrectly folded peptide. When HPLC-analysis showed no further change in peak intensities (usually after ~4 hours), the mixture was loaded onto a preparative RP/C$_{18}$ column and purified following our standard procedure (see below).

Procedure III:

General Procedure for tBoc-Synthesis of Peptides:

Fragment peptides were prepared by manual solid phase peptide synthesis (SPPS) typically on a 0.25 mmol scale using the in situ neutralization/HBTU activation procedure for Boc chemistry as previously described. Each synthetic cycle consisted of Nα-Boc-removal by a one- to two-minute treatment with neat TFA, a one-minute DMF-flow wash, a ten- to twenty-minute coupling time with 1.0 mmol preactivated Boc-amino acid in the presence of excess DIEA, followed by a second DMF-flow wash. Nα-Boc amino acids (1.1 mmol) were preactivated for 3 minutes with 1.0 mmol HBTU (0.5 M in DMF) in the presence of excess DIEA (3 mmol). After coupling of Gln residues, a DCM flow wash was used before and after deprotection using TFA, to prevent possible high-temperature (TFA/DMF)-catalyzed pyrrolidonecarboxylic acid formation. Side-chain protected amino acids were: Boc-Arg (p-toluenesulfonyl)-OH, Boc-Asn(xanthyl)-OH, Boc-Asp(O-cyclohexyl)-OH, Boc-Cys(4-methylbenzyl)-OH, Boc-Glu(O-cyclohexyl)-OH, Boc-His(dinitrophenyl)-OH, Boc-Lys(2-Cl—Z)—OH, Boc-Ser(benzyl)-OH, Boc-Thr(benzyl)-OH, and Boc-Tyr(2-Br—Z)—OH. Other amino acids were used without side-chain protection. Nα-acetylation of peptides was performed by treatment with acetic anhydride (0.1 M)/Pyridine (0.1 M) in DMF for 2×2 minutes). After chain assembly was completed, the peptides were deprotected and cleaved from the resin by treatment with anhydrous HF for one hour at 0° C. with 4% p-cresol as a scavenger. In all cases, the imidazole side chain-dinitrophenyl (Dnp) protecting groups remained on His residues because the Dnp-removal procedure is incompatible with C-terminal thioester groups. However, Dnp is gradually removed by thiols during the ligation reaction yielding unprotected His. After cleavage, the peptide fragments were precipitated with ice-cold diethylether, dissolved in aqueous acetonitrile and lyophilized.

Preparation of Thioester-Generating (-COSR) Resin:

1.1 mmol Nα-Boc Leu was activated with 1 mmol HBTU in the presence of 3 mmol DIEA and coupled for 10 minutes to 0.25 mmol MBHA resin. Next, 1.1 mmol S-trityl mercaptopropionic acid was activated with 1 mmol HBTU in the presence of 3 mmol DIEA and coupled for 30 minutes to Leu-MBHA resin. The resulting trityl-mercaptopropionic acid-leucine resin can be used as a starting resin for polypeptide chain assembly following removal of the trityl protecting group with 2×1-minute treatments with 2.5% triisopropylsilane and 2.5% $H_2O$ in TFA. The thioester bond was formed with the desired amino acid using standard peptide coupling protocols. Treatment of the final peptide with anhydrous HF yielded the C-terminal activated mercaptopropionic acid-leucine (MPAL) thioester (-COSR) peptides for participation in the native chemical ligation reaction.

Native Chemical Ligation (NCL) of Fragment Peptides:

The ligation of fully deprotected fragment peptide thioesters humVEGF$_{26-60}$, humVEG$_{26-67}$, and humVEGF$_{25-67}$ with either the fragment peptides humVEGF$_{61-104}$, humVEGF$_{68-104}$, or humVEGF$_{68-107}$ was performed as follows: peptide fragments were dissolved in a ~1:1 molar ratio at 10 mg/ml in 0.1 M tris buffer, pH 8.0, containing 6 M guanidine. Benzylmercaptan and thiophenol were added to 2% (v/v) resulting in a final peptide concentration of 1-3 mM at a pH~7 (lowered due to addition of thiols and TFA from the lyophilized peptide). The ligation reaction was performed in a heating block at 37° C. and was vortexed periodically to equilibrate the thiol additives. The reaction was monitored by HPLC and ESI-MS until completion. Respective NCLs (humVEGF$_{26-60}$+humVEGF$_{61-104}$; humVEGF$_{26-67}$+humVEGF$_{68-104}$) yielded reduced VEGF$_{26-104}$ with identical HPLC and ESI-MS specifications.

Oxidative Folding of Red-humVEGF$_{26-104}$ and Red-humVEGF$_{25-107}$:

Fully reduced red-humVEGF$_{26-104}$ and red-humVEGF$_{25-107}$ were dissolved in 0.1 M Tris-buffer (pH 8.0), with or without 1 M guanidin.HCl, containing 1.0 mM cystine (SS-form) and 8.0 mM cysteine (SH-form) in a final concentration of 0.1 mg/mL and stirred at room temperature. Immediately, a sharp peak appears at a lower retention time (more polar) corresponding to the correctly folded cysknot structure, in addition to some broad peaks that correspond to incomplete or incorrectly folded peptide. When HPLC-analysis showed no further change in peak intensities (usually after ~4 hours), the mixture was loaded onto a preparative RP/C$_{18}$ column and purified following our standard procedure (see below).

General Procedure for Purification by HPLC:

Crude peptides were purified by reversed-phase high-performance liquid chromatography (RP-HPLC), either on a "DeltaPack" (25×100 or 40×210 mm inner diameter, 15 μm particle size, 100 Å pore size; Waters, USA) or on a "Atlantis" (10×100 mm inner diameter, 5 μm particle size (Waters, USA) RP-18 preparative C$_{18}$ column with a linear AB gradient of 1-2% B/minute where solvent A was 0.05% TFA in water and solvent B was 0.05% TFA in ACN. Alternatively, analytical reversed-phase HPLC was performed on a Varian Prostar system using Vydac C-18 columns (5 μm, 0.46×15 cm) and preparative reversed-phase HPLC was performed on a Waters system using Vydac C-18 columns (10 μm, 1.0/2.5×25 cm). Linear gradients of acetonitrile in water/0.1% TFA were used to elute bound peptides. The flow rates used were 1 ml/minute (analytical), and 5/10 ml/minute (preparative).

Analysis by RP-HPLC/ESI-MS:

Analysis of the purified peptide was performed by reversed-phase high-performance liquid chromatography (RP-HPLC) on an "Acquity" UPLC (Waters, USA) using a RP-18 preparative "BEH" column (2.1×50 inner diameter, 1.7 mm particle size, Waters, USA) with a linear AB gradient (5-55% B, 25% B/minute), where solvent A was 0.05% TFA in water and solvent B was 0.05% TFA in ACN. The primary ion molecular weight of the peptides was determined by electron-spray ionization mass spectrometry.

Analysis by ESI-MS:

Electrospray ionization mass spectrometry (ESI-MS) of HPLC samples was performed on an API-150 single quadrupole mass spectrometer (Applied Biosystems). Peptide masses were calculated from the experimental mass to charge (m/z) ratios from all the observed protonation states of a peptide using Analysis software.

For each peptide the following characteristics were determined:

| Peptide | Oxidation state (RED/OX) | Retention (% ACN) | MW calculated | MW experimental |
|---|---|---|---|---|
| Red-humVEGF$_{26-104}$ | RED | 48.5 | 9065.6 | 9064.4 |
| Oxid-humVEGF$_{26-104}$ | OX | 42.5 | 9059.6 | 9058.5 |
| Red-humVEGF$_{25-107}$ (Boc) | RED | 45.8 | 9569.1 | 9566.4 |
| Oxid-humVEGF$_{25-107}$ (Boc) | OX | 40.5 | 9563.1 | 9560.7 |
| Red-humVEGF$_{25-107}$ (Fmoc) | RED | 45.8 | 9569.1 | 9568.8 |
| Oxid-humVEGF$_{25-107}$ (Fmoc) | OX | 40.5 | 9563.1 | 9561.7 |
| Red-humVEGF$_{25-109}$ | RED | 43.8 | 9869.5 | 9869.6 |
| Oxid-humVEGF$_{25-109}$ | OX | 38.2 | 9863.5 | 9863.8 |

These data and FIG. 1 show that the various forms of hum-VEGF$_{trunc}$ can be synthesized in various different ways with identical outcomes.

Example 1B

Inhibitory Activity of Oxid-humVEGF$_{26-104}$ in Avastin™-Binding to Surface-Immobilized Oxid-humVEGF$_{1-165}$ Binding ELISA: Binding of various mAbs (Avastin™, mAb 293, PDL-antibody) to oxid-humVEGF$_{26-104}$ and hum-VEGF$_{1-165}$ was determined in ELISA. Therefore, polystyrene 96-well plates (Greiner, Germany) were treated with 100 μL/well of 0.2% glutaric dialdehyde in phosphate-buffer (0.1 M, pH=5) for four hours at room temperature while shaking, following by washing (3×10 minutes) with phosphate-buffer (0.1 M, pH=8). Then, the wells were coated with 100 μL/well of a 1 μg/mL solution of oxid-humVEGF$_{26-104}$/humVEGF$_{1-165}$ in phosphate-buffer (0.1 M, pH=8) for three hours at 37° C., followed by overnight standing at room temperature. After washing with 1% TWEEN®-80 (3×), the plates were incubated with the antibody at various different dilutions in horse serum (4% in PBS/1% TWEEN®-80/3% NaCl), starting with 1/10 dilution in the first well and three-fold dilution steps in subsequent wells. Incubation was performed for one hour at 37° C., followed by washing with 1% TWEEN®-80 (3×). Then, the plates were incubated with 100 μL/well of peroxidase-labeled Goat-anti-rat serum (1/1000 dilution in 4% horse serum, see above) for one hour at 25° C., followed by washing with 1% TWEEN®-80 (4×). Finally, the plates were incubated with a 0.5 μg/mL solution of ABTS (2,2'-azine-di(ethylbenzthiazoline sulfonate)) containing 0.006% $H_2O_2$ in citric acid/phosphate-buffer (0.1 M each, pH=4). $OD_{405\ nm}$-values were measured after 45 minutes standing at room temperature in the dark.

Competition ELISA: ELISA binding competition studies were carried out largely following the procedure as described for binding in ELISA (see above). Incubation with antibody was carried out at one fixed antibody-concentration (10 ng/mL of Avastin™; $OD_{405\ nm}$ between 1.0-1.5) in the presence of decreasing amounts of oxid-humVEGF$_{26-104}$ (start at 5 μM; 1/5 dilution steps) and humVEGF$_{1-165}$ (positive control; start at 500 nM; 1/5 dilution steps).

Figure 2:
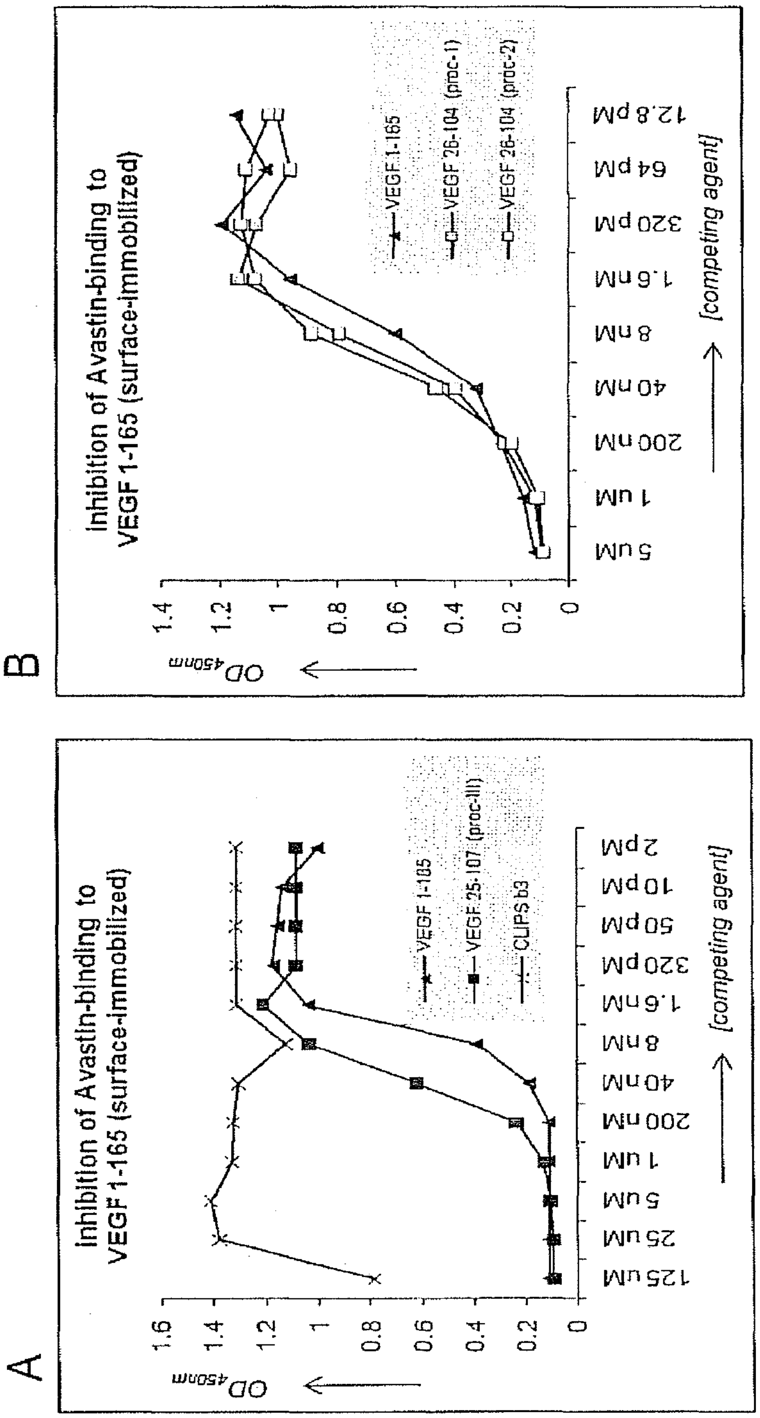
FIG. 2. Panel A) Inhibition of Avastin™-binding to surface-immobilized $humVEGF_{1-165}$ (1 μg/mL; GDA-coupling) in ELISA for varying concentrations (125 μM to 2 pM) of oxid-$humVEGF_{26-104}$ (■), $humVEGF_{1-165}$ (▲), and a backbone-cyclized peptide covering only the β5-turn-β6 loop of humVEGF ($humVEGF_{74-98}$) (x). Panel B) Inhibition of Avastin™-binding to surface-immobilized $humVEGF_{1-165}$ (1 μg/mL; GDA-coupling) in ELISA for varying concentrations (5 μM to 12.8 pM) of $humVEGF_{1-165}$ (▲), oxid-hum $VEGF_{26-104}$ synthesized via procedure-1 (grey square), or oxid-$humVEGF_{26-104}$ synthesized via procedure-2 (white square).
Figure 3:
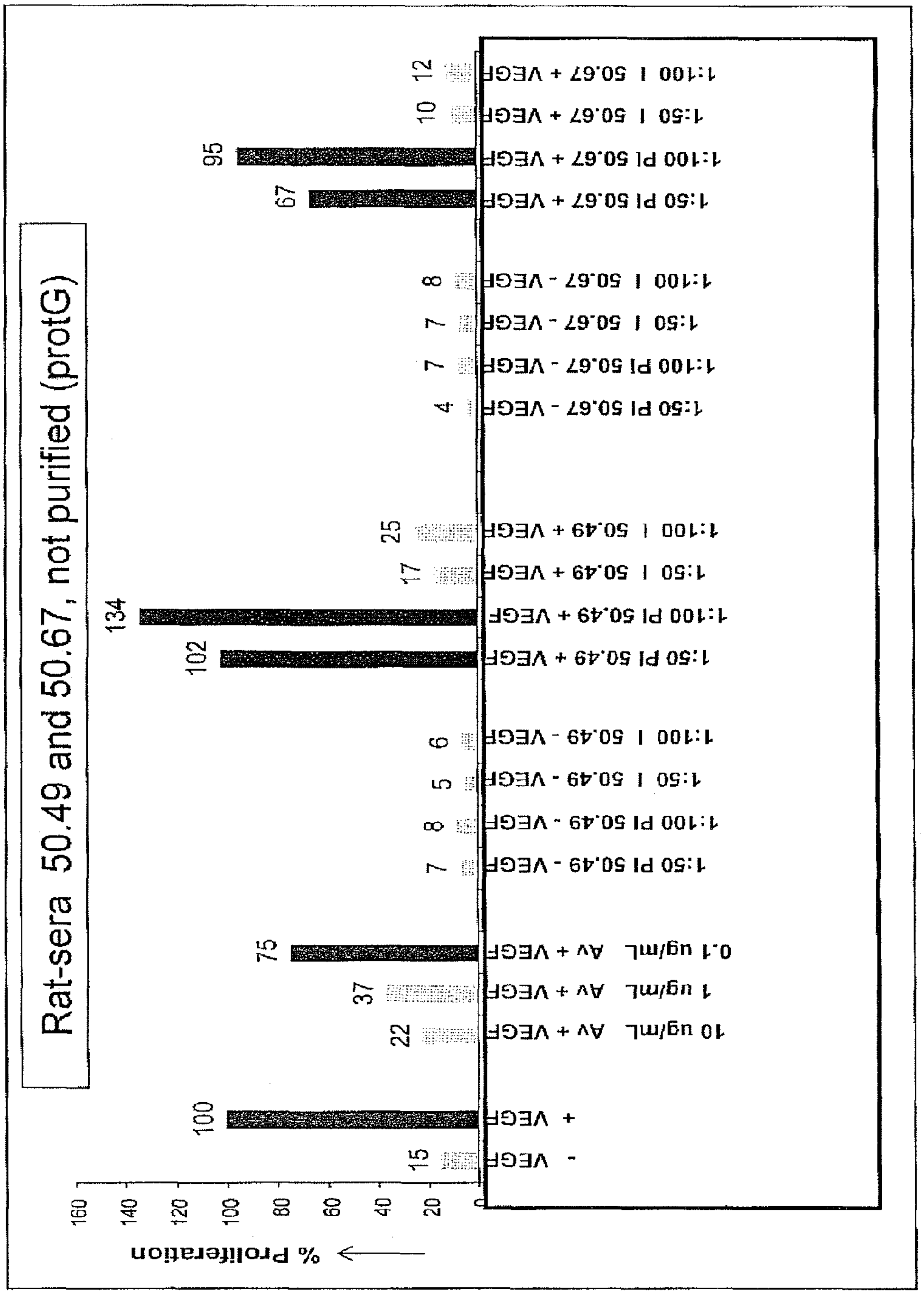
FIG. 3. First neutralization data from BaF3/cell proliferation assay with non-purified rat anti-oxid-$humVEGF_{26-104}$ immune sera (I) 50.49 and 50.67 at 1/50 and 1/100 dilution. mAb Avastin™ (anti-$humVEGF_{1-165}$) was used as positive control, pre-immune (PI) sera (50.49 and 50.67) as negative control. Level of proliferation observed at hum $VEGF_{1-165}$=0.6 ng/mL was set by default to 100%, sera proliferation levels were expressed as % of default. Pre-immune sera were taken just before first immunization. Immune sera were taken six weeks after first immunization. In grey: % of proliferation <50; in black: % of proliferation between 50 and 100.
Figure 4:
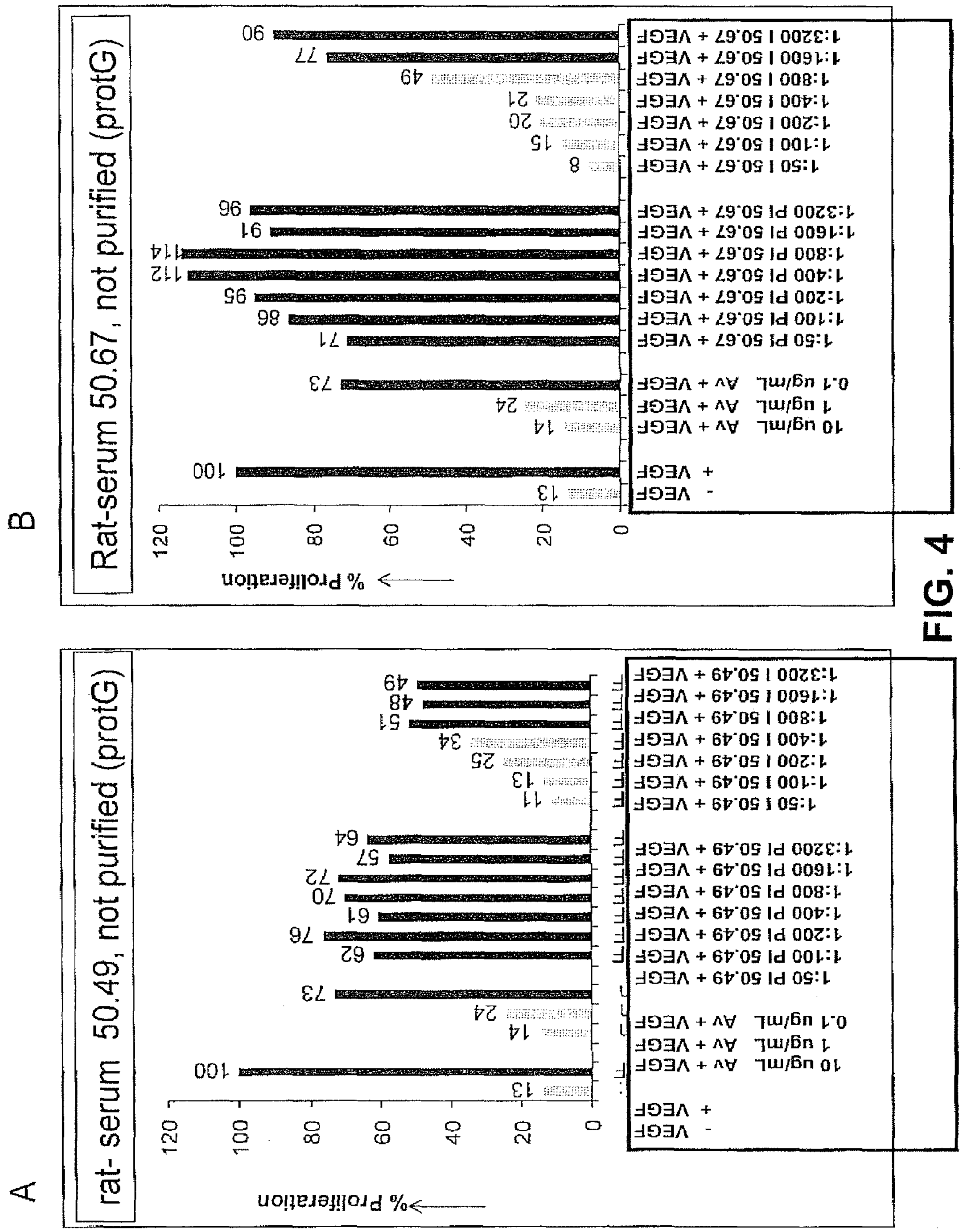
FIG. 4. Neutralization data from BaF3/cell proliferation assay with non-purified anti-oxid-humVEGF$_{26-104}$ rat sera Panel A) 50.49 and Panel B) 50.67 from 1/50 and 1/3200 dilution. For further details, see FIG. 3.
Figure 5:
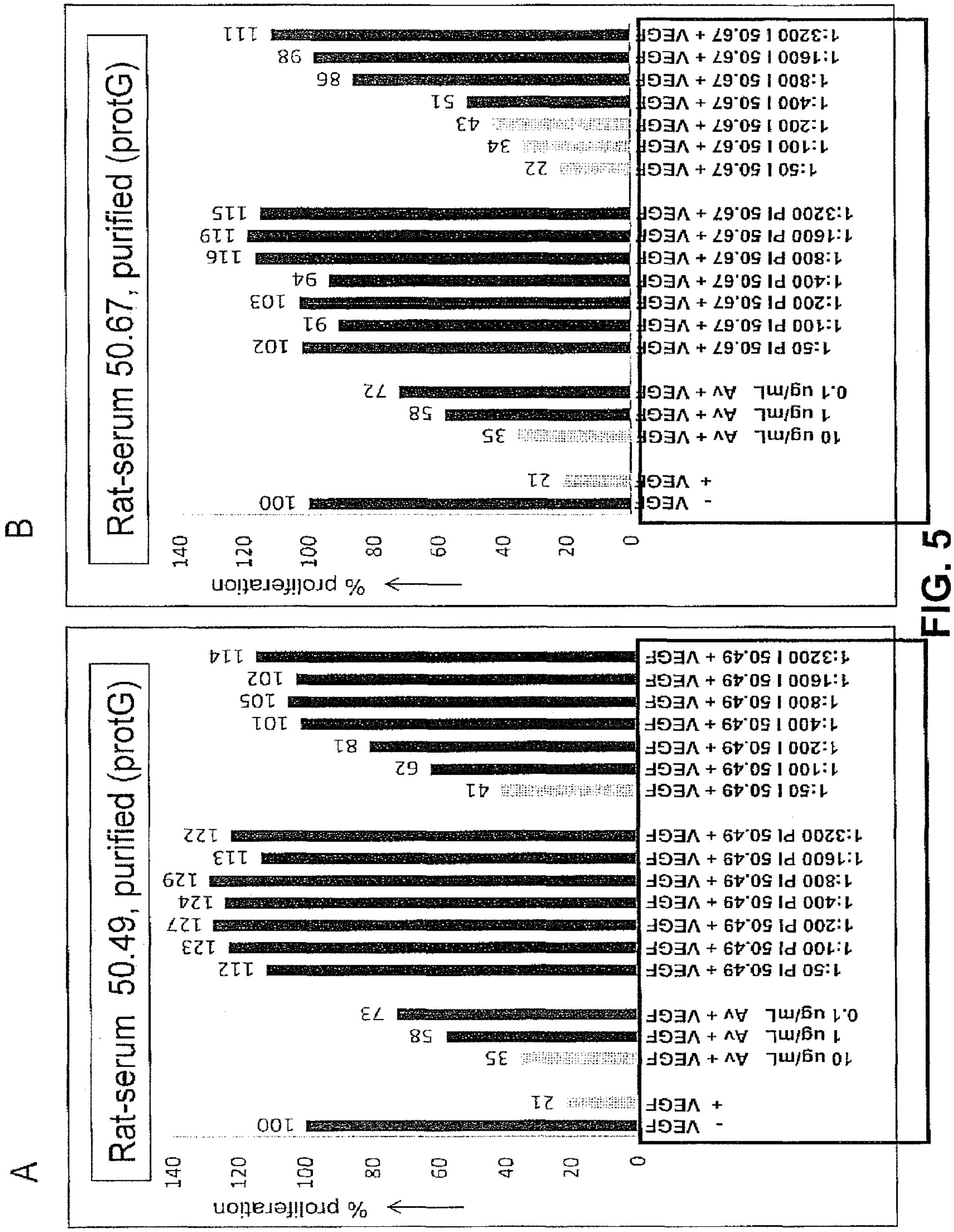
FIG. 5. Neutralization data from BaF3/cell proliferation assay with protG-purified anti-oxid-humVEGF$_{26-104}$ rat sera Panel A) 50.49 and Panel B) 50.67 from 1/50 and 1/3200 dilution. For further details, see FIG. 3.
Figure 6:
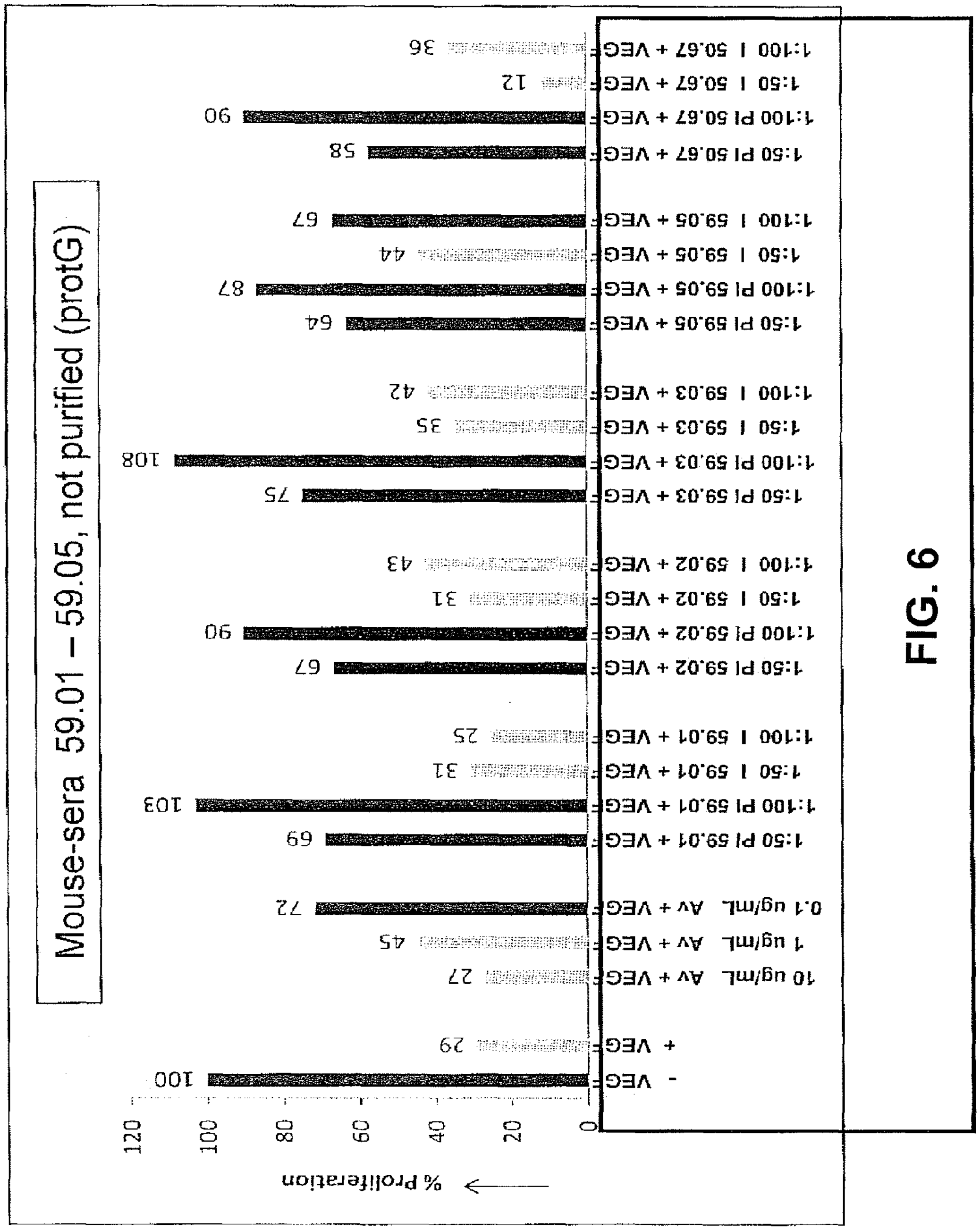
FIG. 6. Neutralization data from BaF3/cell proliferation assay with non-purified mouse anti-oxid-humVEGF$_{26-104}$ immune sera (I) 59.01-59.05 (04 died). mAb Avastin™ (anti-humVEGF$_{1-165}$) and anti-oxid-humVEGF$_{26-104}$ rat serum 50.67 were used as positive control; pre-immune (PI) sera as negative control. Level of proliferation observed at hum-VEGF$_{1-165}$=1.2 ng/mL was set by default to 100%, serum proliferation levels were expressed as % of default. PI: serum taken just before first immunization; I: serum taken six weeks after first immunization.

The data in FIG. 2 show that oxid-humVEGF$_{26-104}$ binds with less than five-fold difference in affinity (as compared to humVEGF$_{1-165}$) to Avastin™, while the (cyclic) peptide-mimic derived from the beta3-loop of humVEGF is >10,000-fold less active in binding to Avastin™. This illustrates the big step forward in reconstruction of the discontinuous Avastin™ binding site on humVEGF using this novel technology of the present invention.

Example 1C

Use of Oxid-humVEGF$_{26-104}$ for Generating VEGF-Neutralizing Antibodies and Sera in Rats and Mice Immunization experiments using oxid-humVEGF$_{26-104}$ (not-conjugated to a carrier protein!!) were carried out both in female Wistar rats and female Balb/C mice. The antisera were analyzed for:

A) binding to surface-immobilized humVEGF$_{1-165}$ (titer determination)

B) ability to inhibit the binding of Avastin™ to surface-immobilized humVEGF$_{1-165}$ C) neutralizing activity for humVEGF$_{1-165}$ in a BaF3-cell proliferation assay The results of these studies are shown below and in FIGS. 3-6.

Immunization Protocols:

Wistar rats: Female Wistar rats were immunized with anti-humVEGF$_{26-104}$ at day 0 with 400 μL (intramuscular+subcutaneous, 200 μL each) of a 375 μg/mL solution of hum-VEGF$_{26-104}$ in PBS/CoVaccine 1:1 (v/v) (PBS=Phosphate-Buffered Saline), followed by a booster (same quantity and concentration) at two and four weeks. Subsequently, the rats were bled after six weeks and the antisera collected. Anti-VEGF titers were determined as described as below.

Balb/C mice: Immunization with oxid-humVEGF$_{26-104}$ was performed in female Balb/C mice, using two different formulations, i.e., with a CFA/IFA adjuvant (group 1: two animals), and with a CoVaccine adjuvant (group 2: three animals). The animals (2) in group 1 were immunized intraperitoneal (i.p.) at day 0 with 250 μL of a 1.0 mg/mL solution of oxid-humVEGF$_{26-104}$ in PBS/CFA 2:3 (v/v) (PBS=Phosphate-Buffered Saline, CFA=Complete Freund's Adjuvance), followed by a booster (same quantity, method and concentration; Incomplete Freund's Adjuvance (IFA) instead of CFA) at four weeks. The animals (3) in group 2 were immunized at day 0 with 210 μL (intramuscular+subcutaneous, 105 μL each) of a 1.25 mg/mL solution of VEGF$_{26-104}$ in PBS/CoVaccin 1:1 (v/v) (PBS=Phosphate-Buffered Saline), followed by a booster (same quantity, method and concentration) at two and four weeks. Subsequently, all five mice were bled after six weeks and the antisera collected. Anti-VEGF titers were determined as described as below.

ELISA Titer Determination:

Titers were calculated by determining the serum dilution for which $OD_{405\ nm}$ is equal to $4\times OD_{405\ nm}$ that of a buffer solution (see "ELISA-binding studies, example 1B"). The titer defines the negative [10] log-value of the dilution factor (1/10=1, 1/100=2, 1/1000=3, 1/10000=4, etc.).

| | humVEGF$_{1-165}$ Titer 0 wpv | humVEGF$_{1-165}$ Titer 6 wpv |
|---|---|---|
| Animal | | |
| 50.49 (Wistar rat 1; CoVaccine) | <<2 | 4.8 |
| 50.67 (Wistar rat 2; CoVaccine) | <<2 | 5.4 |
| 59.01 (Balb/C mouse 1, CFA/IFA) | <<2 | 5.3 |
| 59.02 (Balb/C mouse 2, CFA/IFA) | <<2 | 5.2 |
| 59.03 (Balb/C mouse 3, CoVaccine) | <<2 | 5.4 |
| 59.04 (Balb/C mouse 4, CoVaccine) | <<2 | † |
| 59.05 (Balb/C mouse 5, CoVaccine) | <<2 | 5.3 |
| Control Abs | | |
| Avastin ™ (500 ng/mL start) | — | 4.4 |
| BioVision ™ (5000 ng/mL) | — | 4.2 |

ELISA Competition Studies of Rat Antisera with Avastin™:

ELISA binding competition studies were carried out largely following the procedure as described for binding in ELISA (see above). Incubation with antibody was carried out at a fixed Avastin™-concentration (10 ng/mL; $OD_{405\ nm}$ between 1.0-1.5) in the presence of decreasing amounts of rat antisera (start at 1/5; further 1/3 dilution steps).

Neutralization in BaF3-Cell Proliferation Assay:

The cells that are used in the assay are murine pre-B lymphocytes stable expressing human (h) humVEGF-Receptor 2 (Makinen et al., 2001). These recombinant cells survive/proliferate only in the presence of IL-3 (natural cytokine required for the survival of the parental cells) or humVEGF. For the experiment, IL-3 has to be washed off the medium so that proliferation capability in dependence of humVEGF can be tested.

Ba/F3 R2 cells were grown in DMEM (Gibco #31885) containing 10% fetal bovine serum (Perbio #CH30160.03), 2 mM L-glutamine (Sigma #G7513), 2 ng/ml mIL-3 (Calbiochem #407631) and 500 μg/ml Zeocin (Invitrogen #450430). Cells were grown at 37° C. in a humidified incubator with an atmosphere of 5% CO2/95% air.

Figure 9:
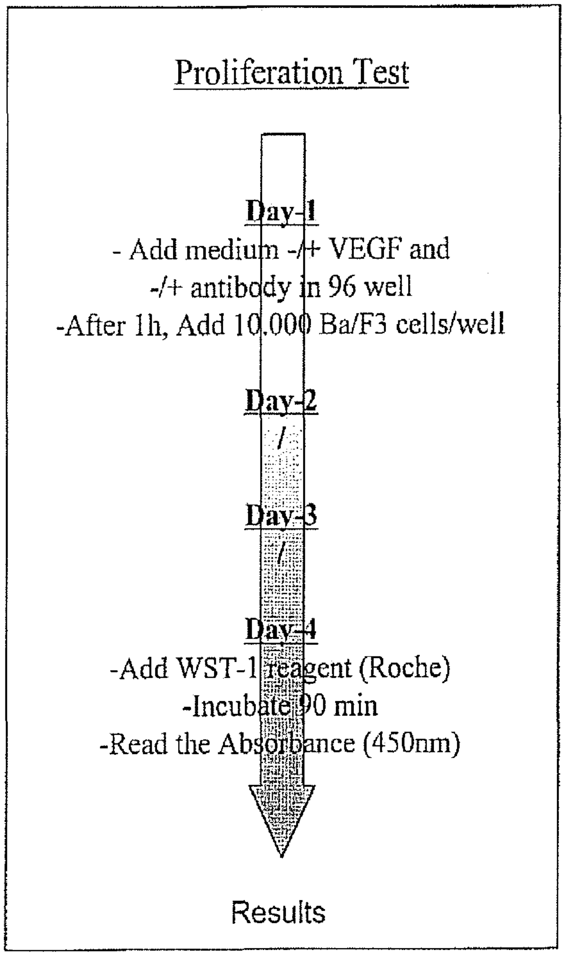
FIG. 9. Schematic overview of the proliferation assay.
Figure 11:
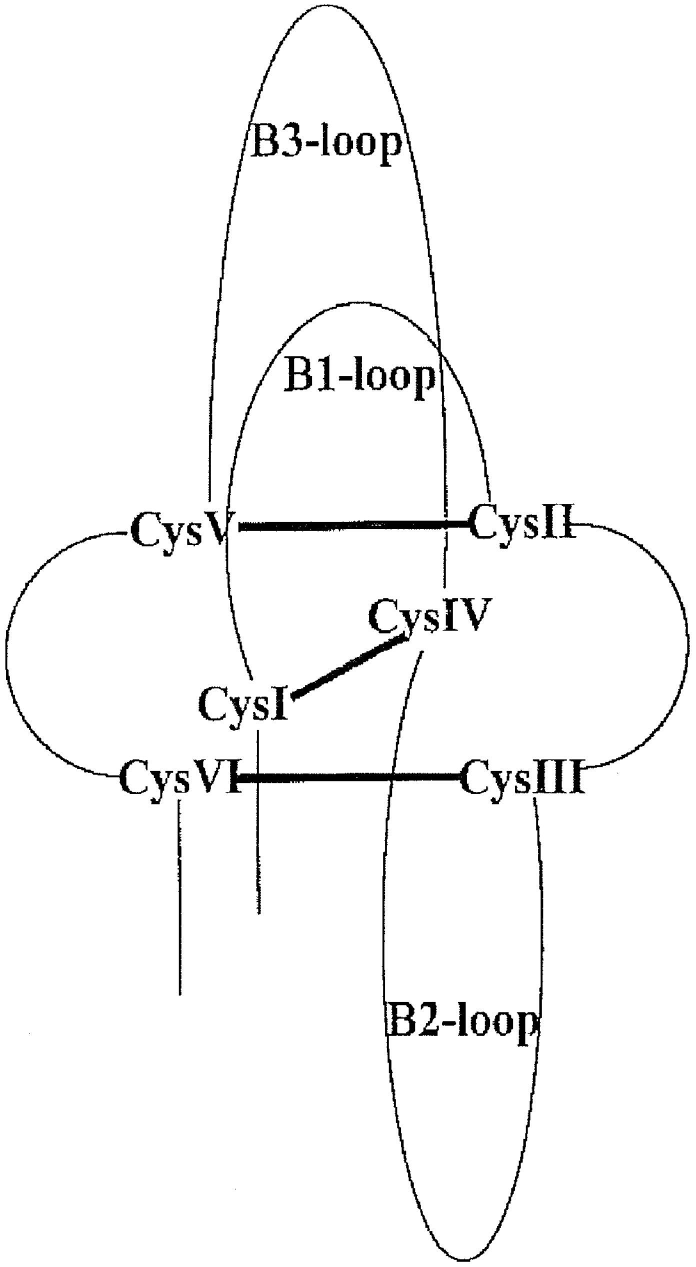
FIG. 11. Schematic representation of the general structure of the various members of the cystine-knot growth factor superfamily.

Differently concentrated humVEGF (+humVEGF) or medium (−humVEGF) was either added directly to the cells (to test the proliferation efficiency) or pre-incubated for one hour with different concentrations of Avastin™ (positive control), different concentrations of rat or mouse sera and then added to the cells (in case of inhibition experiments). Two days later, cell proliferation was measured by adding WST-1 (Roche #1644807). See FIG. 9 for a graphical representation of the assay.

The WST-1 assay is based on the measurement of the mitochondrial succinate dehydrogenase activity. To function correctly, this enzyme requires the integrity of this organelle and is a good indicator of the number of proliferating cells present in the culture. A tetrazolium salt (WST-1) is used as substrate since it generates a soluble dark metabolic (formazon) through the action of the enzyme, which can then be quantified by measuring the absorbance (450 nm) in an ELISA reader. The higher the absorbance measured in the assay, the stronger the proliferation. Absorbance is positively correlated with proliferation. Experiments were repeated three times in triplicate showing overall similar results.

Figure 7:
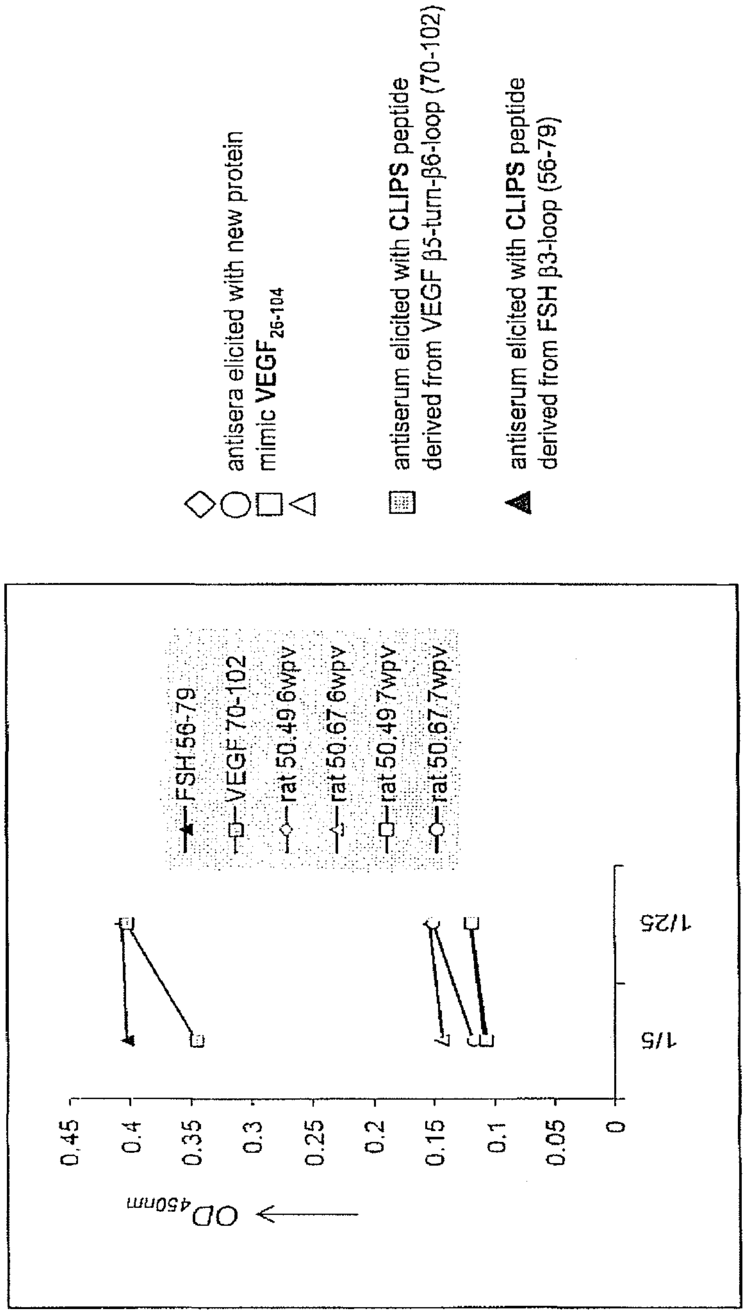
FIG. 7. Inhibition of Avastin™-binding to surface-immobilized humVEGF$_{1-165}$ with non-purified rat immune sera 50.49 and 50.67 at 1/5 and 1/25 dilution. Peptide serum 31.1 (elicited against double-constrained CLIPS/SS-peptide derived from the β3-loop sequence humFSH$_{56-79}$ of Follicle-Stimulating Hormone; serum has high neutralizing activity for FSH in cell-based assay) and serum 45.09 (elicited against backbone-cyclized peptide derived from the β5-turn-β6 loop sequence 70-102 of VEGF; serum has neutralizing activity for humVEGF$_{1-165}$ in BaF3-cell proliferation assay) were used as negative controls. Minimal concentration of Avastin™ (~10 ng/mL) was used (OD$_{450\ nm}$~0.4) in order to secure maximal sensitivity for the inhibition experiments.

The data obtained proves that high levels of antibodies were successfully generated via immunization with oxid-humVEGF$_{26-104}$ (not-conjugated to a carrier protein!!), both in female Wistar rats and female Balb/C mice. The antisera generated in this way exhibit strong neutralizing activity for humVEGF$_{1-165}$ in a BaF3-cell proliferation assay (FIGS. 3-6), and the ability to inhibit binding of Avastin™ to humVEGF (FIG. 7).

Example 1D

Oxid-humVEGF$_{26-104}$ does not Induce BaF3-Cell Proliferating by Itself

In order to check whether oxid-humVEGF$_{26-104}$, the truncated form of humVEGF$_{1-165}$, is also able to induce BaF3-cell proliferation, we measured cell proliferation in the presence of varying amounts of oxid-humVEGF$_{26-104}$ (0.01-20 ng/mL). In order to check if oxid-humVEGF$_{26-104}$ was able to enhance or inhibit the proliferative capacity of humVEGF$_{1-165}$, itself, the experiments with varying amounts of oxid-humVEGF$_{26-104}$ were also run in the presence of humVEGF$_{1-165}$=1.2 ng/mL.

Figure 8:
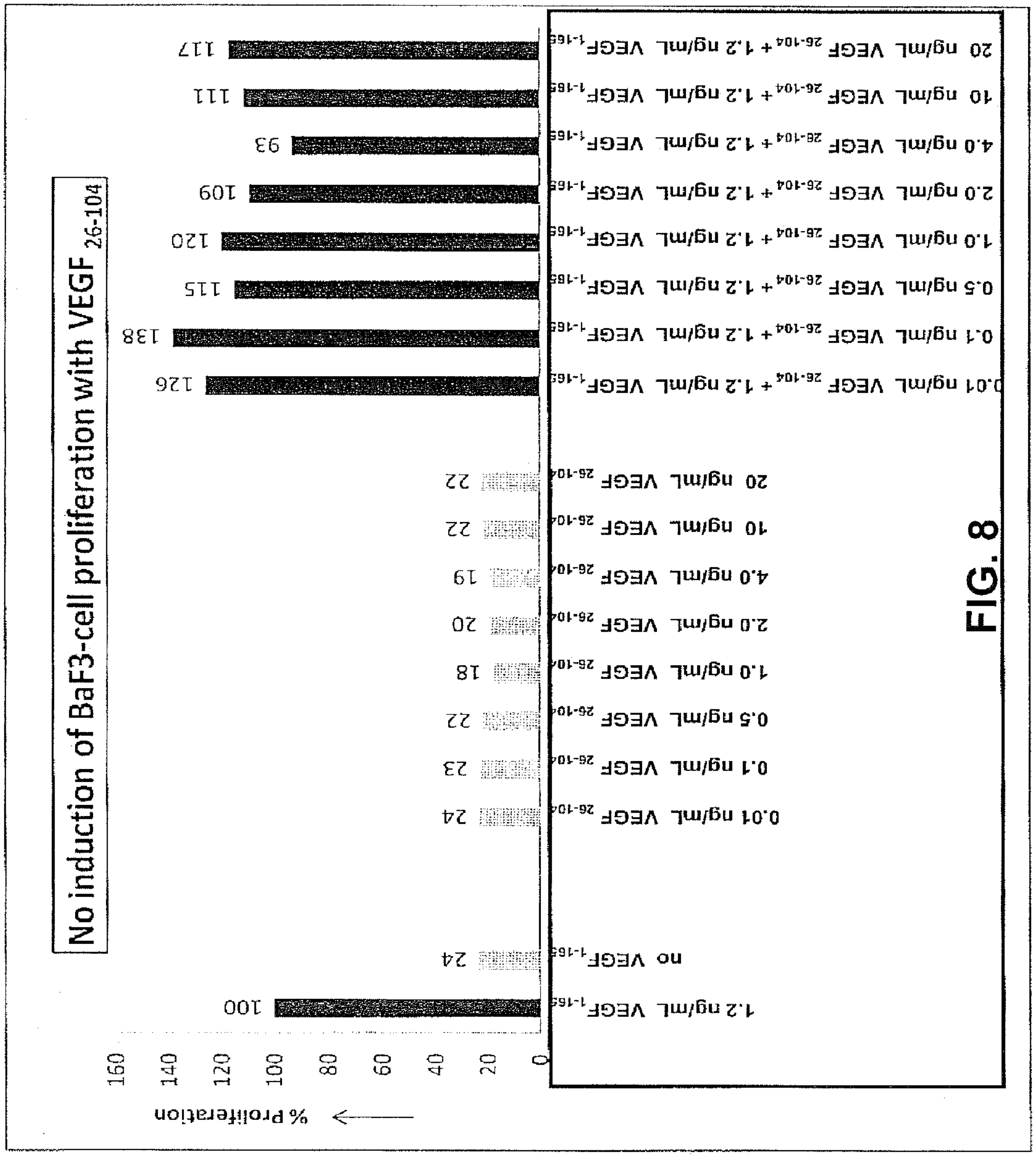
FIG. 8. Proliferation data from BaF3/cell assay with hum-VEGF$_{26-104}$ at various concentration (0.01-20 ng/mL), either in the absence and presence of humVEGF$_{1-165}$. Level of proliferation observed at humVEGF$_{1-165}$=1.2 ng/mL was set by default to 100%, other proliferation levels were expressed as % of default.

The results shown in FIG. 8 clearly demonstrate no activity for oxid-humVEGF$_{26-104}$ in BaF3-cell proliferation nor any affect on the proliferating ability of humVEGF$_{1-165}$.

Example 1E

Passive Immunization Study with Anti-humVEGF$_{26-104}$ Rat-Antisera in Swiss Nu/Nu Mice Inoculated with Human LS174T Tumor Cells: In Vivo Proof of Principle of the Tumor-Reducing Potential of Anti-humVEGF$_{26-104}$ Antisera In order to demonstrate the tumor-reducing potential of anti-humVEGF$_{26-104}$ antisera, the following immunization experiment was carried out in 30 male Swiss nu/nu mice (Charles river), six weeks of age at the beginning of the study. The animals were divided in the following three treatment groups:

Group 1: PBS (n=10; negative control group): intraperitoneal (i.p.) PBS injections (500 μl) after tumor cell inoculation.

Group 2: oxid-humVEGF$_{26-104}$ (n=10): i.p. injections (500 μl) with IgG-purified anti-VEGF peptide rat-antiserum after tumor cell inoculation.

Group 3: AVASTIN™ (n=10; positive control group): i.p. injections (500 μl) with anti-humVEGF mAb AVASTIN™ following tumor cell inoculation.

Figure 12:
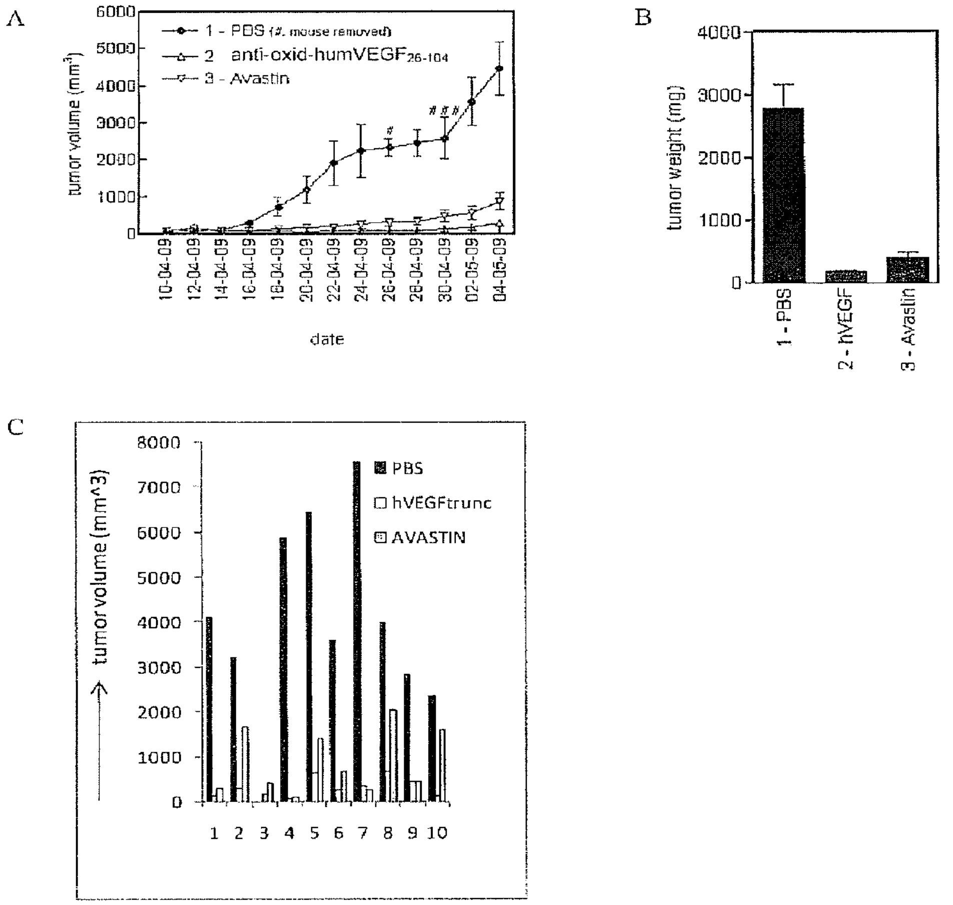
FIG. 12. Panel A) Increase of average tumor volume (mm3) per mice in treatment group 1:PBS (⊙), 2:anti-oxid-hum-VEGF$_{26-104}$ (Δ), and 3:AVASTIN™ (V). In the PBS group, four out of nine mice were euthanized (#) before the planned day because the estimated volume of the tumors exceeded the (pre-set) maximum volume. Panel B) Total average tumor weight (mgs) per mice in each different treatment group at the end of the experiment. Panel C) Total tumor volume (mm3) of individual mice in each different treatment group at the end of the experiment (mouse 3 in PBS-group died before the start of the experiment).

On day 1 of the study, all 30 mice were injected subcutaneously (right flank) with 10 million human LS174T tumor cells suspended in a 100 μL solution. Tumor-take was ~100%. Subsequently, the mice were given on days 1, 8, and 15, i.p. injections (500 μl) with either A) PBS (group 1), B) anti-oxid-humVEGF$_{26-104}$ rat-antiserum (5× conc. rat serum; group 2), and C) AVASTIN™ (group 3). Anti-oxid-humVEGF$_{26-104}$ rat serum was obtained by immunizing a total number of 20 male Whistar rats in a separate experiment 4× with 250-microgram doses of humVEGF$_{26-104}$ using CoVaccine adjuvant (inoculations at days 0, 14, 28, and 49; bled on day 63). The resulting rat sera were purified by affinity chromatography (ProtG-column) and concentrated 5×. The ten most potent antisera (based on in vitro neutralization data in BaF3 assay; see previous Example) of these were pooled and used for inoculation of the ten mice in treatment group 2. Lengths and breadths of the tumors were measured every other day, starting on the first day after tumor cell inoculation. Tumor volumes were estimated using the formula (breadth2×length)/2.[ref 6] The data are shown in FIG. 12.

The data presented above lead to the following conclusions:

1. anti-oxid-humVEG F$_{26-104}$ antisera have the ability to strongly reduce tumor growth in mice.

2. in this experimental setting, the observed effect of treatment with anti-oxid-humVEGF$_{26-104}$ antisera was visibly more pronounced than that for AVASTIN™.

3. treatment of nude mice with anti-oxid-humVEGF$_{26-104}$ antibodies was received well by all animals and is thus not toxic!

Example 1F

Immunogenicity of Oxid-ratVEGF$_{26-104}$ in Rats (SEQ ID NO: 30)

Peptide sequence oxid-ratVEGF$_{26-104}$: Acetyl-C1RPIE

TLVDIFQEYPDEIEYIFKPSAVPLMRC2AGAC3NDEALEC4VPTSESNVT

MQIMRIKPHQSQHIGEMSFLQHSRC5EC6-amide.

Solid-phase synthesis of ratVEGF$_{26-104}$. ratVEGF$_{26-104}$ was synthesized by normal solid-phase synthesis on a Rink-amide resin (downloaded to 0.1 mmol/g) following standard procedures as described for humVEGF$_{26-104}$ (see Example 1). Subsequent oxidative refolding was carried out exactly as described for humVEGF$_{26-104}$. Purification of both red-ratVEGF$_{26-104}$ and oxid-ratVEGF$_{26-104}$ was carried out by preparative High Performance Liquid Chromatography (HPLC). Characterization of both peptides was carried out by analytical HPLC and ElectroSpray Ionization Mass Spectrometry (ESI-MS).

The successful refolding of red-ratVEGF$_{26-104}$ was evidenced by the characteristic shift to lower Rf-values (from 48.5% to 41.3% ACN, see Table below), normally observed when proteins or fragments thereof are oxidative refolded. The characteristic narrow shape of the new peak at lower $R_f$-value provides evidence that an intact cystine-knot structure is indeed formed upon oxidative refolding of red-ratVEGF$_{26-104}$.

Figure 13:
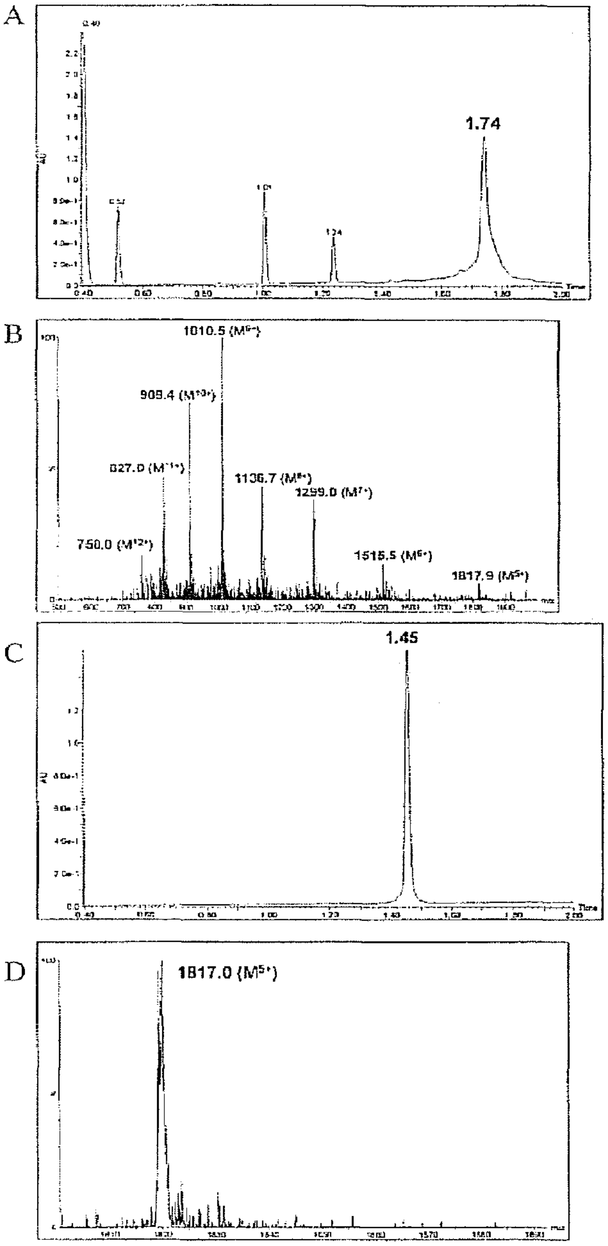
FIG. 13. HPLCs (Panels A/C) and ElectroSpray Ionization Mass Spectra (Panels B/D) of red-ratVEGF$_{26-104}$ (Panels A/B) and oxid-ratVEGF$_{26-104}$ (Panels C/D).

Also, the ESI-MS spectrum undergoes a significant change upon oxidative refolding. First of all, the overall mass goes down by six mass units (formation of three disulfide bonds releases a total of 6H). Moreover, there is a very characteristic shift of MS-signals to higher m/z-values. For example, the MS-spectrum for red-ratVEGF$_{26-104}$ gives the most intense signals for the $M^{9+}$ and $M^{10+}$ charged species, whereas these signals disappear and a much weaker signal at $M^{5+}$ remains (see FIG. 13) that is much less intense. Also, this shift is characteristic for folding of proteins into their oxidized native structure and shows that oxidative refolding of red-ratVEGF$_{26-104}$ has been successful. The reason is that the protein or protein fragment adopts a more condensed structure that is no longer able to pick up so many charges. In contrast to this, the flexible and extended structure of the reduced protein is able to accommodate many more charges.

| Peptide | Oxidation state (RED/OX) | Retention (% ACN) | MW calculated | MW experimental |
|---|---|---|---|---|
| red-ratVEGF$_{26-104}$ | RED $(SH)_6$ | 48.5 | 9087.5 | 9085.3 |
| oxid-ratVEGF$_{26-104}$ | OX $(SS)_3$ | 41.3 | 9081.5 | 9080.0 |

This example describes the results of an immunization study in male Whistar rats with both oxid-hum-VEGF$_{26-104}$ and oxid-ratVEGF$_{26-104}$ with an intact cystine-knot fold (oxid-form). The data unequivocally show that oxid-ratVEGF$_{26-104}$ is equally immunogenic and potent as compared to oxid-humVEGF$_{26-104}$ in generating antibodies in rats. The use of truncated VEGF as described in this patent can thus be used to bypass immune tolerance to "self proteins," like, for example, the full-length homodimeric VEGF protein in this particular case.

A total of four Wistar rats (2×2) were immunized on day 0 with 250 micrograms each of either oxid-ratVEGF$_{26-104}$ (two rats) or oxid-humVEGF$_{26-104}$ (two rats) using CoVaccine as adjuvant, followed by booster inoculations at day 14, 28, and 42. The rats were finally bled at day 56, and the sera were analyzed for antibody titers against ratVEGF$_{1-165}$, humVEGF$_{1-165}$, oxid-ratVEGF$_{26-104}$, and oxid-humVEGF$_{26-104}$. (Part of) the antibody-binding data are shown in Table 1 and FIG. 14.

Figure 14:
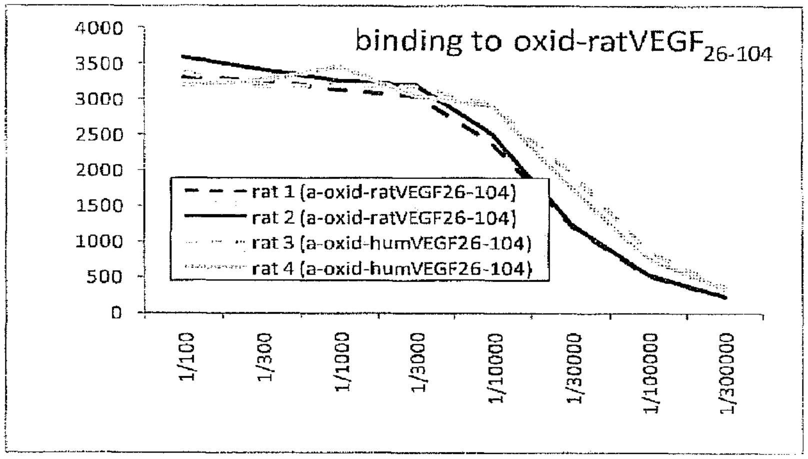
FIG. 14. Plots of the binding in ELISA of anti-oxid-hum-VEGF$_{26-104}$ rat sera 1+2 (black ------ and - - - lines) and anti-oxid-ratVEGF$_{26-104}$ rat sera 3+4 (grey ------ and - - - lines) to both Panel A) oxid-ratVEGF$_{26-104}$ and Panel B) oxid-humVEGF$_{26-104}$.
Figure 14:
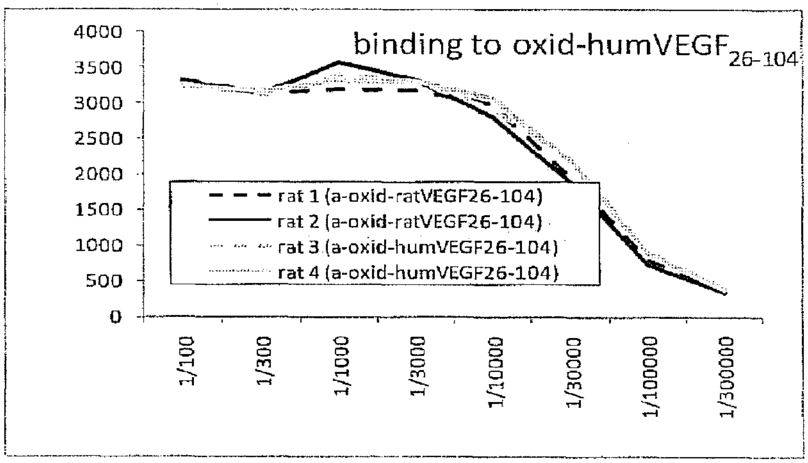

The data in Table 1 and FIG. 14 do not show any detectable difference in binding between antisera elicited with oxid-ratVEGF$_{26-104}$ and those elicited with oxid-humVEGF$_{26-104}$ in rats, which strongly suggests that oxid-ratVEGF$_{26-104}$ is equally immunogenic in rats (homologous species) as compared to oxid-humVEGF$_{26-104}$ (heterologous species), and is able to elicit comparable amounts of antibodies that even show cross-reactivity with the homodimeric VEGF$_{1-165}$ protein (Table 1C).

Furthermore, the experiment provides a very strong basis for the fact that oxid-humVEGF$_{26-104}$ can be used to elicit anti-VEGF in humans, and that oxid-humVEGF$_{26-104}$ will not suffer from lack of immunogenicity as a result of immune tolerance to self proteins.

TABLE 1

List of the binding of rat-antisera in ELISA to A) oxid-ratVEGF$_{26-104}$, B) oxid-humVEGF$_{26-104}$, C) humVEGF$_{1-165}$ homodimer (recombinant full-length humanVEGF), and D) ratVEGF$_{1-165}$ homodimer (recombinant full-length ratVEGF). For comparison, the binding data to the humanized anti-humVEGF mAb AVASTIN ™ are included.

| | titers | 1/100 | 1/300 | 1/1000 | 1/3000 | 1/10000 | 1/30000 | 1/100000 | 1/300000 | titer endblood |
|---|---|---|---|---|---|---|---|---|---|---|
| | ratVEGF26-104 | | | | | | | | | |
| A | rat 1 (a-oxid-ratVEGF26-104) | 3298 | 3263 | 3123 | 3028 | 2357 | 1214 | 514 | 225 | 5.1 |
| | rat 2 (a-oxid-ratVEGF26-104) | 3597 | 3424 | 3262 | 3197 | 2516 | 1241 | 532 | 237 | 5.1 |
| | rat 3 (a-oxid-humVEGF26-104) | 3376 | 3172 | 3209 | 3176 | 2910 | 1951 | 861 | 355 | 5.3 |
| | rat 4 (a-oxid-humVEGF26-104) | 3200 | 3263 | 3465 | 3060 | 2895 | 1736 | 754 | 349 | 5.3 |
| | humanVEGF26-104 | | | | | | | | | |
| B | rat 1 (a-oxid-ratVEGF26-104) | 3334 | 3148 | 3210 | 3174 | 2989 | 1929 | 811 | 366 | 5.3 |
| | rat 2 (a-oxid-ratVEGF26-104) | 3297 | 3121 | 3564 | 3329 | 2801 | 1871 | 728 | 332 | 5.2 |
| | rat 3 (a-oxid-humVEGF26-104) | 3263 | 3098 | 3385 | 3300 | 2908 | 2188 | 898 | 409 | 5.3 |
| | rat 4 (a-oxid-humVEGF26-104) | 3229 | 3174 | 3289 | 3298 | 3051 | 2166 | 873 | 373 | 5.3 |
| | Avastin (a-humVEGF mAb) | 4037 | 3033 | 1839 | 736 | 333 | 158 | 116 | 97 | 15-25 ng/mL |
| | humanVEGF1-165 | | | | | | | | | |
| C | rat 1 (a-oxid-ratVEGF26-104) | 3404 | 3320 | 3449 | 2681 | 1305 | 548 | 280 | 158 | 4.6 |
| | rat 2 (a-oxid-ratVEGF26-104) | 3245 | 3216 | 3672 | 2955 | 1588 | 955 | 301 | 166 | 4.7 |
| | rat 3 (a-oxid-humVEGF26-104) | 3456 | 3406 | 3334 | 3078 | 1776 | 739 | 351 | 176 | 4.7 |
| | rat 4 (a-oxid-humVEGF26-104) | 3758 | 3282 | 3604 | 3313 | 2508 | 1374 | 510 | 235 | 5.1 |
| | Avastin (a-humVEGF mAb) | 3261 | 3016 | 2493 | 1322 | 528 | 222 | 129 | 100 | 5-10 ng/mL |

TABLE 1-continued

List of the binding of rat-antisera in ELISA to A) oxid-ratVEGF$_{26-104}$, B) oxid-humVEGF$_{26-104}$, C) humVEGF$_{1-165}$ homodimer (recombinant full-length humanVEGF), and D) ratVEGF$_{1-165}$ homodimer (recombinant full-length ratVEGF). For comparison, the binding data to the humanized anti-humVEGF mAb AVASTIN ™ are included.

| | titers | 1/100 | 1/300 | 1/1000 | 1/3000 | 1/10000 | 1/30000 | 1/100000 | 1/300000 | titer endblood |
|---|---|---|---|---|---|---|---|---|---|---|
| | | | | | ratVEGF1-165 | | | | | |
| D | rat 1 (a-oxid-ratVEGF26-104) | 2993 | 2519 | 1481 | 731 | 346 | 172 | 122 | 98 | 3.8 |
| | rat 2 (a-oxid-ratVEGF26-104) | 3032 | 3055 | 2717 | 1568 | 753 | 315 | 179 | 122 | 4.2 |
| | Avastin (a-humVEGF mAb) | 236 | 148 | 103 | 89 | 93 | 89 | 91 | 88 | <1000 ng/mL |

Example 1G

Synthesis of humPLGF$_{34-112}$ (humPLGFtrunc)

```
                                   (SEQ ID NO: 14)
Peptide sequence of humPLGF34-112: Acetyl-C1RALERL
VDVVSEYPSEVEHMFSPSAVSLLRC2TGAC3GDENLHC4VPVETANVTMQ
LLKIRSGDRPSYVELTFSQHVRC5EC6-amide.
X0 = acetyl
                      (amino acids 2-31 of SEQ ID NO: 14)
X1 = RALERLVDVVSEYPSEVEHMFSPSAVSLLR (A-mutation
for native C)
X2 = TGA (A-mutation for native C)
                     (amino acids 37-42 of SEQ ID NO: 14)
X3 = GDENLH
                     (amino acids 44-76 of SEQ ID NO: 14)
X4 = VPVETANVTMQLLKIRSGDRPSYVELTFSQHVR
X5 = E
X6 = amide
```

Solid-phase synthesis of red-PLGF$_{34-112}$. Red-PLGF$_{34-112}$ was synthesized by normal solid-phase synthesis on a Rink-amide resin (downloaded to 0.1 mmol/g) following standard procedures as described for red-humVEGF$_{26-104}$ (see Example 1E). Subsequent oxidative refolding was carried out exactly as described for oxid-humVEGF$_{26-104}$.

Purification of both red-humPLGF$_{34-112}$ and oxid-humPLGF$_{34-112}$ was carried out by preparative High Performance Liquid Chromatography (HPLC). Characterization of both red-humPLGF$_{34-112}$ and oxid-humPLGF$_{34-112}$ was carried out by analytical HPLC and ElectroSpray Ionization Mass Spectrometry (ESI-MS).

The successful refolding of red-humPLGF$_{34-112}$ was evidenced by the characteristic shift to lower Rf-values (from 49% to 38.3% ACN, see Table below) that is normally observed when proteins or fragments thereof are oxidative refolded. The characteristic narrow shape of the new peak at lower Rf-value provides evidence that an intact cystine-knot structure is indeed formed upon oxidative refolding of red-humPLGF$_{34-112}$.

Figure 15:
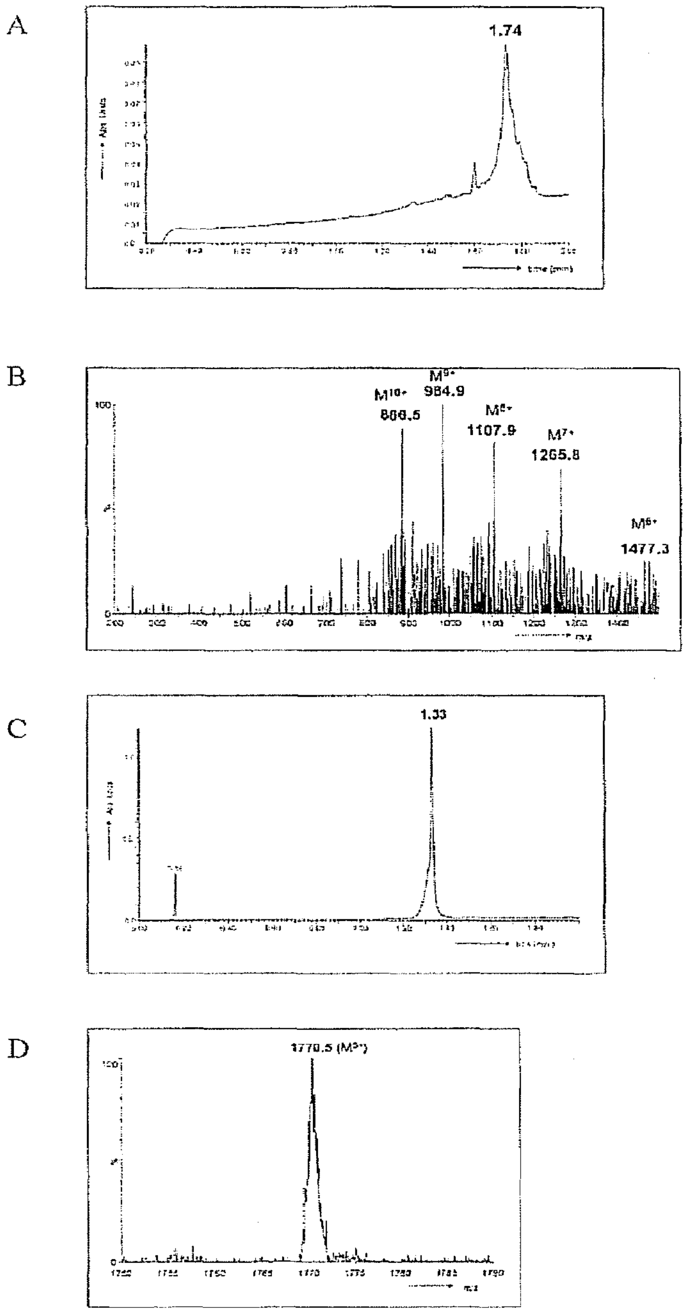
FIG. 15. HPLCs (A/C) and ElectroSpray Ionization Mass Spectra (B/D) of red-humPLGF$_{34-112}$ (A/B) and oxid-hum-PLGF$_{34-112}$ (C/D).

Also the ESI-MS spectrum undergoes a significant change upon oxidative refolding. First of all, the overall mass goes down by six mass units (formation of three disulfide bonds releases a total of 6H). Moreover, there is a very characteristic shift of MS-signals to higher m/z-values. For example, the MS-spectrum for red-humPLGF$_{34-112}$ gives clear signals for the $M^{6+}$ to $M^{10+}$ charged species, whereas these signals disappear and a much weaker signal at $M^{5+}$ remains (see FIG. 15) that is much less intense. Also this shift is characteristic for folding of proteins into their oxidized native structure and shows that refolding of red-humPLGF$_{34-112}$ was successful. The reason is that the protein or protein fragment adopts a more condensed structure that is no longer able to pick up so many charges. In contrast to this, the flexible and extended structure of the reduced protein is able to accommodate many more charges.

| Peptide | Oxidation state (RED/OX) | Retention (% ACN) | MW calculated | MW experimental |
|---|---|---|---|---|
| red-humPLGF$_{34-112}$ | RED $(SH)_6$ | 48.5 | 8855.2 | 8855.3 |
| oxid-humPLGF$_{34-112}$ | OX $(SS)_3$ | 38.3 | 8849.2 | 8847.5 |

Example 1H

Synthesis of humSOST$_{57-144}$ (humSOSTtrunc)

```
                                   (SEQ ID NO: 31)
Peptide sequence for humSOST57-144: Biotine-GGGC1R
ELHFTRYVTDGPCRSAKPVTELVC2SGQC3GPARLLPNAIGRGKWWRPSG
PDFRC4IPDRYRAQRVQLLCPGGEAPRARKVRLVASC5KC6#
X0 = biotine-GGG
                      (amino acids 5-28 of SEQ ID NO: 31)
X1 = RELHFTRYVTDGPCRSAKPVTELV
X2 = SGQ
                     (amino acids 34-57 of SEQ ID NO: 31)
X3 = GPARLLPNAIGRGKWWRPSGPDFR
                     (amino acids 59-88 of SEQ ID NO: 31)
X4 = IPDRYRAQRVQLLCPGGEAPRARKVRLVAS
X5 = K
X6 = amide
```

Synthesis of red-humSOST$_{57-144}$ could not be performed directly on solid-phase on a downloaded resin, as described for humVEGF$_{26-104}$. Therefore, the shorter fragments humSOST-F1/3 were synthesized and subsequently ligated by Native Chemical Ligation (NCL) as described below. Also, the subsequent oxidative refolding of fully red-humSOST$_{57-144}$ was carried out as described below. Solid-phase synthesis of the fragments humSOST-F1/3 was carried out following standard procedures as described for humVEGF$_{26-104}$.

Figure 16:
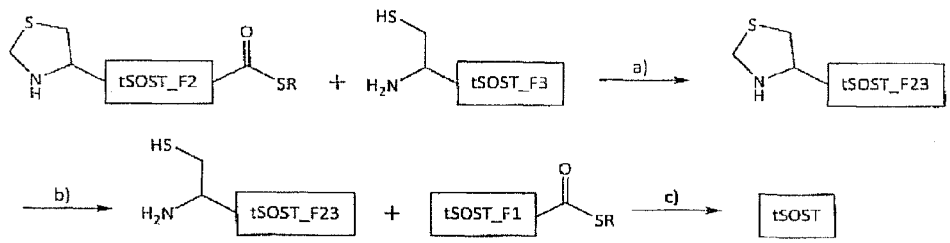
FIG. 16. Three-fragment condensation of humSOST$_{57-144}$ from fragment humSOST-F1, humSOST-F2, and humSOST-F3 by Native Chemical Ligation. Step a) Ligation of the thiaproline-protected humSOST-F2 to humSOST-F3, generating protected humSOST-F2/3. Step b) Deprotection of humSOST-F2/3 with methoxyamine in at pH 4.0. Step c) Ligation of deprotected humSOST-F2/3 to humSOST-F1 generating humSOST$_{57-144}$ at pH 6.5.

Fragment Condensation of humSOST-F1/3 by NCL to give Red-humSOST$_{57-144}$ (for a Schematic Overview see FIG. 16)

First, humSOST-F2 and humSOST-F3 were dissolved (2 mg/ml) in NCL reaction mixture (6 M guanidine, 20 mM TCEP, 200 mM MPAA, 0.2 M disodium hydrogenphosphate, adjusted with 10 M sodium hydroxide to pH 6.5) in a 1.2:1 ratio, and reacted for 24 hours at room temperature. The thiaproline-protected humSOST-F2/3 was obtained in 66.5% yield after reversed phase HPLC purification. Subsequently, the thiaproline was deprotected with 0.02 M methoxyamine in NCL buffer at pH 4.0 for 60 hours. Then, the pH was adjusted to 6.5 and 1.2 equivalents of humSOST-F1 was added and reacted for 1.5 day. The reaction was monitored by RPLC/MS and each day 40 mM TCEP was added to completely reduce all reagents. After completion of the reaction, crude red-humSOST$_{57-144}$ was purified using ion exchange chromatography, and subsequently by reversed phase HPLC giving pure red-humSOST$_{57-144}$ in 24.2% yield (overall 16.1%).

Structure of peptide fragments used for the fragment condensation of reduced SOST$_{67-144}$

| Name | Peptide Sequence |
|---|---|
| humSOST$_{57-144}$ | Biotine-GGGCRELHFTRYVTDGPCRSAKPVTELV CSGQCGPARLLPNAIGRGKWWRPSGPDFRCIPDRYR AQRVQLLCPGGEAPRARKVRLVASCKC (SEQ ID NO: 31)-amide |
| humSOST-F1 | Biotine-GGGCRELHFTRYVTDGPCRSAKPVTELV CSGQ (SEQ ID NO: 32)-thioester |
| humSOST-F2 | BocNH-C(**Thz**)GPARLLPNAIGRGKWWRPSGPDFR (SEQ ID NO: 33)-thioester |
| humSOST-F3 | Amine-CIPDRYRAQRVQLLCPGGEAPRARKVRLVA SCKC(SEQ ID NO: 34)-amide |

C = cysteines involved in cystine-knot formation; *C* = cysteines forming SS-bond between loop-1 and loop-3 of humSOST Oxidate Refolding of Red-humSOST$_{57-144}$ to give Oxid-humSOST$_{57-144}$.

Figure 17:
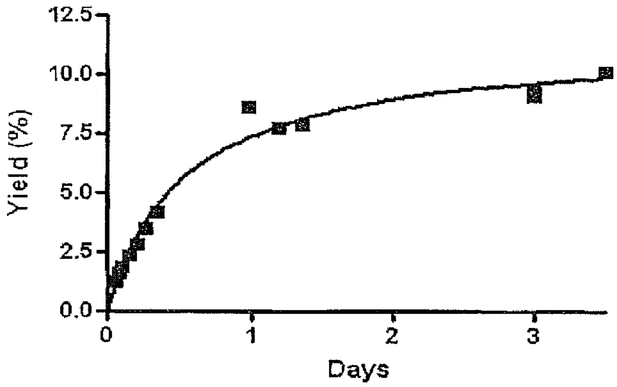
FIG. 17. Oxidative refolding of fully red-humSOST$_{57-144}$ after ion exchange chromatography. The peptide was folded in 0.4 M Arginine, 1.67 mM Glutathione (red), 0.33 mM Glutathione (ox), 55 mM Tris-HCl, 21 mM sodium chloride, 0.88 mM potassium chloride, pH 8.0, yielding 10.2% of the desired product after 3.5 days at 4° C.

Subsequently, red-humSOST$_{57-144}$ was natively refolded by dissolving the peptide (2 mg/ml) in a pH 8.0 buffer solution, containing 55 mM Tris-HCl, 21 mM sodium chloride, 0.88 mM potassium chloride, 0.48 L-arginine, 20 mM Glutathion-SH, and 4 mM Glutathion-SS. The peptide was oxidized over time and yielded 10.2% of oxid-humSOST$_{57-144}$ after 3.5 days at 4° C. (see FIG. 17).

Purification of both red-humSOST$_{57-144}$ and oxid-humSOST$_{57-144}$ was carried out by preparative High Performance Liquid Chromatography (HPLC). Characterization of both compounds was carried out by analytical HPLC and Electro-Spray Ionization Mass Spectrometry (ESI-MS; see below).

| Peptide | Oxidation state (RED/OX) | Retention (% ACN) | MW calculated | MW experi-mental |
|---|---|---|---|---|
| red-humSOST$_{57-144}$ | RED $(SH)_8$ | 35.0 | 10237.2 | 10235.0 |
| oxid-humSOST$_{57-144}$ | OX $(SS)_4$ | 30.0 | 10229.2 | 10229.8 |
| AA$_8$-humSOST$_{57-144}$ | RED $(S—AcNH_2)_8$ | 33.0 | 10694.1 | 10692.5 |

The successful refolding of humSOST$_{57-144}$ was evidenced by the characteristic shift to lower Rf-values (from 35% to 30% ACN, see Table below) that is normally observed when proteins or fragments thereof are oxidative refolded. The characteristic narrow shape of the new peak at lower Rf-value provides evidence that an intact cystine-knot structure is indeed formed upon oxidative refolding.

Figure 18:
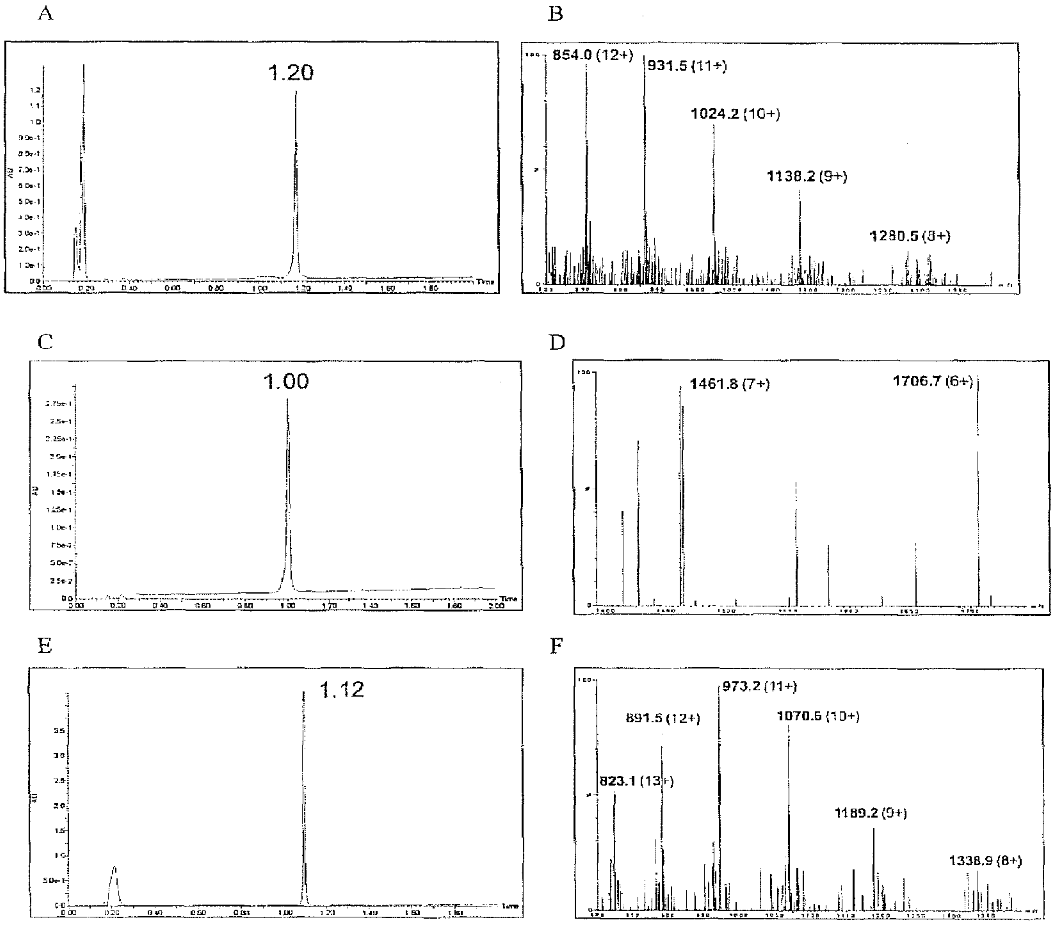
FIG. 18. HPLCs (Panels A/C/E) and ElectroSpray Ionization Mass Spectra (Panels B/D/F) of fully red-humSOST$_{57-144}$ (Panels A/B), oxidatively refolded oxid-humSOST$_{57-144}$ (Panels C/D), octa-acetamido derivatized humSOST$_{57-144}$ (Panels E/F).
Figure 19:
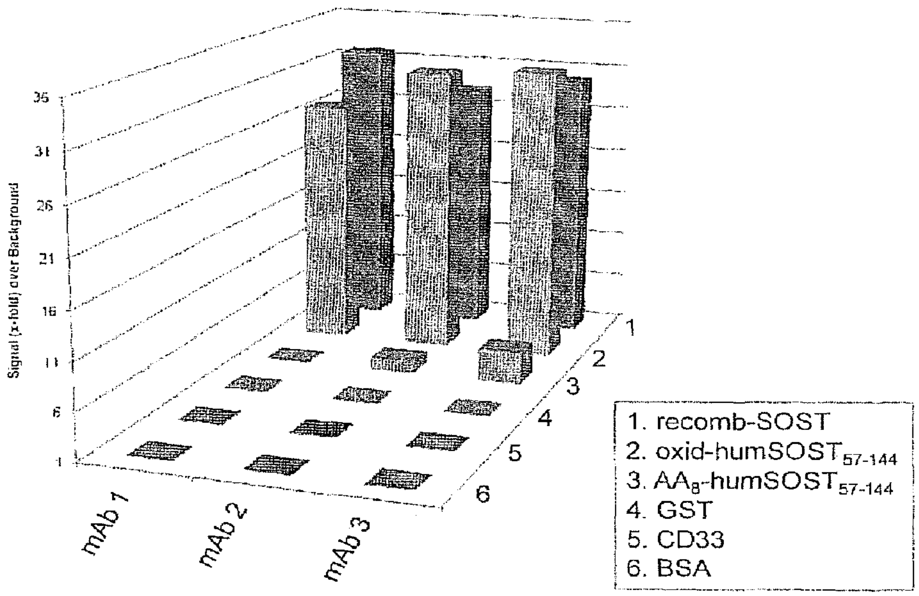
FIG. 19. Binding data in ELISA for antibodies selected biotinylated oxid-humSOST$_{57-144}$ from a PDL-library. The positive binding to 1. Recombinant humSOST, 2. biotinylated oxid-humSOST$_{57-144}$ itself, and the absence of binding to 3. AA$_8$-SOST$_{57-144}$, 4. GST, 5) CD33, and finally 6. Bovine Serum Albumin (BSA) illustrate the high-specificity of the antibody binding.

Also, the ESI-MS spectrum undergoes a significant change upon oxidative refolding. First of all, the overall mass goes down by eight mass units (formation of four disulfide bonds releases a total of 8H). Moreover, there is a very characteristic shift of MS-signals to higher m/z-values. For example, the MS-spectrum for the red-humSOST$_{57-144}$ gives clear signals for the $M^{8+}$ to $M^{12+}$ charged species, whereas these signals disappear and a much weaker signal at $M^{6+}$ and $M^{7+}$ remains (see FIG. 18D) that is much less intense. Also, this shift is characteristic for folding of proteins into their oxidized native structure and shows that refolding of red-humSOST$_{57-144}$ was successful. The reason is that the protein or protein fragment adopts a more condensed structure that is no longer able to pick up so many charges. In contrast to this, the flexible and extended structure of the reduced protein is able to accommodate many more charges.

In order to prove further that oxid-humSOST$_{57-144}$ adopts a native cystine-knot fold, we present binding data of a series of three mAbs that were selected from phage-display libraries using oxid-humSOST$_{57-144}$. It was shown that all three anti-oxid-humSOST$_{57-144}$ antibodies:

bind strongly to oxid-humSOST$_{57-144}$ in ELISA.

bind strongly to recombinant full length humSOST/sclerostin in ELISA.

do not bind at all to AA$_8$-humSOST$_{57-144}$ in ELISA.

do not bind at all to three other, non-related proteins in ELISA.

Altogether, these data show that oxid-humSOST$_{57-144}$ can be used instead of full-length humSOST/sclerostin to select antibodies from phage-display libraries (PDLs), that show full selectivity and specificity to full-length humSOST/sclerostin with respect to non-related proteins, and that oxid-humSOST$_{57-144}$ can, therefore, be used as an "easy-available" protein mimic of full-length humSOST/sclerostin for purposes of antibody generation and selection.

Example 1I

Synthesis of humTGFB2$_{15-111/\Delta 49-77}$-humVEGF$_{62-67}$ (Chimeric humTGFB2-humVEGFtrunc)

In this example, we demonstrate the synthesis of the truncated protein mimic of oxid-humTGFB2$_{15-111}$, in which the beta2-loop (28 amino acids long; X3 in general sequence) was replaced by the humVEGF beta2-loop (aa 62-67). The successful synthesis and oxidative (cystine-knot) folding of this TGFB2$_{15-111/\Delta 49-77}$-humVEGF$_{62-67}$ mainly serves as an example to demonstrate that interchange of beta2-loop sequences amongst different cystine-knot proteins in general leads to chimeric peptides that retain the ability to form an intact cystine-knot fold, just like that observed for the fully homologous trunc-peptides (see other examples).

(SEQ ID NO: 35)

Peptide sequence of humTGFB$_{15-111/\Delta 49-77}$-humVEGF$_{62-67}$: Acetyl-C1ALRPLYIDFKRDLGWKWIHEPKGYNANFC2AGAC3NDEGLEC4VSQDLEPLTILYYIGKTPKIEQLSNMIVKSC5KC6-amide.

X0 = acetyl

-continued

```
              (amino acids 2-29 of SEQ ID NO: 35)
X1 = ALRPLYIDFKRDLGWKWIHEPKGYNANF (A-mutation for

native C)

X2 = AGA

              (amino acids 35-40 of SEQ ID NO: 35)
X3 = NDEGLE (beta2-loop sequence of humVEGF-A; aa

62-67)

              (amino acids 42-71 of SEQ ID NO: 35)
X4 = VSQDLEPLTILYYIGKTPKIEQLSNMIVKS

X5 = K

X6 = amide
```

Solid-phase synthesis of red-humTGFB2$_{15-111/\Delta49-77}$-humVEGF$_{62-67}$. Red-humTGFB2$_{15-111/\Delta49-77}$-humVEGF$_{62-67}$ was synthesized by normal solid-phase synthesis on a Rink-amide resin (downloaded to 0.1 mmol/g) following standard procedures as described for humVEGF$_{26-104}$ (see Example 1). Subsequent oxidative refolding was carried out exactly as described for humVEGF$_{26-104}$. Purification of both red- and oxid-humTGFB2$_{15-111/\Delta49-77}$-humVEGF$_{62-67}$ was carried out by preparative High Performance Liquid Chromatography (HPLC). Characterization of both the red- and oxid-humTGFB2$_{15-111/\Delta49-77}$-humVEGF$_{62-67}$ was carried out by analytical HPLC and ElectroSpray Ionization Mass Spectrometry (ESI-MS).

Figure 20:
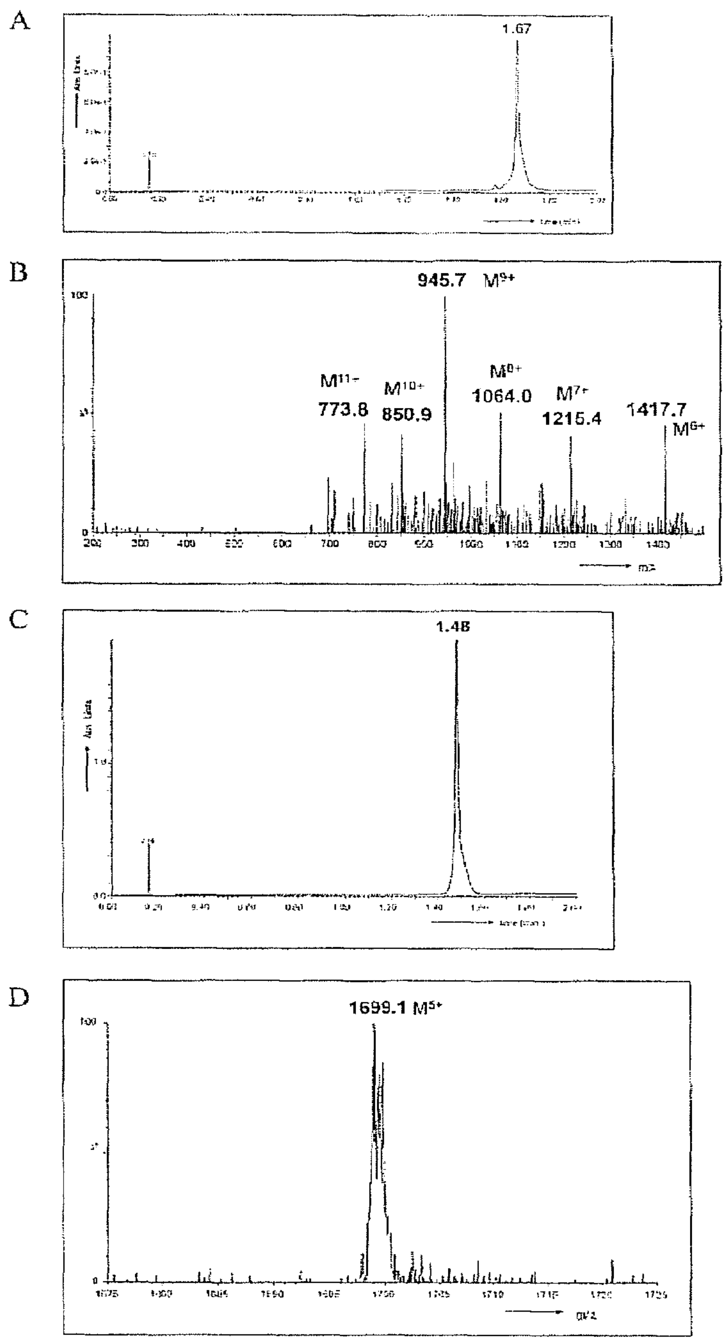
FIG. 20. HPLCs (Panels A/C) and ElectroSpray Ionization Mass Spectra (Panels B/D) of red-humTGFB2$_{15-111/\Delta 49-77}$-humVEGF$_{62-67}$ (Panels A/B) and oxid-humTGFB2$_{15-111/\Delta 49-77}$-humVEGF$_{62-67}$ (Panels C/D).

The successful refolding of red-humTGFB2$_{15-111/\Delta49-77}$-humVEGF$_{62-67}$ was evidenced by the characteristic shift to lower Rf-values upon oxidative refolding (from 46.8% to 42.0% ACN, see Table below) (see other examples). The characteristic narrow shape of the new peak at lower Rf-value provides evidence that an intact cystine-knot structure is indeed formed. Also, the ESI-MS spectrum undergoes a significant change upon oxidative refolding. First of all, the overall mass goes down by six mass units (formation of three disulfide bonds releases a total of 6H). Moreover, there is a very characteristic shift of MS-signals to higher m/z-values. For example, the MS-spectrum for the red-humTGFB2$_{15-111/\Delta49-77}$-humVEGF$_{62-67}$ gives clear signals for the $M^{6+}$ to $M^{11+}$ charged species, whereas these signals completely disappear and a much weaker signal at $M^{5+}$ remains (see FIG. 20) that is much less intense. Also this shift is characteristic for folding of proteins into their oxidized native structure and shows that refolding of humTGFB2$_{15-111/\Delta49-77}$-humVEGF$_{62-67}$ was successful. The reason is that the protein or protein fragment adopts a more condensed structure that is no longer able to pick up so many charges. In contrast to this, the flexible and extended structure of red humTGFB2$_{15-111/\Delta49-77}$-humVEGF$_{62-67}$ is able to accommodate many more charges.

| Peptide | Oxidation state (RED/OX) | Retention (%ACN) | MW calc. | MW exper. |
|---|---|---|---|---|
| red-humTGFB2$_{15-111/\Delta49-77}$-hum VEGF$_{62-67}$ | RED | 46.8 | 8498.1 | 8500.2 |
| oxid-humTGFB2$_{15-111/\Delta49-77}$-hum VEGF$_{62-67}$ | OX | 42.0 | 8492.1 | 8490.5 |

Figure 21:
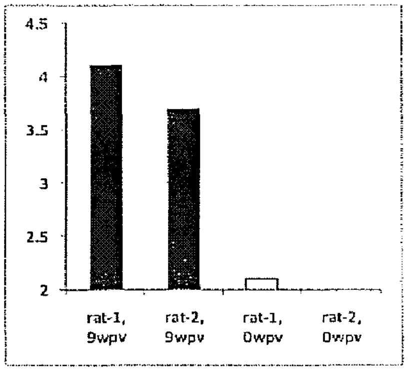
FIG. 21. (Panel A) Antibody titers in ELISA for 9wpv-rat sera (1 and 2+pre-immune sera) that were elicited via immunization with oxid-humTGFB2$_{15-111/\Delta 49-77}$-humVEGF$_{62-67}$. Titers were defined as the −10 log [conc] at which the OD in ELISA is equal to 4× the background signal. (Panel B) Antibody binding in ELISA of 9wpv-rat sera to surface-immobilized 1) humTGFB2trunc-1 (with VEGF b2-loop), 2) humTGFB2trunc-2 (with sequence PGGSPA replacing native humTGF-B2 b2-loop), and 3) humVEGFtrunc.
Figure 21:
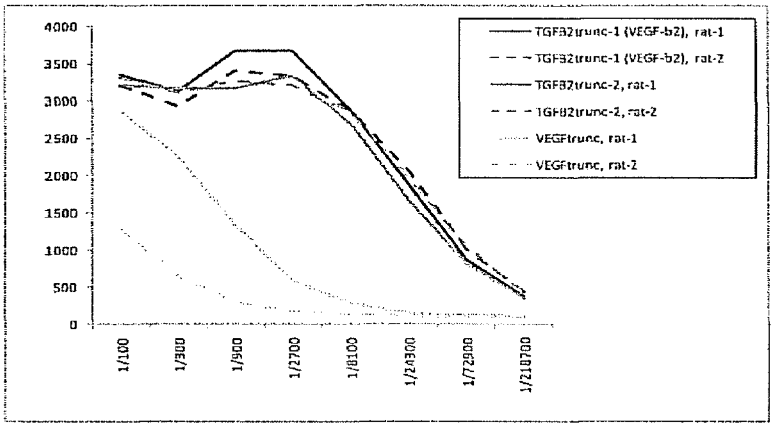

In order to prove that oxid-humTGFB2$_{15-111/\Delta49-77}$-humVEGF$_{62-67}$ can be used to generate anti-TGF-B2 antibodies via immunization, we carried out an immunization experiment in two rats. Each animal received four inoculations (0, 2, 4, and 7.5 wks) with 2×450+2×130 microgram of oxid-humTGFB2$_{15-111/\Delta49-77}$-humVEGF$_{62-67}$. Analysis of the nine weeks post vaccination (wpv) antisera (FIG. 21) showed strong binding in ELISA to full-length TGF-B2 (titers 3.8 and 4.1) compared to those of the pre-immune sera (≤2.1) indicating that antibodies specific for TGF-B2 were generated upon immunization. Moreover, it was observed that the majority of antibodies in the sera were directed towards the TGFB2-part of the peptide in oxid-humTGFB2$_{15-111/\Delta49-77}$-humVEGF$_{62-67}$ rather that to the VEGF-part (humVEGF$_{62-67}$). This indicates the humVEGF$_{62-67}$ sequence is a good substitute for the much longer b2-loop of humTGFB2 (28 amino acids), but that it does not disturb the making of humTGF-B2-specific antibodies, nor the oxidative refolding of red-humTGFB2$_{15-111/\Delta49-77}$-humVEGF$_{62-67}$ into oxid-humTGFB2$_{15-111/\Delta49-77}$-humVEGF$_{62-67}$.

These data prove that oxid-humTGFB2$_{15-111/\Delta49-77}$-humVEGF$_{62-67}$ can be used as a substitute for TGF-B2 for eliciting anti-humTGFB2 antibodies that are fully cross-reactive with the native protein humTGF-B2.

REFERENCES

1. Vitt U. A., Y. H. Sheau, and A. J. W. Hsueh, “Evolution and Classification of Cystine Knot-containing Hormones and Related Extracellular Signaling Molecules,” *Mol. Endocrin.* (2001) 15:681-94.

2. Tamaoki H., R. Miura, M. Kusunoki, Y. Kyogoku, Y. Kobayashi, and L. Moroder, “Folding motifs induced and stabilized by distinct cystine frameworks,” *Prot. Engin.* (1998) 11:649-59.

3. Isaacs N. W., “Cystine Knots,” *Curr. Opin. Struct. Biol.* (1995) 5:391-5.

4. McDonald N., and W. A. Hendrickson, “A structural superfamily of growth factors containing a cystine-knot motif,” *Cell* (1993) 73:421-4.

5. Bork P., “The modular architecture of a new family of growth regulators related to connective tissue growth factor,” *FEBS* (1993) 327:125-130.

6. Tomayko M. M., and C. P. Reynolds, “Determination of subcutaneous tumor size in athymic (nude) mice,” *Cancer Chemother. Pharmacol.* (1989) 24:148-156.

The invention claimed is:

1. A proteinmimic of a member of the cystine-knot growth factor superfamily, wherein the proteinmimic comprises a motif

X0-C1-X1-C2-X2-C3-X3-C4-X4-C5-X5-C6-X6 (SEQ ID NO:2), wherein C1 to C6 are cysteine residues that form a cystine-knot structure in which C1 is linked to C4, C2 is linked to C5, and C3 is linked to C6, wherein X0 comprises KFMDVYQRSY (amino acids 1-10 of SEQ ID NO:12), X1 comprises HPIETLVDIFQEYPDEIEYIFKPSAVPLMR (amino acids 2-31 of SEQ ID NO:27), X2 comprises GGA, X3 comprises NDEGLE (amino acids 37-42 of SEQ ID NO:27), X4 comprises VPTEESNITMQIMRIKPHQGQHIGEMSFLQHNK (amino acids 44-76 of SEQ ID NO:27), X5 comprises E, and X6 comprises RPKKDRARQE (amino acids 90-99 of SEQ ID NO:12), or wherein said protein mimic consists of a sequence having at least 95% sequence identity to SEQ ID NO:27; wherein said protein mimic comprises the consensus sequence P[PSR]CVXXXRC2[GSTA]GCC3 (SEQ ID NO:5) wherein at least one cysteine, other than C2 or C3, is replaced by another amino acid residue and wherein X means any amino acid, [PSR] means P or S or R and [GSTA] means G or S or T or A.

2. A proteinmimic member of the cystine-knot growth factor superfamily, wherein said member of the cystine-knot growth factor superfamily is placental growth factor (PLGF), and wherein said proteinmimic consists of SEQ ID NO:14.

3. A proteinmimic of a member of the cystine-knot growth factor superfamily, wherein said member is sclerostin, and wherein said proteinmimic consists of SEQ ID NO:31.

4. A pharmaceutical composition comprising the proteinmimic of claim 1 and a pharmaceutically acceptable carrier, diluent and/or excipient.

5. The pharmaceutical composition of claim 4, wherein said proteinmimic is coupled to an immunogenic carrier.

6. A method for treating a tumor-related disease wherein inhibition of angiogenesis is desired and/or treating age-related macular degeneration (AMD), the method comprising:

administering a therapeutically effective amount of the proteinmimic of claim 1 to a subject suffering from, or at risk of suffering from said disorder.

7. A method for producing antibodies against a member of the cystine-knot growth factor superfamily, comprising administering a proteinmimic according to claim 1 to a non-human animal, and obtaining antibodies against a member of the cystine-knot growth factor superfamily, which antibodies are produced by said animal.

8. A proteinmimic of a member of the cystine-knot growth factor superfamily, wherein the proteinmimic consists of SEQ ID NO:35.

9. The pharmaceutical composition of claim 5, wherein the immunogenic carrier is diphtheria toxin and/or keyhole limpet haemocyanin.

10. A proteinmimic of human Vascular Endothelial Growth Factor (hVEGF), wherein the proteinmimic comprises a motif

X0-C1-X1-C2-X2-C3-X3-C4-X4-C5-X5-C6-X6 (SEQ ID NO:2), wherein C1 to C6 are cysteine residues that form a cystine-knot structure in which C1 is linked to C4, C2 is linked to C5, and C3 is linked to C6, wherein X0 comprises KFMDVYQRSY (amino acids 1-10 of SEQ ID NO:12), X1 comprises HPIETLVDIFQEYPDEIEYIFKPSAVPLMR (amino acids 2-31 of SEQ ID NO:27), X2 comprises GGA, X3 comprises NDEGLE (amino acids 47-52 of SEQ ID NO:12), X4 comprises VPTEESNITMQIMRIKPHQGQHIGEMSFLQHNK (amino acids 54-86 of SEQ ID NO:12), X5 comprises E, and X6 comprises RPKKDRARQE (amino acids 47-52 of SEQ ID NO:12).

11. A proteinmimic of human Vascular Endothelial Growth Factor (hVEGF), wherein the proteinmimic comprises a motif

C1-X1-C2-X2-C3-X3-C4-X4-C5-X5-C6 (SEQ ID NO:2), wherein C1 to C6 are cysteine residues that form a cystine-knot structure in which C1 is linked to C4, C2 is linked to C5, and C3 is linked to C6, wherein X1 comprises HPIETLVDIFQEYPDEIEYIFKPSAVPLMR (amino acids 2-31 of SEQ ID NO:27), X2 comprises GGA, X3 comprises NDEGLE (amino acids 37-42 of SEQ ID NO:27), X4 comprises VPTEESNITMQIMRIKPHQGQHIGEMSFLQHNK (amino acids 44-76 of SEQ ID NO:27), and X5 comprises E.

12. The proteinmimic of claim 11, consisting of SEQ ID NO:27.

* * * * *

SEQUENCE LISTING

<160> NUMBER OF SEQ ID NOS: 180

<210> SEQ ID NO 1
<211> LENGTH: 42
<212> TYPE: PRT
<213> ORGANISM: Artificial
<220> FEATURE:
<223> OTHER INFORMATION: cystine knot consensus sequence short
<220> FEATURE:
<221> NAME/KEY: misc_feature
<222> LOCATION: (2)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid
<220> FEATURE:
<221> NAME/KEY: misc_feature
<222> LOCATION: (25)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: DISULFID
<222> LOCATION: (1)..(24)
<220> FEATURE:
<221> NAME/KEY: DISULFID
<222> LOCATION: (17)..(40)
<220> FEATURE:
<221> NAME/KEY: DISULFID
<222> LOCATION: (20)..(42)

<400> SEQUENCE: 1

```
Cys Xaa Xaa Xaa Xaa Xaa Xaa Xaa Xaa Xaa Xaa Xaa Xaa Xaa Xaa Xaa
1               5                   10                  15

Cys Xaa Xaa Cys Xaa Xaa Xaa Cys Xaa Xaa Xaa Xaa Xaa Xaa Xaa Xaa
            20                  25                  30

Xaa Xaa Xaa Xaa Xaa Xaa Xaa Cys Xaa Cys
        35                  40
```

<210> SEQ ID NO 2
<211> LENGTH: 187
<212> TYPE: PRT
<213> ORGANISM: Artificial
<220> FEATURE:
<223> OTHER INFORMATION: cystine-knot protein consensus long
<220> FEATURE:
<221> NAME/KEY: misc_feature
<222> LOCATION: (1)..(10)
<223> OTHER INFORMATION: Xaa can be any naturally occurring amino acid
<220> FEATURE:
<221> NAME/KEY: misc_feature
<222> LOCATION: (12)..(61)
<223> OTHER INFORMATION: Xaa can be any naturally occurring amino acid
<220> FEATURE:
<221> NAME/KEY: misc_feature
<222> LOCATION: (63)..(86)
<223> OTHER INFORMATION: Xaa can be any naturally occurring amino acid
<220> FEATURE:
<221> NAME/KEY: misc_feature
<222> LOCATION: (88)..(123)
<223> OTHER INFORMATION: Xaa can be any naturally occurring amino acid
<220> FEATURE:
<221> NAME/KEY: misc_feature
<222> LOCATION: (125)..(174)
<223> OTHER INFORMATION: Xaa can be any naturally occurring amino acid
<220> FEATURE:
<221> NAME/KEY: misc_feature -continued
<222> LOCATION: (176)..(176)
<223> OTHER INFORMATION: Xaa can be any naturally occurring amino acid
<220> FEATURE:
<221> NAME/KEY: DISULFID
<222> LOCATION: (11)..(124)
<220> FEATURE:
<221> NAME/KEY: DISULFID
<222> LOCATION: (62)..(175)
<220> FEATURE:
<221> NAME/KEY: DISULFID
<222> LOCATION: (87)..(177)
<220> FEATURE:
<221> NAME/KEY: misc_feature
<222> LOCATION: (178)..(187)
<223> OTHER INFORMATION: Xaa can be any naturally occurring amino acid

<400> SEQUENCE: 2

```
Xaa Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Cys Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Cys Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Cys Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Cys Xaa
                165                 170                 175

Cys Xaa Xaa Xaa Xaa Xaa Xaa Xaa Xaa Xaa Xaa
            180                 185
```

<210> SEQ ID NO 3
<211> LENGTH: 74
<212> TYPE: PRT
<213> ORGANISM: Artificial
<220> FEATURE:
<223> OTHER INFORMATION: proteinmimic TGFB2

<400> SEQUENCE: 3

```
Cys Ala Leu Arg Pro Leu Tyr Ile Asp Phe Lys Arg Asp Leu Gly Trp
1               5                   10                  15

Lys Trp Ile His Glu Pro Lys Gly Tyr Asn Ala Asn Phe Cys Ala Gly
            20                  25                  30

Ala Cys Asn Asp Glu Gly Leu Glu Cys Val Ser Gln Asp Leu Glu Pro
        35                  40                  45

Leu Thr Ile Leu Tyr Tyr Ile Gly Lys Thr Pro Lys Ile Glu Gln Leu
    50                  55                  60

Ser Asn Met Ile Val Lys Ser Cys Lys Cys
65                  70
```

<210> SEQ ID NO 4
<211> LENGTH: 14
<212> TYPE: PRT
<213> ORGANISM: Artificial
<220> FEATURE:
<223> OTHER INFORMATION: partial consensus
<220> FEATURE:
<221> NAME/KEY: VARIANT
<222> LOCATION: (1)..(1)
<223> OTHER INFORMATION: S, R or E
<220> FEATURE:
<221> NAME/KEY: VARIANT
<222> LOCATION: (3)..(3)
<223> OTHER INFORMATION: R or L
<220> FEATURE:
<221> NAME/KEY: VARIANT
<222> LOCATION: (5)..(5)
<223> OTHER INFORMATION: I, V or T
<220> FEATURE:
<221> NAME/KEY: VARIANT
<222> LOCATION: (6)..(6)
<223> OTHER INFORMATION: E
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: W
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 4

```
Gly Cys Lys Gly Leu Asp Xaa Xaa Xaa Tyr Xaa Ser Xaa Cys
1               5                   10
```

<210> SEQ ID NO 5
<211> LENGTH: 13
<212> TYPE: PRT
<213> ORGANISM: Artificial
<220> FEATURE:
<223> OTHER INFORMATION: partial consensus
<220> FEATURE:
<221> NAME/KEY: VARIANT
<222> LOCATION: (2)..(2)
<223> OTHER INFORMATION: S or R
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: S, T or A

<400> SEQUENCE: 5

```
Pro Pro Cys Val Xaa Xaa Xaa Arg Cys Gly Gly Cys Cys
1               5                   10
```

<210> SEQ ID NO 6
<211> LENGTH: 16
<212> TYPE: PRT
<213> ORGANISM: Artificial
<220> FEATURE:
<223> OTHER INFORMATION: partial consensus
<220> FEATURE:
<221> NAME/KEY: VARIANT -continued
<222> LOCATION: (1)..(1)
<223> OTHER INFORMATION: I, V or M
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: VARIANT
<222> LOCATION: (7)..(7)
<223> OTHER INFORMATION: Y
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 6

```
Leu Xaa Xaa Pro Xaa Xaa Phe Xaa Xaa Xaa Xaa Cys Xaa Gly Xaa Cys
1               5                   10                  15
```

<210> SEQ ID NO 7
<211> LENGTH: 7
<212> TYPE: PRT
<213> ORGANISM: Artificial
<220> FEATURE:
<223> OTHER INFORMATION: partial consensus
<220> FEATURE:
<221> NAME/KEY: VARIANT
<222> LOCATION: (2)..(2)
<223> OTHER INFORMATION: T, A, G or M
<220> FEATURE:
<221> NAME/KEY: VARIANT
<222> LOCATION: (4)..(4)
<223> OTHER INFORMATION: F, Y or L
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: VARIANT
<222> LOCATION: (7)..(7)
<223> OTHER INFORMATION: T

<400> SEQUENCE: 7

```
Cys Ser Gly His Cys Xaa Ser
1               5
```

<210> SEQ ID NO 8
<211> LENGTH: 18
<212> TYPE: PRT
<213> ORGANISM: Artificial
<220> FEATURE:
<223> OTHER INFORMATION: partial consensus
<220> FEATURE:
<221> NAME/KEY: VARIANT
<222> LOCATION: (1)..(1)
<223> OTHER INFORMATION: A
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)

-continued

<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: VARIANT
<222> LOCATION: (16)..(16)
<223> OTHER INFORMATION: T, D, A or I
<220> FEATURE:
<221> NAME/KEY: VARIANT
<222> LOCATION: (17)..(17)
<223> OTHER INFORMATION: E or Y

<400> SEQUENCE: 8

Pro Val Ala Xaa Xaa Cys Xaa Cys Xaa Xaa Cys Xaa Xaa Xaa Xaa Ser
1 5 10 15

Asp Cys

<210> SEQ ID NO 9
<211> LENGTH: 13
<212> TYPE: PRT
<213> ORGANISM: Artificial
<220> FEATURE:
<223> OTHER INFORMATION: partial consensus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (6)..(6)
<223> OTHER INFORMATION: Y
<220> FEATURE:
<221> NAME/KEY: VARIANT
<222> LOCATION: (8)..(8)
<223> OTHER INFORMATION: Q or S
<220> FEATURE:
<221> NAME/KEY: VARIANT
<222> LOCATION: (10)..(10)
<223> OTHER INFORMATION: Y

<400> SEQUENCE: 9

Cys Xaa Gly Cys Cys Phe Ser Arg Ala Phe Pro Thr Pro
1 5 10

<210> SEQ ID NO 10
<211> LENGTH: 37
<212> TYPE: PRT
<213> ORGANISM: Artificial
<220> FEATURE:
<223> OTHER INFORMATION: partial consensus short version
<220> FEATURE:
<221> NAME/KEY: misc_feature
<222> LOCATION: (3)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: VARIANT
<222> LOCATION: (19)..(19)
<223> OTHER INFORMATION: N
<220> FEATURE:
<221> NAME/KEY: misc_feature
<222> LOCATION: (20)..(31)
<223> OTHER INFORMATION: Xaa can be any naturally occurring amino acid
<220> FEATURE:
<221> NAME/KEY: misc_feature -continued
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid

<400> SEQUENCE: 10

Cys Cys Xaa Xaa Xaa Xaa Xaa Xaa Xaa Xaa Xaa Xaa Xaa Xaa Xaa Cys
1               5                   10                  15

Xaa Xaa Gly Xaa Xaa Xaa Xaa Xaa Xaa Xaa Xaa Xaa Xaa Xaa Xaa Cys
            20                  25                  30

Xaa Cys Xaa Xaa Cys
        35

<210> SEQ ID NO 11
<211> LENGTH: 39
<212> TYPE: PRT
<213> ORGANISM: Artificial
<220> FEATURE:
<223> OTHER INFORMATION: partial consensus long version
<220> FEATURE:
<221> NAME/KEY: misc_feature
<222> LOCATION: (3)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: VARIANT
<222> LOCATION: (19)..(19)
<223> OTHER INFORMATION: N
<220> FEATURE:
<221> NAME/KEY: misc_feature
<222> LOCATION: (20)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(38)
<223> OTHER INFORMATION: Xaa can be any naturally occurring amino acid

<400> SEQUENCE: 11

Cys Cys Xaa Xaa Xaa Xaa Xaa Xaa Xaa Xaa Xaa Xaa Xaa Xaa Xaa Cys
1               5                   10                  15

Xaa Xaa Gly Xaa Xaa Xaa Xaa Xaa Xaa Xaa Xaa Xaa Xaa Xaa Xaa Cys
            20                  25                  30

Xaa Cys Xaa Xaa Xaa Xaa Cys
        35

<210> SEQ ID NO 12
<211> LENGTH: 99
<212> TYPE: PRT
<213> ORGANISM: Artificial
<220> FEATURE:
<223> OTHER INFORMATION: proteinmimic hVEGF

<400> SEQUENCE: 12

Lys Phe Met Asp Val Tyr Gln Arg Ser Tyr Cys His Pro Ile Glu Thr
1               5                   10                  15

Leu Val Asp Ile Phe Gln Glu Tyr Asp Pro Glu Ile Glu Tyr Ile Phe
            20                  25                  30

Lys Pro Ser Ala Val Pro Leu Met Arg Cys Gly Gly Ala Cys Asn Asp
        35                  40                  45

```
Glu Gly Leu Glu Cys Val Pro Thr Glu Glu Ser Asn Ile Thr Met Gln
    50                  55                  60

Ile Met Arg Ile Lys Pro His Gln Gly Gln His Ile Gly Glu Met Ser
65                  70                  75                  80

Phe Leu Gln His Asn Lys Cys Glu Cys Arg Pro Lys Lys Asp Arg Ala
                85                  90                  95

Arg Gln Glu


<210> SEQ ID NO 13
<211> LENGTH: 99
<212> TYPE: PRT
<213> ORGANISM: Artificial
<220> FEATURE:
<223> OTHER INFORMATION: proteinmimic hPLGF

<400> SEQUENCE: 13

Pro Phe Gln Glu Val Trp Gly Arg Ser Tyr Cys Arg Ala Leu Glu Arg
1               5                   10                  15

Leu Val Asp Val Val Ser Glu Tyr Pro Ser Glu Val Glu His Met Phe
            20                  25                  30

Ser Pro Ser Ala Val Ser Leu Leu Arg Cys Thr Gly Ala Cys Gly Asp
        35                  40                  45

Glu Asn Leu His Cys Val Pro Val Glu Thr Ala Asn Val Thr Met Gln
    50                  55                  60

Leu Leu Lys Ile Arg Ser Gly Asp Arg Pro Ser Tyr Val Glu Leu Thr
65                  70                  75                  80

Phe Ser Gln His Val Arg Cys Glu Cys Arg His Ser Pro Gly Arg Gln
                85                  90                  95

Ser Pro Asp


<210> SEQ ID NO 14
<211> LENGTH: 79
<212> TYPE: PRT
<213> ORGANISM: Artificial
<220> FEATURE:
<223> OTHER INFORMATION: proteinmimic hPLGF
<220> FEATURE:
<221> NAME/KEY: MOD_RES
<222> LOCATION: (1)..(1)
<223> OTHER INFORMATION: ACETYLATION

<400> SEQUENCE: 14

Cys Arg Ala Leu Glu Arg Leu Val Asp Val Val Ser Glu Tyr Pro Ser
1               5                   10                  15

Glu Val Glu His Met Phe Ser Pro Ser Ala Val Ser Leu Leu Arg Cys
            20                  25                  30

Thr Gly Ala Cys Gly Asp Glu Asn Leu His Cys Val Pro Val Glu Thr
        35                  40                  45

Ala Asn Val Thr Met Gln Leu Leu Lys Ile Arg Ser Gly Asp Arg Pro
    50                  55                  60

Ser Tyr Val Glu Leu Thr Phe Ser Gln His Val Arg Cys Glu Cys
65                  70                  75


<210> SEQ ID NO 15
<211> LENGTH: 103
<212> TYPE: PRT
<213> ORGANISM: Artificial
<220> FEATURE:
<223> OTHER INFORMATION: proteinmimic hPDGF-A
```

<400> SEQUENCE: 15

```
Ser Ile Glu Glu Ala Val Pro Ala Val Cys Lys Thr Arg Thr Val Ile
1               5                   10                  15

Tyr Glu Ile Pro Arg Ser Gln Val Asp Pro Thr Ser Ala Asn Phe Leu
            20                  25                  30

Ile Trp Pro Pro Cys Val Glu Val Lys Arg Cys Thr Gly Cys Cys Asn
        35                  40                  45

Thr Ser Ser Val Lys Cys Gln Pro Ser Arg Val His His Arg Ser Val
    50                  55                  60

Lys Val Ala Lys Val Glu Tyr Val Arg Lys Lys Pro Lys Leu Lys Glu
65                  70                  75                  80

Val Gln Val Arg Leu Glu Glu His Leu Glu Cys Ala Cys Ala Thr Ser
                85                  90                  95

Leu Asn Pro Asp Tyr Arg Glu
            100
```

<210> SEQ ID NO 16
<211> LENGTH: 106
<212> TYPE: PRT
<213> ORGANISM: Artificial
<220> FEATURE:
<223> OTHER INFORMATION: proteinmimic hPDGF-C

<400> SEQUENCE: 16

```
Leu Leu Thr Glu Glu Val Arg Leu Tyr Ser Cys Thr Pro Arg Asn Phe
1               5                   10                  15

Ser Val Ser Ile Arg Glu Glu Leu Lys Arg Thr Asp Thr Ile Phe Trp
            20                  25                  30

Pro Gly Cys Leu Leu Val Lys Arg Cys Gly Gly Asn Cys Ala Cys Cys
        35                  40                  45

Leu His Asn Cys Asn Glu Cys Gln Cys Val Pro Ser Lys Val Thr Lys
    50                  55                  60

Lys Tyr His Glu Val Leu Gln Leu Arg Pro Lys Thr Gly Val Arg Gly
65                  70                  75                  80

Leu His Lys Ser Leu Thr Asp Val Ala Leu Glu His His Glu Glu Cys
                85                  90                  95

Asp Cys Val Cys Arg Gly Ser Thr Gly Gly
            100                 105
```

<210> SEQ ID NO 17
<211> LENGTH: 98
<212> TYPE: PRT
<213> ORGANISM: Artificial
<220> FEATURE:
<223> OTHER INFORMATION: proteinmimic hVEGF-C

<400> SEQUENCE: 17

```
Ser Ile Asp Asn Glu Trp Arg Lys Thr Gln Cys Met Pro Arg Glu Val
1               5                   10                  15

Ala Ile Asp Val Gly Lys Glu Phe Gly Val Ala Thr Asn Thr Phe Phe
            20                  25                  30

Lys Pro Pro Cys Val Ser Val Tyr Arg Cys Gly Gly Cys Cys Pro Asp
        35                  40                  45

Asp Gly Leu Glu Cys Val Pro Thr Gly Gln His Gln Val Arg Met Gln
    50                  55                  60

Ile Leu Met Ile Arg Tyr Pro Ser Ser Gln Leu Gly Glu Met Ser Leu
65                  70                  75                  80
```

-continued

```
Glu Glu His Ser Gln Cys Glu Cys Arg Pro Lys Lys Lys Asp Ser Ala
                85                  90                  95

Val Lys


<210> SEQ ID NO 18
<211> LENGTH: 94
<212> TYPE: PRT
<213> ORGANISM: Artificial
<220> FEATURE:
<223> OTHER INFORMATION: proteinmimic hFSH

<400> SEQUENCE: 18

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Lys Cys Asp Ser Asp Ser Thr Asp Cys Thr
                85                  90


<210> SEQ ID NO 19
<211> LENGTH: 100
<212> TYPE: PRT
<213> ORGANISM: Artificial
<220> FEATURE:
<223> OTHER INFORMATION: proteinmimic hCG

<400> SEQUENCE: 19

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys
            100


<210> SEQ ID NO 20
<211> LENGTH: 116
<212> TYPE: PRT
<213> ORGANISM: Artificial
<220> FEATURE:
<223> OTHER INFORMATION: proteinmimic hNGF

<400> SEQUENCE: 20

Pro Ile Phe His Arg Gly Glu Phe Ser Val Cys Asp Ser Val Ser Val
1               5                   10                  15

Trp Val Gly Asp Lys Thr Thr Ala Thr Asp Ile Lys Gly Lys Glu Val
            20                  25                  30
```

```
Met Val Leu Gly Glu Val Asn Ile Asn Asn Ser Val Phe Lys Gln Tyr
        35                  40                  45

Phe Phe Glu Thr Lys Cys Arg Asp Pro Asn Pro Val Asp Ser Gly Cys
    50                  55                  60

Arg Gly Ile Asp Ser Lys His Trp Asn Ser Tyr Cys Thr Thr Thr His
65                  70                  75                  80

Thr Phe Val Lys Ala Leu Thr Met Asp Gly Lys Gln Ala Ala Trp Arg
                85                  90                  95

Phe Ile Arg Ile Asp Thr Ala Cys Val Cys Val Leu Ser Arg Lys Ala
            100                 105                 110

Val Arg Arg Ala
        115


<210> SEQ ID NO 21
<211> LENGTH: 108
<212> TYPE: PRT
<213> ORGANISM: Artificial
<220> FEATURE:
<223> OTHER INFORMATION: proteinmimic hTGF beta 2

<400> SEQUENCE: 21

Ala Tyr Cys Phe Arg Asn Val Gln Asp Asn Cys Cys Leu Arg Pro Leu
1               5                   10                  15

Tyr Ile Asp Phe Lys Arg Asp Leu Gly Trp Lys Trp Ile His Glu Pro
            20                  25                  30

Lys Gly Tyr Asn Ala Asn Phe Cys Ala Gly Ala Cys Pro Tyr Leu Trp
        35                  40                  45

Ser Ser Asp Thr Gln His Ser Arg Val Leu Ser Leu Tyr Asn Thr Ile
    50                  55                  60

Asn Pro Glu Ala Ser Ala Ser Pro Cys Cys Val Ser Gln Asp Leu Glu
65                  70                  75                  80

Pro Leu Thr Ile Leu Tyr Tyr Ile Gly Lys Thr Pro Lys Ile Glu Gln
                85                  90                  95

Leu Ser Asn Met Ile Val Lys Ser Cys Lys Cys Ser
            100                 105


<210> SEQ ID NO 22
<211> LENGTH: 108
<212> TYPE: PRT
<213> ORGANISM: Artificial
<220> FEATURE:
<223> OTHER INFORMATION: proteinmimic sclerostin

<400> SEQUENCE: 22

Phe Glu Thr Lys Asp Val Ser Glu Tyr Ser Cys Arg Glu Leu His Phe
1               5                   10                  15

Thr Arg Tyr Val Thr Asp Gly Pro Cys Arg Ser Ala Lys Pro Val Thr
            20                  25                  30

Glu Leu Val Cys Ser Gly Gln Cys Gly Pro Ala Arg Leu Leu Pro Asn
        35                  40                  45

Ala Ile Gly Arg Gly Lys Trp Trp Arg Pro Ser Gly Pro Asp Phe Arg
    50                  55                  60

Cys Ile Pro Asp Arg Tyr Arg Ala Gln Arg Val Gln Leu Leu Cys Pro
65                  70                  75                  80

Gly Gly Glu Ala Pro Arg Ala Arg Lys Val Arg Leu Val Ala Ser Cys
                85                  90                  95

Lys Cys Lys Arg Leu Thr Arg Phe His Asn Gln Ser
```

100 105

<210> SEQ ID NO 23
<211> LENGTH: 91
<212> TYPE: PRT
<213> ORGANISM: Artificial
<220> FEATURE:
<223> OTHER INFORMATION: proteinmimic sclerostin

<400> SEQUENCE: 23

Gly Gly Gly Cys Arg Glu Leu His Phe Thr Arg Tyr Val Thr Asp Gly
1 5 10 15

Pro Cys Arg Ser Ala Lys Pro Val Thr Glu Leu Val Cys Ser Gly Gln
20 25 30

Cys Gly Pro Ala Arg Leu Leu Pro Asn Ala Ile Gly Arg Gly Lys Trp
35 40 45

Trp Arg Pro Ser Gly Pro Asp Phe Arg Cys Ile Pro Asp Arg Tyr Arg
50 55 60

Ala Gln Arg Val Gln Leu Leu Cys Pro Gly Gly Glu Ala Pro Arg Ala
65 70 75 80

Arg Lys Val Arg Leu Val Ala Ser Cys Lys Cys
85 90

<210> SEQ ID NO 24
<211> LENGTH: 74
<212> TYPE: PRT
<213> ORGANISM: Artificial
<220> FEATURE:
<223> OTHER INFORMATION: humTGFB2 trunc1

<400> SEQUENCE: 24

Cys Ala Leu Arg Pro Leu Tyr Ile Asp Phe Lys Arg Asp Leu Gly Trp
1 5 10 15

Lys Trp Ile His Glu Pro Lys Gly Tyr Asn Ala Asn Phe Cys Ala Gly
20 25 30

Ala Cys Asn Asp Glu Gly Leu Glu Cys Val Ser Gln Asp Leu Glu Pro
35 40 45

Leu Thr Ile Leu Tyr Tyr Ile Gly Lys Thr Pro Lys Ile Glu Gln Leu
50 55 60

Ser Asn Met Ile Val Lys Ser Cys Lys Cys
65 70

<210> SEQ ID NO 25
<211> LENGTH: 74
<212> TYPE: PRT
<213> ORGANISM: Artificial
<220> FEATURE:
<223> OTHER INFORMATION: humTGFB2 trunc 2

<400> SEQUENCE: 25

Cys Ala Leu Arg Pro Leu Tyr Ile Asp Phe Lys Arg Asp Leu Gly Trp
1 5 10 15

Lys Trp Ile His Glu Pro Lys Gly Tyr Asn Ala Asn Phe Cys Ala Gly
20 25 30

Ala Cys Pro Gly Gly Ser Pro Ala Cys Val Ser Gln Asp Leu Glu Pro
35 40 45

Leu Thr Ile Leu Tyr Tyr Ile Gly Lys Thr Pro Lys Ile Glu Gln Leu
50 55 60

Ser Asn Met Ile Val Lys Ser Cys Lys Cys
65 70

<210> SEQ ID NO 26
<211> LENGTH: 79
<212> TYPE: PRT
<213> ORGANISM: Artificial
<220> FEATURE:
<223> OTHER INFORMATION: VEGFtrunc

<400> SEQUENCE: 26

```
Cys His Pro Ile Glu Thr Leu Val Asp Ile Phe Gln Glu Tyr Pro Asp
1               5                   10                  15

Glu Ile Glu Tyr Ile Phe Lys Pro Ser Ala Val Pro Leu Met Arg Cys
            20                  25                  30

Gly Gly Ala Cys Asn Asp Glu Gly Leu Glu Cys Val Pro Thr Glu Glu
        35                  40                  45

Ser Asn Ile Thr Met Gln Ile Met Arg Ile Lys Pro His Gln Gly Gln
    50                  55                  60

His Ile Gly Glu Met Ser Phe Leu Gln His Asn Lys Cys Glu Cys
65                  70                  75
```

<210> SEQ ID NO 27
<211> LENGTH: 79
<212> TYPE: PRT
<213> ORGANISM: Artificial
<220> FEATURE:
<223> OTHER INFORMATION: VEGF26-104
<220> FEATURE:
<221> NAME/KEY: MOD_RES
<222> LOCATION: (1)..(1)
<223> OTHER INFORMATION: ACETYLATION

<400> SEQUENCE: 27

```
Cys His Pro Ile Glu Thr Leu Val Asp Ile Phe Gln Glu Tyr Pro Asp
1               5                   10                  15

Glu Ile Glu Tyr Ile Phe Lys Pro Ser Ala Val Pro Leu Met Arg Cys
            20                  25                  30

Gly Gly Ala Cys Asn Asp Glu Gly Leu Glu Cys Val Pro Thr Glu Glu
        35                  40                  45

Ser Asn Ile Thr Met Gln Ile Met Arg Ile Lys Pro His Gln Gly Gln
    50                  55                  60

His Ile Gly Glu Met Ser Phe Leu Gln His Asn Lys Cys Glu Cys
65                  70                  75
```

<210> SEQ ID NO 28
<211> LENGTH: 83
<212> TYPE: PRT
<213> ORGANISM: Artificial
<220> FEATURE:
<223> OTHER INFORMATION: VEGF25-107
<220> FEATURE:
<221> NAME/KEY: MOD_RES
<222> LOCATION: (1)..(1)
<223> OTHER INFORMATION: ACETYLATION

<400> SEQUENCE: 28

```
Tyr Cys His Pro Ile Glu Thr Leu Val Asp Ile Phe Gln Glu Tyr Pro
1               5                   10                  15

Asp Glu Ile Glu Tyr Ile Phe Lys Pro Ser Ala Val Pro Leu Met Arg
            20                  25                  30

Cys Gly Gly Ala Cys Asn Asp Glu Gly Leu Glu Cys Val Pro Thr Glu
        35                  40                  45

Glu Ser Asn Ile Thr Met Gln Ile Met Arg Ile Lys Pro His Gln Gly
```

50 55 60

Gln His Ile Gly Glu Met Ser Phe Leu Gln His Asn Lys Cys Glu Cys
65 70 75 80

Arg Pro Lys

<210> SEQ ID NO 29
<211> LENGTH: 85
<212> TYPE: PRT
<213> ORGANISM: Artificial
<220> FEATURE:
<223> OTHER INFORMATION: VEGF25-109
<220> FEATURE:
<221> NAME/KEY: MOD_RES
<222> LOCATION: (1)..(1)
<223> OTHER INFORMATION: ACETYLATION

<400> SEQUENCE: 29

Tyr Cys His Pro Ile Glu Thr Leu Val Asp Ile Phe Gln Glu Tyr Pro
1 5 10 15

Asp Glu Ile Glu Tyr Ile Phe Lys Pro Ser Ala Val Pro Leu Met Arg
20 25 30

Cys Gly Gly Ser Cys Asn Asp Glu Gly Leu Glu Cys Val Pro Thr Glu
35 40 45

Glu Ser Asn Ile Thr Met Gln Ile Met Arg Ile Lys Pro His Gln Gly
50 55 60

Gln His Ile Gly Glu Met Ser Phe Leu Gln His Asn Lys Cys Glu Cys
65 70 75 80

Arg Pro Lys Lys Asp
85

<210> SEQ ID NO 30
<211> LENGTH: 79
<212> TYPE: PRT
<213> ORGANISM: Artificial
<220> FEATURE:
<223> OTHER INFORMATION: ratVEGF26-104
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (79)..(79)
<223> OTHER INFORMATION: AMIDATION

<400> SEQUENCE: 30

Cys Arg Pro Ile Glu Thr Leu Val Asp Ile Phe Gln Glu Tyr Pro Asp
1 5 10 15

Glu Ile Glu Tyr Ile Phe Lys Pro Ser Ala Val Pro Leu Met Arg Cys
20 25 30

Ala Gly Ala Cys Asn Asp Glu Ala Leu Glu Cys Val Pro Thr Ser Glu
35 40 45

Ser Asn Val Thr Met Gln Ile Met Arg Ile Lys Pro His Gln Ser Gln
50 55 60

His Ile Gly Glu Met Ser Phe Leu Gln His Ser Arg Cys Glu Cys
65 70 75

<210> SEQ ID NO 31
<211> LENGTH: 91
<212> TYPE: PRT
<213> ORGANISM: Artificial
<220> FEATURE:
<223> OTHER INFORMATION: humSOST57-144

<220> FEATURE:
<221> NAME/KEY: MISC_FEATURE
<222> LOCATION: (1)..(1)
<223> OTHER INFORMATION: bound to biotine
<220> FEATURE:
<221> NAME/KEY: MOD_RES
<222> LOCATION: (91)..(91)
<223> OTHER INFORMATION: AMIDATION

<400> SEQUENCE: 31

```
Gly Gly Gly Cys Arg Glu Leu His Phe Thr Arg Tyr Val Thr Asp Gly
1               5                   10                  15

Pro Cys Arg Ser Ala Lys Pro Val Thr Glu Leu Val Cys Ser Gly Gln
            20                  25                  30

Cys Gly Pro Ala Arg Leu Leu Pro Asn Ala Ile Gly Arg Gly Lys Trp
        35                  40                  45

Trp Arg Pro Ser Gly Pro Asp Phe Arg Cys Ile Pro Asp Arg Tyr Arg
    50                  55                  60

Ala Gln Arg Val Gln Leu Leu Cys Pro Gly Gly Glu Ala Pro Arg Ala
65                  70                  75                  80

Arg Lys Val Arg Leu Val Ala Ser Cys Lys Cys
                85                  90
```

<210> SEQ ID NO 32
<211> LENGTH: 32
<212> TYPE: PRT
<213> ORGANISM: Artificial
<220> FEATURE:
<223> OTHER INFORMATION: humSOST-F1
<220> FEATURE:
<221> NAME/KEY: MISC_FEATURE
<222> LOCATION: (1)..(1)
<223> OTHER INFORMATION: bound to biotine
<220> FEATURE:
<221> NAME/KEY: MISC_FEATURE
<222> LOCATION: (32)..(32)
<223> OTHER INFORMATION: thioester

<400> SEQUENCE: 32

```
Gly Gly Gly Cys Arg Glu Leu His Phe Thr Arg Tyr Val Thr Asp Gly
1               5                   10                  15

Pro Cys Arg Ser Ala Lys Pro Val Thr Glu Leu Val Cys Ser Gly Gln
            20                  25                  30
```

<210> SEQ ID NO 33
<211> LENGTH: 25
<212> TYPE: PRT
<213> ORGANISM: Artificial
<220> FEATURE:
<223> OTHER INFORMATION: humSOST-F2
<220> FEATURE:
<221> NAME/KEY: MOD_RES
<222> LOCATION: (1)..(1)
<223> OTHER INFORMATION: BLOCKED
<220> FEATURE:
<221> NAME/KEY: MISC_FEATURE
<222> LOCATION: (1)..(1)
<223> OTHER INFORMATION: contains thiazole residue
<220> FEATURE:
<221> NAME/KEY: MISC_FEATURE
<222> LOCATION: (25)..(25)
<223> OTHER INFORMATION: thioester

<400> SEQUENCE: 33

```
Cys Gly Pro Ala Arg Leu Leu Pro Asn Ala Ile Gly Arg Gly Lys Trp
1               5                   10                  15

Trp Arg Pro Ser Gly Pro Asp Phe Arg
```

20 25

<210> SEQ ID NO 34
<211> LENGTH: 34
<212> TYPE: PRT
<213> ORGANISM: Artificial
<220> FEATURE:
<223> OTHER INFORMATION: humSOST-F3
<220> FEATURE:
<221> NAME/KEY: MOD_RES
<222> LOCATION: (34)..(34)
<223> OTHER INFORMATION: AMIDATION

<400> SEQUENCE: 34

Cys Ile Pro Asp Arg Tyr Arg Ala Gln Arg Val Gln Leu Leu Cys Pro
1 5 10 15

Gly Gly Glu Ala Pro Arg Ala Arg Lys Val Arg Leu Val Ala Ser Cys
20 25 30

Lys Cys

<210> SEQ ID NO 35
<211> LENGTH: 74
<212> TYPE: PRT
<213> ORGANISM: Artificial
<220> FEATURE:
<223> OTHER INFORMATION: humTGFB2-humVEGF
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (74)..(74)
<223> OTHER INFORMATION: AMIDATION

<400> SEQUENCE: 35

Cys Ala Leu Arg Pro Leu Tyr Ile Asp Phe Lys Arg Asp Leu Gly Trp
1 5 10 15

Lys Trp Ile His Glu Pro Lys Gly Tyr Asn Ala Asn Phe Cys Ala Gly
20 25 30

Ala Cys Asn Asp Glu Gly Leu Glu Cys Val Ser Gln Asp Leu Glu Pro
35 40 45

Leu Thr Ile Leu Tyr Tyr Ile Gly Lys Thr Pro Lys Ile Glu Gln Leu
50 55 60

Ser Asn Met Ile Val Lys Ser Cys Lys Cys
65 70

<210> SEQ ID NO 36
<211> LENGTH: 112
<212> TYPE: PRT
<213> ORGANISM: Artificial
<220> FEATURE:
<223> OTHER INFORMATION: proteinmimic protein 60A firefly

<400> SEQUENCE: 36

Leu Leu Glu Pro Met Glu Ser Thr Arg Ser Cys Gln Met Gln Thr Leu
1 5 10 15

Tyr Ile Asp Phe Lys Asp Leu Gly Trp His Asp Trp Ile Ile Ala Pro
20 25 30

Glu Gly Tyr Gly Ala Phe Tyr Cys Ser Gly Glu Cys Asn Phe Pro Leu
35 40 45

Asn Ala His Met Asn Ala Thr Asn His Ala Ile Val Gln Thr Leu Val
50 55 60

His Leu Leu Glu Pro Lys Lys Val Pro Lys Pro Cys Cys Ala Pro Thr
65 70 75 80

Arg Leu Gly Ala Leu Pro Val Leu Tyr His Leu Asn Asp Glu Asn Val
85 90 95

Asn Leu Lys Lys Tyr Arg Asn Met Ile Val Lys Ser Cys Gly Cys His
100 105 110

<210> SEQ ID NO 37
<211> LENGTH: 108
<212> TYPE: PRT
<213> ORGANISM: Artificial
<220> FEATURE:
<223> OTHER INFORMATION: proteinmimic artemin

<400> SEQUENCE: 37

Ser Arg Ala Arg Ala Ala Gly Ala Arg Gly Cys Arg Leu Arg Ser Gln
1 5 10 15

Leu Val Pro Val Arg Ala Leu Gly Leu Gly His Arg Ser Asp Glu Leu
20 25 30

Val Arg Phe Arg Phe Cys Ser Gly Ser Cys Arg Arg Ala Arg Ser Pro
35 40 45

His Asp Leu Ser Leu Ala Ser Leu Leu Gly Ala Gly Ala Leu Arg Pro
50 55 60

Pro Pro Gly Ser Arg Pro Val Ser Gln Pro Cys Cys Arg Pro Thr Arg
65 70 75 80

Tyr Glu Ala Val Ser Phe Met Asp Val Asn Ser Thr Trp Arg Thr Val
85 90 95

Asp Arg Leu Ser Ala Thr Ala Cys Gly Cys Leu Gly
100 105

<210> SEQ ID NO 38
<211> LENGTH: 112
<212> TYPE: PRT
<213> ORGANISM: Artificial
<220> FEATURE:
<223> OTHER INFORMATION: proteinmimic hBMP-10

<400> SEQUENCE: 38

Arg Ile Arg Arg Asn Ala Lys Gly Asn Tyr Cys Lys Arg Thr Pro Leu
1 5 10 15

Tyr Ile Asp Phe Lys Glu Ile Gly Trp Asp Ser Trp Ile Ile Ala Pro
20 25 30

Pro Gly Tyr Glu Ala Tyr Glu Cys Arg Gly Val Cys Asn Tyr Pro Leu
35 40 45

Ala Glu His Leu Thr Pro Thr Lys His Ala Ile Ile Gln Ala Leu Val
50 55 60

His Leu Lys Asn Ser Gln Lys Ala Ser Lys Ala Cys Cys Val Pro Thr
65 70 75 80

Lys Leu Glu Pro Ile Ser Ile Leu Tyr Leu Asp Lys Gly Val Val Thr
85 90 95

Tyr Lys Phe Lys Tyr Glu Gly Met Ala Val Ser Glu Cys Gly Cys Arg
100 105 110

<210> SEQ ID NO 39
<211> LENGTH: 112
<212> TYPE: PRT
<213> ORGANISM: Artificial
<220> FEATURE:
<223> OTHER INFORMATION: proteinmimic hBMP-15

<400> SEQUENCE: 39

Lys His Ser Gly Pro Pro Glu Asn Asn Gln Cys Ser Leu His Pro Phe
1 5 10 15

Gln Ile Ser Phe Arg Gln Leu Gly Trp Asp His Trp Ile Ile Ala Pro
20 25 30

Pro Phe Tyr Thr Pro Asn Tyr Cys Lys Gly Thr Cys Leu Arg Val Leu
35 40 45

Arg Asp Gly Leu Asn Ser Pro Asn His Ala Ile Ile Gln Asn Leu Ile
50 55 60

Asn Gln Leu Val Asp Gln Ser Val Pro Arg Pro Ser Cys Val Pro Tyr
65 70 75 80

Lys Tyr Val Pro Ile Ser Val Leu Met Ile Glu Ala Asn Gly Ser Ile
85 90 95

Leu Tyr Lys Glu Tyr Glu Gly Met Ile Ala Glu Ser Cys Thr Cys Arg
100 105 110

<210> SEQ ID NO 40
<211> LENGTH: 111
<212> TYPE: PRT
<213> ORGANISM: Artificial
<220> FEATURE:
<223> OTHER INFORMATION: proteinmimic hBMP-2

<400> SEQUENCE: 40

His Lys Gln Arg Lys Arg Leu Lys Ser Ser Cys Lys Arg His Pro Leu
1 5 10 15

Tyr Val Asp Phe Ser Asp Val Gly Trp Asn Asp Trp Ile Val Ala Pro
20 25 30

Pro Gly Tyr His Ala Phe Tyr Cys His Gly Glu Cys Pro Phe Pro Leu
35 40 45

Ala Asp His Leu Asn Ser Thr Asn His Ala Ile Val Gln Thr Leu Val
50 55 60

Asn Ser Val Asn Ser Lys Ile Pro Lys Ala Cys Cys Val Pro Thr Glu
65 70 75 80

Leu Ser Ala Ile Ser Met Leu Tyr Leu Asp Glu Asn Glu Lys Val Val
85 90 95

Leu Lys Asn Tyr Gln Asp Met Val Val Glu Gly Cys Gly Cys Arg
100 105 110

<210> SEQ ID NO 41
<211> LENGTH: 106
<212> TYPE: PRT
<213> ORGANISM: Artificial
<220> FEATURE:
<223> OTHER INFORMATION: proteinmimic hBMP-3

<400> SEQUENCE: 41

Gln Trp Ile Glu Pro Arg Asn Cys Ala Arg Arg Tyr Leu Lys Val Asp
1 5 10 15

Phe Ala Asp Ile Gly Trp Ser Glu Trp Ile Ile Ser Pro Lys Ser Phe
20 25 30

Asp Ala Tyr Tyr Cys Ser Gly Ala Cys Gln Phe Pro Met Pro Lys Ser
35 40 45

Asn His Ala Thr Ile Gln Ser Ile Val Arg Ala Val Gly Val Val Pro
50 55 60

Gly Ile Pro Glu Pro Cys Cys Val Pro Glu Lys Met Ser Ser Leu Ser
65 70 75 80

```
Ile Leu Phe Phe Asp Glu Asn Lys Asn Val Val Leu Lys Val Tyr Pro
                85                  90                  95

Asn Met Thr Val Glu Ser Cys Ala Cys Arg
            100                 105


<210> SEQ ID NO 42
<211> LENGTH: 110
<212> TYPE: PRT
<213> ORGANISM: Artificial
<220> FEATURE:
<223> OTHER INFORMATION: proteinmimic hBMP-3b

<400> SEQUENCE: 42

Gln Trp Asp Glu Pro Arg Val Cys Ser Arg Arg Tyr Leu Lys Val Asp
1               5                   10                  15

Phe Ala Asp Ile Gly Trp Asn Glu Trp Ile Ile Ser Pro Lys Ser Phe
            20                  25                  30

Asp Ala Tyr Tyr Cys Ala Gly Ala Cys Glu Phe Pro Met Pro Lys Ile
        35                  40                  45

Val Arg Pro Ser Asn His Ala Thr Ile Gln Ser Ile Val Arg Ala Val
    50                  55                  60

Gly Ile Ile Pro Gly Ile Pro Glu Pro Cys Cys Val Pro Asp Lys Met
65                  70                  75                  80

Asn Ser Leu Gly Val Leu Phe Leu Asp Glu Asn Arg Asn Val Val Leu
                85                  90                  95

Lys Val Tyr Pro Asn Met Ser Val Asp Thr Cys Ala Cys Arg
            100                 105                 110


<210> SEQ ID NO 43
<211> LENGTH: 111
<212> TYPE: PRT
<213> ORGANISM: Artificial
<220> FEATURE:
<223> OTHER INFORMATION: proteinmimic hBMP-4

<400> SEQUENCE: 43

Ser Gln Arg Ala Arg Lys Lys Asn Lys Asn Cys Arg Arg His Ser Leu
1               5                   10                  15

Tyr Val Asp Phe Ser Asp Val Gly Trp Asn Asp Trp Ile Val Ala Pro
            20                  25                  30

Pro Gly Tyr Gln Ala Phe Tyr Cys His Gly Asp Cys Pro Phe Pro Leu
        35                  40                  45

Ala Asp His Leu Asn Ser Thr Asn His Ala Ile Val Gln Thr Leu Val
    50                  55                  60

Asn Ser Val Asn Ser Ser Ile Pro Lys Ala Cys Cys Val Pro Thr Glu
65                  70                  75                  80

Leu Ser Ala Ile Ser Met Leu Tyr Leu Asp Glu Tyr Asp Lys Val Val
                85                  90                  95

Leu Lys Asn Tyr Gln Glu Met Val Val Glu Gly Cys Gly Cys Arg
            100                 105                 110


<210> SEQ ID NO 44
<211> LENGTH: 112
<212> TYPE: PRT
<213> ORGANISM: Artificial
<220> FEATURE:
<223> OTHER INFORMATION: proteinmimic hBMP-5

<400> SEQUENCE: 44

Asp Tyr Asn Thr Ser Glu Gln Lys Gln Ala Cys Lys Lys His Glu Leu
```

-continued

```
1               5                   10                  15

Tyr Val Ser Phe Arg Asp Leu Gly Trp Gln Asp Trp Ile Ile Ala Pro
            20                  25                  30

Glu Gly Tyr Ala Ala Phe Tyr Cys Asp Gly Glu Cys Ser Phe Pro Leu
        35                  40                  45

Asn Ala His Met Asn Ala Thr Asn His Ala Ile Val Gln Thr Leu Val
    50                  55                  60

His Leu Met Phe Pro Asp His Val Pro Lys Pro Cys Cys Ala Pro Thr
65                  70                  75                  80

Lys Leu Asn Ala Ile Ser Val Leu Tyr Phe Asp Asp Ser Ser Asn Val
                85                  90                  95

Ile Leu Lys Lys Tyr Arg Asn Met Val Val Arg Ser Cys Gly Cys His
            100                 105                 110


<210> SEQ ID NO 45
<211> LENGTH: 112
<212> TYPE: PRT
<213> ORGANISM: Artificial
<220> FEATURE:
<223> OTHER INFORMATION: proteinmimic hBMP-6

<400> SEQUENCE: 45

Asp Tyr Asn Ser Ser Glu Leu Lys Thr Ala Cys Arg Lys His Glu Leu
1               5                   10                  15

Tyr Val Ser Phe Gln Asp Leu Gly Trp Gln Asp Trp Ile Ile Ala Pro
            20                  25                  30

Lys Gly Tyr Ala Ala Asn Tyr Cys Asp Gly Glu Cys Ser Phe Pro Leu
        35                  40                  45

Asn Ala His Met Asn Ala Thr Asn His Ala Ile Val Gln Thr Leu Val
    50                  55                  60

His Leu Met Asn Pro Glu Tyr Val Pro Lys Pro Cys Cys Ala Pro Thr
65                  70                  75                  80

Lys Leu Asn Ala Ile Ser Val Leu Tyr Phe Asp Asp Asn Ser Asn Val
                85                  90                  95

Ile Leu Lys Lys Tyr Arg Asn Met Val Val Arg Ala Cys Gly Cys His
            100                 105                 110


<210> SEQ ID NO 46
<211> LENGTH: 112
<212> TYPE: PRT
<213> ORGANISM: Artificial
<220> FEATURE:
<223> OTHER INFORMATION: proteinmimic hBMP-7

<400> SEQUENCE: 46

Ala Glu Asn Ser Ser Ser Asp Arg Gln Ala Cys Lys Lys His Glu Leu
1               5                   10                  15

Tyr Val Ser Phe Arg Asp Leu Gly Trp Gln Asp Trp Ile Ile Ala Pro
            20                  25                  30

Glu Gly Tyr Ala Ala Tyr Tyr Cys Glu Gly Glu Cys Ala Phe Pro Leu
        35                  40                  45

Asn Ser Tyr Met Asn Ala Thr Asn His Ala Ile Val Gln Thr Leu Val
    50                  55                  60

His Phe Ile Asn Pro Glu Thr Val Pro Lys Pro Cys Cys Ala Pro Thr
65                  70                  75                  80

Gln Leu Asn Ala Ile Ser Val Leu Tyr Phe Asp Asp Ser Ser Asn Val
                85                  90                  95
```

```
Ile Leu Lys Lys Tyr Arg Asn Met Val Val Arg Ala Cys Gly Cys His
            100                 105                 110
```

<210> SEQ ID NO 47
<211> LENGTH: 111
<212> TYPE: PRT
<213> ORGANISM: Artificial
<220> FEATURE:
<223> OTHER INFORMATION: proteinmimic hBMP-8

<400> SEQUENCE: 47

```
Asp Val Arg Gly Ser His Gly Arg Gln Val Cys Arg Arg His Glu Leu
1               5                   10                  15

Tyr Val Ser Phe Gln Asp Leu Gly Trp Leu Asp Trp Val Ile Ala Pro
            20                  25                  30

Gln Gly Tyr Ser Ala Tyr Tyr Cys Glu Gly Glu Cys Ser Phe Pro Leu
        35                  40                  45

Asp Ser Cys Met Asn Ala Thr His Ala Ile Leu Gln Ser Leu Val His
    50                  55                  60

Ser Met Lys Pro Asn Ala Val Pro Lys Ala Cys Cys Ala Pro Thr Lys
65                  70                  75                  80

Leu Ser Ala Thr Ser Val Leu Tyr Tyr Asp Ser Ser Asn Asn Val Ile
                85                  90                  95

Leu Arg Lys His Arg Asn Met Val Val Lys Ala Cys Gly Cys His
            100                 105                 110
```

<210> SEQ ID NO 48
<211> LENGTH: 111
<212> TYPE: PRT
<213> ORGANISM: Artificial
<220> FEATURE:
<223> OTHER INFORMATION: proteinmimic DLDRGF C. elegans

<400> SEQUENCE: 48

```
Ser His Ala Lys Pro Val Cys Asn Ala Glu Ala Gln Ser Lys Gly Cys
1               5                   10                  15

Cys Leu Tyr Asp Leu Glu Ile Glu Phe Glu Lys Ile Gly Trp Asp Trp
            20                  25                  30

Ile Val Ala Pro Arg Tyr Asn Ala Tyr Met Cys Arg Gly Asp Cys Pro
        35                  40                  45

Ser Gln Phe Arg Ala Ala Asn Met His Ala Gln Ile Lys Thr Ser Leu
    50                  55                  60

His Arg Leu Lys Pro Asp Thr Val Pro Ala Pro Cys Cys Val Pro Ala
65                  70                  75                  80

Ser Tyr Asn Pro Met Val Leu Ile Gln Lys Thr Asp Thr Gly Val Ser
                85                  90                  95

Leu Gln Thr Tyr Asp Asp Leu Leu Ala Lys Asp Cys His Cys Ile
            100                 105                 110
```

<210> SEQ ID NO 49
<211> LENGTH: 112
<212> TYPE: PRT
<213> ORGANISM: Artificial
<220> FEATURE:
<223> OTHER INFORMATION: proteinmimic decapentaplegic Drosophila

<400> SEQUENCE: 49

```
Pro Thr Arg Arg Lys Asn His Asp Asp Thr Cys Arg Arg His Ser Leu
1               5                   10                  15

Tyr Val Asp Phe Ser Asp Val Gly Trp Asp Asp Trp Ile Val Ala Pro
```

-continued

```
            20                  25                  30

Leu Gly Tyr Asp Ala Tyr Tyr Cys His Gly Lys Cys Pro Phe Pro Leu
        35                  40                  45

Ala Asp His Phe Asn Ser Thr Asn His Ala Val Val Gln Thr Leu Val
    50                  55                  60

Asn Asn Met Asn Pro Gly Lys Val Pro Lys Ala Cys Cys Val Pro Thr
65                  70                  75                  80

Gln Leu Asp Ser Val Ala Met Leu Tyr Leu Asn Asp Gln Ser Thr Val
                85                  90                  95

Val Leu Lys Asn Tyr Gln Glu Met Thr Val Val Gly Cys Gly Cys Arg
            100                 105                 110


<210> SEQ ID NO 50
<211> LENGTH: 112
<212> TYPE: PRT
<213> ORGANISM: Artificial
<220> FEATURE:
<223> OTHER INFORMATION: proteinmimic decapentaplegic red flour beetle

<400> SEQUENCE: 50

Arg Arg His Arg Lys Asn Leu Lys Asp Pro Cys Arg Arg Arg Gln Met
1               5                   10                  15

Tyr Val Asp Phe Gly Ser Val Gly Trp Asn Asp Trp Ile Val Ala Pro
            20                  25                  30

Leu Gly Tyr Asp Ala Tyr Tyr Cys Gly Gly Glu Cys Glu Tyr Pro Ile
        35                  40                  45

Pro Asp His Met Asn Thr Thr Asn His Ala Ile Val Gln Ser Leu Val
    50                  55                  60

Asn Ser Met Lys Pro Lys Glu Val Pro Gly Pro Cys Cys Val Pro Thr
65                  70                  75                  80

Gln Leu Gly Gln Met Ser Met Leu Tyr Leu Gly Ser Asp Gly Ser Val
                85                  90                  95

Ile Leu Lys Asn Tyr Lys Glu Met Val Val Val Gly Cys Gly Cys Arg
            100                 105                 110


<210> SEQ ID NO 51
<211> LENGTH: 108
<212> TYPE: PRT
<213> ORGANISM: Artificial
<220> FEATURE:
<223> OTHER INFORMATION: proteinmimic derriereprtoein frog

<400> SEQUENCE: 51

Pro Thr Pro Ser Asn Ile Cys Lys Lys Arg Arg Leu Tyr Ile Asp Phe
1               5                   10                  15

Lys Asp Val Gly Trp Gln Asn Trp Val Ile Ala Pro Arg Gly Tyr Met
            20                  25                  30

Ala Asn Tyr Cys His Gly Glu Cys Pro Tyr Pro Leu Thr Glu Met Leu
        35                  40                  45

Arg Gly Thr Asn His Ala Val Leu Gln Thr Leu Val His Ser Val Glu
    50                  55                  60

Pro Glu Asn Thr Pro Leu Pro Cys Cys Ala Pro Thr Lys Leu Ser Pro
65                  70                  75                  80

Ile Ser Met Leu Tyr Tyr Asp Asn Asn Asp Asn Val Val Leu Arg His
                85                  90                  95

Tyr Glu Asp Met Val Val Asp Glu Cys Gly Cys Lys
            100                 105
```

<210> SEQ ID NO 52
<211> LENGTH: 109
<212> TYPE: PRT
<213> ORGANISM: Artificial
<220> FEATURE:
<223> OTHER INFORMATION: proteinmimic dorsalin-1 chicken

<400> SEQUENCE: 52

```
Ser Ile Gly Ala Asn His Cys Arg Arg Thr Ser Leu His Val Asn Phe
1               5                   10                  15

Lys Glu Ile Gly Trp Asp Ser Trp Ile Ile Ala Pro Lys Asp Tyr Glu
            20                  25                  30

Ala Phe Glu Cys Lys Gly Gly Cys Phe Phe Pro Leu Thr Asp Asn Val
        35                  40                  45

Thr Pro Thr Lys His Ala Ile Val Gln Thr Leu Val His Leu Gln Asn
    50                  55                  60

Pro Lys Lys Ala Ser Lys Ala Cys Cys Val Pro Thr Lys Leu Asp Ala
65                  70                  75                  80

Ile Ser Ile Leu Tyr Lys Asp Asp Ala Gly Val Pro Thr Leu Ile Tyr
                85                  90                  95

Asn Tyr Glu Gly Met Lys Val Ala Glu Cys Gly Cys Arg
            100                 105
```

<210> SEQ ID NO 53
<211> LENGTH: 112
<212> TYPE: PRT
<213> ORGANISM: Artificial
<220> FEATURE:
<223> OTHER INFORMATION: proteinmimic DVR-1frog

<400> SEQUENCE: 53

```
Ser Lys Leu Pro Phe Thr Ala Ser Asn Ile Cys Lys Lys Arg His Leu
1               5                   10                  15

Tyr Val Glu Phe Lys Asp Val Gly Trp Gln Asn Trp Val Ile Ala Pro
            20                  25                  30

Gln Gly Tyr Met Ala Asn Tyr Cys Tyr Gly Glu Cys Pro Tyr Pro Leu
        35                  40                  45

Thr Glu Ile Leu Asn Gly Ser Asn His Ala Ile Leu Gln Thr Leu Val
    50                  55                  60

His Ser Ile Glu Pro Glu Asp Ile Pro Leu Pro Cys Cys Val Pro Thr
65                  70                  75                  80

Lys Met Ser Pro Ile Ser Met Leu Phe Tyr Asp Asn Asn Asp Asn Val
                85                  90                  95

Val Leu Arg His Tyr Glu Asn Met Ala Val Asp Glu Cys Gly Cys Arg
            100                 105                 110
```

<210> SEQ ID NO 54
<211> LENGTH: 112
<212> TYPE: PRT
<213> ORGANISM: Artificial
<220> FEATURE:
<223> OTHER INFORMATION: proteinmimic DVR-1 homolog urchin

<400> SEQUENCE: 54

```
Ser Ala Ser Ser Leu Asn Ser Asp Trp Gln Cys Lys Arg Lys Asn Leu
1               5                   10                  15

Phe Val Asn Phe Glu Asp Leu Asp Trp Gln Glu Trp Ile Ile Ala Pro
            20                  25                  30

Leu Gly Tyr Val Ala Phe Tyr Cys Gln Gly Glu Cys Ala Phe Pro Leu
```

35 40 45

Asn Gly His Ala Asn Ala Thr Asn His Ala Ile Val Gln Thr Leu Val
50 55 60

His His Met Ser Pro Ser His Val Pro Gln Pro Cys Cys Ala Pro Thr
65 70 75 80

Lys Leu Ser Pro Ile Thr Val Leu Tyr Tyr Asp Asp Ser Arg Asn Val
85 90 95

Val Leu Lys Lys Tyr Lys Asn Met Val Val Arg Ala Cys Gly Cys Leu
100 105 110

<210> SEQ ID NO 55
<211> LENGTH: 109
<212> TYPE: PRT
<213> ORGANISM: Artificial
<220> FEATURE:
<223> OTHER INFORMATION: proteinmimic growth/differentiation factor 11

<400> SEQUENCE: 55

Asn Leu Gly Leu Asp Cys Asp Glu His Ser Ser Glu Ser Arg Cys Cys
1 5 10 15

Arg Tyr Pro Leu Thr Val Asp Phe Glu Ala Phe Gly Trp Asp Trp Ile
20 25 30

Ile Ala Pro Lys Arg Tyr Lys Ala Asn Tyr Cys Ser Gly Gln Cys Glu
35 40 45

Tyr Met Phe Met Gln Lys Tyr Pro His Thr His Leu Val Gln Gln Ala
50 55 60

Asn Pro Arg Gly Ser Ala Gly Pro Cys Cys Thr Pro Thr Lys Met Ser
65 70 75 80

Pro Ile Asn Met Leu Tyr Phe Asn Asp Lys Gln Gln Ile Ile Tyr Gly
85 90 95

Lys Ile Pro Gly Met Val Val Asp Arg Cys Gly Cys Ser
100 105

<210> SEQ ID NO 56
<211> LENGTH: 114
<212> TYPE: PRT
<213> ORGANISM: Artificial
<220> FEATURE:
<223> OTHER INFORMATION: proteinmimic growth/differentiation factor 15

<400> SEQUENCE: 56

Ala Arg Ala Arg Asn Gly Asp His Cys Pro Leu Gly Pro Gly Arg Cys
1 5 10 15

Cys Arg Leu His Thr Val Arg Ala Ser Leu Glu Asp Leu Gly Trp Ala
20 25 30

Asp Trp Val Leu Ser Pro Arg Glu Val Gln Val Thr Met Cys Ile Gly
35 40 45

Ala Cys Pro Ser Gln Phe Arg Ala Ala Asn Met His Ala Gln Ile Lys
50 55 60

Thr Ser Leu His Arg Leu Lys Pro Asp Thr Val Pro Ala Pro Cys Cys
65 70 75 80

Val Pro Ala Ser Tyr Asn Pro Met Val Leu Ile Gln Lys Thr Asp Thr
85 90 95

Gly Val Ser Leu Gln Thr Tyr Asp Asp Leu Leu Ala Lys Asp Cys His
100 105 110

Cys Ile

<210> SEQ ID NO 57
<211> LENGTH: 116
<212> TYPE: PRT
<213> ORGANISM: Artificial
<220> FEATURE:
<223> OTHER INFORMATION: proteinmimic embryonic growth/differentiation
      factor 1

<400> SEQUENCE: 57

```
Pro Val Leu Gly Gly Gly Pro Gly Gly Ala Cys Arg Ala Arg Arg Leu
1               5                   10                  15

Tyr Val Ser Phe Arg Glu Val Gly Trp His Arg Trp Val Ile Ala Pro
            20                  25                  30

Arg Gly Phe Leu Ala Asn Tyr Cys Gln Gly Gln Cys Ala Leu Pro Val
        35                  40                  45

Ala Leu Ser Gly Ser Gly Gly Pro Pro Ala Leu Asn His Ala Val Leu
    50                  55                  60

Arg Ala Leu Met His Ala Ala Ala Pro Gly Ala Ala Asp Leu Pro Cys
65                  70                  75                  80

Cys Val Pro Ala Arg Leu Ser Pro Ile Ser Val Leu Phe Phe Asp Asn
                85                  90                  95

Ser Asp Asn Val Val Leu Arg Gln Tyr Glu Asp Met Val Val Asp Glu
            100                 105                 110

Cys Gly Cys Arg
        115
```

<210> SEQ ID NO 58
<211> LENGTH: 110
<212> TYPE: PRT
<213> ORGANISM: Artificial
<220> FEATURE:
<223> OTHER INFORMATION: proteinmimic growth/differentiation factor 2

<400> SEQUENCE: 58

```
Ser Ala Gly Ala Gly Ser His Cys Gln Lys Thr Ser Leu Arg Val Asn
1               5                   10                  15

Phe Glu Asp Ile Gly Trp Asp Ser Trp Ile Ile Ala Pro Lys Glu Tyr
            20                  25                  30

Glu Ala Tyr Glu Cys Lys Gly Gly Cys Phe Phe Pro Leu Ala Asp Asp
        35                  40                  45

Val Thr Pro Thr Lys His Ala Ile Val Gln Thr Leu Val His Leu Lys
    50                  55                  60

Phe Pro Thr Lys Val Gly Lys Ala Cys Cys Val Pro Thr Lys Leu Ser
65                  70                  75                  80

Pro Ile Ser Val Leu Tyr Lys Asp Asp Met Gly Val Pro Thr Leu Lys
                85                  90                  95

Tyr His Tyr Glu Gly Met Ser Val Ala Glu Cys Gly Cys Arg
            100                 105                 110
```

<210> SEQ ID NO 59
<211> LENGTH: 111
<212> TYPE: PRT
<213> ORGANISM: Artificial
<220> FEATURE:
<223> OTHER INFORMATION: proteinmimic growth/differentiation factor 3

<400> SEQUENCE: 59

```
Pro Val Pro Lys Leu Ser Cys Lys Asn Leu Cys His Arg His Gln Leu
1               5                   10                  15

Phe Ile Asn Phe Arg Asp Leu Gly Trp His Lys Trp Ile Ile Ala Pro
```

```
            20                  25                  30

Lys Gly Phe Met Ala Asn Tyr Cys His Gly Glu Cys Pro Phe Ser Leu
        35                  40                  45

Thr Ile Ser Leu Asn Ser Ser Asn Tyr Ala Phe Met Gln Ala Leu Met
    50                  55                  60

His Ala Val Asp Pro Glu Ile Pro Gln Ala Val Cys Ile Pro Thr Lys
65                  70                  75                  80

Leu Ser Pro Ile Ser Met Leu Tyr Gln Asp Asn Asn Asp Asn Val Ile
                85                  90                  95

Leu Arg His Tyr Glu Asp Met Val Val Asp Glu Cys Gly Cys Gly
            100                 105                 110


<210> SEQ ID NO 60
<211> LENGTH: 112
<212> TYPE: PRT
<213> ORGANISM: Artificial
<220> FEATURE:
<223> OTHER INFORMATION: proteinmimic growth/differentiation factor 5

<400> SEQUENCE: 60

Lys Arg Pro Ser Lys Asn Leu Lys Ala Arg Cys Ser Arg Lys Ala Leu
1               5                   10                  15

His Val Asn Phe Lys Glu Met Gly Trp Asp Asp Trp Ile Ile Ala Pro
            20                  25                  30

Leu Glu Tyr Glu Ala Phe His Cys Glu Gly Leu Cys Glu Phe Pro Leu
        35                  40                  45

Arg Ser His Leu Glu Pro Thr Asn His Ala Val Ile Gln Thr Leu Met
    50                  55                  60

Asn Ser Met Asp Pro Glu Ser Thr Pro Pro Thr Cys Cys Val Pro Thr
65                  70                  75                  80

Arg Leu Ser Pro Ile Ser Ile Leu Phe Ile Asp Ser Ala Asn Asn Val
                85                  90                  95

Val Tyr Lys Gln Tyr Glu Asp Met Val Val Glu Ser Cys Gly Cys Arg
            100                 105                 110


<210> SEQ ID NO 61
<211> LENGTH: 112
<212> TYPE: PRT
<213> ORGANISM: Artificial
<220> FEATURE:
<223> OTHER INFORMATION: proteinmimic growth/differentiation factor 6

<400> SEQUENCE: 61

Lys Arg His Gly Lys Lys Ser Arg Leu Arg Cys Ser Lys Lys Pro Leu
1               5                   10                  15

His Val Asn Phe Lys Glu Leu Gly Trp Asp Asp Trp Ile Ile Ala Pro
            20                  25                  30

Leu Glu Tyr Glu Ala Tyr His Cys Glu Gly Val Cys Asp Phe Pro Leu
        35                  40                  45

Arg Ser His Leu Glu Pro Thr Asn His Ala Ile Ile Gln Thr Leu Met
    50                  55                  60

Asn Ser Met Asp Pro Gly Ser Thr Pro Pro Ser Cys Cys Val Pro Thr
65                  70                  75                  80

Lys Leu Thr Pro Ile Ser Ile Leu Tyr Ile Asp Ala Gly Asn Asn Val
                85                  90                  95

Val Tyr Lys Gln Tyr Glu Asp Met Val Val Glu Ser Cys Gly Cys Arg
            100                 105                 110
```

<210> SEQ ID NO 62
<211> LENGTH: 112
<212> TYPE: PRT
<213> ORGANISM: Artificial
<220> FEATURE:
<223> OTHER INFORMATION: proteinmimic growth/differentiation factor 7

<400> SEQUENCE: 62

```
Arg Gly His Gly Arg Arg Gly Arg Ser Arg Cys Ser Arg Lys Pro Leu
1               5                   10                  15

His Val Asp Phe Lys Glu Leu Gly Trp Asp Asp Trp Ile Ile Ala Pro
            20                  25                  30

Leu Asp Tyr Glu Ala Tyr His Cys Glu Gly Leu Cys Asp Phe Pro Leu
        35                  40                  45

Arg Ser His Leu Glu Pro Thr Asn His Ala Ile Ile Gln Thr Leu Leu
    50                  55                  60

Asn Ser Met Ala Pro Asp Ala Ala Pro Ala Ser Cys Cys Val Pro Ala
65                  70                  75                  80

Arg Leu Ser Pro Ile Ser Ile Leu Tyr Ile Asp Ala Ala Asn Asn Val
                85                  90                  95

Val Tyr Lys Gln Tyr Glu Asp Met Val Val Glu Ala Cys Gly Cys Arg
            100                 105                 110
```

<210> SEQ ID NO 63
<211> LENGTH: 109
<212> TYPE: PRT
<213> ORGANISM: Artificial
<220> FEATURE:
<223> OTHER INFORMATION: proteinmimic growth/differentiation factor 8

<400> SEQUENCE: 63

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Glu Cys Glu
        35                  40                  45

Phe Val Phe Leu Gln Lys Tyr Pro His Thr His Leu Val His Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105
```

<210> SEQ ID NO 64
<211> LENGTH: 112
<212> TYPE: PRT
<213> ORGANISM: Artificial
<220> FEATURE:
<223> OTHER INFORMATION: proteinmimic growth/differentiation factor 9

<400> SEQUENCE: 64

```
Phe Arg Gln Phe Leu Leu Pro Gln Asn Glu Cys Glu Leu His Asp Phe
1               5                   10                  15

Arg Leu Ser Phe Ser Gln Leu Lys Trp Asp Asn Trp Ile Val Ala Pro
            20                  25                  30

His Arg Tyr Asn Pro Arg Tyr Cys Lys Gly Asp Cys Pro Arg Ala Val
```

-continued 35 40 45

Gly His Arg Tyr Gly Ser Pro Val His Thr Met Val Gln Asn Ile Ile
50 55 60

Tyr Glu Lys Leu Asp Ser Ser Val Pro Arg Pro Ser Cys Val Pro Ala
65 70 75 80

Lys Tyr Ser Pro Leu Ser Val Leu Thr Ile Glu Pro Asp Gly Ser Ile
85 90 95

Ala Tyr Lys Glu Tyr Glu Asp Met Ile Ala Thr Lys Cys Thr Cys Arg
100 105 110

<210> SEQ ID NO 65
<211> LENGTH: 104
<212> TYPE: PRT
<213> ORGANISM: Artificial
<220> FEATURE:
<223> OTHER INFORMATION: proteinmimic gklial cell-line derived neurotrophic factor

<400> SEQUENCE: 65

Arg Gly Gly Gln Arg Gly Lys Asn Arg Gly Cys Val Leu Thr Ala Ile
1 5 10 15

His Leu Asn Val Thr Asp Leu Gly Leu Gly Tyr Glu Thr Lys Glu Glu
20 25 30

Leu Ile Phe Arg Tyr Cys Ser Gly Ser Cys Asp Ala Ala Glu Thr Thr
35 40 45

Tyr Asp Lys Ile Leu Lys Asn Leu Ser Arg Asn Arg Arg Leu Val Ser
50 55 60

Asp Lys Val Gly Gln Ala Cys Cys Arg Pro Ile Ala Phe Asp Asp Asp
65 70 75 80

Leu Ser Phe Leu Asp Asp Asn Leu Val Tyr His Ile Leu Arg Lys His
85 90 95

Ser Ala Lys Arg Cys Gly Cys Ile
100

<210> SEQ ID NO 66
<211> LENGTH: 115
<212> TYPE: PRT
<213> ORGANISM: Artificial
<220> FEATURE:
<223> OTHER INFORMATION: proteinmimic inhibin alpha

<400> SEQUENCE: 66

Pro Pro Glu Glu Pro Ala Ala His Ala Asn Cys His Arg Val Ala Leu
1 5 10 15

Asn Ile Ser Phe Gln Glu Leu Gly Trp Glu Arg Trp Ile Val Tyr Pro
20 25 30

Pro Ser Phe Ile Phe His Tyr Cys His Gly Gly Cys Gly Leu His Ile
35 40 45

Pro Pro Asn Leu Ser Leu Pro Val Pro Gly Ala Pro Pro Thr Pro Ala
50 55 60

Gln Pro Tyr Ser Leu Leu Pro Gly Ala Gln Pro Cys Cys Ala Ala Leu
65 70 75 80

Pro Gly Thr Met Arg Pro Leu His Val Arg Thr Thr Ser Asp Gly Gly
85 90 95

Tyr Ser Phe Lys Tyr Glu Thr Val Pro Asn Leu Leu Thr Gln His Cys
100 105 110

Ala Cys Ile
115

<210> SEQ ID NO 67
<211> LENGTH: 120
<212> TYPE: PRT
<213> ORGANISM: Artificial
<220> FEATURE:
<223> OTHER INFORMATION: proteinmimic inhibin beta Drosophila

<400> SEQUENCE: 67

```
Thr Arg Arg Val Arg Arg Arg Ala Val Asp Cys Gly Gly Ala Leu Asn
1               5                   10                  15

Gly Gln Cys Cys Lys Glu Ser Phe Tyr Val Ser Phe Lys Ala Leu Gly
            20                  25                  30

Trp Asp Asp Trp Ile Ile Ala Pro Arg Gly Tyr Phe Ala Asn Tyr Cys
        35                  40                  45

Arg Gly Asp Cys Thr Gly Ser Phe Arg Thr Pro Asp Thr Phe Gln Thr
    50                  55                  60

Phe His Ala His Phe Ile Glu Glu Tyr Arg Lys Met Gly Leu Met Asn
65                  70                  75                  80

Gly Met Arg Pro Cys Cys Ala Pro Ile Lys Phe Ser Ser Met Ser Leu
                85                  90                  95

Ile Tyr Tyr Gly Asp Asp Gly Ile Ile Lys Arg Asp Leu Pro Lys Met
            100                 105                 110

Val Val Asp Glu Cys Gly Cys Pro
        115                 120
```

<210> SEQ ID NO 68
<211> LENGTH: 123
<212> TYPE: PRT
<213> ORGANISM: Artificial
<220> FEATURE:
<223> OTHER INFORMATION: proteinmimic human inhibin beta-A

<400> SEQUENCE: 68

```
Pro His Arg Arg Arg Arg Arg Gly Leu Glu Cys Asp Gly Lys Val Asn
1               5                   10                  15

Ile Cys Cys Lys Lys Gln Phe Phe Val Ser Phe Lys Asp Ile Gly Trp
            20                  25                  30

Asn Asp Trp Ile Ile Ala Pro Ser Gly Tyr His Ala Asn Tyr Cys Glu
        35                  40                  45

Gly Glu Cys Pro Ser His Ile Ala Gly Thr Ser Gly Ser Ser Leu Ser
    50                  55                  60

Phe His Ser Thr Val Ile Asn His Tyr Arg Met Arg Gly His Ser Pro
65                  70                  75                  80

Phe Ala Asn Leu Lys Ser Cys Cys Val Pro Thr Lys Leu Arg Pro Met
                85                  90                  95

Ser Met Leu Tyr Tyr Asp Asp Gly Gln Asn Ile Ile Lys Lys Asp Ile
            100                 105                 110

Gln Asn Met Ile Val Glu Glu Cys Gly Cys Ser
        115                 120
```

<210> SEQ ID NO 69
<211> LENGTH: 122
<212> TYPE: PRT
<213> ORGANISM: Artificial
<220> FEATURE:
<223> OTHER INFORMATION: proteinmimic human inhibin beta-B

<400> SEQUENCE: 69

```
Arg His Arg Ile Arg Lys Arg Gly Leu Glu Cys Asp Gly Arg Thr Asn
1               5                   10                  15

Leu Cys Cys Arg Gln Gln Phe Phe Ile Asp Phe Arg Leu Ile Gly Trp
            20                  25                  30

Asn Asp Trp Ile Ile Ala Pro Thr Gly Tyr Tyr Gly Asn Tyr Cys Glu
        35                  40                  45

Gly Ser Cys Pro Ala Tyr Leu Ala Gly Val Pro Gly Ser Ala Ser Ser
    50                  55                  60

Phe His Thr Ala Val Val Asn Gln Tyr Arg Met Arg Gly Leu Asn Pro
65                  70                  75                  80

Gly Thr Val Asn Ser Cys Cys Ile Pro Thr Lys Leu Ser Thr Met Ser
                85                  90                  95

Met Leu Tyr Phe Asp Asp Glu Tyr Asn Ile Val Lys Arg Asp Val Pro
            100                 105                 110

Asn Met Ile Val Glu Glu Cys Gly Cys Ala
        115                 120


<210> SEQ ID NO 70
<211> LENGTH: 123
<212> TYPE: PRT
<213> ORGANISM: Artificial
<220> FEATURE:
<223> OTHER INFORMATION: proteinmimic human inhibin beta-C

<400> SEQUENCE: 70

Lys His Gln Ile His Arg Arg Gly Ile Asp Cys Gln Gly Gly Ser Arg
1               5                   10                  15

Met Cys Cys Arg Gln Glu Phe Phe Val Asp Phe Arg Glu Ile Gly Trp
            20                  25                  30

His Asp Trp Ile Ile Gln Pro Glu Gly Tyr Ala Met Asn Phe Cys Ile
        35                  40                  45

Gly Gln Cys Pro Leu His Ile Ala Gly Met Pro Gly Ile Ala Ala Ser
    50                  55                  60

Phe His Thr Ala Val Leu Asn Leu Leu Lys Ala Asn Thr Ala Ala Gly
65                  70                  75                  80

Thr Thr Gly Gly Gly Ser Cys Cys Val Pro Thr Ala Arg Arg Pro Leu
                85                  90                  95

Ser Leu Leu Tyr Tyr Asp Arg Asp Ser Asn Ile Val Lys Thr Asp Ile
            100                 105                 110

Pro Asp Met Val Val Glu Ala Cys Gly Cys Ser
        115                 120


<210> SEQ ID NO 71
<211> LENGTH: 121
<212> TYPE: PRT
<213> ORGANISM: Artificial
<220> FEATURE:
<223> OTHER INFORMATION: proteinmimic human inhibin beta-E

<400> SEQUENCE: 71

Ala Gly Arg Ala Arg Arg Arg Thr Pro Thr Cys Glu Pro Ala Thr Pro
1               5                   10                  15

Leu Cys Cys Arg Arg Asp His Tyr Val Asp Phe Gln Glu Leu Gly Trp
            20                  25                  30

Arg Asp Trp Ile Leu Gln Pro Glu Gly Tyr Gln Leu Asn Tyr Cys Ser
        35                  40                  45

Gly Gln Cys Pro Pro His Leu Ala Gly Ser Pro Gly Ile Ala Ala Ser
    50                  55                  60
```

Phe His Ser Ala Val Phe Ser Leu Leu Lys Ala Asn Asn Pro Trp Pro
65 70 75 80

Ala Ser Thr Ser Cys Cys Val Pro Thr Ala Arg Arg Pro Leu Ser Leu
85 90 95

Leu Tyr Leu Asp His Asn Gly Asn Val Val Lys Thr Asp Val Pro Asp
100 105 110

Met Val Val Glu Ala Cys Gly Cys Ser
115 120

<210> SEQ ID NO 72
<211> LENGTH: 123
<212> TYPE: PRT
<213> ORGANISM: Artificial
<220> FEATURE:
<223> OTHER INFORMATION: proteinmimic human left-right determination factor 2

<400> SEQUENCE: 72

Asp Leu Arg Asp Tyr Gly Ala Gln Gly Asp Cys Asp Pro Glu Ala Pro
1 5 10 15

Met Thr Glu Gly Thr Arg Cys Cys Arg Gln Glu Met Tyr Ile Asp Leu
20 25 30

Gln Gly Met Lys Trp Ala Lys Asn Trp Val Leu Glu Pro Pro Gly Phe
35 40 45

Leu Ala Tyr Glu Cys Val Gly Thr Cys Gln Gln Pro Pro Glu Ala Leu
50 55 60

Ala Phe Asn Trp Pro Phe Leu Gly Pro Arg Gln Cys Ile Ala Ser Glu
65 70 75 80

Thr Ala Ser Leu Pro Met Ile Val Ser Ile Lys Glu Gly Gly Arg Thr
85 90 95

Arg Pro Gln Val Val Ser Leu Pro Asn Met Arg Val Gln Lys Cys Ser
100 105 110

Cys Ala Ser Asp Gly Ala Leu Val Pro Arg Arg
115 120

<210> SEQ ID NO 73
<211> LENGTH: 109
<212> TYPE: PRT
<213> ORGANISM: Artificial
<220> FEATURE:
<223> OTHER INFORMATION: proteinmimic Mullerian-inhibiting factor

<400> SEQUENCE: 73

Ser Ala Gly Ala Thr Ala Ala Asp Gly Pro Cys Ala Leu Arg Glu Leu
1 5 10 15

Ser Val Asp Leu Arg Ala Glu Arg Ser Val Leu Ile Pro Glu Thr Tyr
20 25 30

Gln Ala Asn Asn Cys Gln Gly Val Cys Gly Trp Pro Gln Ser Asp Arg
35 40 45

Asn Pro Arg Tyr Gly Asn His Val Val Leu Leu Leu Lys Met Gln Val
50 55 60

Arg Gly Ala Ala Leu Ala Arg Pro Pro Cys Cys Val Pro Thr Ala Tyr
65 70 75 80

Ala Gly Lys Leu Leu Ile Ser Leu Ser Glu Glu Arg Ile Ser Ala His
85 90 95

His Val Pro Asn Met Val Ala Thr Glu Cys Gly Cys Arg
100 105

<210> SEQ ID NO 74
<211> LENGTH: 109
<212> TYPE: PRT
<213> ORGANISM: Artificial
<220> FEATURE:
<223> OTHER INFORMATION: proteinmimic nodal homolog 2-A African clawed frog

<400> SEQUENCE: 74

```
Ser Ala Gly Ala Thr Ala Ala Asp Gly Pro Cys Ala Leu Arg Glu Leu
1               5                   10                  15

Ser Val Asp Leu Arg Ala Glu Arg Ser Val Leu Ile Pro Glu Thr Tyr
            20                  25                  30

Gln Ala Asn Asn Cys Gln Gly Val Cys Gly Trp Pro Gln Ser Asp Arg
        35                  40                  45

Asn Pro Arg Tyr Gly Asn His Val Val Leu Leu Leu Lys Met Gln Val
    50                  55                  60

Arg Gly Ala Ala Leu Ala Arg Pro Pro Cys Cys Val Pro Thr Ala Tyr
65                  70                  75                  80

Ala Gly Lys Leu Leu Ile Ser Leu Ser Glu Glu Arg Ile Ser Ala His
                85                  90                  95

His Val Pro Asn Met Val Ala Thr Glu Cys Gly Cys Arg
            100                 105
```

<210> SEQ ID NO 75
<211> LENGTH: 110
<212> TYPE: PRT
<213> ORGANISM: Artificial
<220> FEATURE:
<223> OTHER INFORMATION: proteinmimic nodal homolog 4A African clawed frog

<400> SEQUENCE: 75

```
Val Pro Pro Ala Asp Ser Ser Arg Thr Leu Cys Arg Arg Val Asp Phe
1               5                   10                  15

Phe Val Asp Phe Lys Gln Ile Gly Trp Asp Ser Trp Ile Ile His Pro
            20                  25                  30

Met Lys Tyr Asn Ala Tyr Arg Cys Glu Gly Glu Cys Pro Ser Pro Val
        35                  40                  45

Asn Glu Ser Val Lys Pro Asn Asn His Ala Tyr Met Gln Ser Leu Leu
    50                  55                  60

Asn Tyr Val Lys Gly Lys Ala Pro Glu Val Cys Cys Val Pro Ile Arg
65                  70                  75                  80

Met Ser Ser Leu Ser Met Val Tyr Tyr Asp His Asp Asp Ile Ala Phe
                85                  90                  95

Gln Asn His Glu Gly Met Ile Val Glu Glu Cys Gly Cys Gln
            100                 105                 110
```

<210> SEQ ID NO 76
<211> LENGTH: 110
<212> TYPE: PRT
<213> ORGANISM: Artificial
<220> FEATURE:
<223> OTHER INFORMATION: proteinmimic human nodal homolog

<400> SEQUENCE: 76

```
His His Leu Pro Asp Arg Ser Gln Leu Cys Arg Lys Val Lys Phe Gln
1               5                   10                  15

Val Asp Phe Asn Leu Ile Gly Trp Gly Ser Trp Ile Ile Tyr Pro Lys
            20                  25                  30
```

Gln Tyr Asn Ala Tyr Arg Cys Glu Gly Glu Cys Pro Asn Pro Val Gly
35 40 45

Glu Glu Phe His Pro Thr Asn His Ala Tyr Ile Gln Ser Leu Leu Lys
50 55 60

Arg Tyr Gln Pro His Arg Val Pro Ser Thr Cys Cys Ala Pro Val Lys
65 70 75 80

Thr Lys Pro Leu Ser Met Leu Tyr Val Asp Asn Gly Arg Val Leu Leu
85 90 95

Asp His His Lys Asp Met Ile Val Glu Glu Cys Gly Cys Leu
100 105 110

<210> SEQ ID NO 77
<211> LENGTH: 101
<212> TYPE: PRT
<213> ORGANISM: Artificial
<220> FEATURE:
<223> OTHER INFORMATION: proteinmimic human neurturin

<400> SEQUENCE: 77

Arg Leu Gly Ala Arg Pro Cys Gly Leu Arg Glu Leu Glu Val Arg Val
1 5 10 15

Ser Glu Leu Gly Leu Gly Tyr Ala Ser Asp Glu Thr Val Leu Phe Arg
20 25 30

Tyr Cys Ala Gly Ala Cys Glu Ala Ala Ala Arg Val Tyr Asp Leu Gly
35 40 45

Leu Arg Arg Leu Arg Gln Arg Arg Arg Leu Arg Arg Glu Arg Val Arg
50 55 60

Ala Gln Pro Cys Cys Arg Pro Thr Ala Tyr Glu Asp Glu Val Ser Phe
65 70 75 80

Leu Asp Ala His Ser Arg Tyr His Thr Val His Glu Leu Ser Ala Arg
85 90 95

Glu Cys Ala Cys Val
100

<210> SEQ ID NO 78
<211> LENGTH: 95
<212> TYPE: PRT
<213> ORGANISM: Artificial
<220> FEATURE:
<223> OTHER INFORMATION: proteinmimic human persephin

<400> SEQUENCE: 78

Ala Leu Ser Gly Pro Cys Gln Leu Trp Ser Leu Thr Leu Ser Val Ala
1 5 10 15

Glu Leu Gly Leu Gly Tyr Ala Ser Glu Glu Lys Val Ile Phe Arg Tyr
20 25 30

Cys Ala Gly Ser Cys Pro Arg Gly Ala Arg Thr Gln His Gly Leu Ala
35 40 45

Leu Ala Arg Leu Gln Gly Gln Glu Arg Ala His Gly Gly Pro Cys Cys
50 55 60

Arg Pro Thr Arg Tyr Thr Asp Val Ala Phe Leu Asp Asp Arg His Arg
65 70 75 80

Trp Gln Arg Leu Pro Gln Leu Ser Ala Ala Ala Cys Gly Cys Gly
85 90 95

<210> SEQ ID NO 79
<211> LENGTH: 111
<212> TYPE: PRT

<213> ORGANISM: Artificial
<220> FEATURE:
<223> OTHER INFORMATION: proteinmimic protein screw Drosophila

<400> SEQUENCE: 79

Pro Val Asp Leu Tyr Arg Pro Pro Gln Ser Cys Glu Arg Leu Asn Phe
1 5 10 15

Thr Val Asp Phe Lys Glu Leu His Met His Asn Trp Val Ile Ala Pro
20 25 30

Lys Lys Phe Glu Ala Tyr Phe Cys Gly Gly Gly Cys Asn Phe Pro Leu
35 40 45

Gly Thr Lys Met Asn Ala Thr Asn His Ala Ile Val Gln Thr Leu Met
50 55 60

His Leu Lys Gln Pro His Leu Pro Lys Pro Cys Cys Val Pro Thr Val
65 70 75 80

Leu Gly Ala Ile Thr Ile Leu Arg Tyr Leu Asn Glu Asp Ile Ile Asp
85 90 95

Leu Thr Lys Tyr Gln Lys Ala Val Ala Lys Glu Cys Gly Cys His
100 105 110

<210> SEQ ID NO 80
<211> LENGTH: 108
<212> TYPE: PRT
<213> ORGANISM: Artificial
<220> FEATURE:
<223> OTHER INFORMATION: proteinmimic human TGF beta-1

<400> SEQUENCE: 80

Asn Tyr Cys Phe Ser Ser Thr Glu Lys Asn Cys Cys Val Arg Gln Leu
1 5 10 15

Tyr Ile Asp Phe Arg Lys Asp Leu Gly Trp Lys Trp Ile His Glu Pro
20 25 30

Lys Gly Tyr His Ala Asn Phe Cys Leu Gly Pro Cys Pro Tyr Ile Trp
35 40 45

Ser Leu Asp Thr Gln Tyr Ser Lys Val Leu Ala Leu Tyr Asn Gln His
50 55 60

Asn Pro Gly Ala Ser Ala Ala Pro Cys Cys Val Pro Gln Ala Leu Glu
65 70 75 80

Pro Leu Pro Ile Val Tyr Tyr Val Gly Arg Lys Pro Lys Val Glu Gln
85 90 95

Leu Ser Asn Met Ile Val Arg Ser Cys Lys Cys Ser
100 105

<210> SEQ ID NO 81
<211> LENGTH: 108
<212> TYPE: PRT
<213> ORGANISM: Artificial
<220> FEATURE:
<223> OTHER INFORMATION: proteinmimic human TGF beta-2

<400> SEQUENCE: 81

Ala Tyr Cys Phe Arg Asn Val Gln Asp Asn Cys Cys Leu Arg Pro Leu
1 5 10 15

Tyr Ile Asp Phe Lys Arg Asp Leu Gly Trp Lys Trp Ile His Glu Pro
20 25 30

Lys Gly Tyr Asn Ala Asn Phe Cys Ala Gly Ala Cys Pro Tyr Leu Trp
35 40 45

Ser Ser Asp Thr Gln His Ser Arg Val Leu Ser Leu Tyr Asn Thr Ile
50 55 60

Asn Pro Glu Ala Ser Ala Ser Pro Cys Cys Val Ser Gln Asp Leu Glu
65 70 75 80

Pro Leu Thr Ile Leu Tyr Tyr Ile Gly Lys Thr Pro Lys Ile Glu Gln
85 90 95

Leu Ser Asn Met Ile Val Lys Ser Cys Lys Cys Ser
100 105

<210> SEQ ID NO 82
<211> LENGTH: 108
<212> TYPE: PRT
<213> ORGANISM: Artificial
<220> FEATURE:
<223> OTHER INFORMATION: proteinmimic human TGF beta-3

<400> SEQUENCE: 82

Asn Tyr Cys Phe Arg Asn Leu Glu Glu Asn Cys Cys Val Arg Pro Leu
1 5 10 15

Tyr Ile Asp Phe Arg Gln Asp Leu Gly Trp Lys Trp Val His Glu Pro
20 25 30

Lys Gly Tyr Tyr Ala Asn Phe Cys Ser Gly Pro Cys Pro Tyr Leu Arg
35 40 45

Ser Ala Asp Thr Thr His Ser Thr Val Leu Gly Leu Tyr Asn Thr Leu
50 55 60

Asn Pro Glu Ala Ser Ala Ser Pro Cys Cys Val Pro Gln Asp Leu Glu
65 70 75 80

Pro Leu Thr Ile Leu Tyr Tyr Val Gly Arg Thr Pro Lys Val Glu Gln
85 90 95

Leu Ser Asn Met Val Val Lys Ser Cys Lys Cys Ser
100 105

<210> SEQ ID NO 83
<211> LENGTH: 112
<212> TYPE: PRT
<213> ORGANISM: Artificial
<220> FEATURE:
<223> OTHER INFORMATION: proteinmimic univin urchin

<400> SEQUENCE: 83

Ser Phe Pro Thr Ala Ser Leu Thr Asn Leu Cys Gln Arg His Arg Leu
1 5 10 15

Phe Val Ser Phe Arg Asp Val Gly Trp Glu Asn Trp Ile Ile Ala Pro
20 25 30

Met Gly Tyr Gln Ala Tyr Tyr Cys Asp Gly Glu Cys Pro Phe Pro Leu
35 40 45

Gly Glu Arg Leu Asn Gly Thr Asn His Ala Ile Ile Gln Thr Leu Val
50 55 60

Asn Ser Ile Asp Asn Arg Ala Val Pro Lys Val Cys Cys Ala Pro Thr
65 70 75 80

Lys Leu Ser Gly Ile Ser Met Leu Tyr Phe Asp Asn Asn Glu Asn Val
85 90 95

Val Leu Arg Gln Tyr Glu Asp Met Val Val Glu Ala Cys Gly Cys Arg
100 105 110

<210> SEQ ID NO 84
<211> LENGTH: 103
<212> TYPE: PRT
<213> ORGANISM: Artificial
<220> FEATURE:
<223> OTHER INFORMATION: proteinmimic Mullerian inhibitory substance hatcheri

<400> SEQUENCE: 84

Gly Leu Asp Ser Pro Ser Gly Ser Asn Ile Cys Gly Leu Arg Ser Leu
1 5 10 15

Thr Val Ser Phe Glu Lys Leu Leu Leu Gly Pro Gln Thr Ala Asn Ile
20 25 30

Asn Asn Cys Gln Gly Ser Cys Ala Phe Pro Leu Thr Asn Gly Asn Asn
35 40 45

His Ala Val Leu Leu Asn Ser His Val Glu Ser Gly Asn Ala Asn Glu
50 55 60

Arg Ala Pro Cys Cys Val Pro Val Ala Tyr Asp Pro Leu Glu Val Met
65 70 75 80

Asp Trp Asn Ala Glu Glu Ser Phe Leu Ser Ile Lys Pro Asp Met Ile
85 90 95

Val Lys Glu Cys Gly Cys Arg
100

<210> SEQ ID NO 85
<211> LENGTH: 111
<212> TYPE: PRT
<213> ORGANISM: Artificial
<220> FEATURE:
<223> OTHER INFORMATION: proteinmimic decaplentaplegic-like protein sea anemone

<400> SEQUENCE: 85

Gly Gly Ala Lys Arg Arg Arg Pro Gln Tyr Cys Arg Arg His Pro Leu
1 5 10 15

Tyr Val Asp Phe Thr Asp Val Gly Trp Asn Asp Trp Ile Val Ala Pro
20 25 30

Pro Gly Tyr His Ala Phe Tyr Cys Thr Gly Val Cys Pro Tyr Pro Ile
35 40 45

Ala Lys His Leu Asn Ala Thr Asn His Ala Ile Val Gln Thr Ile Met
50 55 60

Asn Thr Val Asp Ser Asn Val Pro Asn Ala Cys Cys Ile Pro Thr Thr
65 70 75 80

Leu Asn Pro Ile Ser Ile Leu Ser Leu Asn Glu Phe Asp Lys Val Val
85 90 95

Leu Lys Asn Tyr Lys Asp Met Val Ile Glu Gly Cys Gly Cys Arg
100 105 110

<210> SEQ ID NO 86
<211> LENGTH: 112
<212> TYPE: PRT
<213> ORGANISM: Artificial
<220> FEATURE:
<223> OTHER INFORMATION: proteinmimic decaplentaplegic hormone analog roundworm

<400> SEQUENCE: 86

His His Asn Thr Glu Ala Glu Ser Asn Leu Cys Arg Arg Thr Asp Phe
1 5 10 15

Tyr Val Asp Phe Asp Asp Leu Asn Trp Gln Asp Trp Ile Met Ala Pro
20 25 30

Lys Gly Tyr Asp Ala Tyr Gln Cys Gln Gly Ser Cys Pro Asn Pro Met
35 40 45

Pro Ala Gln Leu Asn Ala Thr Asn His Ala Ile Ile Gln Ser Leu Leu
50 55 60

His Ser Leu Arg Pro Asp Glu Val Pro Pro Pro Cys Cys Val Pro Thr
65 70 75 80

Glu Thr Ser Pro Leu Ser Ile Leu Tyr Met Asp Val Asp Lys Val Ile
85 90 95

Val Ile Arg Glu Tyr Ala Asp Met Arg Val Glu Ser Cys Gly Cys Arg
100 105 110

<210> SEQ ID NO 87
<211> LENGTH: 111
<212> TYPE: PRT
<213> ORGANISM: Artificial
<220> FEATURE:
<223> OTHER INFORMATION: proteinmimic CG1901-PB isoform B Drosophila

<400> SEQUENCE: 87

Thr Asn Asn Cys Tyr Lys Leu His Gln Arg Cys Cys Arg Asn Gln Leu
1 5 10 15

Asp Val Ala Phe Lys Ser Ile Lys Gly Phe Glu Phe Ile Leu Pro Gln
20 25 30

Lys Val Phe Asp Ala Gly Tyr Cys His Gly Arg Cys Pro Pro Arg His
35 40 45

Asn Pro Ala His His His Ala Leu Leu Gln Ser Leu Ile Trp Gln Glu
50 55 60

Asp His Lys Arg Ala Pro Arg Pro Cys Cys Thr Pro Ser Lys Leu Glu
65 70 75 80

Met Leu Glu Ile Leu His Val Asp Glu Asn His Ser Asp Lys Leu Lys
85 90 95

Ile Ser Thr Trp Ser Asp Met Gln Val Val Glu Cys Ala Cys Ser
100 105 110

<210> SEQ ID NO 88
<211> LENGTH: 114
<212> TYPE: PRT
<213> ORGANISM: Artificial
<220> FEATURE:
<223> OTHER INFORMATION: proteinmimic CG16987-PA isoform A Drosophila

<400> SEQUENCE: 88

Ser Ile Asn Cys Ser Ser Gly Met Thr Glu Cys Cys Arg Glu His Leu
1 5 10 15

Tyr Ile Ser Phe Arg Asp Ile Gly Trp Ser Asn Trp Ile Leu Lys Pro
20 25 30

Glu Gly Tyr Asn Ala Tyr Phe Cys Arg Gly Ser Cys Ser Ser Val Ala
35 40 45

Ser Val Thr Gln Ala Ala Ser His His Ser Ser Ile Met Lys Ile Leu
50 55 60

Ser Thr Ser Gly Ala Asn Lys Ser Leu Glu Leu Val Pro Cys Cys Thr
65 70 75 80

Ala Lys Gln Tyr Ser Ser Leu Gln Leu Val Val Met Asp Ser Ser Asn
85 90 95

Thr Ala Thr Val Lys Thr Leu Pro Asn Met Val Val Glu Ser Cys Gly
100 105 110

Cys Arg

<210> SEQ ID NO 89
<211> LENGTH: 102
<212> TYPE: PRT
<213> ORGANISM: Artificial

-continued

<220> FEATURE:
<223> OTHER INFORMATION: proteinmimic myoglianin Drosophila

<400> SEQUENCE: 89

Asp Cys Thr Glu Asn Asp His Asp Met Arg Cys Cys Arg Tyr Pro Leu
1               5                   10                  15

Lys Val Asn Phe Thr Ser Phe Gly Trp His Phe Val Val Ala Pro Thr
            20                  25                  30

Ser Phe Asp Ala Tyr Phe Cys Ser Gly Asp Cys Lys Val Gly Tyr Leu
        35                  40                  45

Glu Gln Tyr Pro His Thr His Leu Ala Ala Leu Thr Thr Ser Ala Thr
    50                  55                  60

Pro Cys Cys Ser Pro Thr Lys Met Ser Ser Leu Ser Leu Leu Tyr Phe
65                  70                  75                  80

Asp Asp Asn His Asn Leu Val Leu Ser Val Ile Pro Asn Met Ser Val
                85                  90                  95

Glu Gly Cys Ser Cys Ser
            100

<210> SEQ ID NO 90
<211> LENGTH: 112
<212> TYPE: PRT
<213> ORGANISM: Artificial
<220> FEATURE:
<223> OTHER INFORMATION: proteinmimic CBR-DBL-1 protein roundworm

<400> SEQUENCE: 90

His His Asn Thr Glu Ala Glu Ser Asn Leu Cys Arg Arg Thr Asp Leu
1               5                   10                  15

Tyr Val Asp Phe Asp Asp Leu Gly Trp Gln Asp Trp Ile Met Ala Pro
            20                  25                  30

Lys Gly Tyr Asp Ala Tyr Gln Cys Gln Gly Ser Cys Pro Asn Pro Met
        35                  40                  45

Pro Ala Gln Leu Asn Ala Thr Asn His Ala Ile Ile Gln Ser Leu Leu
    50                  55                  60

His Ser Leu Lys Pro Asp Glu Val Pro Pro Pro Cys Cys Val Pro Thr
65                  70                  75                  80

Glu Thr Ser Pro Leu Ser Ile Leu Tyr Met Asp Val Asp Lys Val Ile
                85                  90                  95

Val Ile Arg Glu Tyr Ala Asp Met Arg Val Asp Ser Cys Gly Cys Arg
            100                 105                 110

<210> SEQ ID NO 91
<211> LENGTH: 106
<212> TYPE: PRT
<213> ORGANISM: Artificial
<220> FEATURE:
<223> OTHER INFORMATION: proteinmimic CBR-UNC-129 protein roundworm

<400> SEQUENCE: 91

Arg Val Val Leu Leu Gln Asn Lys Asn Arg Cys His Lys Glu Gly Thr
1               5                   10                  15

Leu Val Ser Leu Lys His Phe Gly Trp Asp Lys Phe Val Met Glu Pro
            20                  25                  30

Arg Thr Ile Glu Thr Ser Phe Cys Lys Gly Lys Cys Ala Lys Pro Met
        35                  40                  45

Leu Ala Ser Gly Lys Ala Ser Asn His Ala Met Leu Gln Ser Leu Phe
    50                  55                  60

-continued

```
Ala Ala Glu Pro Val Cys Cys Ala Pro Thr Asn Leu Lys Ser Leu Asn
65                  70                  75                  80

Phe Leu Tyr Arg Asp Glu Lys Gly Arg Thr Val Ile Arg Asn Tyr Ser
                85                  90                  95

Lys Met Leu Ile Gly Ser Cys Ser Cys Leu
            100                 105


<210> SEQ ID NO 92
<211> LENGTH: 100
<212> TYPE: PRT
<213> ORGANISM: Artificial
<220> FEATURE:
<223> OTHER INFORMATION: proteinmimic hCG-beta v1

<400> SEQUENCE: 92

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys
            100


<210> SEQ ID NO 93
<211> LENGTH: 100
<212> TYPE: PRT
<213> ORGANISM: Artificial
<220> FEATURE:
<223> OTHER INFORMATION: proteinmimic hCG-beta v2

<400> SEQUENCE: 93

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys
            100


<210> SEQ ID NO 94
<211> LENGTH: 100
<212> TYPE: PRT
<213> ORGANISM: Artificial
<220> FEATURE:
<223> OTHER INFORMATION: proteinmimic hCG-beta
```

<400> SEQUENCE: 94

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys
            100

<210> SEQ ID NO 95
<211> LENGTH: 94
<212> TYPE: PRT
<213> ORGANISM: Artificial
<220> FEATURE:
<223> OTHER INFORMATION: proteinmimic hFSH

<400> SEQUENCE: 95

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Lys Cys Asp Ser Asp Ser Thr Asp Cys Thr
                85                  90

<210> SEQ ID NO 96
<211> LENGTH: 102
<212> TYPE: PRT
<213> ORGANISM: Artificial
<220> FEATURE:
<223> OTHER INFORMATION: proteinmimic glycoprotein hormone beta-5

<400> SEQUENCE: 96

Ser Ser Gly Asn Leu Arg Thr Phe Val Gly Cys Ala Val Arg Glu Phe
1               5                   10                  15

Thr Phe Leu Ala Lys Lys Pro Gly Cys Arg Gly Leu Arg Ile Thr Thr
            20                  25                  30

Asp Ala Cys Trp Gly Arg Cys Glu Thr Trp Glu Lys Pro Ile Leu Glu
        35                  40                  45

Pro Pro Tyr Ile Glu Ala His His Arg Val Cys Thr Tyr Asn Glu Thr
    50                  55                  60

Lys Gln Val Thr Val Lys Leu Pro Asn Cys Ala Pro Gly Val Asp Pro
65                  70                  75                  80

Phe Tyr Thr Tyr Pro Val Ala Ile Arg Cys Asp Cys Gly Ala Cys Ser
                85                  90                  95

Thr Ala Thr Thr Glu Cys
100

<210> SEQ ID NO 97
<211> LENGTH: 102
<212> TYPE: PRT
<213> ORGANISM: Artificial
<220> FEATURE:
<223> OTHER INFORMATION: proteinmimic gonadotropin beta-1 eel

<400> SEQUENCE: 97

Ser Ser Gly Asn Leu Arg Thr Phe Val Gly Cys Ala Val Arg Glu Phe
1 5 10 15

Thr Phe Leu Ala Lys Lys Pro Gly Cys Arg Gly Leu Arg Ile Thr Thr
20 25 30

Asp Ala Cys Trp Gly Arg Cys Glu Thr Trp Glu Lys Pro Ile Leu Glu
35 40 45

Pro Pro Tyr Ile Glu Ala His His Arg Val Cys Thr Tyr Asn Glu Thr
50 55 60

Lys Gln Val Thr Val Lys Leu Pro Asn Cys Ala Pro Gly Val Asp Pro
65 70 75 80

Phe Tyr Thr Tyr Pro Val Ala Ile Arg Cys Asp Cys Gly Ala Cys Ser
85 90 95

Thr Ala Thr Thr Glu Cys
100

<210> SEQ ID NO 98
<211> LENGTH: 97
<212> TYPE: PRT
<213> ORGANISM: Artificial
<220> FEATURE:
<223> OTHER INFORMATION: proteinmimic gonadotropin beta-2 eel

<400> SEQUENCE: 98

Ser Leu Leu Leu Pro Cys Glu Pro Ile Asn Glu Thr Ile Ser Val Glu
1 5 10 15

Lys Asp Gly Cys Pro Lys Cys Leu Val Phe Gln Thr Ser Ile Cys Ser
20 25 30

Gly His Cys Ile Thr Lys Asp Pro Ser Tyr Lys Ser Pro Leu Ser Thr
35 40 45

Val Tyr Gln Arg Val Cys Thr Tyr Arg Asp Val Arg Tyr Glu Thr Val
50 55 60

Arg Leu Pro Asp Cys Arg Pro Gly Val Asp Pro His Val Thr Phe Pro
65 70 75 80

Val Ala Leu Ser Cys Asp Cys Asn Leu Cys Thr Met Asp Thr Ser Asp
85 90 95

Cys

<210> SEQ ID NO 99
<211> LENGTH: 97
<212> TYPE: PRT
<213> ORGANISM: Artificial
<220> FEATURE:
<223> OTHER INFORMATION: proteinmimic gonadotropin beta eel

<400> SEQUENCE: 99

Ser Val Leu Gln Pro Cys Gln Pro Ile Asn Glu Thr Ile Ser Val Glu
1 5 10 15

Lys Asp Gly Cys Pro Lys Cys Leu Val Phe Gln Thr Ser Ile Cys Ser
20 25 30

Gly His Cys Ile Thr Lys Asp Pro Ser Tyr Lys Ser Pro Leu Ser Thr
35 40 45

Val Tyr Gln Arg Val Cys Thr Tyr Arg Asp Val Arg Tyr Glu Thr Val
50 55 60

Arg Leu Pro Asp Cys Arg Pro Gly Val Asp Pro His Val Thr Phe Pro
65 70 75 80

Val Ala Leu Ser Cys Asp Cys Asn Leu Cys Thr Met Asp Thr Ser Asp
85 90 95

Cys

<210> SEQ ID NO 100
<211> LENGTH: 100
<212> TYPE: PRT
<213> ORGANISM: Artificial
<220> FEATURE:
<223> OTHER INFORMATION: proteinmimic hLH beta

<400> SEQUENCE: 100

Ser Arg Glu Pro Leu Arg Pro Trp Cys His Pro Ile Asn Ala Ile Leu
1 5 10 15

Ala Val Glu Lys Glu Gly Cys Pro Val Cys Ile Thr Val Asn Thr Thr
20 25 30

Ile Cys Ala Gly Tyr Cys Pro Thr Met Met Arg Val Leu Gln Ala Val
35 40 45

Leu Pro Pro Leu Pro Gln Val Val Cys Thr Tyr Arg Asp Val Arg Phe
50 55 60

Glu Ser Ile Arg Leu Pro Gly Cys Pro Arg Gly Val Asp Pro Val Val
65 70 75 80

Ser Phe Pro Val Ala Leu Ser Cys Arg Cys Gly Pro Cys Arg Arg Ser
85 90 95

Thr Ser Asp Cys
100

<210> SEQ ID NO 101
<211> LENGTH: 95
<212> TYPE: PRT
<213> ORGANISM: Artificial
<220> FEATURE:
<223> OTHER INFORMATION: proteinmimic hTSH beta

<400> SEQUENCE: 101

Phe Cys Ile Pro Thr Glu Tyr Thr Met His Ile Glu Arg Arg Glu Cys
1 5 10 15

Ala Tyr Cys Leu Thr Ile Asn Thr Thr Ile Cys Ala Gly Tyr Cys Met
20 25 30

Thr Arg Asp Ile Asn Gly Lys Leu Phe Leu Pro Lys Tyr Ala Leu Ser
35 40 45

Gln Asp Val Cys Thr Tyr Arg Asp Phe Ile Tyr Arg Thr Val Glu Ile
50 55 60

Pro Gly Cys Pro Leu His Val His Pro Tyr Phe Ser Tyr Pro Val Ala
65 70 75 80

Leu Ser Cys Lys Cys Gly Lys Cys Asn Thr Asp Tyr Ser Asp Cys
85 90 95

<210> SEQ ID NO 102
<211> LENGTH: 100
<212> TYPE: PRT
<213> ORGANISM: Artificial
<220> FEATURE:
<223> OTHER INFORMATION: proteinmimic protein roundworm

<400> SEQUENCE: 102

```
Cys Met Arg Leu Val Pro Gly Phe Asn Pro Leu Arg Gln Val Asp Ala
1               5                   10                  15

Asn Gly Lys Glu Cys Arg Gly Asn Val Glu Leu Pro Phe Cys Lys Gly
            20                  25                  30

Tyr Cys Lys Thr Ser Glu Ser Gly Thr His Gly Phe Pro Pro Arg Val
        35                  40                  45

Gln Asn Ser Lys Val Cys Thr Leu Val Thr Thr Ser Thr Arg Lys Val
    50                  55                  60

Val Leu Asp Asp Cys Asp Asp Gly Ala Asp Glu Ser Val Lys Phe Val
65                  70                  75                  80

Met Val Pro His Gly Thr Asp Cys Glu Cys Ser Ala Val Pro Leu Glu
                85                  90                  95

Gln His His Ser
            100
```

<210> SEQ ID NO 103
<211> LENGTH: 117
<212> TYPE: PRT
<213> ORGANISM: Artificial
<220> FEATURE:
<223> OTHER INFORMATION: proteinmimic hBDNF

<400> SEQUENCE: 103

```
Asp Pro Ala Arg Arg Gly Glu Leu Ser Val Cys Asp Ser Ile Ser Glu
1               5                   10                  15

Trp Val Thr Ala Ala Asp Lys Lys Thr Ala Val Asp Met Ser Gly Gly
            20                  25                  30

Thr Val Thr Val Leu Glu Lys Val Pro Val Ser Lys Gly Gln Leu Lys
        35                  40                  45

Gln Tyr Phe Tyr Glu Thr Lys Cys Asn Pro Met Gly Tyr Thr Lys Glu
    50                  55                  60

Gly Cys Arg Gly Ile Asp Lys Arg His Trp Asn Ser Gln Cys Arg Thr
65                  70                  75                  80

Thr Gln Ser Tyr Val Arg Ala Leu Thr Met Asp Ser Lys Lys Arg Ile
                85                  90                  95

Gly Trp Arg Phe Ile Arg Ile Asp Thr Ser Cys Val Cys Thr Leu Thr
            100                 105                 110

Ile Lys Arg Gly Arg
        115
```

<210> SEQ ID NO 104
<211> LENGTH: 116
<212> TYPE: PRT
<213> ORGANISM: Artificial
<220> FEATURE:
<223> OTHER INFORMATION: proteinmimic viper venom nerve growth factor 1

<400> SEQUENCE: 104

```
Pro Val His Asn Gln Gly Glu Tyr Ser Val Cys Asp Ser Val Ser Val
1               5                   10                  15

Trp Val Ala Asn Lys Thr Thr Ala Thr Asp Ile Arg Gly Asn Leu Val
            20                  25                  30

Thr Val Met Val Asp Ile Asn Leu Asn Asn Asn Val Tyr Lys Gln Tyr
        35                  40                  45
```

Phe Phe Glu Thr Lys Cys Arg Asn Pro Asn Pro Val Pro Ser Gly Cys
    50                  55                  60

Arg Gly Ile Asp Ala Arg His Trp Asn Ser Tyr Cys Thr Thr Thr His
65                  70                  75                  80

Thr Tyr Val Arg Ala Leu Thr Lys Glu Gly Asn Gln Ala Ser Trp Arg
                85                  90                  95

Phe Ile Arg Ile Asp Thr Ala Cys Val Cys Val Ile Ser Arg Ile Thr
            100                 105                 110

Glu Asn Phe Gly
        115

<210> SEQ ID NO 105
<211> LENGTH: 114
<212> TYPE: PRT
<213> ORGANISM: Artificial
<220> FEATURE:
<223> OTHER INFORMATION: proteinmimic snake venom nerve growth factor 2

<400> SEQUENCE: 105

Pro Val Asn Asp His Gly Glu Tyr Ser Val Cys Asp Ser Val Ser Val
1               5                   10                  15

Trp Val Asn Lys Thr Thr Ala Thr Asp Ile Lys Gly Lys Pro Val Thr
            20                  25                  30

Val Met Val Asp Val Asn Leu Asn Asn His Val Tyr Lys Gln Tyr Phe
        35                  40                  45

Phe Glu Thr Lys Cys Lys Asn Pro Asn Pro Val Pro Ser Gly Cys Arg
    50                  55                  60

Gly Ile Asp Ser Arg His Trp Asn Ser Tyr Cys Thr Thr Thr Gln Ser
65                  70                  75                  80

Phe Val Lys Ala Leu Thr Lys Glu Gly Asn Gln Ala Ser Trp Arg Phe
                85                  90                  95

Ile Arg Ile Asp Thr Ala Cys Val Cys Val Ile Ser Arg Lys Thr Gly
            100                 105                 110

Asn Phe

<210> SEQ ID NO 106
<211> LENGTH: 116
<212> TYPE: PRT
<213> ORGANISM: Artificial
<220> FEATURE:
<223> OTHER INFORMATION: proteinmimic snake venom nerve growth factor 3

<400> SEQUENCE: 106

Pro Val His Asn Gln Gly Glu His Ser Val Cys Asp Ser Val Ser Asp
1               5                   10                  15

Trp Val Ile Lys Thr Thr Ala Thr Asp Ile Arg Gly Asn Met Val Thr
            20                  25                  30

Val Met Val Asp Ile Asn Arg Asp Asn Glu Val Tyr Lys Gln Tyr Phe
        35                  40                  45

Phe Glu Thr Lys Cys Arg Asn Pro Asn Pro Asn Pro Val Gln Ser Glu
    50                  55                  60

Cys Arg Gly Ile Asp Ser Arg Leu Trp Asn Ser Tyr Cys Thr Thr Thr
65                  70                  75                  80

Arg Thr Phe Val Arg Ala Leu Thr Met Glu Gly Asn Gln Ala Ser Trp
                85                  90                  95

Arg Phe Ile Arg Ile Asp Thr Ala Cys Val Cys Val Ile Ile Arg Lys
            100                 105                 110

```
Thr Asp Asn Phe
        115


<210> SEQ ID NO 107
<211> LENGTH: 116
<212> TYPE: PRT
<213> ORGANISM: Artificial
<220> FEATURE:
<223> OTHER INFORMATION: proteinmimic snake venom nerve growth factor 4

<400> SEQUENCE: 107

Pro Val His Asn Gln Gly Glu His Ser Val Cys Asp Ser Val Ser Asp
1               5                   10                  15

Trp Val Ile Lys Thr Thr Ala Thr Asp Ile Arg Gly Asn Val Val Thr
            20                  25                  30

Val Met Glu Asp Ile Asn Leu Asn Asn Glu Val Tyr Lys Gln Tyr Phe
        35                  40                  45

Phe Glu Thr Lys Cys Arg Asn Pro Asn Pro Asn Pro Val Gln Ser Glu
    50                  55                  60

Cys Arg Gly Ile Asp Ser Arg Leu Trp Asn Ser Tyr Cys Thr Thr Thr
65                  70                  75                  80

Gln Thr Phe Val Arg Ala Leu Thr Met Glu Gly Asn Gln Ala Ser Trp
                85                  90                  95

Arg Phe Ile Arg Ile Asp Thr Ala Cys Val Cys Val Ile Ile Arg Lys
            100                 105                 110

Thr Asp Asn Phe
        115


<210> SEQ ID NO 108
<211> LENGTH: 115
<212> TYPE: PRT
<213> ORGANISM: Artificial
<220> FEATURE:
<223> OTHER INFORMATION: proteinmimic snake venom nerve growth factor 5

<400> SEQUENCE: 108

Pro Val Tyr Asn Arg Gly Glu His Ser Val Cys Asp Ser Val Ser Val
1               5                   10                  15

Trp Val Thr Asn Lys Thr Lys Ala Thr Asp Ile Lys Gly Asn Met Val
            20                  25                  30

Thr Val Met Val Asp Ile Asn Leu Asn Asn Glu Val Tyr Lys Gln Tyr
        35                  40                  45

Phe Phe Glu Thr Lys Cys Arg Asn Pro Asn Pro Val Pro Ser Gly Cys
    50                  55                  60

Arg Gly Thr Asp Ser Arg His Trp Asn Ser Tyr Cys Thr Thr Thr Gln
65                  70                  75                  80

Thr Phe Val Arg Ala Leu Thr Met Glu Gly Asn Gln Ala Ser Trp Arg
                85                  90                  95

Phe Ile Arg Ile Asp Thr Ala Cys Val Cys Val Ile Ile Arg Lys Thr
            100                 105                 110

Asp Asn Phe
        115


<210> SEQ ID NO 109
<211> LENGTH: 115
<212> TYPE: PRT
<213> ORGANISM: Artificial
<220> FEATURE:
<223> OTHER INFORMATION: proteinmimic snake venom nerve growth factor
```

<400> SEQUENCE: 109

```
Pro Val His Asn Leu Gly Glu His Ser Val Cys Asp Ser Ile Ser Val
1               5                   10                  15

Trp Val Thr Asn Lys Thr Lys Ala Thr Asp Ile Lys Asp Asn Met Val
            20                  25                  30

Thr Val Met Val Asp Ile Asn Leu Asn Asn Glu Val Tyr Lys Gln Tyr
        35                  40                  45

Phe Phe Glu Thr Lys Cys Arg Asn Pro Asn Pro Val Pro Ser Gly Cys
    50                  55                  60

Arg Gly Thr Asp Ser Arg His Trp Asn Ser Tyr Cys Thr Thr Thr Gln
65                  70                  75                  80

Thr Phe Val Lys Ala Leu Thr Met Glu Gly Asn Arg Ala Ser Trp Arg
                85                  90                  95

Phe Ile Arg Ile Asp Thr Ala Cys Val Cys Val Ile Ser Arg Lys Thr
            100                 105                 110

Asp Asn Phe
        115
```

<210> SEQ ID NO 110
<211> LENGTH: 116
<212> TYPE: PRT
<213> ORGANISM: Artificial
<220> FEATURE:
<223> OTHER INFORMATION: proteinmimic hBNGF

<400> SEQUENCE: 110

```
Pro Ile Phe His Arg Gly Glu Phe Ser Val Cys Asp Ser Val Ser Val
1               5                   10                  15

Trp Val Gly Asp Lys Thr Thr Ala Thr Asp Ile Lys Gly Lys Glu Val
            20                  25                  30

Met Val Leu Gly Glu Val Asn Ile Asn Asn Ser Val Phe Lys Gln Tyr
        35                  40                  45

Phe Phe Glu Thr Lys Cys Arg Asp Pro Asn Pro Val Asp Ser Gly Cys
    50                  55                  60

Arg Gly Ile Asp Ser Lys His Trp Asn Ser Tyr Cys Thr Thr Thr His
65                  70                  75                  80

Thr Phe Val Lys Ala Leu Thr Met Asp Gly Lys Gln Ala Ala Trp Arg
                85                  90                  95

Phe Ile Arg Ile Asp Thr Ala Cys Val Cys Val Leu Ser Arg Lys Ala
            100                 105                 110

Val Arg Arg Ala
        115
```

<210> SEQ ID NO 111
<211> LENGTH: 116
<212> TYPE: PRT
<213> ORGANISM: Artificial
<220> FEATURE:
<223> OTHER INFORMATION: proteinmimic rBNGF

<400> SEQUENCE: 111

```
Pro Val Phe His Met Gly Glu Phe Ser Val Cys Asp Ser Val Ser Val
1               5                   10                  15

Trp Val Gly Asp Lys Thr Thr Ala Thr Asp Ile Lys Gly Lys Glu Val
            20                  25                  30

Thr Val Leu Gly Glu Val Asn Ile Asn Asn Ser Val Phe Lys Gln Tyr
        35                  40                  45
```

-continued

Phe Phe Glu Thr Lys Cys Arg Ala Pro Asn Pro Val Glu Ser Gly Cys
    50                  55                  60

Arg Gly Ile Asp Ser Lys His Trp Asn Ser Tyr Cys Thr Thr Thr His
65                  70                  75                  80

Thr Phe Val Lys Ala Leu Thr Thr Asp Asp Lys Gln Ala Ala Trp Arg
                85                  90                  95

Phe Ile Arg Ile Asp Thr Ala Cys Val Cys Val Leu Ser Arg Lys Ala
            100                 105                 110

Ala Arg Arg Gly
        115

<210> SEQ ID NO 112
<211> LENGTH: 116
<212> TYPE: PRT
<213> ORGANISM: Artificial
<220> FEATURE:
<223> OTHER INFORMATION: proteinmimic hNTF-3

<400> SEQUENCE: 112

His Lys Ser His Arg Gly Glu Tyr Ser Val Cys Asp Ser Glu Ser Leu
1               5                   10                  15

Trp Val Thr Asp Lys Ser Ser Ala Ile Asp Ile Arg Gly His Gln Val
            20                  25                  30

Thr Val Leu Gly Glu Ile Lys Thr Gly Asn Ser Pro Val Lys Gln Tyr
        35                  40                  45

Phe Tyr Glu Thr Arg Cys Lys Glu Ala Arg Pro Val Lys Asn Gly Cys
    50                  55                  60

Arg Gly Ile Asp Asp Lys His Trp Asn Ser Gln Cys Lys Thr Ser Gln
65                  70                  75                  80

Thr Tyr Val Arg Ala Leu Thr Ser Glu Asn Asn Lys Leu Val Gly Trp
                85                  90                  95

Arg Trp Ile Arg Ile Asp Thr Ser Cys Val Cys Ala Leu Ser Arg Lys
            100                 105                 110

Ile Gly Arg Thr
        115

<210> SEQ ID NO 113
<211> LENGTH: 116
<212> TYPE: PRT
<213> ORGANISM: Artificial
<220> FEATURE:
<223> OTHER INFORMATION: proteinmimic hNTF-4/5

<400> SEQUENCE: 113

His Lys Ser His Arg Gly Glu Tyr Ser Val Cys Asp Ser Glu Ser Leu
1               5                   10                  15

Trp Val Thr Asp Lys Ser Ser Ala Ile Asp Ile Arg Gly His Gln Val
            20                  25                  30

Thr Val Leu Gly Glu Ile Lys Thr Gly Asn Ser Pro Val Lys Gln Tyr
        35                  40                  45

Phe Tyr Glu Thr Arg Cys Lys Glu Ala Arg Pro Val Lys Asn Gly Cys
    50                  55                  60

Arg Gly Ile Asp Asp Lys His Trp Asn Ser Gln Cys Lys Thr Ser Gln
65                  70                  75                  80

Thr Tyr Val Arg Ala Leu Thr Ser Glu Asn Asn Lys Leu Val Gly Trp
                85                  90                  95

Arg Trp Ile Arg Ile Asp Thr Ser Cys Val Cys Ala Leu Ser Arg Lys
            100                 105                 110

Ile Gly Arg Thr
115

<210> SEQ ID NO 114
<211> LENGTH: 131
<212> TYPE: PRT
<213> ORGANISM: Artificial
<220> FEATURE:
<223> OTHER INFORMATION: proteinmimic neurtrophin-7 zebrafish

<400> SEQUENCE: 114

Asp Phe Leu His Arg Gly Glu Tyr Ser Val Cys Asp Ser Glu Glu His
1 5 10 15

Trp Val Gly Asn Leu Thr His Ala Thr Asp Leu Gly Gly Asn Glu Val
20 25 30

Met Val Leu Pro His Phe Arg Ile Asn Asn Val Val Lys Lys Gln Leu
35 40 45

Phe Tyr Glu Thr Thr Cys Arg Val Lys Lys Pro Ile Gly Ala Pro Lys
50 55 60

Pro Gly Gln Gly Ala Ser Gly Val Lys Ala Gly Thr Ser Ser Cys Arg
65 70 75 80

Gly Ile Asp Ser Lys His Trp Val Ser Tyr Cys Thr Asn Thr His Thr
85 90 95

Tyr Val Arg Ala Leu Thr Ser Tyr Lys Asn Gln Ile Ala Trp Arg Phe
100 105 110

Ile Arg Ile Asn Ala Ala Cys Val Cys Val Leu Ser Arg Asn Ser Trp
115 120 125

Arg His Gly
130

<210> SEQ ID NO 115
<211> LENGTH: 103
<212> TYPE: PRT
<213> ORGANISM: Artificial
<220> FEATURE:
<223> OTHER INFORMATION: proteinmimic hPDGF A

<400> SEQUENCE: 115

Ser Ile Glu Glu Ala Val Pro Ala Val Cys Lys Thr Arg Thr Val Ile
1 5 10 15

Tyr Glu Ile Pro Arg Ser Gln Val Asp Pro Thr Ser Ala Asn Phe Leu
20 25 30

Ile Trp Pro Pro Cys Val Glu Val Lys Arg Cys Thr Gly Cys Cys Asn
35 40 45

Thr Ser Ser Val Lys Cys Gln Pro Ser Arg Val His His Arg Ser Val
50 55 60

Lys Val Ala Lys Val Glu Tyr Val Arg Lys Lys Pro Lys Leu Lys Glu
65 70 75 80

Val Gln Val Arg Leu Glu Glu His Leu Glu Cys Ala Cys Ala Thr Ser
85 90 95

Leu Asn Pro Asp Tyr Arg Glu
100

<210> SEQ ID NO 116
<211> LENGTH: 104
<212> TYPE: PRT
<213> ORGANISM: Artificial
<220> FEATURE:
<223> OTHER INFORMATION: proteinmimic hPDGF B

<400> SEQUENCE: 116

Thr Ile Ala Glu Pro Ala Met Ile Ala Glu Cys Lys Thr Arg Thr Glu
1               5                   10                  15

Val Phe Glu Ile Ser Arg Arg Leu Ile Asp Arg Thr Asn Ala Asn Phe
            20                  25                  30

Leu Val Trp Pro Pro Cys Val Glu Val Gln Arg Cys Ser Gly Cys Cys
        35                  40                  45

Asn Asn Arg Asn Val Gln Cys Arg Pro Thr Gln Val Gln Leu Arg Pro
    50                  55                  60

Val Gln Val Arg Lys Ile Glu Ile Val Arg Lys Lys Pro Ile Phe Lys
65                  70                  75                  80

Lys Ala Thr Val Thr Leu Glu Asp His Leu Ala Cys Lys Cys Glu Thr
                85                  90                  95

Val Ala Ala Ala Arg Pro Val Thr
            100

<210> SEQ ID NO 117
<211> LENGTH: 106
<212> TYPE: PRT
<213> ORGANISM: Artificial
<220> FEATURE:
<223> OTHER INFORMATION: proteinmimic hPDGF C

<400> SEQUENCE: 117

Leu Leu Thr Glu Glu Val Arg Leu Tyr Ser Cys Thr Pro Arg Asn Phe
1               5                   10                  15

Ser Val Ser Ile Arg Glu Glu Leu Lys Arg Thr Asp Thr Ile Phe Trp
            20                  25                  30

Pro Gly Cys Leu Leu Val Lys Arg Cys Gly Gly Asn Cys Ala Cys Cys
        35                  40                  45

Leu His Asn Cys Asn Glu Cys Gln Cys Val Pro Ser Lys Val Thr Lys
    50                  55                  60

Lys Tyr His Glu Val Leu Gln Leu Arg Pro Lys Thr Gly Val Arg Gly
65                  70                  75                  80

Leu His Lys Ser Leu Thr Asp Val Ala Leu Glu His His Glu Glu Cys
                85                  90                  95

Asp Cys Val Cys Arg Gly Ser Thr Gly Gly
            100                 105

<210> SEQ ID NO 118
<211> LENGTH: 110
<212> TYPE: PRT
<213> ORGANISM: Artificial
<220> FEATURE:
<223> OTHER INFORMATION: proteinmimic hPDGF D

<400> SEQUENCE: 118

Arg Leu Asn Asp Asp Ala Lys Arg Tyr Ser Cys Thr Pro Arg Asn Tyr
1               5                   10                  15

Ser Val Asn Ile Arg Glu Glu Leu Lys Leu Ala Asn Val Val Phe Phe
            20                  25                  30

Pro Arg Cys Leu Leu Val Gln Arg Cys Gly Gly Asn Cys Gly Cys Cys
        35                  40                  45

Gly Thr Val Asn Trp Arg Ser Cys Thr Cys Asn Ser Gly Lys Thr Val
    50                  55                  60

Lys Lys Tyr His Glu Val Leu Gln Phe Glu Pro Gly His Ile Lys Arg
65                  70                  75                  80

```
Arg Gly Arg Ala Lys Thr Met Ala Leu Val Asp Ile Gln Leu Asp His
                85                  90                  95

His Glu Arg Cys Asp Cys Ile Cys Ser Ser Arg Pro Pro Arg
            100                 105                 110


<210> SEQ ID NO 119
<211> LENGTH: 99
<212> TYPE: PRT
<213> ORGANISM: Artificial
<220> FEATURE:
<223> OTHER INFORMATION: proteinmimic human placenta growth factor

<400> SEQUENCE: 119

Pro Phe Gln Glu Val Trp Gly Arg Ser Tyr Cys Arg Ala Leu Glu Arg
1               5                   10                  15

Leu Val Asp Val Val Ser Glu Tyr Pro Ser Glu Val Glu His Met Phe
            20                  25                  30

Ser Pro Ser Cys Val Ser Leu Leu Arg Cys Thr Gly Cys Cys Gly Asp
        35                  40                  45

Glu Asn Leu His Cys Val Pro Val Glu Thr Ala Asn Val Thr Met Gln
    50                  55                  60

Leu Leu Lys Ile Arg Ser Gly Asp Arg Pro Ser Tyr Val Glu Leu Thr
65                  70                  75                  80

Phe Ser Gln His Val Arg Cys Glu Cys Arg His Ser Pro Gly Arg Gln
                85                  90                  95

Ser Pro Asp


<210> SEQ ID NO 120
<211> LENGTH: 104
<212> TYPE: PRT
<213> ORGANISM: Artificial
<220> FEATURE:
<223> OTHER INFORMATION: proteinmimic PDGF-related protein monkey
      sarcoma virus

<400> SEQUENCE: 120

Ser Val Ala Glu Pro Ala Met Ile Ala Glu Cys Lys Thr Arg Thr Glu
1               5                   10                  15

Val Phe Glu Ile Ser Arg Arg Leu Ile Asp Arg Thr Asn Ala Asn Phe
            20                  25                  30

Leu Val Trp Pro Pro Cys Val Glu Val Gln Arg Cys Ser Gly Cys Cys
        35                  40                  45

Asn Asn Arg Asn Val Gln Cys Arg Pro Thr Gln Val Gln Leu Arg Pro
    50                  55                  60

Val Gln Val Arg Lys Ile Glu Ile Val Arg Lys Lys Pro Ile Phe Lys
65                  70                  75                  80

Lys Ala Thr Val Thr Leu Glu Asp His Leu Ala Cys Lys Cys Glu Ile
                85                  90                  95

Val Ala Ala Ala Arg Ala Val Thr
            100


<210> SEQ ID NO 121
<211> LENGTH: 104
<212> TYPE: PRT
<213> ORGANISM: Artificial
<220> FEATURE:
<223> OTHER INFORMATION: proteinmimic snake VEGF toxin

<400> SEQUENCE: 121
```

Ser Val Ala Glu Pro Ala Met Ile Ala Glu Cys Lys Thr Arg Thr Glu
1 5 10 15

Val Phe Glu Ile Ser Arg Arg Leu Ile Asp Arg Thr Asn Ala Asn Phe
20 25 30

Leu Val Trp Pro Pro Cys Val Glu Val Gln Arg Cys Ser Gly Cys Cys
35 40 45

Asn Asn Arg Asn Val Gln Cys Arg Pro Thr Gln Val Gln Leu Arg Pro
50 55 60

Val Gln Val Arg Lys Ile Glu Ile Val Arg Lys Lys Pro Ile Phe Lys
65 70 75 80

Lys Ala Thr Val Thr Leu Glu Asp His Leu Ala Cys Lys Cys Glu Ile
85 90 95

Val Ala Ala Ala Arg Ala Val Thr
100

<210> SEQ ID NO 122
<211> LENGTH: 100
<212> TYPE: PRT
<213> ORGANISM: Artificial
<220> FEATURE:
<223> OTHER INFORMATION: proteinmimic snake VEGF toxin

<400> SEQUENCE: 122

Pro Phe Leu Glu Val His Glu Arg Ser Ala Cys Gln Ala Arg Glu Thr
1 5 10 15

Leu Val Ser Ile Leu Gln Glu Tyr Pro Asp Glu Ile Ser Asp Ile Phe
20 25 30

Arg Pro Ser Cys Val Ala Val Leu Arg Cys Ser Gly Cys Cys Thr Asp
35 40 45

Glu Ser Leu Lys Cys Thr Pro Val Gly Lys His Thr Val Asp Leu Gln
50 55 60

Ile Met Arg Val Asn Pro Arg Thr Gln Ser Ser Lys Met Glu Val Met
65 70 75 80

Lys Phe Thr Glu His Thr Ala Cys Glu Cys Arg Pro Arg Arg Lys Gln
85 90 95

Gly Glu Pro Asp
100

<210> SEQ ID NO 123
<211> LENGTH: 99
<212> TYPE: PRT
<213> ORGANISM: Artificial
<220> FEATURE:
<223> OTHER INFORMATION: proteinmimic hVEGF A

<400> SEQUENCE: 123

Lys Phe Met Asp Val Tyr Gln Arg Ser Tyr Cys His Pro Ile Glu Thr
1 5 10 15

Leu Val Asp Ile Phe Gln Glu Tyr Pro Asp Glu Ile Glu Tyr Ile Phe
20 25 30

Lys Pro Ser Cys Val Pro Leu Met Arg Cys Gly Gly Ala Cys Asn Asp
35 40 45

Glu Gly Leu Glu Cys Val Pro Thr Glu Glu Ser Asn Ile Thr Met Gln
50 55 60

Ile Met Arg Ile Lys Pro His Gln Gly Gln His Ile Gly Glu Met Ser
65 70 75 80

Phe Leu Gln His Asn Lys Cys Glu Cys Arg Pro Lys Lys Asp Arg Ala
85 90 95

Arg Gln Glu

<210> SEQ ID NO 124
<211> LENGTH: 98
<212> TYPE: PRT
<213> ORGANISM: Artificial
<220> FEATURE:
<223> OTHER INFORMATION: proteinmimic hVEGF B

<400> SEQUENCE: 124

```
Ser Trp Ile Asp Val Tyr Thr Arg Ala Thr Cys Gln Pro Arg Glu Val
1               5                   10                  15

Val Val Pro Leu Thr Val Glu Leu Met Gly Thr Val Ala Lys Gln Leu
            20                  25                  30

Val Pro Ser Cys Val Thr Val Gln Arg Cys Gly Gly Cys Cys Pro Asp
        35                  40                  45

Asp Gly Leu Glu Cys Val Pro Thr Gly Gln His Gln Val Arg Met Gln
    50                  55                  60

Ile Leu Met Ile Arg Tyr Pro Ser Ser Gln Leu Gly Glu Met Ser Leu
65                  70                  75                  80

Glu Glu His Ser Gln Cys Glu Cys Arg Pro Lys Lys Lys Asp Ser Ala
                85                  90                  95

Val Lys
```

<210> SEQ ID NO 125
<211> LENGTH: 101
<212> TYPE: PRT
<213> ORGANISM: Artificial
<220> FEATURE:
<223> OTHER INFORMATION: proteinmimic hVEGF C

<400> SEQUENCE: 125

```
Ser Ile Asp Asn Glu Trp Arg Lys Thr Gln Cys Met Pro Arg Glu Val
1               5                   10                  15

Ala Ile Asp Val Gly Lys Glu Phe Gly Val Ala Thr Asn Thr Phe Phe
            20                  25                  30

Lys Pro Pro Cys Val Ser Val Tyr Arg Cys Gly Gly Cys Cys Asn Ser
        35                  40                  45

Glu Gly Leu Gln Cys Met Asn Thr Ser Thr Ser Tyr Leu Ser Lys Thr
    50                  55                  60

Leu Phe Glu Ile Thr Val Pro Leu Ser Gln Gly Pro Lys Pro Val Thr
65                  70                  75                  80

Ile Ser Phe Ala Asn His Thr Ser Cys Arg Cys Met Ser Lys Leu Asp
                85                  90                  95

Val Tyr Arg Gln Val
            100
```

<210> SEQ ID NO 126
<211> LENGTH: 101
<212> TYPE: PRT
<213> ORGANISM: Artificial
<220> FEATURE:
<223> OTHER INFORMATION: proteinmimic hVEGF D

<400> SEQUENCE: 126

```
Val Ile Asp Glu Glu Trp Gln Arg Thr Gln Cys Ser Pro Arg Glu Thr
1               5                   10                  15

Ala Val Glu Val Ala Ser Glu Leu Gly Lys Ser Thr Asn Thr Phe Phe
            20                  25                  30
```

```
Lys Pro Pro Cys Val Asn Val Phe Arg Cys Gly Gly Cys Cys Asn Glu
        35                  40                  45

Glu Ser Leu Ile Cys Met Asn Thr Ser Thr Ser Tyr Ile Ser Lys Gln
    50                  55                  60

Leu Phe Glu Ile Ser Val Pro Leu Thr Ser Val Pro Glu Leu Val Pro
65                  70                  75                  80

Val Lys Val Ala Asn His Thr Gly Cys Lys Cys Leu Pro Thr Ala Pro
                85                  90                  95

Arg His Pro Tyr Ser
            100
```

<210> SEQ ID NO 127
<211> LENGTH: 99
<212> TYPE: PRT
<213> ORGANISM: Artificial
<220> FEATURE:
<223> OTHER INFORMATION: proteinmimic VEGF homolog NZ2 virus

<400> SEQUENCE: 127

```
Gly Trp Ser Glu Val Leu Lys Gly Ser Glu Cys Lys Pro Arg Pro Ile
1               5                   10                  15

Val Val Pro Val Ser Glu Thr His Pro Glu Leu Thr Ser Gln Arg Phe
            20                  25                  30

Asn Pro Pro Cys Val Thr Leu Met Arg Cys Gly Gly Cys Cys Asn Asp
        35                  40                  45

Glu Ser Leu Glu Cys Val Pro Thr Glu Glu Val Asn Val Ser Met Glu
    50                  55                  60

Leu Leu Gly Ala Ser Gly Ser Gly Ser Asn Gly Met Gln Arg Leu Ser
65                  70                  75                  80

Phe Val Glu His Lys Lys Cys Asp Cys Arg Pro Arg Phe Thr Thr Thr
                85                  90                  95

Pro Pro Thr
```

<210> SEQ ID NO 128
<211> LENGTH: 107
<212> TYPE: PRT
<213> ORGANISM: Artificial
<220> FEATURE:
<223> OTHER INFORMATION: proteinmimic VEGF homolog NZ7 virus

<400> SEQUENCE: 128

```
Asp Trp Met Arg Thr Leu Asp Lys Ser Gly Cys Lys Pro Arg Asp Thr
1               5                   10                  15

Val Val Tyr Leu Gly Glu Glu Tyr Pro Glu Ser Thr Asn Leu Gln Tyr
            20                  25                  30

Asn Pro Arg Cys Val Thr Val Lys Arg Cys Ser Gly Cys Cys Asn Gly
        35                  40                  45

Asp Gly Gln Ile Cys Thr Ala Val Glu Thr Arg Asn Thr Thr Val Thr
    50                  55                  60

Val Ser Val Thr Gly Val Ser Ser Ser Ser Gly Thr Asn Ser Gly Val
65                  70                  75                  80

Ser Thr Asn Leu Gln Arg Ile Ser Val Thr Glu His Thr Lys Cys Asp
                85                  90                  95

Cys Ile Gly Arg Thr Thr Thr Thr Pro Thr Thr
            100                 105
```

<210> SEQ ID NO 129

<211> LENGTH: 99
<212> TYPE: PRT
<213> ORGANISM: Artificial
<220> FEATURE:
<223> OTHER INFORMATION: proteinmimic VEGF A-A zebrafish

<400> SEQUENCE: 129

Pro Phe Met Asp Val Tyr Lys Lys Ser Ala Cys Lys Thr Arg Glu Leu
1 5 10 15

Leu Val Asp Ile Ile Gln Glu Tyr Pro Asp Glu Ile Glu His Thr Tyr
20 25 30

Ile Pro Ser Cys Val Val Leu Met Arg Cys Ala Gly Cys Cys Asn Asp
35 40 45

Glu Ala Leu Glu Cys Val Pro Thr Glu Thr Arg Asn Val Thr Met Glu
50 55 60

Val Leu Arg Val Lys Gln Arg Val Ser Gln His Asn Phe Gln Leu Ser
65 70 75 80

Phe Thr Glu His Thr Lys Cys Glu Cys Arg Pro Lys Ala Glu Val Lys
85 90 95

Ala Lys Lys

<210> SEQ ID NO 130
<211> LENGTH: 102
<212> TYPE: PRT
<213> ORGANISM: Artificial
<220> FEATURE:
<223> OTHER INFORMATION: proteinmimic VEGF-like protein orf virus

<400> SEQUENCE: 130

Lys Trp Pro Glu Val Leu Glu Gly Ser Lys Cys Lys Pro Arg Pro Thr
1 5 10 15

Val Leu Ser Val Asn Gly Glu His Pro Glu Leu Thr Ser Gln Arg Phe
20 25 30

Asn Pro Pro Cys Val Thr Leu Met Arg Cys Gly Gly Cys Cys Asn Asp
35 40 45

Glu Ser Leu Glu Cys Val Pro Thr Glu Glu Ala Asn Val Thr Met Glu
50 55 60

Phe Met Gly Val Gly Val Ser Ser Thr Gly Ser Ser Val Ser Thr Gln
65 70 75 80

His Leu Glu Phe Val Glu His Thr Lys Cys Asp Cys Pro Arg Gly Gly
85 90 95

Gln Gln Thr Thr Pro Pro
100

<210> SEQ ID NO 131
<211> LENGTH: 104
<212> TYPE: PRT
<213> ORGANISM: Artificial
<220> FEATURE:
<223> OTHER INFORMATION: proteinmimic C-sis proto-onocogene cat

<400> SEQUENCE: 131

Thr Val Ala Glu Pro Ala Met Ile Ala Glu Cys Lys Thr Arg Thr Glu
1 5 10 15

Val Phe Glu Val Ser Arg Arg Leu Ile Asp Arg Thr Asn Ala Asn Phe
20 25 30

Leu Val Trp Pro Pro Cys Val Glu Val Gln Arg Cys Ser Gly Cys Cys
35 40 45

Asn Asn Arg Asn Val Gln Cys Arg Pro Thr Gln Val Gln Leu Arg Leu 50 55 60

Val Gln Val Arg Lys Ile Glu Ile Val Arg Lys Arg Pro Val Phe Lys
65 70 75 80

Lys Ala Thr Val Thr Leu Glu Asp His Leu Ala Cys Lys Cys Glu Thr
85 90 95

Val Val Ala Ala Arg Pro Val Thr
100

<210> SEQ ID NO 132
<211> LENGTH: 92
<212> TYPE: PRT
<213> ORGANISM: Artificial
<220> FEATURE:
<223> OTHER INFORMATION: proteinmimic salmon glycoprotein hormone alpha

<400> SEQUENCE: 132

Ser Asp Met Thr Asn Val Gly Cys Glu Glu Cys Lys Leu Lys Glu Asn
1 5 10 15

Lys Val Phe Ser Asn Pro Gly Ala Pro Val Tyr Gln Cys Thr Gly Cys
20 25 30

Cys Phe Ser Arg Ala Tyr Pro Thr Pro Leu Gln Ser Lys Lys Ala Met
35 40 45

Leu Val Pro Lys Asn Ile Thr Ser Glu Ala Thr Cys Cys Val Ala Lys
50 55 60

Glu Gly Glu Arg Val Val Val Asp Asn Ile Lys Leu Thr Asn His Thr
65 70 75 80

Glu Cys Trp Cys Asn Thr Cys Tyr His His Lys Ser
85 90

<210> SEQ ID NO 133
<211> LENGTH: 82
<212> TYPE: PRT
<213> ORGANISM: Artificial
<220> FEATURE:
<223> OTHER INFORMATION: proteinmimic salmon glycoprotein hormone alpha

<400> SEQUENCE: 133

Cys Glu Glu Cys Thr Leu Lys Pro Asn Thr Ile Phe Pro Asn Ile Met
1 5 10 15

Gln Cys Thr Gly Cys Cys Phe Ser Arg Ala Tyr Pro Thr Pro Leu Arg
20 25 30

Ser Lys Gln Thr Met Leu Val Pro Lys Asn Ile Thr Ser Glu Ala Thr
35 40 45

Cys Cys Val Ala Lys Glu Gly Glu Arg Val Thr Thr Lys Asp Gly Phe
50 55 60

Pro Val Thr Asn His Thr Glu Cys His Cys Ser Thr Cys Tyr Tyr His
65 70 75 80

Lys Ser

<210> SEQ ID NO 134
<211> LENGTH: 92
<212> TYPE: PRT
<213> ORGANISM: Artificial
<220> FEATURE:
<223> OTHER INFORMATION: proteinmimic human glycoprotein hormone alpha

<400> SEQUENCE: 134

Ala Pro Asp Val Gln Asp Cys Pro Glu Cys Thr Leu Gln Glu Asn Pro
1 5 10 15

```
Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90
```

<210> SEQ ID NO 135
<211> LENGTH: 93
<212> TYPE: PRT
<213> ORGANISM: Artificial
<220> FEATURE:
<223> OTHER INFORMATION: proteinmimic macaque glycoprotein hormone alpha

<400> SEQUENCE: 135

```
Gly Glu Phe Thr Met Gln Asp Cys Pro Glu Cys Lys Pro Arg Glu Asn
1               5                   10                  15

Lys Phe Phe Ser Lys Pro Gly Ala Pro Ile Tyr Gln Cys Met Gly Cys
            20                  25                  30

Cys Phe Ser Arg Ala Tyr Pro Thr Pro Leu Arg Ser Lys Lys Thr Met
        35                  40                  45

Leu Val Gln Lys Asn Val Thr Ser Glu Ser Thr Cys Cys Val Ala Lys
    50                  55                  60

Ser Leu Thr Arg Val Met Val Met Gly Asn Val Arg Val Glu Asn His
65                  70                  75                  80

Thr Gln Cys His Cys Ser Thr Cys Tyr Tyr His Lys Phe
                85                  90
```

<210> SEQ ID NO 136
<211> LENGTH: 88
<212> TYPE: PRT
<213> ORGANISM: Artificial
<220> FEATURE:
<223> OTHER INFORMATION: proteinmimic noggin

<400> SEQUENCE: 136

```
Leu Gln Met Trp Leu Trp Ser Gln Thr Phe Cys Pro Val Leu Tyr Ala
1               5                   10                  15

Trp Asn Asp Leu Gly Ser Arg Phe Trp Pro Arg Tyr Val Lys Val Gly
            20                  25                  30

Ser Cys Phe Ser Lys Arg Ser Cys Ser Val Pro Glu Gly Met Val Cys
        35                  40                  45

Lys Pro Ser Lys Ser Val His Leu Thr Val Leu Arg Trp Arg Cys Gln
    50                  55                  60

Arg Arg Gly Gly Gln Arg Cys Gly Trp Ile Pro Ile Gln Tyr Pro Ile
65                  70                  75                  80

Ile Ser Glu Cys Lys Cys Ser Cys
                85
```

<210> SEQ ID NO 137
<211> LENGTH: 91
<212> TYPE: PRT
<213> ORGANISM: Artificial
<220> FEATURE:
<223> OTHER INFORMATION: proteinmimic noggin-1 zebrafish

<400> SEQUENCE: 137

Leu Gln Met Trp Leu Trp Ser Tyr Ser Phe Cys Pro Val Leu Tyr Ala
1 5 10 15

Trp Asn Asp Leu Gly Ser Arg Phe Trp Pro Arg Phe Val Arg Ala Gly
20 25 30

Ser Cys Tyr Thr Lys Arg Ser Cys Ser Val Pro Glu Gly Met Val Cys
35 40 45

Lys Pro Ala Lys Ser Thr His Ile Thr Leu Leu Arg Trp Arg Cys Val
50 55 60

Ala Arg Arg Gly Ala Leu Lys Cys Ala Trp Ile Pro Val Gln Tyr Pro
65 70 75 80

Ile Ile Thr Glu Cys Lys Cys Ser Cys Ala Asn
85 90

<210> SEQ ID NO 138
<211> LENGTH: 89
<212> TYPE: PRT
<213> ORGANISM: Artificial
<220> FEATURE:
<223> OTHER INFORMATION: proteinmimic noggin-2 zebrafish

<400> SEQUENCE: 138

Phe Leu Gln Trp Leu Trp Met Tyr Thr His Cys Pro Val Leu Tyr Thr
1 5 10 15

Trp Lys Asp Leu Gly Leu Arg Phe Trp Pro Arg Tyr Ile Lys Glu Gly
20 25 30

Asn Cys Phe Ser Glu Arg Ser Cys Ser Phe Pro Glu Gly Met Ser Cys
35 40 45

Lys Pro Val Lys Ala Val Thr Lys Thr Phe Leu Arg Trp Tyr Cys Gln
50 55 60

Gly Phe Met Arg Gln Lys Tyr Cys Thr Trp Ile Gln Val Gln Tyr Pro
65 70 75 80

Ile Ile Ser Gln Cys Lys Cys Ser Cys
85

<210> SEQ ID NO 139
<211> LENGTH: 91
<212> TYPE: PRT
<213> ORGANISM: Artificial
<220> FEATURE:
<223> OTHER INFORMATION: proteinmimic noggin-3 zebrafish

<400> SEQUENCE: 139

Leu Gln Leu Trp Leu Trp Ser Tyr Thr Phe Cys Pro Val Val His Thr
1 5 10 15

Trp Gln Asp Leu Gly Asn Arg Phe Trp Pro Arg Tyr Leu Lys Val Gly
20 25 30

Ser Cys Tyr Asn Lys Arg Ser Cys Ser Val Pro Glu Gly Met Val Cys
35 40 45

Lys Pro Pro Lys Ser Ser His Leu Thr Val Leu Arg Trp Arg Cys Val
50 55 60

Gln Arg Lys Gly Gly Leu Lys Cys Ala Trp Ile Pro Val Gln Tyr Pro
65 70 75 80

Val Ile Ser Glu Cys Lys Cys Ser Cys Pro Asn
85 90

<210> SEQ ID NO 140
<211> LENGTH: 93

<212> TYPE: PRT
<213> ORGANISM: Artificial
<220> FEATURE:
<223> OTHER INFORMATION: proteinmimic noggin-4 chicken

<400> SEQUENCE: 140

```
Leu Arg Arg Trp Leu Val Glu Arg Ala Ser Cys Arg Leu Thr Ser Ala
1               5                   10                  15

Trp Val Asp Leu Gly Pro Val Phe Trp Pro Arg Trp Val Arg His Thr
            20                  25                  30

Ala Cys Arg Thr Gly Pro Pro Ala Cys Ser Trp Pro Pro Gly Met Ala
        35                  40                  45

Cys Arg Pro Ala Gln Leu Ala His Leu Lys Leu Leu Ala Trp His Cys
    50                  55                  60

Trp Ala Ala Arg Pro Pro Gly Pro Pro His Cys Ala Trp Arg Gln Val
65                  70                  75                  80

Pro Tyr Pro Val Val Val Ala Cys Lys Cys Ser Cys Arg
                85                  90
```

<210> SEQ ID NO 141
<211> LENGTH: 90
<212> TYPE: PRT
<213> ORGANISM: Artificial
<220> FEATURE:
<223> OTHER INFORMATION: proteinmimic noggin-5 zebrafish

<400> SEQUENCE: 141

```
Met Arg Arg Trp Met Trp Ser Tyr Thr Arg Cys Pro Val Leu Ser Met
1               5                   10                  15

Trp Lys Asp Leu Gly Val Arg Phe Trp Pro Arg Tyr Val Lys Glu Gly
            20                  25                  30

Gln Cys Ser Thr Glu Arg Ser Cys Ser Leu Pro Glu Gly Met Phe Cys
        35                  40                  45

Lys Pro Val Gln Ser Val Ser Val Thr Leu Leu Arg Trp His Cys Gln
    50                  55                  60

Gln Gly Ser Arg Ala Leu Lys Arg Cys Ala Trp Ile Arg Ala His Tyr
65                  70                  75                  80

Pro Val Ile Ser Gln Cys Ala Cys Ala Cys
                85                  90
```

<210> SEQ ID NO 142
<211> LENGTH: 119
<212> TYPE: PRT
<213> ORGANISM: Artificial
<220> FEATURE:
<223> OTHER INFORMATION: proteinmimic noggin-I sponge

<400> SEQUENCE: 142

```
Ala Ile Arg Arg Thr Leu Asn Thr Leu Asn Cys Arg Val Thr Tyr Asn
1               5                   10                  15

Trp Ala Asp Ala Gly Val Asn Phe Phe Pro Arg Tyr Phe Ser Ala Gly
            20                  25                  30

Ser Cys Phe Glu Arg Arg Cys Ser Ile Pro Asp Arg Ala Asp Phe Leu
        35                  40                  45

Cys Arg Pro Asp Val Phe Asn Gln Glu Gln Met Gly Thr Leu Thr Ala
    50                  55                  60

Leu Arg Trp Asp Cys Cys Trp Glu Val Val Glu Thr Ile Val Arg Gly
65                  70                  75                  80

Arg Arg Gly Arg Thr Phe Arg Arg Leu Ser Arg Arg Tyr Asn Cys Gly
```

```
                85                  90                  95

Trp Arg Arg Ile Arg Phe Pro Ile Val Cys Asp Cys Asp Cys Asn Cys
            100                 105                 110

Pro Gly Asn Arg Pro Arg Ile
        115


<210> SEQ ID NO 143
<211> LENGTH: 151
<212> TYPE: PRT
<213> ORGANISM: Artificial
<220> FEATURE:
<223> OTHER INFORMATION: proteinmimic noggin-like protein dugesia
      japonica

<400> SEQUENCE: 143

Ile Arg Arg Trp Met Val Gln Gln Ala Ala Cys Lys Ile Asp Tyr Leu
1               5                   10                  15

Trp Lys Arg Leu Asp Asp Thr His Trp Pro Ser Phe Ile Lys His Gly
            20                  25                  30

Val Cys Asn Ser Arg Glu Ser Cys Ser Trp Pro Pro Gly Met Asn Cys
        35                  40                  45

Arg Pro Asn Asp Gln Lys Leu Leu Lys Ile Leu Lys Trp Thr Cys Ile
    50                  55                  60

Ser Asp Pro Leu Gly Lys Arg Trp Asn Glu Phe Arg Glu Ser Ile Phe
65                  70                  75                  80

Ala Asp Lys Arg Lys Arg Arg Leu Arg Arg His Lys Ile Lys Arg His
                85                  90                  95

Leu Ser Gln Lys Arg Lys Thr Asn Lys Val Ile Arg Pro Lys Arg Met
            100                 105                 110

Lys Arg Leu Val Lys Arg Tyr Leu Tyr Arg Thr Ser Lys Tyr Val Ser
        115                 120                 125

Gly Tyr Leu Cys Gln Trp Lys Pro Ile Asp Tyr Thr Val His Gln Ser
    130                 135                 140

Cys Thr Cys Ser Cys Gln Gly
145                 150


<210> SEQ ID NO 144
<211> LENGTH: 151
<212> TYPE: PRT
<213> ORGANISM: Artificial
<220> FEATURE:
<223> OTHER INFORMATION: proteinmimic noggin-like protein 1 flatworm

<400> SEQUENCE: 144

Ile Arg Arg Trp Met Val Gln Gln Ala Thr Cys Lys Thr Asp Tyr Ile
1               5                   10                  15

Trp Lys Arg Leu Asp Glu Thr His Trp Pro Ser Trp Ile Lys His Gly
            20                  25                  30

Ile Cys Ser Ser Thr Glu Pro Cys Ser Trp Pro Pro Gly Met Ala Cys
        35                  40                  45

Lys Gln Ser Asp Lys Lys Thr Leu Lys Val Leu Lys Trp Thr Cys Leu
    50                  55                  60

Ser Asp Pro Leu Gly Glu Lys Trp Asn Ala Phe Arg Glu Leu Met His
65                  70                  75                  80

Glu Asp Arg Lys Arg Arg Arg Leu Arg Arg His Gln Phe Lys Arg His
                85                  90                  95

Leu Ser Gln Lys Arg Lys Ile Gly Val Lys Lys Val Lys Lys Pro Lys
            100                 105                 110
```

Gln Leu Lys Arg Leu Val Lys Arg Tyr Leu Tyr Lys Thr Ser Lys Tyr
        115                 120                 125

Ala Ser Gly Tyr Leu Cys Gln Trp Lys Pro Ile Asp Tyr Thr Val Tyr
    130                 135                 140

Glu Ser Cys Thr Cys Ser Cys
145                 150

<210> SEQ ID NO 145
<211> LENGTH: 98
<212> TYPE: PRT
<213> ORGANISM: Artificial
<220> FEATURE:
<223> OTHER INFORMATION: proteinmimic coagulogen horseshoe crab

<400> SEQUENCE: 145

Phe Phe Pro Phe His His Phe Pro Ser Glu Cys Pro Val Ser Val Ser
1               5                   10                  15

Ala Cys Glu Pro Thr Phe Gly Tyr Thr Thr Ser Asn Glu Leu Arg Ile
            20                  25                  30

Ile Val Gln Ala Pro Lys Ala Gly Phe Arg Gln Cys Val Trp Gln His
        35                  40                  45

Lys Cys Arg Ala Tyr Gly Ser Asn Phe Cys Gln Arg Thr Gly Arg Cys
    50                  55                  60

Thr Gln Gln Arg Ser Val Val Arg Leu Val Thr Tyr Asp Leu Glu Lys
65                  70                  75                  80

Gly Val Phe Phe Cys Glu Asn Val Arg Thr Cys Cys Gly Cys Pro Cys
                85                  90                  95

Arg Ser

<210> SEQ ID NO 146
<211> LENGTH: 98
<212> TYPE: PRT
<213> ORGANISM: Artificial
<220> FEATURE:
<223> OTHER INFORMATION: proteinmimic coagulogen crab

<400> SEQUENCE: 146

Phe Pro Pro Phe Val His Phe Thr Ser Glu Cys Pro Val Ser Thr Arg
1               5                   10                  15

Asp Cys Glu Pro Val Phe Gly Tyr Thr Val Ala Gly Glu Phe Arg Val
            20                  25                  30

Ile Val Gln Ala Pro Arg Ala Gly Phe Arg Gln Cys Val Trp Gln His
        35                  40                  45

Lys Cys Arg Tyr Gly Ser Asn Asn Cys Gly Phe Ser Gly Arg Cys Thr
    50                  55                  60

Gln Gln Arg Ser Val Val Arg Leu Val Thr Tyr Asn Leu Glu Lys Asp
65                  70                  75                  80

Gly Phe Leu Cys Glu Ser Phe Arg Thr Cys Cys Gly Cys Pro Cys Arg
                85                  90                  95

Asn Tyr

<210> SEQ ID NO 147
<211> LENGTH: 107
<212> TYPE: PRT
<213> ORGANISM: Artificial
<220> FEATURE:
<223> OTHER INFORMATION: proteinmimic bursicon Drosophila

<400> SEQUENCE: 147

```
Thr Asp Asn Asp Ile Thr His Leu Gly Asp Cys Gln Val Thr Pro Val
1               5                   10                  15

Ile His Val Leu Gln Tyr Pro Gly Cys Val Pro Lys Pro Ile Pro Ser
            20                  25                  30

Phe Ala Cys Val Gly Arg Cys Ala Ser Tyr Ile Gln Val Ser Gly Ser
        35                  40                  45

Lys Ile Trp Gln Met Glu Arg Ser Cys Met Cys Cys Gln Glu Ser Gly
    50                  55                  60

Glu Arg Glu Ala Ala Val Ser Leu Phe Cys Pro Lys Val Lys Pro Gly
65                  70                  75                  80

Glu Arg Lys Phe Lys Lys Val Leu Thr Lys Ala Pro Leu Glu Cys Met
                85                  90                  95

Cys Arg Pro Cys Thr Ser Ile Glu Glu Ser Gly
            100                 105


<210> SEQ ID NO 148
<211> LENGTH: 121
<212> TYPE: PRT
<213> ORGANISM: Artificial
<220> FEATURE:
<223> OTHER INFORMATION: proteinmimic bursicon partner Drosophila

<400> SEQUENCE: 148

Arg Tyr Ser Gln Gly Thr Gly Asp Glu Asn Cys Glu Thr Leu Lys Ser
1               5                   10                  15

Glu Ile His Leu Ile Lys Glu Glu Phe Asp Glu Leu Gly Arg Met Gln
            20                  25                  30

Arg Thr Cys Asn Ala Asp Val Ile Val Asn Lys Cys Glu Gly Leu Cys
        35                  40                  45

Asn Ser Gln Val Gln Pro Ser Val Ile Thr Pro Thr Gly Phe Leu Lys
    50                  55                  60

Glu Cys Tyr Cys Cys Arg Glu Ser Phe Leu Lys Glu Lys Val Ile Thr
65                  70                  75                  80

Leu Thr His Cys Tyr Asp Pro Asp Gly Thr Arg Leu Thr Ser Pro Gly
                85                  90                  95

Glu Met Gly Ser Met Asp Ile Arg Leu Arg Glu Pro Thr Glu Cys Lys
            100                 105                 110

Cys Phe Lys Cys Gly Asp Phe Thr Arg
        115                 120


<210> SEQ ID NO 149
<211> LENGTH: 90
<212> TYPE: PRT
<213> ORGANISM: Artificial
<220> FEATURE:
<223> OTHER INFORMATION: proteinmimic CEF-10 chicken

<400> SEQUENCE: 149

Ser Tyr Ala Ser Leu Lys Lys Gly Lys Lys Cys Thr Lys Thr Lys Lys
1               5                   10                  15

Ser Pro Ser Pro Val Arg Phe Thr Tyr Ala Gly Cys Ser Ser Val Lys
            20                  25                  30

Lys Tyr Arg Pro Lys Tyr Cys Gly Ser Cys Val Asp Gly Arg Cys Cys
        35                  40                  45

Thr Pro Gln Gln Thr Arg Thr Val Lys Ile Arg Phe Arg Cys Asp Asp
    50                  55                  60

Gly Glu Thr Phe Thr Lys Ser Val Met Met Ile Gln Ser Cys Arg Cys
```

-continued

```
65                  70                  75                  80

Asn Tyr Asn Cys Pro His Ala Asn Glu Ala
                85                  90


<210> SEQ ID NO 150
<211> LENGTH: 100
<212> TYPE: PRT
<213> ORGANISM: Artificial
<220> FEATURE:
<223> OTHER INFORMATION: proteinmimic human cerberus

<400> SEQUENCE: 150

Ile Lys Ser His Glu Val His Trp Glu Thr Cys Arg Thr Val Pro Phe
1               5                   10                  15

Ser Gln Thr Ile Thr His Glu Gly Cys Glu Lys Val Val Val Gln Asn
            20                  25                  30

Asn Leu Cys Phe Gly Lys Cys Gly Ser Val His Phe Pro Gly Ala Ala
        35                  40                  45

Gln His Ser His Thr Ser Cys Ser His Cys Leu Pro Ala Lys Phe Thr
    50                  55                  60

Thr Met His Leu Pro Leu Asn Cys Thr Glu Leu Ser Ser Val Ile Lys
65                  70                  75                  80

Val Val Met Leu Val Glu Glu Cys Gln Cys Lys Val Lys Thr Glu His
                85                  90                  95

Glu Asp Gly His
            100


<210> SEQ ID NO 151
<211> LENGTH: 90
<212> TYPE: PRT
<213> ORGANISM: Artificial
<220> FEATURE:
<223> OTHER INFORMATION: proteinmimic hCTGF

<400> SEQUENCE: 151

Leu Glu Glu Asn Ile Lys Lys Gly Lys Lys Cys Ile Arg Thr Pro Lys
1               5                   10                  15

Ile Ser Lys Pro Ile Lys Phe Glu Leu Ser Gly Cys Thr Ser Met Lys
            20                  25                  30

Thr Tyr Arg Ala Lys Phe Cys Gly Val Cys Thr Asp Gly Arg Cys Cys
        35                  40                  45

Thr Pro His Arg Thr Thr Thr Leu Pro Val Glu Phe Lys Cys Pro Asp
    50                  55                  60

Gly Glu Val Met Lys Lys Asn Met Met Phe Ile Lys Thr Cys Ala Cys
65                  70                  75                  80

His Tyr Asn Cys Pro Gly Asp Asn Asp Ile
                85                  90


<210> SEQ ID NO 152
<211> LENGTH: 90
<212> TYPE: PRT
<213> ORGANISM: Artificial
<220> FEATURE:
<223> OTHER INFORMATION: proteinmimic hCYR61

<400> SEQUENCE: 152

Val Tyr Ser Ser Leu Lys Lys Gly Lys Lys Cys Ser Lys Thr Lys Lys
1               5                   10                  15

Ser Pro Glu Pro Val Arg Phe Thr Tyr Ala Gly Cys Leu Ser Val Lys
            20                  25                  30
```

```
Lys Tyr Arg Pro Lys Tyr Cys Gly Ser Cys Val Asp Gly Arg Cys Cys
        35                  40                  45

Thr Pro Gln Leu Thr Arg Thr Val Lys Met Arg Phe Arg Cys Glu Asp
    50                  55                  60

Gly Glu Thr Phe Ser Lys Asn Val Met Met Ile Gln Ser Cys Lys Cys
65                  70                  75                  80

Asn Tyr Asn Cys Pro His Ala Asn Glu Ala
                85                  90


<210> SEQ ID NO 153
<211> LENGTH: 99
<212> TYPE: PRT
<213> ORGANISM: Artificial
<220> FEATURE:
<223> OTHER INFORMATION: proteinmimic hDDFM5

<400> SEQUENCE: 153

Leu Asn Pro Gln Glu Val Ile Gln Gly Met Cys Lys Ala Val Pro Phe
1               5                   10                  15

Val Gln Val Phe Ser Arg Pro Gly Cys Ser Ala Ile Arg Leu Arg Asn
            20                  25                  30

His Leu Cys Phe Gly His Cys Ser Ser Leu Tyr Ile Pro Gly Ser Asp
        35                  40                  45

Pro Thr Pro Leu Val Leu Cys Asn Ser Cys Met Pro Ala Arg Lys Arg
    50                  55                  60

Trp Ala Pro Val Val Leu Trp Cys Leu Thr Gly Ser Ser Ala Ser Arg
65                  70                  75                  80

Arg Arg Val Lys Ile Ser Thr Met Leu Ile Glu Gly Cys His Cys Ser
                85                  90                  95

Pro Lys Ala


<210> SEQ ID NO 154
<211> LENGTH: 100
<212> TYPE: PRT
<213> ORGANISM: Artificial
<220> FEATURE:
<223> OTHER INFORMATION: proteinmimic DDFM5 xenla

<400> SEQUENCE: 154

Ile Gly Gln Asp Ala Leu Lys Arg Ser Arg Cys His Ala Leu Pro Phe
1               5                   10                  15

Ile Gln Asn Val Phe Arg Lys Asn Cys Phe Pro Val Arg Leu Pro Asn
            20                  25                  30

Lys Phe Cys Phe Gly Gln Cys Asn Ser Phe Tyr Val Pro Gly Trp Pro
        35                  40                  45

Ala Gly Leu Ser Gln Pro Cys Thr Ser Cys Ala Pro Ser Arg Ser Arg
    50                  55                  60

Arg Ile Ser Leu Pro Leu Arg Cys Arg Ser Gly His Leu Ala Trp Gln
65                  70                  75                  80

Glu Val Glu Leu Val Glu Glu Cys Glu Cys Glu Thr Arg Tyr Asp Arg
                85                  90                  95

Asn Thr Val Glu
            100


<210> SEQ ID NO 155
<211> LENGTH: 101
<212> TYPE: PRT
<213> ORGANISM: Artificial
```

-continued

<220> FEATURE:
<223> OTHER INFORMATION: proteinmimic gramlin-1

<400> SEQUENCE: 155

Thr Glu Arg Lys Tyr Leu Lys Arg Asp Trp Cys Lys Thr Gln Pro Leu
1 5 10 15

Lys Gln Thr Ile His Glu Glu Gly Cys Asn Ser Arg Thr Ile Ile Asn
20 25 30

Arg Phe Cys Tyr Gly Gln Cys Asn Ser Phe Tyr Ile Pro Arg His Ile
35 40 45

Arg Lys Glu Glu Gly Ser Phe Gln Ser Cys Ser Phe Cys Lys Pro Lys
50 55 60

Lys Phe Thr Thr Met Met Val Thr Leu Asn Cys Pro Glu Leu Gln Pro
65 70 75 80

Pro Thr Lys Lys Lys Arg Val Thr Arg Val Lys Gln Cys Arg Cys Ile
85 90 95

Ser Ile Asp Leu Asp
100

<210> SEQ ID NO 156
<211> LENGTH: 101
<212> TYPE: PRT
<213> ORGANISM: Artificial
<220> FEATURE:
<223> OTHER INFORMATION: proteinmimic gramlin-2

<400> SEQUENCE: 156

Thr Glu Arg Lys Tyr Leu Lys Arg Asp Trp Cys Lys Thr Gln Pro Leu
1 5 10 15

Arg Gln Thr Val Ser Glu Glu Gly Cys Arg Ser Arg Thr Ile Leu Asn
20 25 30

Arg Phe Cys Tyr Gly Gln Cys Asn Ser Phe Tyr Ile Pro Arg His Val
35 40 45

Lys Lys Glu Glu Glu Ser Phe Gln Ser Cys Ala Phe Cys Lys Pro Gln
50 55 60

Arg Val Thr Ser Val Leu Val Glu Leu Glu Cys Pro Gly Leu Asp Pro
65 70 75 80

Pro Phe Arg Leu Lys Lys Ile Gln Lys Val Lys Gln Cys Lys Cys Met
85 90 95

Ser Val Asn Leu Ser
100

<210> SEQ ID NO 157
<211> LENGTH: 100
<212> TYPE: PRT
<213> ORGANISM: Artificial
<220> FEATURE:
<223> OTHER INFORMATION: proteinm,imic mucin-19

<400> SEQUENCE: 157

Lys Lys Cys Cys Tyr Thr Cys Lys Asn Asn Cys Arg Ser Ser Leu Val
1 5 10 15

Asn Val Thr Val Ile Tyr Ser Gly Cys Lys Lys Arg Val Gln Met Ala
20 25 30

Lys Cys Thr Gly Glu Cys Glu Lys Thr Ala Lys Tyr Asn His Asp Ile
35 40 45

Leu Leu Leu Glu His Ser Cys Leu Cys Cys Arg Glu Glu Asn Tyr Glu
50 55 60

-continued

```
Leu Arg Asp Ile Val Leu Asp Cys Pro Asp Gly Ser Thr Ile Pro Tyr
65                  70                  75                  80

Gln Tyr Lys His Ile Thr Thr Cys Ser Cys Leu Asp Ile Cys Gln Leu
                85                  90                  95

Tyr Thr Thr Phe
            100


<210> SEQ ID NO 158
<211> LENGTH: 100
<212> TYPE: PRT
<213> ORGANISM: Artificial
<220> FEATURE:
<223> OTHER INFORMATION: proteinmimic mucin-2

<400> SEQUENCE: 158

Cys Thr Pro Arg Asn Glu Thr Arg Val Pro Cys Ser Thr Val Pro Val
1               5                   10                  15

Thr Thr Glu Val Ser Tyr Ala Gly Cys Thr Lys Thr Val Leu Met Asn
            20                  25                  30

His Cys Ser Gly Ser Cys Gly Thr Phe Val Met Tyr Ser Ala Lys Ala
        35                  40                  45

Gln Ala Leu Asp His Ser Cys Ser Cys Cys Lys Glu Glu Lys Thr Ser
    50                  55                  60

Gln Arg Glu Val Val Leu Ser Cys Pro Asn Gly Gly Ser Leu Thr His
65                  70                  75                  80

Thr Tyr Thr His Ile Glu Ser Cys Gln Cys Gln Asp Thr Val Cys Gly
                85                  90                  95

Leu Pro Thr Gly
            100


<210> SEQ ID NO 159
<211> LENGTH: 99
<212> TYPE: PRT
<213> ORGANISM: Artificial
<220> FEATURE:
<223> OTHER INFORMATION: proteinmimic mucin-5AC

<400> SEQUENCE: 159

Pro Pro Pro Pro Tyr Gln Asn Gln Ser Thr Cys Ala Val Tyr His Arg
1               5                   10                  15

Ser Leu Ile Ile Gln Gln Gln Gly Cys Ser Ser Ser Glu Pro Val Arg
            20                  25                  30

Leu Ala Tyr Cys Arg Gly Asn Cys Gly Asp Ser Ser Ser Met Tyr Ser
        35                  40                  45

Leu Glu Gly Asn Thr Val Glu His Arg Cys Gln Cys Cys Gln Glu Leu
    50                  55                  60

Arg Thr Ser Leu Arg Asn Val Thr Leu His Cys Thr Asp Gly Ser Ser
65                  70                  75                  80

Arg Ala Phe Ser Tyr Thr Glu Val Glu Glu Cys Gly Cys Met Gly Arg
                85                  90                  95

Arg Cys Pro


<210> SEQ ID NO 160
<211> LENGTH: 95
<212> TYPE: PRT
<213> ORGANISM: Artificial
<220> FEATURE:
<223> OTHER INFORMATION: proteinmimic mucin-5B

<400> SEQUENCE: 160
```

```
Gly Cys Cys Tyr Ser Cys Glu Glu Asp Ser Cys Gln Val Arg Ile Asn
1               5                   10                  15

Thr Thr Ile Leu Trp His Gln Gly Cys Glu Thr Glu Val Asn Ile Thr
            20                  25                  30

Phe Cys Glu Gly Ser Cys Pro Gly Ala Ser Lys Tyr Ser Ala Glu Ala
        35                  40                  45

Gln Ala Met Gln His Gln Cys Thr Cys Cys Gln Glu Arg Arg Val His
    50                  55                  60

Glu Glu Thr Val Pro Leu His Cys Pro Asn Gly Ser Ala Ile Leu His
65                  70                  75                  80

Thr Tyr Thr His Val Asp Glu Cys Gly Cys Thr Pro Phe Cys Val
                85                  90                  95


<210> SEQ ID NO 161
<211> LENGTH: 100
<212> TYPE: PRT
<213> ORGANISM: Artificial
<220> FEATURE:
<223> OTHER INFORMATION: proteinmimic mucin-6

<400> SEQUENCE: 161

Gly Thr Pro Thr Pro Thr Ser Pro Gly Val Cys Ser Val Arg Glu Gln
1               5                   10                  15

Gln Glu Glu Ile Thr Phe Lys Gly Cys Met Ala Asn Val Thr Val Thr
            20                  25                  30

Arg Cys Glu Gly Ala Cys Ile Ser Ala Ala Ser Phe Asn Ile Ile Thr
        35                  40                  45

Gln Gln Val Asp Ala Arg Cys Ser Cys Cys Arg Pro Leu His Ser Tyr
    50                  55                  60

Glu Gln Gln Leu Glu Leu Pro Cys Pro Asp Pro Ser Thr Pro Gly Arg
65                  70                  75                  80

Arg Leu Val Leu Thr Leu Gln Val Phe Ser His Cys Val Cys Ser Ser
                85                  90                  95

Val Ala Cys Gly
            100


<210> SEQ ID NO 162
<211> LENGTH: 105
<212> TYPE: PRT
<213> ORGANISM: Artificial
<220> FEATURE:
<223> OTHER INFORMATION: proteinmimic Norrie disease protein

<400> SEQUENCE: 162

Ser Phe Ile Met Asp Ser Asp Pro Arg Arg Cys Met Arg His His Tyr
1               5                   10                  15

Val Asp Ser Ile Ser His Pro Leu Tyr Lys Cys Ser Ser Lys Met Val
            20                  25                  30

Leu Leu Ala Arg Cys Glu Gly His Cys Ser Gln Ala Ser Arg Ser Glu
        35                  40                  45

Pro Leu Val Ser Phe Ser Thr Val Leu Lys Gln Pro Phe Arg Ser Ser
    50                  55                  60

Cys His Cys Cys Arg Pro Gln Thr Ser Lys Leu Lys Ala Leu Arg Leu
65                  70                  75                  80

Arg Cys Ser Gly Gly Met Arg Leu Thr Ala Thr Tyr Arg Tyr Ile Leu
                85                  90                  95

Ser Cys His Cys Glu Glu Cys Asn Ser
```

100 105

<210> SEQ ID NO 163
<211> LENGTH: 90
<212> TYPE: PRT
<213> ORGANISM: Artificial
<220> FEATURE:
<223> OTHER INFORMATION: proteinmimic NOV-homolog

<400> SEQUENCE: 163

```
Glu Gln Pro Thr Asp Lys Lys Gly Lys Lys Cys Leu Arg Thr Lys Lys
1               5                   10                  15

Ser Leu Lys Ala Ile His Leu Gln Phe Lys Asn Cys Thr Ser Leu His
            20                  25                  30

Thr Tyr Lys Pro Arg Phe Cys Gly Val Cys Ser Asp Gly Arg Cys Cys
        35                  40                  45

Thr Pro His Asn Thr Lys Thr Ile Gln Ala Glu Phe Gln Cys Ser Pro
    50                  55                  60

Gly Gln Ile Val Lys Lys Pro Val Met Val Ile Gly Thr Cys Thr Cys
65                  70                  75                  80

His Thr Asn Cys Pro Lys Asn Asn Glu Ala
                85                  90
```

<210> SEQ ID NO 164
<211> LENGTH: 96
<212> TYPE: PRT
<213> ORGANISM: Artificial
<220> FEATURE:
<223> OTHER INFORMATION: proteinmimic otogelin-like protein

<400> SEQUENCE: 164

```
Cys Lys Ile Cys Lys Arg Glu Glu Arg Ile Cys Gln Lys Val Ile Ile
1               5                   10                  15

Lys Ser Val Ile Arg Lys Gln Asp Cys Met Ser Gln Ser Pro Ile Asn
            20                  25                  30

Val Ala Ser Cys Asp Gly Lys Cys Pro Ser Ala Thr Ile Tyr Asn Ile
        35                  40                  45

Asn Ile Glu Ser His Leu Arg Phe Cys Lys Cys Cys Arg Glu Asn Gly
    50                  55                  60

Val Arg Asn Leu Ser Val Pro Leu Tyr Cys Ser Gly Asn Gly Thr Glu
65                  70                  75                  80

Ile Met Tyr Thr Leu Gln Glu Pro Ile Asp Cys Thr Cys Gln Trp Asn
                85                  90                  95
```

<210> SEQ ID NO 165
<211> LENGTH: 95
<212> TYPE: PRT
<213> ORGANISM: Artificial
<220> FEATURE:
<223> OTHER INFORMATION: proteinmimic otogelin

<400> SEQUENCE: 165

```
Cys Arg Thr Cys Lys Glu Asp Gly Arg Ser Cys Lys Lys Val Thr Ile
1               5                   10                  15

Arg Met Thr Ile Arg Lys Asn Glu Cys Arg Ser Ser Thr Pro Val Asn
            20                  25                  30

Leu Val Ser Cys Asp Gly Arg Cys Pro Ser Ala Ser Ile Tyr Asn Tyr
        35                  40                  45

Asn Ile Asn Thr Tyr Ala Arg Phe Cys Lys Cys Cys Arg Glu Val Gly
    50                  55                  60
```

Leu Gln Arg Arg Ser Val Gln Leu Phe Cys Thr Asn Ala Thr Trp Val
65 70 75 80

Pro Tyr Thr Val Gln Glu Pro Thr Asp Cys Ala Cys Gln Trp Ser
85 90 95

<210> SEQ ID NO 166
<211> LENGTH: 86
<212> TYPE: PRT
<213> ORGANISM: Artificial
<220> FEATURE:
<223> OTHER INFORMATION: proteinmimic slit homolog 1

<400> SEQUENCE: 166

Ser Gly Glu Leu Cys Glu Gln Glu Ser Glu Cys Arg Gly Asp Pro Val
1 5 10 15

Arg Asp Phe His Gln Val Gln Arg Gly Tyr Ala Ile Cys Gln Thr Thr
20 25 30

Arg Pro Leu Ser Trp Val Glu Cys Arg Gly Ser Cys Pro Gly Gln Gly
35 40 45

Cys Cys Gln Gly Leu Arg Leu Lys Arg Arg Lys Phe Thr Phe Glu Cys
50 55 60

Ser Asp Gly Thr Ser Phe Ala Glu Glu Val Glu Lys Pro Thr Lys Cys
65 70 75 80

Gly Cys Ala Leu Cys Ala
85

<210> SEQ ID NO 167
<211> LENGTH: 86
<212> TYPE: PRT
<213> ORGANISM: Artificial
<220> FEATURE:
<223> OTHER INFORMATION: proteinmimic slit homolog 2

<400> SEQUENCE: 167

Thr Gly Asp Ser Cys Asp Arg Glu Ile Ser Cys Arg Gly Glu Arg Ile
1 5 10 15

Arg Asp Tyr Tyr Gln Lys Gln Gln Gly Tyr Ala Ala Cys Gln Thr Thr
20 25 30

Lys Lys Val Ser Arg Leu Glu Cys Arg Gly Gly Cys Ala Gly Gly Gln
35 40 45

Cys Cys Gly Pro Leu Arg Ser Lys Arg Arg Lys Tyr Ser Phe Glu Cys
50 55 60

Thr Asp Gly Ser Ser Phe Val Asp Glu Val Glu Lys Val Val Lys Cys
65 70 75 80

Gly Cys Thr Arg Cys Val
85

<210> SEQ ID NO 168
<211> LENGTH: 85
<212> TYPE: PRT
<213> ORGANISM: Artificial
<220> FEATURE:
<223> OTHER INFORMATION: proteinmimic slit homolog 3

<400> SEQUENCE: 168

Ser Gly Glu His Cys Gln Gln Glu Asn Pro Cys Leu Gly Gln Val Val
1 5 10 15

Arg Glu Val Ile Arg Arg Gln Lys Gly Tyr Ala Ser Cys Ala Thr Ala
20 25 30

-continued

```
Ser Lys Val Pro Ile Met Glu Cys Arg Gly Gly Cys Gly Pro Gln Cys
        35                  40                  45

Cys Gln Pro Thr Arg Ser Lys Arg Arg Lys Tyr Val Phe Gln Cys Thr
    50                  55                  60

Asp Gly Ser Ser Phe Val Glu Glu Val Glu Arg His Leu Glu Cys Gly
65                  70                  75                  80

Cys Leu Ala Cys Ser
                85


<210> SEQ ID NO 169
<211> LENGTH: 82
<212> TYPE: PRT
<213> ORGANISM: Artificial
<220> FEATURE:
<223> OTHER INFORMATION: proteinmimic slit Drosophila

<400> SEQUENCE: 169

Glu Pro Pro Thr Val Thr Ala Ala Ser Thr Cys Arg Lys Glu Gln Val
1               5                   10                  15

Arg Glu Tyr Tyr Thr Glu Asn Asp Cys Arg Ser Arg Gln Pro Leu Lys
            20                  25                  30

Tyr Ala Lys Cys Val Gly Gly Cys Gly Ser Gln Cys Cys Ala Ala Lys
        35                  40                  45

Ile Val Arg Arg Arg Lys Val Arg Met Val Cys Ser Asn Asn Arg Lys
    50                  55                  60

Tyr Ile Lys Asn Leu Asp Ile Val Arg Lys Cys Gly Cys Thr Lys Lys
65                  70                  75                  80

Cys Tyr


<210> SEQ ID NO 170
<211> LENGTH: 111
<212> TYPE: PRT
<213> ORGANISM: Artificial
<220> FEATURE:
<223> OTHER INFORMATION: proteinmimic hSDCP1

<400> SEQUENCE: 170

Leu Asp Arg Asn Thr Arg Val Gln Val Gly Cys Arg Glu Leu Arg Ser
1               5                   10                  15

Thr Lys Tyr Ile Ser Asp Gly Gln Cys Thr Ser Ile Ser Pro Leu Lys
            20                  25                  30

Glu Leu Val Cys Ala Gly Glu Cys Leu Pro Leu Pro Val Leu Pro Asn
        35                  40                  45

Trp Ile Gly Gly Gly Tyr Gly Thr Lys Tyr Trp Ser Arg Arg Ser Ser
    50                  55                  60

Gln Glu Trp Arg Cys Val Asn Asp Lys Thr Arg Thr Gln Arg Ile Gln
65                  70                  75                  80

Leu Gln Cys Gln Asp Gly Ser Thr Arg Thr Tyr Lys Ile Thr Val Val
                85                  90                  95

Thr Ala Cys Lys Cys Lys Arg Tyr Thr Arg Gln His Asn Glu Ser
            100                 105                 110


<210> SEQ ID NO 171
<211> LENGTH: 108
<212> TYPE: PRT
<213> ORGANISM: Artificial
<220> FEATURE:
<223> OTHER INFORMATION: proteinmimic sclerostin

<400> SEQUENCE: 171
```

-continued

Phe Glu Thr Lys Asp Val Ser Glu Tyr Ser Cys Arg Glu Leu His Phe
1               5                   10                  15

Thr Arg Tyr Val Thr Asp Gly Pro Cys Arg Ser Ala Lys Pro Val Thr
            20                  25                  30

Glu Leu Val Cys Ala Gly Glu Cys Gly Pro Ala Arg Leu Leu Pro Asn
        35                  40                  45

Ala Ile Gly Arg Gly Lys Trp Trp Arg Pro Ser Gly Pro Asp Phe Arg
    50                  55                  60

Cys Ile Pro Asp Arg Tyr Arg Ala Gln Arg Val Gln Leu Leu Cys Pro
65                  70                  75                  80

Gly Gly Glu Ala Pro Arg Ala Arg Lys Val Arg Leu Val Ala Ser Cys
                85                  90                  95

Lys Cys Lys Arg Leu Thr Arg Phe His Asn Gln Ser
            100                 105

<210> SEQ ID NO 172
<211> LENGTH: 116
<212> TYPE: PRT
<213> ORGANISM: Artificial
<220> FEATURE:
<223> OTHER INFORMATION: proteinmimic SCO-spondin

<400> SEQUENCE: 172

Val Leu Glu Pro Gly Ser Cys Cys Pro Ser Cys Arg Arg Glu Ala Pro
1               5                   10                  15

Glu Glu Gln Ser Pro Ser Cys Gln Leu Leu Thr Glu Leu Arg Asn Phe
            20                  25                  30

Thr Lys Gly Thr Cys Tyr Leu Asp Gln Val Glu Val Ser Tyr Cys Ser
        35                  40                  45

Gly Tyr Cys Pro Ser Ser Thr His Val Met Pro Glu Glu Pro Tyr Leu
    50                  55                  60

Gln Ser Gln Cys Asp Cys Cys Ser Tyr Arg Leu Asp Pro Glu Ser Pro
65                  70                  75                  80

Val Arg Ile Leu Asn Leu Arg Cys Leu Gly Gly His Thr Glu Pro Val
                85                  90                  95

Val Leu Pro Val Ile His Ser Cys Gln Cys Ser Ser Cys Gln Gly Gly
            100                 105                 110

Asp Phe Ser Lys
        115

<210> SEQ ID NO 173
<211> LENGTH: 100
<212> TYPE: PRT
<213> ORGANISM: Artificial
<220> FEATURE:
<223> OTHER INFORMATION: proteinmimic van Willebrand factor

<400> SEQUENCE: 173

Thr Cys Cys Asp Thr Cys Glu Glu Pro Glu Cys Asn Asp Ile Thr Ala
1               5                   10                  15

Arg Leu Gln Tyr Val Lys Val Gly Ser Cys Lys Ser Glu Val Glu Val
            20                  25                  30

Asp Ile His Tyr Cys Gln Gly Lys Cys Ala Ser Lys Ala Met Tyr Ser
        35                  40                  45

Ile Asp Ile Asn Asp Val Gln Asp Gln Cys Ser Cys Cys Ser Pro Thr
    50                  55                  60

Arg Thr Glu Pro Met Gln Val Ala Leu His Cys Thr Asn Gly Ser Val

-continued

```
65                  70                  75                  80

Val Tyr His Glu Val Leu Asn Ala Met Glu Cys Lys Cys Ser Pro Arg
                85                  90                  95

Lys Cys Ser Lys
            100


<210> SEQ ID NO 174
<211> LENGTH: 90
<212> TYPE: PRT
<213> ORGANISM: Artificial
<220> FEATURE:
<223> OTHER INFORMATION: proteinmimic WNT1-inducible signalling pathway
      protein 1

<400> SEQUENCE: 174

Ile His Thr Leu Ile Lys Ala Gly Lys Lys Cys Leu Ala Val Tyr Gln
1               5                   10                  15

Pro Glu Ala Ser Met Asn Phe Thr Leu Ala Gly Cys Ile Ser Thr Arg
            20                  25                  30

Ser Tyr Gln Pro Lys Tyr Cys Gly Val Cys Met Asp Asn Arg Cys Cys
        35                  40                  45

Ile Pro Tyr Lys Ser Lys Thr Ile Asp Val Ser Phe Gln Cys Pro Asp
    50                  55                  60

Gly Leu Gly Phe Ser Arg Gln Val Leu Trp Ile Asn Ala Cys Phe Cys
65                  70                  75                  80

Asn Leu Ser Cys Arg Asn Pro Asn Asp Ile
                85                  90


<210> SEQ ID NO 175
<211> LENGTH: 90
<212> TYPE: PRT
<213> ORGANISM: Artificial
<220> FEATURE:
<223> OTHER INFORMATION: proteinmimic WNT1-inducible-signalling pathway
      protein 3

<400> SEQUENCE: 175

Leu Lys Thr Ile Lys Ile Pro Lys Gly Lys Cys Gln Pro Thr Phe Gln
1               5                   10                  15

Leu Ser Lys Ala Glu Lys Phe Val Phe Ser Gly Cys Ser Ser Thr Gln
            20                  25                  30

Ser Tyr Lys Pro Thr Phe Cys Gly Ile Cys Leu Asp Lys Arg Cys Cys
        35                  40                  45

Ile Pro Asn Lys Ser Lys Met Ile Thr Ile Gln Phe Asp Cys Pro Asn
    50                  55                  60

Glu Gly Ser Phe Lys Trp Lys Met Leu Trp Ile Thr Ser Cys Val Cys
65                  70                  75                  80

Gln Arg Asn Cys Arg Glu Pro Gly Asp Ile
                85                  90


<210> SEQ ID NO 176
<211> LENGTH: 113
<212> TYPE: PRT
<213> ORGANISM: Artificial
<220> FEATURE:
<223> OTHER INFORMATION: proteinmimic hemaolectin Drosophila

<400> SEQUENCE: 176

Ser Glu Pro Leu Val Glu Asp Lys Ser Ser Cys Leu Pro Val Ser Leu
1               5                   10                  15
```

-continued

```
Ala Glu Ser Arg Thr Lys Glu Ile Leu Lys Phe Pro Val Gln Gly His
            20                  25                  30

Gly Thr Cys Val Asn Ala Asp Pro Ile Gln Gly Phe Thr Asp Cys Glu
        35                  40                  45

Gly Ala Cys Ser Ser Gly Ser Lys Tyr Asn Thr Leu Thr Asp Met His
    50                  55                  60

Glu Lys Phe Cys Thr Cys Cys Ser Ile Lys Ser Tyr His Pro Ile Ser
65                  70                  75                  80

Val Lys Met Ile Cys Asp Asp Gly His Thr Phe Thr Gln Lys His Glu
                85                  90                  95

Val Pro Ser Asn Cys Gly Cys Ser Pro Cys Ser Glu Phe Ser Asp Ser
            100                 105                 110

Ala
```

<210> SEQ ID NO 177
<211> LENGTH: 106
<212> TYPE: PRT
<213> ORGANISM: Artificial
<220> FEATURE:
<223> OTHER INFORMATION: proteinmimic human glycoprotein hormone alpha-2

<400> SEQUENCE: 177

```
Gln Glu Ala Val Ile Pro Gly Cys His Leu His Pro Phe Asn Val Thr
1               5                   10                  15

Val Arg Ser Asp Arg Gln Gly Thr Cys Gln Gly Ser His Val Ala Gln
            20                  25                  30

Ala Cys Val Gly His Cys Glu Ser Ser Ala Phe Pro Ser Arg Tyr Ser
        35                  40                  45

Val Leu Val Ala Ser Gly Tyr Arg His Asn Ile Thr Ser Val Ser Gln
    50                  55                  60

Cys Cys Thr Ile Ser Gly Leu Lys Lys Val Lys Val Gln Leu Gln Cys
65                  70                  75                  80

Val Gly Ser Arg Arg Glu Glu Leu Glu Ile Phe Thr Ala Arg Ala Cys
                85                  90                  95

Gln Cys Asp Met Cys Arg Leu Ser Arg Tyr
            100                 105
```

<210> SEQ ID NO 178
<211> LENGTH: 108
<212> TYPE: PRT
<213> ORGANISM: Artificial
<220> FEATURE:
<223> OTHER INFORMATION: proteinmimic mouse glycoprotein hormone alpha-2

<400> SEQUENCE: 178

```
His Ser Pro Glu Thr Ala Ile Pro Gly Cys His Leu His Pro Phe Asn
1               5                   10                  15

Val Thr Val Arg Ser Asp Arg Leu Gly Thr Cys Gln Gly Ser His Val
            20                  25                  30

Ala Gln Ala Cys Val Gly His Cys Glu Ser Ser Ala Phe Pro Ser Arg
        35                  40                  45

Tyr Ser Val Leu Val Ala Ser Gly Tyr Arg His Asn Ile Thr Ser Ser
    50                  55                  60

Ser Gln Cys Cys Thr Ile Ser Ser Leu Arg Lys Val Arg Val Trp Leu
65                  70                  75                  80
```

Gln Cys Val Gly Asn Gln Arg Gly Glu Leu Glu Ile Phe Thr Ala Arg
85 90 95

Ala Cys Gln Cys Asp Met Cys Arg Phe Ser Arg Tyr
100 105

<210> SEQ ID NO 179
<211> LENGTH: 113
<212> TYPE: PRT
<213> ORGANISM: Artificial
<220> FEATURE:
<223> OTHER INFORMATION: proteinmimic jagged-1

<400> SEQUENCE: 179

Leu Asp Ala Asn Glu Cys Glu Ala Lys Pro Cys Val Asn Ala Lys Ser
1 5 10 15

Cys Lys Asn Leu Ile Ala Ser Tyr Tyr Cys Asp Cys Leu Pro Gly Trp
20 25 30

Asn Gly Gln Asn Cys Asp Ile Asn Ile Asn Asp Cys Leu Gly Gln Cys
35 40 45

Gln Asn Asp Ala Ser Cys Arg Asp Leu Val Asn Gly Tyr Arg Cys Ile
50 55 60

Cys Pro Pro Gly Tyr Ala Gly Asp His Cys Glu Arg Asp Ile Asp Glu
65 70 75 80

Cys Ala Ser Asn Pro Cys Leu Asn Gly Gly His Cys Gln Asn Glu Ile
85 90 95

Asn Arg Phe Gln Cys Leu Cys Pro Thr Gly Phe Ser Gly Asn Leu Cys
100 105 110

Gln

<210> SEQ ID NO 180
<211> LENGTH: 113
<212> TYPE: PRT
<213> ORGANISM: Artificial
<220> FEATURE:
<223> OTHER INFORMATION: proteinmimic jagged-2

<400> SEQUENCE: 180

Leu Asp Ala Asn Glu Cys Glu Gly Lys Pro Cys Leu Asn Ala Phe Ser
1 5 10 15

Cys Lys Asn Leu Ile Gly Gly Tyr Tyr Cys Asp Cys Ile Pro Gly Trp
20 25 30

Lys Gly Ile Asn Cys His Ile Asn Val Asn Asp Cys Arg Gly Gln Cys
35 40 45

Gln His Gly Gly Thr Cys Lys Asp Leu Val Asn Gly Tyr Gln Cys Val
50 55 60

Cys Pro Arg Gly Phe Gly Gly Arg His Cys Glu Leu Glu Arg Asp Glu
65 70 75 80

Cys Ala Ser Ser Pro Cys His Ser Gly Gly Leu Cys Glu Asp Leu Ala
85 90 95

Asp Gly Phe His Cys His Cys Pro Gln Gly Phe Ser Gly Pro Leu Cys
100 105 110

Glu